(12) United States Patent
Lee et al.

(10) Patent No.: US 9,371,294 B2
(45) Date of Patent: Jun. 21, 2016

(54) CYCLOALKENYL ARYL DERIVATIVES FOR CETP INHIBITOR

(75) Inventors: SeoHee Lee, Yongin-si (KR); Jung Taek Oh, Yongin-si (KR); JaeKwang Lee, Yongin-si (KR); JaeWon Lee, Yongin-si (KR); Suyeal Bae, Yongin-si (KR); Nina Ha, Yongin-si (KR); Sera Lee, Yongin-si (KR)

(73) Assignee: CHONG KUN DANG PHARMACEUTICAL CORP. (KR)

( * ) Notice: Subject to any disclaimer, the term of this patent is extended or adjusted under 35 U.S.C. 154(b) by 186 days.

(21) Appl. No.: 14/110,271

(22) PCT Filed: Apr. 12, 2012

(86) PCT No.: PCT/KR2012/002739
§ 371 (c)(1),
(2), (4) Date: Oct. 7, 2013

(87) PCT Pub. No.: WO2012/141487
PCT Pub. Date: Oct. 18, 2012

(65) Prior Publication Data
US 2014/0031335 A1 Jan. 30, 2014
US 2015/0119376 A2 Apr. 30, 2015

(30) Foreign Application Priority Data

Apr. 12, 2011 (KR) .................. 10-2011-0033943

(51) Int. Cl.
| | | |
|---|---|---|
| C07D 401/14 | (2006.01) | |
| C07D 403/10 | (2006.01) | |
| C07D 405/14 | (2006.01) | |
| C07D 263/24 | (2006.01) | |
| C07D 263/16 | (2006.01) | |
| C07D 263/22 | (2006.01) | |
| C07D 401/06 | (2006.01) | |
| C07D 413/06 | (2006.01) | |
| C07D 413/08 | (2006.01) | |
| C07D 413/10 | (2006.01) | |
| C07D 417/12 | (2006.01) | |

(52) U.S. Cl.
CPC ............ *C07D 263/24* (2013.01); *C07D 263/16* (2013.01); *C07D 263/22* (2013.01); *C07D 401/06* (2013.01); *C07D 413/06* (2013.01); *C07D 413/08* (2013.01); *C07D 413/10* (2013.01); *C07D 417/12* (2013.01)

(58) Field of Classification Search
None
See application file for complete search history.

(56) References Cited

U.S. PATENT DOCUMENTS

| | | | |
|---|---|---|---|
| 5,929,094 A | 7/1999 | Durette et al. | |
| 8,759,383 B2 * | 6/2014 | Tung ................... | A61K 31/421 514/374 |
| 2008/0242711 A1 | 10/2008 | Tung | |
| 2010/0081673 A1 | 4/2010 | Hutchinson et al. | |

FOREIGN PATENT DOCUMENTS

| | | |
|---|---|---|
| WO | 98/35937 A1 | 8/1998 |
| WO | 2006/014357 A1 | 9/2006 |
| WO | 2007-079186 A2 | 7/2007 |
| WO | 2007-081569 A2 | 7/2007 |
| WO | 2010039474 A1 | 4/2010 |

OTHER PUBLICATIONS

International Search Report for PCT/KR2012/002739 dated Oct. 23, 2012.
Morris, G. A., et al., Tetrahedron Lett., 2001, 42, 2093.
Goldbourt et al., Arterioscler Thromb Vasc Biol, 1997, 17, 107-113.
Taylor et al, Circulation, 2004, 110, 3512-3517.
Barter et al., Arterioscler Thromb Vasc Biol, 2003, 23, 160-167.
Forrest et al, British Journal of Pharmacology (2008) 154, 1465-1473.
Hisashi Shinkai. Expert Opinion on Therapeutic Patents, 2009, 19(9), 1229-1237.
Niesor et al, Journal of Lipid reserch, 2010, 51, 3443-3453.
Martin G. Banwell et al. Org. Lett. 2004, 6, 2741.
Erin F. Dimauro et al., J. Med. Chem. 2006, 49, 5671.
Jingjun Yin et al., J. Org. Chem. 2006, 840.
Akio Baba et al., Tetrahedron 2009, 65, 5462.
Kim et al, J. Am. Chem. Soc. 1997, 119, 681-69.

* cited by examiner

*Primary Examiner* — Kamal Saeed
(74) *Attorney, Agent, or Firm* — Heslin, Rothenberg, Farley & Mesiti P.C.

(57) ABSTRACT

The present invention relates to cycloalkenyl aryl derivatives, isomers thereof, pharmaceutically acceptable salts thereof, hydrates thereof, or solvates thereof; a method for preparing the derivatives; and pharmaceutical compositions containing the same. The compounds of the present invention show the effect of CETP activity inhibition. It means that the compounds can increase HDL-cholesterol and decrease LDL-cholesterol.

10 Claims, No Drawings

CYCLOALKENYL ARYL DERIVATIVES FOR CETP INHIBITOR

CROSS REFERENCE TO RELATED APPLICATIONS

This application is a national stage filing under section 371 of International Application No. PCT/KR2012/002739 filed Apr. 12, 2012 and published as WO 2012/141487, and claims priority to Korean Patent Application No. 10-2011-0033943 filed on Apr. 12, 2011, the entire disclosure of these applications being hereby incorporated herein by reference.

TECHNICAL FIELD

The present invention relates to novel cycloalkenyl aryl derivatives, and more particularly to novel cycloalkenyl aryl derivatives having CETP inhibitory activity, isomers thereof, pharmaceutically acceptable salts thereof, hydrates thereof, or solvates thereof, the use thereof for preparing pharmaceutical compositions, pharmaceutical compositions containing the same, methods of treating disease using these compositions, and methods for preparing novel cycloalkenyl aryl derivatives.

BACKGROUND ART

Hyperlipidemia refers to high blood cholesterol levels and is asymptomatic. However, hyperlipidemia is a very significant condition, because it causes angina pectoris, myocardial infarction and arteriosclerosis. Statins, drugs that are commonly used to treat hyperlipidemia, exhibit therapeutic effects mainly by lowering LDL-C, but their effects on the prevention of cardiovascular diseases are still very insufficient. A recent study reported that elevated concentration of high-density lipoprotein (HDL-C) is very effective in preventing cardiovascular diseases as effective as lower low-density lipoprotein cholesterol (LDL-C) (Goldbourt et al, Arterioscler Thromb Vasc Biol, 1997, 17, 107-113). Among drugs that are used to increase HDL-C, the most effective drug is Niacin. However, this drug needs to be taken in relatively large doses and causes side effects such as facial flushing (Taylor et al, Circulation, 2004, 110, 3512-3517).

Meanwhile, cholesterol ester transfer protein (CETP) is a protein that participates in reverse cholesterol transport (the reverse transport of cholesterol from peripheral tissue to the liver). When CETP is inhibited, HDL-C can be effectively increased, thus preventing cardiovascular diseases. Accordingly, the development of compounds capable of inhibiting CETP activity is very important (Barter et al., Arterioscler Thromb Vasc Biol, 2003, 23, 160-167).

CETP inhibitors known to date can be divided according to structure into Torcetrapib (WO 02/088085) and Anacetrapib (WO 2006/014357), which are 3,5-bis-trifluoromethyl-benzene derivatives, and Dalcetrapib (WO 98/35937) which is a benzenethiol derivative.

However, among these CETP inhibitors, Torcetrapib causes a increases in blood pressure and an increase in mortality, and thus clinical trials thereof were terminated. It was reported that such side effects occur because Torcetrapib increases the levels of hormones, such as aldosterone and cortisol, associated with a significant elevation in blood pressure, and increases the thickness of the vascular wall to cause inflammation, thus increasing mortality (Ferrest et al, British Journal of Pharmacology, (2008) 154, 1465-1473). The other CETP inhibitor Dalcetrapib has not been reported to cause such side effects, but is known to have insufficient rise in HDL-C (Hisashi Shinkai. Expert Opinion on Therapeutic Patents, 2009, 19(9), 1229-1237). Among such CETP inhibitors, Anacetrapib and Dalcetrapib are in clinical trials for the purpose of treating hyperlipidemia and cardiovascular diseases by increasing HDL-C and decreasing LDL-C(Niesor et al, Journal of lipid Research, 2010, 51, 3443-3453).

DISCLOSURE

Technical Problem

It is an object of the present invention to provide novel cycloalkenyl aryl derivatives, isomers thereof, pharmaceutically acceptable salts thereof, hydrates thereof, or solvates thereof, and preparation methods thereof.

Another object of the present invention is to provide novel cycloalkenyl aryl derivatives, which have less side effects and can effectively inhibit CETP, isomers thereof, pharmaceutically acceptable salts thereof, hydrates thereof, or solvates thereof, and preparation methods thereof.

Still another object of the present invention is to provide methods for preparing novel cycloalkenyl aryl derivatives.

Technical Solution

To achieve the above objects, the present invention provides cycloalkenyl aryl derivatives of the following formula 1, isomers thereof, pharmaceutically acceptable salts thereof, hydrates thereof, or solvates thereof, and preparation methods thereof:

[Formula 1]

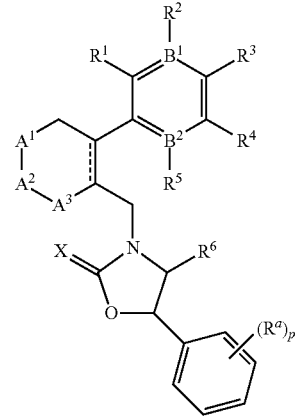

wherein $B^1$ and $B^2$ are each independently N or C, with the proviso that both $B^1$ and $B^2$ cannot be N at the same time, and if one of $B^1$ and $B^2$ is N, $R^2$ or $R^5$ is absent;

$R^1$ and $R^2$ are each independently H, —F, —OH, —NH$_2$, —C(=O)H, —CH$_2$OH, —OC$_1$-C$_6$ alkyl, —SC$_1$-C$_6$ alkyl, —CH$_2$OC$_1$-C$_6$ alkyl, —NH(C$_1$-C$_6$ alkyl), —NH(C=O)(C$_1$-C$_6$ alkyl), —N(C$_1$-C$_6$ alkyl)$_2$, or

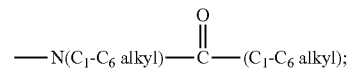

or
$R^1$ and $R^2$ together with the carbon atoms to which they are bonded may form a 5- or 6-membered heterocyclic aromatic or non-aromatic ring compound having 1 to 3 hetero atoms selected independently from the group consisting of N, O, S, and C(=O), wherein the heterocyclic aromatic or non-aromatic ring compound may optionally be substituted with $R^8$;

$R^3$ is —H, —F, —OH, —$C_1$-$C_6$ alkyl, or —O$C_1$—$C_6$ alkyl;

$R^4$ is —H, halogen, —CN, —$NO_2$, —$C_1$-$C_6$ alkyl, —$C_2$-$C_6$alkenyl, —$C_3$-$C_6$ cycloalkyl,

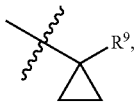

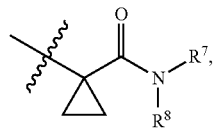

—$OR^7$, —$CH_2OR^7$, —$CH_2NR^7R^8$, —$SR^7$, —C(=O)$R^7$, —$CO_2R^7$, —CH$R^7CO_2R^8$, —C(=O)N$R^7R^8$,

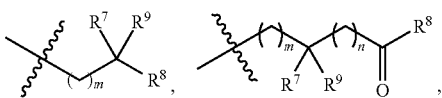

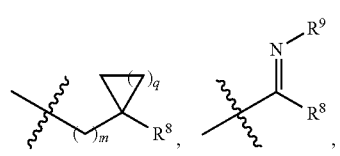

—N$R^7R^8$, —N$R^7$C(=O)$R^8$, —N$R^7CO_2R^8$,

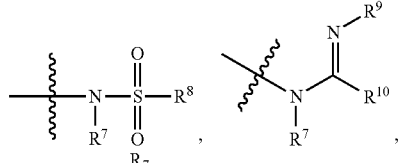

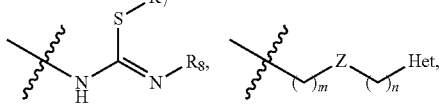

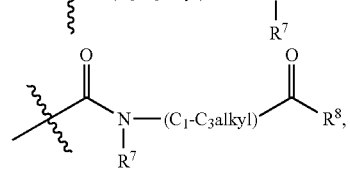

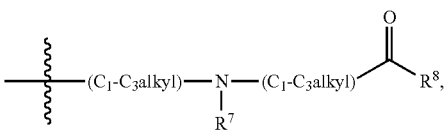

N$R^7$C(=O)N$R^8R^9$, —N$R^7$C(=S)N$R^8R^9$, Ar or Het; or $R^3$ and $R^4$ together with the carbon atoms to which they are bonded may form a 5- or 6-membered cycloalkyl or heterocyclic ring compound having 0 to 3 hetero atoms selected independently from the group consisting of N, O, S, and C(=O), wherein the cycloalkyl or heterocyclic ring compound may optionally be substituted with $R^8$;

Ar is a C6 monocyclic aromatic compound, which is unsubstituted or optionally substituted with one or more selected from the group consisting of halogen, —OH, —$NH_2$, —$C_1$-$C_6$ alkyl and —O$C_1$—$C_6$ alkyl; Het is a 5- or 6-membered heterocyclic ring compound containing 0 to 2 double bonds and having 1 to 4 hetero atoms selected independently from the group consisting of N, O, S, C(=O) and C(=S), and may be unsubstituted or may optionally be substituted with $R^8$;

$R^5$ is —H, —F, —OH, —$CF_3$, —$C_1$-$C_6$alkyl, or —O$C_1$—$C_6$ alkyl;

$R^6$ is —H or —$C_1$-$C_6$ alkyl;

$R^7$ is —H, halogen, —C(=O)($C_1$-$C_3$ alkyl), —$C_1$-$C_6$ alkyl, —O$C_1$—$C_6$ alkyl, —$C_3$-$C_6$ cycloalkyl, or —OC(=O)($C_1$-$C_3$ alkyl);

$R^8$ is —H, halogen, —OH, —CN, —$NH_2$, —NH($C_1$-$C_3$ alkyl), —C(=O)$NH_2$, —$CO_2H$,

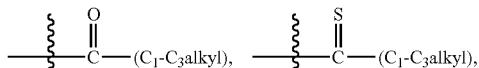

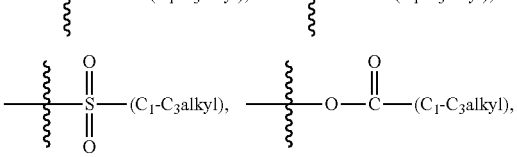

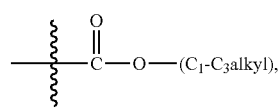

—O$C_1$—$C_6$ alkyl, —O$C_1$—$C_6$ alkyl, —$C_3$—$C_6$ cycloalkyl, -Ph or

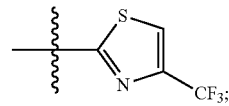 [SMILES: *c1nc(C(F)(F)F)cs1]

$R^9$ is —H, —CN, —$C_1$-$C_6$ alkyl, —O$C_1$—$C_6$ alkyl, or —C(=O)($C_1$-$C_3$ alkyl);

$R^{10}$ is —NH($C_1$-$C_3$ alkyl), —N($C_1$-$C_3$ alkyl)$_2$, or —S($C_1$-$C_3$ alkyl);

Z is —CH$_2$—,

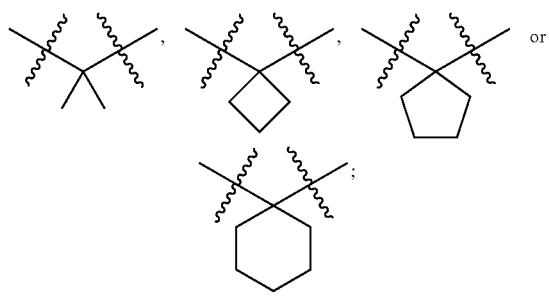

R$^a$ is —H, —Cl or —CF$_3$;
p is an integer ranging from 0 to 2;
A$^1$ and A$^2$ are each independently —O—, —(CR$^{11}$R$^{12}$)—, or —NR$^{13}$, wherein R$^{11}$ and R$^{12}$ are each independently —H, —F, or —C$_1$-C$_6$ alkyl, or R$^{11}$ and R$^{12}$ together form a 3- or 4-membered spirocyclic non-aromatic ring compound, and R$^{13}$ is —H, —C$_1$-C$_6$ alkyl, —C(=O)(C$_1$-C$_6$ alkyl), —CO$_2$(C$_1$-C$_6$ alkyl), —SO$_2$(C$_1$-C$_6$ alkyl), or —C$_3$-C$_6$ cycloalkyl;
A$^3$ is —(CH$_2$)$_n$—;
X is S or O;
m is an integer ranging from 0 to 3;
n is an integer ranging from 0 to 2;
q is an integer ranging from 1 to 3;
wherein said —C$_1$-C$_3$ alkyl, —C$_3$-C$_6$ cycloalkyl —C$_1$-C$_6$ alkyl or —C$_2$-C$_6$ alkenyl is unsubstituted or substituted with one or more selected from the group consisting of halogen, —OH, —CF$_3$, —CN, —CO$_2$H, —C(=O)CH$_3$, —OC(=O)CH$_3$, —C$_1$-C$_3$alkyl, —OC$_1$-C$_3$alkyl, and -Ph.

Preferably, the present invention provides cycloalkenyl aryl derivatives according to the above definition, isomers thereof, pharmaceutically acceptable salts thereof, hydrates thereof, or solvates thereof:
wherein B$^1$ and B$^2$ are each independently N or C, with the proviso that both B$^1$ and B$^2$ cannot be N at the same time, and if any one of B$^1$ and B$^2$ is N, R$^2$ or R$^5$ is absent;
R$^1$ is —F, —OH, —NH$_2$, —C(=O)H, —CH$_2$OH, —OCH$_3$, —OCF$_3$, —SCH$_3$, —CH$_2$OCH$_3$, —NHCH$_3$,

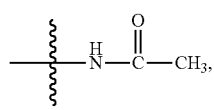

—N(CH$_3$)$_2$, or

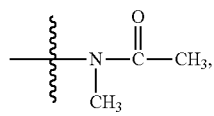

R$^2$ is —H; or
R$^1$ and R$^2$ together with the carbon atoms to which they are bonded may form a 5- or 6-membered heterocyclic aromatic or non-aromatic ring compound having 1 to 3 hetero atoms selected independently from the group consisting of N, O, S, and C(=O), wherein the heterocyclic aromatic or non-aromatic ring compound may optionally be substituted with R$^8$;
R$^3$ is —H, —F, —OH, —CH$_3$, —CF$_3$, —CH$_2$CH$_3$, or —OCH$_3$;

R$^4$ is —H, —F, —Cl, —CN, —NO$_2$, —CH$_3$, —CH$_2$CH$_3$, —CH(CH$_3$)$_2$, —C(CH$_3$)$_3$, —CF$_3$, —CH(CF$_3$)$_2$, —CH(CH$_3$)(CF$_3$), —C(OCH$_3$)(CF$_3$)$_2$, —CH(OH)CH$_3$, —C(OH)(CH$_3$)$_2$, —C(OH)(CF$_3$)$_2$, —C(=CF$_2$)CF$_3$, -cyclopropyl,

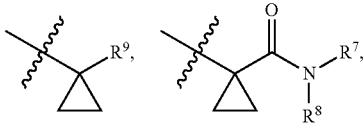

—OCH$_3$, —OCH$_2$CH$_3$, —OCH(CH$_3$)$_2$, —OC(CH$_3$)$_3$, —OCF$_3$, —OCH$_2$CF$_3$, —CH$_2$OH, —CH$_2$OCH$_3$, —CH$_2$NR$^7$R$^8$, —SCH$_3$, —C(=O)R$^7$, —CO$_2$R$^7$, —CHR$^7$CO$_2$R$^8$, —C(=O)NR$^7$R$^8$,

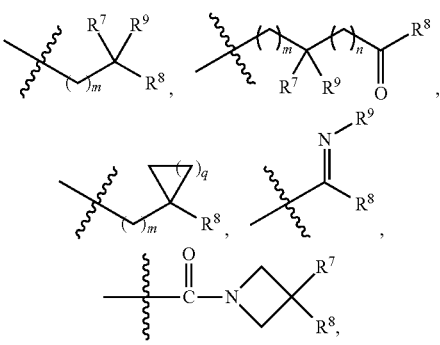

—NR$^7$R$^8$, —NR$^7$C(=O)R$^8$, —NR$^4$CO$_2$R$^8$,

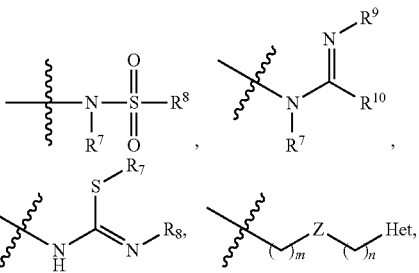

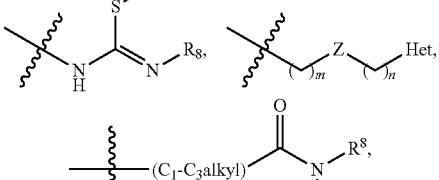

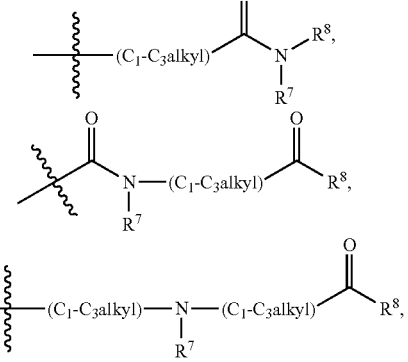

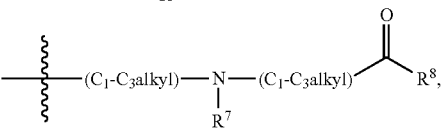

—NR$^7$C(=O)NR$^8$R$^9$, —NR$^7$C(=S)NR$^8$R$^9$, Ar or Het; or
R$^3$ and R$^4$ together with the carbon atoms to which they are bonded may form a 5- or 6-membered cycloalkyl or heterocyclic ring compound having 0 to 3 hetero atoms selected independently from the group consisting of N, O, S, and C(=O), wherein the cycloalkyl or heterocyclic ring compound may optionally be substituted with $R^8$;

Ar is a C6 monocyclic aromatic compound, which is unsubstituted or optionally substituted with one or more selected from the group consisting of —F, —Cl, —OH, —$NH_2$, —$CH_3$ and —$OCH_3$;

Het is selected from

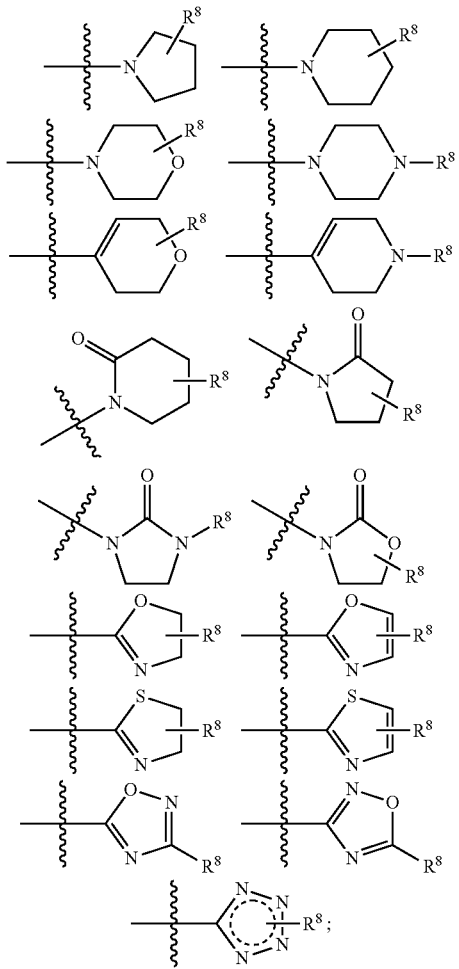

$R^5$ is —H;
$R^6$ is —H or —$CH_3$;
$R^7$ is —H, halogen, —C(=O)($C_1$-$C_3$ alkyl), —$C_1$-$C_6$ alkyl, —$OC_1$—$C_6$ alkyl, —$C_3$-$C_6$ cycloalkyl, or —OC(=O)($C_1$-$C_3$ alkyl);
$R^8$ is —H, halogen, —OH, —CN, —$NH_2$, —NH($C_1$-$C_3$ alkyl), —C(=O)$NH_2$, —$CO_2$H,

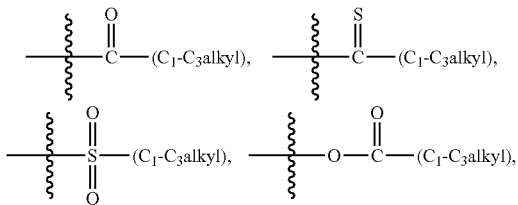

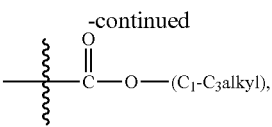

—$C_1$-$C_6$ alkyl, —$OC_1$—$C_6$ alkyl,
—$C_3$-$C_6$ cycloalkyl, -Ph or

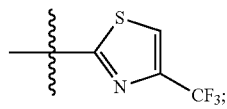

$R^9$ is —H, —CN, —$C_1$-$C_6$ alkyl, —$OC_1$—$C_6$ alkyl, or —C(=O)($C_1$-$C_3$ alkyl);
$R^{10}$ is —NH($C_1$-$C_3$ alkyl), —N($C_1$-$C_3$ alkyl)$_2$, or —S($C_1$-$C_3$ alkyl);
Z is —$CH_2$—,

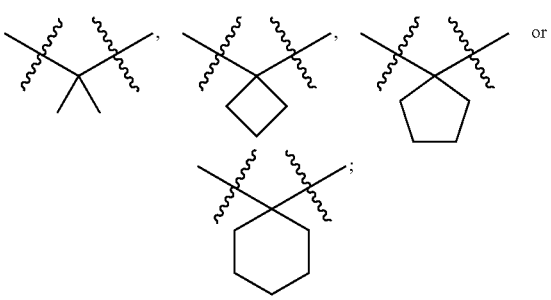

$R^a$ is —H, —Cl or —$CF_3$;
p is 2;
$A^1$ is —$CH_2$—, —C($CH_3$)$_2$—, or —$NR^{13}$;
$A^2$ is —O—, —($CR^{11}R^{12}$) or —$NR^{13}$, wherein $R^{11}$ and $R^{12}$ are each independently —H, —F, —$CH_3$, —$CF_3$, —$CH_2CH_3$, —CH($CH_3$)$_2$, or —C($CH_3$)$_3$, or $R^{11}$ and $R^{12}$ together form a 3- or 4-membered spirocyclic non-aromatic ring compound, and $R^{13}$ is —H, —$CH_3$, —$CF_3$, —$CH_2CH_3$, —CH($CH_3$)$_2$, —$CH_2CF_3$, —C(=O)$CH_3$, —C(=O)$CF_3$, —$CO_2$C($CH_3$)$_3$, —$SO_2CH_3$, —$SO_2CF_3$, or

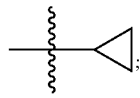

$A^3$ is —($CH_2$)$_n$—;
X is S or O;
m is an integer ranging from 0 to 3;
n is an integer ranging from 0 to 2;
q is an integer ranging from 1 to 3;
wherein said —$C_1$-$C_3$ alkyl, —$C_3$-$C_6$ cycloalkyl, —$C_1$-$C_6$ alkyl or —$C_2$-$C_6$ alkenyl is unsubstituted or substituted with one or more selected from the group consisting of —F, —Cl, —Br, —OH, —$CF_3$, —CN, —$CO_2$H, —C(=O)$CH_3$, —OC(=O)$CH_3$, —$C_1$-$C_3$ alkyl, —$OC_1$—$C_3$ alkyl, and -Ph.

Specific examples of preferred compounds of formula 1 according to the present invention include:

| | |
|---|---|
| 15 | (4S,5R)-5-(3,5-bis(trifluoromethyl)phenyl)-3-((2-(5-isopropyl-2-methoxyphenyl)-5,5-dimethylcyclohex-1-enyl)methyl)-4-methyloxazolidine-2-thione |
| 16 | (4S,5R)-5-(3,5-bis(trifluoromethyl)phenyl)-3-((2-(2-methoxyphenyl)-5,5-dimethylcyclohex-1-enyl)methyl)-4-methyloxazolidine-2-thione |
| 17 | (4S,5R)-5-(3,5-bis(trifluoromethyl)phenyl)-3-((2-(4-fluoro-5-isopropyl-2-methoxyphenyl)-5,5-dimethylcyclohex-1-enyl)methyl)-4-methyloxazolidine-2-thione |
| 18 | (4S,5R)-5-(3,5-bis(trifluoromethyl)phenyl)-3-((2-(2-methoxyphenyl)-5,5-dimethylcyclohex-1-enyl)methyl)-4-methyloxazolidin-2-one |
| 19 | (4S,5R)-5-(3,5-bis(trifluoromethyl)phenyl)-3-((2-(4-fluoro-5-isopropyl-2-methoxyphenyl)-5,5-dimethylcyclohex-1-enyl)methyl)-4-methyloxazolidin-2-one |
| 25 | (4S,5R)-5-(3,5-bis(trifluoromethyl)phenyl)-3-((2-(4-fluoro-5-isopropyl-2-methoxyphenyl)-5-methylcyclohex-1-enyl)methyl)-4-methyloxazolidin-2-one |
| 26 | (4S,5R)-5-(3,5-bis(trifluoromethyl)phenyl)-3-((2-(4-fluoro-5-isopropyl-2-methoxyphenyl)-5-methylcyclohex-1-enyl)methyl)-4-methyloxazolidine-2-thione |
| 27 | (4S,5R)-5-(3,5-bis(trifluoromethyl)phenyl)-3-((2-(4-fluoro-5-isopropyl-2-methoxyphenyl)cyclohex-1-enyl)methyl)-4-methyloxazolidin-2-one |
| 28 | (4S,5R)-5-(3,5-bis(trifluoromethyl)phenyl)-3-((2-(4-fluoro-5-isopropyl-2-methoxyphenyl)cyclohex-1-enyl)methyl)-4-methyloxazolidine-2-thione |
| 29 | (4S,5R,Z)-5-(3,5-bis(trifluoromethyl)phenyl)-3-((2-(4-fluoro-5-isopropyl-2-methoxyphenyl)cyclohept-1-enyl)methyl)-4-methyloxazolidin-2-one |
| 30 | (4S,5R)-5-(3,5-bis(trifluoromethyl)phenyl)-3-((4-(4-fluoro-5-isopropyl-2-methoxyphenyl)-5,6-dihydro-2H-pyran-3-yl)methyl)-4-methyloxazolidin-2-one |
| 31 | (4S,5R)-5-(3,5-bis(trifluoromethyl)phenyl)-3-((2-(4-fluoro-5-isopropyl-2-methoxyphenyl)cyclopent-1-enyl)methyl)-4-methyloxazolidin-2-one |
| 32 | (4S,5R)-5-(3,5-bis(trifluoromethyl)phenyl)-3-((2-(5-isopropyl-2-methoxyphenyl)cyclopent-1-enyl)methyl)-4-methyloxazolidin-2-one |
| 34 | 3-(2-(((4S,5R)-5-(3,5-bis(trifluoromethyl)phenyl)-4-methyl-2-oxooxazolidin-3-yl)methyl)cyclohex-1-enyl)-4-methoxybenzoic acid |
| 36 | methyl 3-(2-(((4S,5R)-5-(3,5-bis(trifluoromethyl)phenyl)-4-methyl-2-oxooxazolidin-3-yl)methyl)cyclohex-1-enyl)-4-methoxybenzoate |
| 37 | 3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzoic acid |
| 41 | methyl 3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzoate |
| 42 | (4S,5R,Z)-5-(3,5-bis(trifluoromethyl)phenyl)-3-((2-(5-isopropyl-2-methoxyphenyl)cyclohept-1-enyl)methyl)-4-methyloxazolidin-2-one |
| 43 | (4S,5R)-5-(3,5-bis(trifluoromethyl)phenyl)-3-((5-ethyl-2-(4-fluoro-5-isopropyl-2-methoxyphenyl)cyclohex-1-enyl)methyl)-4-methyloxazolidin-2-one |
| 44 | (4S,5R)-5-(3,5-bis(trifluoromethyl)phenyl)-3-((2-(5-isopropyl-2-methoxyphenyl)-4,4-dimethylcyclohex-1-enyl)methyl)-4-methyloxazolidin-2-one |
| 46 | (4S,5R)-5-(3,5-bis(trifluoromethyl)phenyl)-3-((2-(5-(hydroxymethyl)-2-methoxyphenyl)cyclohex-1-enyl)methyl)-4-methyloxazolidin-2-one |
| 47 | (4S,5R)-5-(3,5-bis(trifluoromethyl)phenyl)-3-((2-(2-methoxy-5-(methoxymethyl)phenyl)cyclohex-1-enyl)methyl)-4-methyloxazolidin-2-one |
| 48 | (4S,5R)-5-(3,5-bis(trifluoromethyl)phenyl)-3-((2-(4-fluoro-5-isopropyl-2-methoxyphenyl)-5-(trifluoromethyl)cyclohex-1-enyl)methyl)-4-methyloxazolidin-2-one |
| 49 | (4S,5R)-5-(3,5-bis(trifluoromethyl)phenyl)-3-((2-(3'-chloro-4,6'-dimethoxybiphenyl-3-yl)cyclohex-1-enyl)methyl)-4-methyloxazolidin-2-one |
| 50 | (4S,5R)-5-(3,5-bis(trifluoromethyl)phenyl)-3-((2-(5-chloro-2-methoxyphenyl)cyclohex-1-enyl)methyl)-4-methyloxazolidin-2-one |
| 51 | (4S,5R)-3-((2-(1H-indol-4-yl)-5,5-dimethylcyclohex-1-enyl)methyl)-5-(3,5-bis(trifluoromethyl)phenyl)-4-methyloxazolidin-2-one |
| 52 | (4S,5R)-5-(3,5-bis(trifluoromethyl)phenyl)-3-((2-(2-methoxy-5-nitrophenyl)-5,5-dimethylcyclohex-1-enyl)methyl)-4-methyloxazolidin-2-one |
| 55 | (4S,5R)-5-(3,5-bis(trifluoromethyl)phenyl)-3-((4-(2-methoxyphenyl)-5,6-dihydro-2H-pyran-3-yl)methyl)-4-methyloxazolidin-2-one |
| 56 | (4S,5R)-5-(3,5-bis(trifluoromethyl)phenyl)-3-((2-(5-(dimethylamino)-2-methoxyphenyl)-5,5-dimethylcyclohex-1-enyl)methyl)-4-methyloxazolidin-2-one |
| 57 | 2-(2-(((4S,5R)-5-(3,5-bis(trifluoromethyl)phenyl)-4-methyl-2-oxooxazolidin-3-yl)methyl)cyclohex-1-enyl)-5-methoxybenzaldehyde |
| 58 | (4S,5R)-5-(3,5-bis(trifluoromethyl)phenyl)-3-((2-(2-(hydroxymethyl)-4-methoxyphenyl)cyclohex-1-enyl)methyl)-4-methyloxazolidin-2-one |
| 59 | (4S,5R)-5-(3,5-bis(trifluoromethyl)phenyl)-3-((2-(4-methoxy-2-(methoxymethyl)phenyl)cyclohex-1-enyl)methyl)-4-methyloxazolidin-2-one |
| 60 | (4S,5R)-5-(3,5-bis(trifluoromethyl)phenyl)-4-methyl-3-((2-(quinolin-8-yl)cyclohex-1-enyl)methyl)oxazolidin-2-one |
| 61 | (4S,5R)-5-(3,5-bis(trifluoromethyl)phenyl)-4-methyl-3-((2-(1-methyl-1H-indazol-4-yl)cyclohex-1-enyl)methyl)oxazolidin-2-one |
| 62 | (4S,5R)-5-(3,5-bis(trifluoromethyl)phenyl)-3-((2-(5-(3-isopropyl-1,2,4-oxadiazol-5-yl)-2-methoxyphenyl)cyclohex-1-enyl)methyl)-4-methyloxazolidin-2-one |
| 63 | (4S,5R)-5-(3,5-bis(trifluoromethyl)phenyl)-3-((2-(4-fluoro-2-hydroxy-5-isopropylphenyl)-5,5-dimethylcyclohex-1-enyl)methyl)-4-methyloxazolidin-2-one |
| 64 | (4S,5R)-5-(3,5-bis(trifluoromethyl)phenyl)-3-((2-(4-fluoro-2-hydroxy-5-isopropylphenyl)-5-methylcyclohex-1-enyl)methyl)-4-methyloxazolidin-2-one |
| 65 | (4S,5R)-5-(3,5-bis(trifluoromethyl)phenyl)-3-((2-(4-fluoro-2-hydroxy-5-isopropylphenyl)-5-(trifluoromethyl)cyclohex-1-enyl)methyl)-4-methyloxazolidin-2-one |
| 66 | (4S,5R)-5-(3,5-bis(trifluoromethyl)phenyl)-3-((2-(2-methoxy-5-morpholinophenyl)cyclohex-1-enyl)methyl)-4-methyloxazolidin-2-one |
| 67 | 3-(2-(((4S,5R)-5-(3,5-bis(trifluoromethyl)phenyl)-4-methyl-2-oxooxazolidin-3-yl)methyl)cyclohex-1-enyl)-4-methoxy-N-methylbenzamide |
| 68 | 3-(2-(((4S,5R)-5-(3,5-bis(trifluoromethyl)phenyl)-4-methyl-2-oxooxazolidin-3-yl)methyl)cyclohex-1-enyl)-N-ethyl-4-methoxybenzamide |
| 69 | 3-(2-(((4S,5R)-5-(3,5-bis(trifluoromethyl)phenyl)-4-methyl-2-oxooxazolidin-3-yl)methyl)cyclohex-1-enyl)-4-methoxy-N-(2,2,2-trifluoroethyl)benzamide |
| 70 | 3-(2-(((4S,5R)-5-(3,5-bis(trifluoromethyl)phenyl)-4-methyl-2-oxooxazolidin-3-yl)methyl)cyclohex-1-enyl)-N-isopropyl-4-methoxybenzamide |
| 71 | N-(3-(2-(((4S,5R)-5-(3,5-bis(trifluoromethyl)phenyl)-4-methyl-2-oxooxazolidin-3-yl)methyl)cyclohex-1-enyl)-4-methoxyphenyl)acetamide |
| 72 | N-(3-(2-(((4S,5R)-5-(3,5-bis(trifluoromethyl)phenyl)-4-methyl-2-oxooxazolidin-3-yl)methyl)cyclohex-1-enyl)-4-methoxyphenyl)isobutyramide |
| 76 | (4S,5R)-5-(3,5-bis(trifluoromethyl)phenyl)-3-((2-(5-(3-cyclopropyl-1,2,4-oxadiazol-5-yl)-2-methoxyphenyl)cyclohex-1-enyl)methyl)-4-methyloxazolidin-2-one |
| 79 | 3-(2-(((4S,5R)-5-(3,5-bis(trifluoromethyl)phenyl)-4-methyl-2-oxooxazolidin-3-yl)methyl)cyclohex-1-enyl)-4-methoxybenzaldehyde |
| 80 | (4S,5R)-5-(3,5-bis(trifluoromethyl)phenyl)-3-((2-(5-(1-hydroxyethyl)-2-methoxyphenyl)cyclohex-1-enyl)methyl)-4-methyloxazolidin-2-one |
| 81 | (4S,5R)-3-((2-(5-acetyl-2-methoxyphenyl)cyclohex-1-enyl)methyl)-5-(3,5-bis(trifluoromethyl)phenyl)-4-methyloxazolidin-2-one |
| 82 | (4S,5R)-5-(3,5-bis(trifluoromethyl)phenyl)-3-((2-(5-(2-hydroxypropan-2-yl)-2-methoxyphenyl)cyclohex-1-enyl)methyl)-4-methyloxazolidin-2-one |
| 83 | (4S,5R)-5-(3,5-bis(trifluoromethyl)phenyl)-4-methyl-3-((2-(2-(trifluoromethoxy)phenyl)cyclohex-1-enyl)methyl)oxazolidin-2-one |
| 84 | (4S,5R)-5-(3,5-bis(trifluoromethyl)phenyl)-3-((2-(2-fluoro-5-(trifluoromethyl)phenyl)cyclohex-1-enyl)methyl)-4-methyloxazolidin-2-one |
| 85 | 1-(3-(2-(((4S,5R)-5-(3,5-bis(trifluoromethyl)phenyl)-4-methyl-2-oxooxazolidin-3-yl)methyl)cyclohex-1-enyl)-4-methoxyphenyl)ethyl acetate |
| 86 | N-(3-(2-(((4S,5R)-5-(3,5-bis(trifluoromethyl)phenyl)-4-methyl-2-oxooxazolidin-3-yl)methyl)cyclohex-1-enyl)-4-methoxyphenyl)-N-methylisobutyramide |

| # | Name |
|---|---|
| 87 | 3-(2-(((4S,5R)-5-(3,5-bis(trifluoromethyl)phenyl)-4-methyl-2-oxooxazolidin-3-yl)methyl)cyclohex-1-enyl)-N-isopropyl-4-methoxy-N-methylbenzamide |
| 96 | (4S,5R)-5-(3,5-bis(trifluoromethyl)phenyl)-3-((2-(2-methoxy-5-(trifluoromethyl)phenyl)-5-methylcyclohex-1-enyl)methyl)-4-methyloxazolidin-2-one |
| 97 | (4S,5R)-5-(3,5-bis(trifluoromethyl)phenyl)-3-((2-(2-methoxy-5-(trifluoromethyl)phenyl)-5,5-dimethylcyclohex-1-enyl)methyl)-4-methyloxazolidin-2-one |
| 101 | (4S,5R)-5-(3,5-bis(trifluoromethyl)phenyl)-3-((5-tert-butyl-2-(4-fluoro-5-isopropyl-2-methoxyphenyl)cyclohex-1-enyl)methyl)-4-methyloxazolidin-2-one |
| 103 | (4S,5R)-5-(3,5-bis(trifluoromethyl)phenyl)-3-((2-(5-(1-hydroxyethyl)-2-methoxyphenyl)-5,5-dimethylcyclohex-1-enyl)methyl)-4-methyloxazolidin-2-one |
| 104 | (4S,5R)-5-(3,5-bis(trifluoromethyl)phenyl)-3-((2-(5-(2-hydroxypropan-2-yl)-2-methoxyphenyl)-5,5-dimethylcyclohex-1-enyl)methyl)-4-methyloxazolidin-2-one |
| 107 | (4S,5R)-5-(3,5-bis(trifluoromethyl)phenyl)-3-((2-(5-isopropyl-2-methoxyphenyl)-5,5-dimethylcyclohex-1-enyl)methyl)-4-methyloxazolidin-2-one |
| 108 | (4S,5R)-5-(3,5-bis(trifluoromethyl)phenyl)-3-((2-(5-isopropyl-2-methoxyphenyl)-5-(trifluoromethyl)cyclohex-1-enyl)methyl)-4-methyloxazolidin-2-one |
| 109 | (4S,5R)-5-(3,5-bis(trifluoromethyl)phenyl)-3-((2-(4-fluoro-5-isopropyl-2-methoxyphenyl)-4,4-dimethylcyclohex-1-enyl)methyl)-4-methyloxazolidin-2-one |
| 110 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)acetamide |
| 111 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)isobutyramide |
| 112 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-methylacetamide |
| 113 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-methylisobutyramide |
| 114 | (4S,5R)-5-(3,5-bis(trifluoromethyl)phenyl)-3-((2-(2-(methoxymethyl)-4-(trifluoromethyl)phenyl)-5,5-dimethylcyclohex-1-enyl)methyl)-4-methyloxazolidin-2-one |
| 115 | (4S,5R)-5-(3,5-bis(trifluoromethyl)phenyl)-3-((2-(5-tert-butyl-2-methoxyphenyl)-5,5-dimethylcyclohex-1-enyl)methyl)-4-methyloxazolidin-2-one |
| 116 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)-N-(2,2,2-trifluoroethyl)acetamide |
| 117 | (4S,5R)-5-(3,5-bis(trifluoromethyl)phenyl)-3-((2-(2-methoxy-5-(trifluoromethoxy)phenyl)-5,5-dimethylcyclohex-1-enyl)methyl)-4-methyloxazolidin-2-one |
| 118 | N-acetyl-N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)acetamide |
| 120 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2,2-trifluoro-N-methylacetamide |
| 121 | (4S,5R)-5-(3,5-bis(trifluoromethyl)phenyl)-3-((2-(2-methoxy-5-(2-oxopyrrolidin-1-yl)phenyl)-5,5-dimethylcyclohex-1-enyl)methyl)-4-methyloxazolidin-2-one |
| 122 | (4S,5R)-5-(3,5-bis(trifluoromethyl)phenyl)-3-((2-(2-methoxy-5-(2-oxopiperidin-1-yl)phenyl)-5,5-dimethylcyclohex-1-enyl)methyl)-4-methyloxazolidin-2-one |
| 123 | (4S,5R)-5-(3,5-bis(trifluoromethyl)phenyl)-3-((5,5-difluoro-2-(4-fluoro-5-isopropyl-2-methoxyphenyl)cyclohex-1-enyl)methyl)-4-methyloxazolidin-2-one |
| 124 | methyl 3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl(methyl)carbamate |
| 128 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-methylmethanesulfonamide |
| 130 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3,3,3-trifluoro-N-methylpropanamide |
| 132 | (4S,5R)-5-(3,5-bis(trifluoromethyl)phenyl)-3-((2-(4-fluoro-2-methoxy-5-(1,1,1-trifluoropropan-2-yl)phenyl)-5,5-dimethylcyclohex-1-enyl)methyl)-4-methyloxazolidin-2-one |
| 133 | methyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)acetate |
| 134 | 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)acetic acid |
| 136 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)cyclopropanesulfonamide |
| 137 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)trifluoromethanesulfonamide |
| 138 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-methylcyclopropanesulfonamide |
| 140 | 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3-methylthiourea |
| 141 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)trifluoro-N-methylmethanesulfonamide |
| 142 | (4S,5R)-5-(3,5-bis(trifluoromethyl)phenyl)-3-((2-(2-methoxy-5-(2-oxoimidazolidin-1-yl)phenyl)-5,5-dimethylcyclohex-1-enyl)methyl)-4-methyloxazolidin-2-one |
| 143 | (4S,5R)-5-(3,5-bis(trifluoromethyl)phenyl)-3-((2-(2-methoxy-5-(2-oxooxazolidin-3-yl)phenyl)-5,5-dimethylcyclohex-1-enyl)methyl)-4-methyloxazolidin-2-one |
| 144 | (4S,5R)-3-((2-(2-amino-5-isopropylphenyl)-5,5-dimethylcyclohex-1-enyl)methyl)-5-(3,5-bis(trifluoromethyl)phenyl)-4-methyloxazolidin-2-one |
| 145 | N-(2-(2-(((4S,5R)-5-(3,5-bis(trifluoromethyl)phenyl)-4-methyl-2-oxooxazolidin-3-yl)methyl)-4,4-dimethylcyclohex-1-enyl)-4-isopropylphenyl)-N-methylacetamide |
| 146 | 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-1,1-dimethylurea |
| 147 | (4S,5R)-5-(3,5-bis(trifluoromethyl)phenyl)-3-((2-(2-methoxy-5-(methylthio)phenyl)-5,5-dimethylcyclohex-1-enyl)methyl)-4-methyloxazolidin-2-one |
| 148 | (4S,5R)-5-(3,5-bis(trifluoromethyl)phenyl)-3-((5,5-dimethyl-2-(2-(methylthio)-5-(trifluoromethoxy)phenyl)cyclohex-1-enyl)methyl)-4-methyloxazolidin-2-one |
| 149 | (Z)-3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-cyano-1,1-dimethylguanidine |
| 151 | (E)-1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-cyano-3-methylguanidine |
| 153 | (E)-1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-cyano-1,3,3-trimethylguanidine |
| 156 | (Z)-methyl N-3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl-N'-methylcarbamimidothioate |
| 157 | 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-1,3,3-trimethylurea |
| 159 | methyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)propanoate |
| 160 | (4S,5R)-5-(3,5-bis(trifluoromethyl)phenyl)-3-((2-(2-methoxy-5-(1,1,1-trifluoropropan-2-ylamino)phenyl)-5,5-dimethylcyclohex-1-enyl)methyl)-4-methyloxazolidin-2-one |
| 161 | (4S,5R)-5-(3,5-bis(trifluoromethyl)phenyl)-3-((2-(2-methoxy-5-(methyl(1,1,1-trifluoropropan-2-yl)amino)phenyl)-5,5-dimethylcyclohex-1-enyl)methyl)-4-methyloxazolidin-2-one |
| 162 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2,2-trifluoroacetamide |
| 163 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-bromoacetamide |
| 166 | N-(2-(2-(((4S,5R)-5-(3,5-bis(trifluoromethyl)phenyl)-4-methyl-2-oxooxazolidin-3-yl)methyl)-4,4-dimethylcyclohex-1-enyl)-4-isopropylphenyl)acetamide |

| | |
|---|---|
| 167 | (4S,5R)-5-(3,5-bis(trifluoromethyl)phenyl)-3-((2-(5-isopropyl-2-(methylamino)phenyl)-5,5-dimethylcyclohex-1-enyl)methyl)-4-methyloxazolidin-2-one |
| 168 | (4S,5R)-5-(3,5-bis(trifluoromethyl)phenyl)-3-((2-(dimethylamino)-5-isopropylphenyl)-5,5-dimethylcyclohex-1-enyl)methyl)-4-methyloxazolidin-2-one |
| 170 | (4S,5R)-5-(3,5-bis(trifluoromethyl)phenyl)-3-((2-(2-methoxy-5-(2,2,2-trifluoroacetyl)phenyl)-5,5-dimethylcyclohex-1-enyl)methyl)-4-methyloxazolidin-2-one |
| 171 | (4S,5R)-5-(3,5-bis(trifluoromethyl)phenyl)-3-((2-(2-methoxy-5-(perfluoroprop-1-en-2-yl)phenyl)-5,5-dimethylcyclohex-1-enyl)methyl)-4-methyloxazolidin-2-one |
| 172 | (4S,5R)-5-(3,5-bis(trifluoromethyl)phenyl)-3-((2-(5-(1,1,1,3,3,3-hexafluoropropan-2-yl)-2-methoxyphenyl)-5,5-dimethylcyclohex-1-enyl)methyl)-4-methyloxazolidin-2-one |
| 173 | tert-butyl 3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenykisopropyl)carbamate |
| 174 | tert-butyl 3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenykethyl)carbamate |
| 177 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-ethylacetamide |
| 178 | (4S,5R,Z)-5-(3,5-bis(trifluoromethyl)phenyl)-3-((2-(2-methoxy-5-(2,2,2-trifluoro-1-(methoxyimino)ethyl)phenyl)-5,5-dimethylcyclohex-1-enyl)methyl)-4-methyloxazolidin-2-one |
| 179 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-(2-hydroxy-2-methylpropyl)acetamide |
| 180 | (4S,5R)-5-(3,5-bis(trifluoromethyl)phenyl)-3-((2-(5-(3,3-difluoroazetidine-1-carbonyl)-2-methoxyphenyl)cyclohex-1-enyl)methyl)-4-methyloxazolidin-2-one |
| 181 | (4S,5R)-5-(3,5-bis(trifluoromethyl)phenyl)-3-((2-(5-(1,1,1,3,3,3-hexafluoro-2-hydroxypropan-2-yl)-2-methoxyphenyl)-5,5-dimethylcyclohex-1-enyl)methyl)-4-methyloxazolidin-2-one |
| 182 | (4S,5R)-5-(3,5-bis(trifluoromethyl)phenyl)-3-((2-(5-(1,1,1,3,3,3-hexafluoro-2-methoxypropan-2-yl)-2-methoxyphenyl)-5,5-dimethylcyclohex-1-enyl)methyl)-4-methyloxazolidin-2-one |
| 183 | (4S,5R)-5-(3,5-bis(trifluoromethyl)phenyl)-3-((2-(5-((2-hydroxy-2-methylpropyl)(methyl)amino)-2-methoxyphenyl)-5,5-dimethylcyclohex-1-enyl)methyl)-4-methyloxazolidin-2-one |
| 184 | (4S,5R)-3-((2-(5-acetyl-4-fluoro-2-methoxyphenyl)-5,5-dimethylcyclohex-1-enyl)methyl)-5-(3,5-bis(trifluoromethyl)phenyl)-4-methyloxazolidin-2-one |
| 185 | (4S,5R)-5-(3,5-bis(trifluoromethyl)phenyl)-3-((2-(5-(4,5-dihydrooxazol-2-yl)-2-methoxyphenyl)-5,5-dimethylcyclohex-1-enyl)methyl)-4-methyloxazolidin-2-one |
| 187 | (4S,5R)-5-(3,5-bis(trifluoromethyl)phenyl)-3-((2-(5-(3-hydroxyazetidine-1-carbonyl)-2-methoxyphenyl)-5,5-dimethylcyclohex-1-enyl)methyl)-4-methyloxazolidin-2-one |
| 188 | (4S,5R)-5-(3,5-bis(trifluoromethyl)phenyl)-3-((2-(5-((R)-4-isopropyl-4,5-dihydrooxazol-2-yl)-2-methoxyphenyl)-5,5-dimethylcyclohex-1-enyl)methyl)-4-methyloxazolidin-2-one |
| 189 | 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)cyclopropanecarbonitrile |
| 190 | 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)cyclopropanecarboxamide |
| 191 | (4S,5R)-5-(3,5-bis(trifluoromethyl)phenyl)-3-((2-(4-fluoro-2-methoxy-5-(2,2,2-trifluoroacetyl)phenyl)-5,5-dimethylcyclohex-1-enyl)methyl)-4-methyloxazolidin-2-one |
| 192 | (4S,5R)-5-(3,5-bis(trifluoromethyl)phenyl)-3-((2-(5-(cyclopropane carbonyl)-4-fluoro-2-methoxyphenyl)-5,5-dimethylcyclohex-1-enyl)methyl)-4-methyloxazolidin-2-one |
| 193 | (4S,5R)-5-(3,5-bis(trifluoromethyl)phenyl)-3-((2-(2-methoxy-5-(trifluoromethyl)phenyl)-5-(trifluoromethyl)cyclohex-1-enyl)methyl)-4-methyloxazolidin-2-one |
| 194 | (4S,5R)-5-(3,5-bis(trifluoromethyl)phenyl)-3-((2-(2-methoxy-5-nitrophenyl)-5-(trifluoromethyl)cyclohex-1-enyl)methyl)-4-methyloxazolidin-2-one |
| 195 | (4S,5R)-3-((2-(5-amino-2-methoxyphenyl)-5-(trifluoromethyl)cyclohex-1-enyl)methyl)-5-(3,5-bis(trifluoromethyl)phenyl)-4-methyloxazolidin-2-one |
| 196 | N-(3-(2-(((4S,5R)-5-(3,5-bis(trifluoromethyl)phenyl)-4-methyl-2-oxooxazolidin-3-yl)methyl)-4-(trifluoromethyl)cyclohex-1-enyl)-4-methoxyphenyl)acetamide |
| 197 | methyl 5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxybenzoate |
| 204 | 5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxybenzoic acid |
| 206 | (4S,5R)-5-(3,5-bis(trifluoromethyl)phenyl)-3-((2-(2-methoxy-5-nitro-4-(trifluoromethyl)phenyl)-5,5-dimethylcyclohex-1-enyl)methyl)-4-methyloxazolidin-2-one |
| 207 | (4S,5R)-3-((2-(5-amino-2-methoxy-4-(trifluoromethyl)phenyl)-5,5-dimethylcyclohex-1-enyl)methyl)-5-(3,5-bis(trifluoromethyl)phenyl)-4-methyloxazolidin-2-one |
| 209 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)trifluoro-N-methylmethanesulfonamide |
| 210 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)-N-methylacetamide |
| 212 | (4S,5R)-5-(3,5-bis(trifluoromethyl)phenyl)-3-((2-(2-methoxy-5-(methyl(4-(trifluoromethyl)thiazol-2-yl)amino)phenyl)-5,5-dimethylcyclohex-1-enyl)methyl)-4-methyloxazolidin-2-one |
| 213 | (4S,5R)-5-(3,5-bis(trifluoromethyl)phenyl)-3-((2-(2-methoxy-5-(4-(trifluoromethyl)thiazol-2-ylamino)phenyl)-5,5-dimethylcyclohex-1-enyl)methyl)-4-methyloxazolidin-2-one |
| 215 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxyphenyl)-N-methylacetamide |
| 216 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxyphenyl)acetamide |
| 217 | (4S,5R)-3-((2-(5-amino-4-fluoro-2-methoxyphenyl)-5,5-dimethylcyclohex-1-enyl)methyl)-5-(3,5-bis(trifluoromethyl)phenyl)-4-methyloxazolidin-2-one |
| 218 | (4S,5R)-5-(3,5-bis(trifluoromethyl)phenyl)-3-((2-(4-fluoro-2-methoxy-5-nitrophenyl)-5,5-dimethylcyclohex-1-enyl)methyl)-4-methyloxazolidin-2-one |
| 219 | tert-butyl 3-(((4S,5R)-5-(3,5-bis(trifluoromethyl)phenyl)-4-methyl-2-oxooxazolidin-3-yl)methyl)-4-(4-fluoro-5-isopropyl-2-methoxyphenyl)-5,6-dihydropyridine-1(2H)-carboxylate |
| 222 | (4S,5R)-5-(3,5-bis(trifluoromethyl)phenyl)-3-((2-(4-fluoro-2-methoxy-5-(2,2,2-trifluoro ethoxy)phenyl)-5,5-dimethylcyclohex-1-enyl)methyl)-4-methyloxazolidin-2-one |
| 223 | (4S,5R)-5-(3,5-bis(trifluoromethyl)phenyl)-3-((2-(6-methoxybenzo[d][1,3]dioxol-5-yl)-5,5-dimethylcyclohex-1-enyl)methyl)-4-methyloxazolidin-2-one |
| 224 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)-N-methylisobutyramide |
| 225 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)-N-methylpropionamide |
| 226 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)-N-methylmethanesulfonamide |
| 227 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)-2,2,2-trifluoro-N-methylacetamide |
| 228 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)trifluoromethanesulfonamide |
| 229 | (4S,5R)-5-(3,5-bis(trifluoromethyl)phenyl)-3-((2-(2,4-dimethoxy-5-nitrophenyl)-5,5-dimethylcyclohex-1-enyl)methyl)-4-methyloxazolidin-2-one |
| 230 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2,4-dimethoxyphenyl)-N-methylacetamide |
| 231 | (4S,5R)-5-(3,5-bis(trifluoromethyl)phenyl)-3-((4-(4-fluoro-5-isopropyl-2-methoxyphenyl)-1-methyl-1,2,5,6-tetrahydropyridin-3-yl)methyl)-4-methyloxazolidin-2-one |

| | |
|---|---|
| 232 | (4S,5R)-5-(3,5-bis(trifluoromethyl)phenyl)-3-((2-(4-hydroxy-2-methoxy-5-nitrophenyl)-5,5-dimethylcyclohex-1-enyl)methyl)-4-methyloxazolidin-2-one |
| 233 | (4S,5R)-5-(3,5-bis(trifluoromethyl)phenyl)-3-((2-(2-methoxy-5-(methylamino)-4-(trifluoromethyl)phenyl)-5,5-dimethylcyclohex-1-enyl)methyl)-4-methyloxazolidin-2-one |
| 234 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-ethyl-4-methoxyphenyl)-N-methylacetamide |
| 235 | (4S,5R)-5-(3,5-bis(trifluoromethyl)phenyl)-3-((2-(5-((2-hydroxy-2-methylpropyl)(methyl)amino)-2-methoxy-4-(trifluoromethyl)phenyl)-5,5-dimethylcyclohex-1-enyl)methyl)-4-methyloxazolidin-2-one |
| 237 | (4S,5R)-5-(3,5-bis(trifluoromethyl)phenyl)-3-((2-(5-cyclopropyl-4-fluoro-2-methoxyphenyl)-5,5-dimethylcyclohex-1-enyl)methyl)-4-methyloxazolidin-2-one |
| 240 | 1-((5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)(methyl)amino)-2-methyl-1-oxopropan-2-yl acetate |
| 241 | (4S,5R)-5-(3,5-bis(trifluoromethyl)phenyl)-3-((2-(4-fluoro-5-isopropoxy-2-methoxyphenyl)-5,5-dimethylcyclohex-1-enyl)methyl)-4-methyloxazolidin-2-one |
| 243 | 1-((3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)(methyl)amino)-2-methyl-1-oxopropan-2-yl acetate |
| 244 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-hydroxy-N,2-dimethylpropanamide |
| 245 | (4S,5R)-5-(3,5-bis(trifluoromethyl)phenyl)-3-((4-(4-fluoro-5-isopropyl-2-methoxyphenyl)-1-(trifluoromethyl)-1,2,5,6-tetrahydropyridin-3-yl)methyl)-4-methyloxazolidin-2-one |
| 246 | (4S,5R)-5-(3,5-bis(trifluoromethyl)phenyl)-3-((2-(2-methoxy-4-methyl-5-nitrophenyl)-5,5-dimethylcyclohex-1-enyl)methyl)-4-methyloxazolidin-2-one |
| 247 | (4S,5R)-3-((2-(5-amino-2-methoxy-4-methylphenyl)-5,5-dimethylcyclohex-1-enyl)methyl)-5-(3,5-bis(trifluoromethyl)phenyl)-4-methyloxazolidin-2-one |
| 248 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-methylphenyl)acetamide |
| 249 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-methylphenyl)-N-methylacetamide |
| 250 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-methylphenyl)trifluoromethanesulfonamide |
| 251 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-methylphenyl)trifluoro-N-methylmethanesulfonamide |
| 259 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-methylethanethioamide |
| 261 | (4S,5R)-5-(3,5-bis(trifluoromethyl)phenyl)-3-((4-(4-fluoro-5-isopropyl-2-methoxyphenyl)-1-(2,2,2-trifluoroacetyl)-1,2,5,6-tetrahydropyridin-3-yl)methyl)-4-methyloxazolidin-2-one |
| 262 | (4S,5R)-5-(3,5-bis(trifluoromethyl)phenyl)-3-((4-(4-fluoro-5-isopropyl-2-methoxyphenyl)-1-(trifluoromethylsulfonyl)-1,2,5,6-tetrahydropyridin-3-yl)methyl)-4-methyloxazolidin-2-one |
| 263 | (4S,5R)-3-((1-acetyl-4-(4-fluoro-5-isopropyl-2-methoxyphenyl)-1,2,5,6-tetrahydropyridin-3-yl)methyl)-5-(3,5-bis(trifluoromethyl)phenyl)-4-methyloxazolidin-2-one |
| 264 | (4S,5R)-5-(3,5-bis(trifluoromethyl)phenyl)-3-((4-(4-fluoro-5-isopropyl-2-methoxyphenyl)-1-(methylsulfonyl)-1,2,5,6-tetrahydropyridin-3-yl)methyl)-4-methyloxazolidin-2-one |
| 265 | (4S,5R)-5-(3,5-bis(trifluoromethyl)phenyl)-3-((4-(4-fluoro-5-isopropyl-2-methoxyphenyl)-1-isopropyl-1,2,5,6-tetrahydropyridin-3-yl)methyl)-4-methyloxazolidin-2-one |
| 267 | (4S,5R)-5-(3,5-bis(trifluoromethyl)phenyl)-3-((4-(4-fluoro-5-isopropyl-2-methoxyphenyl)-1,2,5,6-tetrahydropyridin-3-yl)methyl)-4-methyloxazolidin-2-one |
| 268 | (4S,5R)-5-(3,5-bis(trifluoromethyl)phenyl)-3-((4-(4-fluoro-5-isopropyl-2-methoxyphenyl)-1-(2,2,2-trifluoroethyl)-1,2,5,6-tetrahydropyridin-3-yl)methyl)-4-methyloxazolidin-2-one |
| 271 | N-(3-(2-(((4S,5R)-5-(3,5-bis(trifluoromethyl)phenyl)-4-methyl-2-thiooxooxazolidin-3-yl)methyl)-4,4-dimethylcyclohex-1-enyl)-4-methoxyphenyl)-N-methylacetamide |
| 272 | methyl 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)propanoate |
| 273 | 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)propanoic acid |
| 274 | (4S,5R)-5-(3,5-bis(trifluoromethyl)phenyl)-3-46-(4-fluoro-5-isopropyl-2-methoxyphenyl)spiro[2.5]oct-5-en-5-yl)methyl)-4-methyloxazolidin-2-one |
| 275 | tert-butyl 6-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxyindoline-1-carboxylate |
| 276 | (4S,5R)-5-(3,5-bis(trifluoromethyl)phenyl)-3-((2-(5-methoxyindolin-6-yl)-5,5-dimethylcyclohex-1-enyl)methyl)-4-methyloxazolidin-2-one |
| 277 | (4S,5R)-3-((2-(1-acetyl-5-methoxyindolin-6-yl)-5,5-dimethylcyclohex-1-enyl)methyl)-5-(3,5-bis(trifluoromethyl)phenyl)-4-methyloxazolidin-2-one |
| 278 | (4S,5R)-5-(3,5-bis(trifluoromethyl)phenyl)-3-((2-(5-methoxy-1-(2,2,2-trifluoroethyl)indolin-6-yl)-5,5-dimethylcyclohex-1-enyl)methyl)-4-methyloxazolidin-2-one |
| 280 | (4S,5R)-5-(3,5-bis(trifluoromethyl)phenyl)-3-((2-(5-methoxy-1-(methylsulfonyl)indolin-6-yl)-5,5-dimethylcyclohex-1-enyl)methyl)-4-methyloxazolidin-2-one |
| 281 | tert-butyl 4-(((4S,5R)-5-(3,5-bis(trifluoromethyl)phenyl)-4-methyl-2-oxooxazolidin-3-yl)methyl)-3-(4-fluoro-5-isopropyl-2-methoxyphenyl)-5,6-dihydropyridine-1(2H)-carboxylate |
| 282 | (4S,5R)-5-(3,5-bis(trifluoromethyl)phenyl)-3-((3-(4-fluoro-5-isopropyl-2-methoxyphenyl)-1,2,5,6-tetrahydropyridin-4-yl)methyl)-4-methyloxazolidin-2-one |
| 283 | (4S,5R)-5-(3,5-bis(trifluoromethyl)phenyl)-3-((3-(4-fluoro-5-isopropyl-2-methoxyphenyl)-1-(2,2,2-trifluoroethyl)-1,2,5,6-tetrahydropyridin-4-yl)methyl)-4-methyloxazolidin-2-one |
| 284 | (4S,5R)-5-(3,5-bis(trifluoromethyl)phenyl)-3-((3-(4-fluoro-5-isopropyl-2-methoxyphenyl)-1-(trifluoromethylsulfonyl)-1,2,5,6-tetrahydropyridin-4-yl)methyl)-4-methyloxazolidin-2-one |
| 285 | methyl 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2-dimethylpropanoate |
| 286 | 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2-dimethylpropanoic acid |
| 291 | (R)-N-3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3,3,3-trifluoro-2-methoxy-2-phenylpropanamide |
| 292 | (S)-N-3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3,3,3-trifluoro-2-methoxy-2-phenylpropanamide |
| 293 | (4S,5R)-5-(3,5-bis(trifluoromethyl)phenyl)-3-46-(2-methoxyphenyl)spiro[2.5]oct-5-en-5-yl)methyl)-4-methyloxazolidin-2-one |
| 294 | (4S,5R)-5-(3,5-bis(trifluoromethyl)phenyl)-3-46-(2-methoxy-5-nitrophenyl)spiro[2.5]oct-5-en-5-yl)methyl)-4-methyloxazolidin-2-one |
| 295 | (4S,5R)-3-((6-(5-amino-2-methoxyphenyl)spiro[2.5]oct-5-en-5-yl)methyl)-5-(3,5-bis(trifluoromethyl)phenyl)-4-methyloxazolidin-2-one |
| 296 | (R)-N-(3-(5-(((4S,5R)-5-(3,5-bis(trifluoromethyl)phenyl)-4-methyl-2-oxooxazolidin-3-yl)methyl)spiro[2.5]oct-5-en-6-yl)-4-methoxyphenyl)-3,3,3-trifluoro-2-methoxy-2-phenylpropanamide |
| 297 | (S)-N-(3-(5-(((4S,5R)-5-(3,5-bis(trifluoromethyl)phenyl)-4-methyl-2-oxooxazolidin-3-yl)methyl)spiro[2.5]oct-5-en-6-yl)-4-methoxyphenyl)-3,3,3-trifluoro-2-methoxy-2-phenylpropanamide |
| 298 | (R)-N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3,3,3-trifluoro-2-methoxy-N-methyl-2-phenylpropanamide |
| 299 | 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)propanamide |
| 300 | 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)propanenitrile |
| 301 | (4S,5R)-3-((2-(5-(2-(2H-tetrazol-5-yl)ethyl)-2-methoxyphenyl)-5,5-dimethylcyclohex-1-enyl)methyl)-5-(3,5-bis(trifluoromethyl)phenyl)-4-methyloxazolidin-2-one |
| 302 | (4S,5R)-5-(3,5-bis(trifluoromethyl)phenyl)-3-((2-(4-fluoro-2-methoxy-5-(1-methylcyclopropyl)phenyl)-5,5-dimethylcyclohex-1-enyl)methyl)-4-methyloxazolidin-2-one |
| 303 | (4S,5R)-5-(3,5-bis(trifluoromethyl)phenyl)-3-46-(4-fluoro-2-methoxy-5-(1-methylcyclopropyl)phenyl)spiro[2.5]oct-5-en-5-yl)methyl)-4-methyloxazolidin-2-one |

| # | Name |
|---|---|
| 304 | (4S,5R)-5-(3,5-bis(trifluoromethyl)phenyl)-3-((2-(3',5'-difluoro-4-methoxy-4'-(methoxymethoxy)biphenyl-3-yl)-5,5-dimethylcyclohex-1-enyl)methyl)-4-methyloxazolidin-2-one |
| 305 | (4S,5R)-5-(3,5-bis(trifluoromethyl)phenyl)-3-((2-(3',5'-difluoro-4'-hydroxy-4-methoxybiphenyl-3-yl)-5,5-dimethylcyclohex-1-enyl)methyl)-4-methyloxazolidin-2-one |
| 306 | 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2-dimethylpropanamide |
| 307 | 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2-dimethylpropanenitrile |
| 308 | methyl 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3-methylbutanoate |
| 309 | 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3-methylbutanoic acid |
| 310 | methyl 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2-dimethylbutanoate |
| 311 | 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2-dimethylbutanoic acid |
| 312 | ethyl 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclobutanecarboxylate |
| 313 | 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclobutanecarboxylic acid |
| 314 | 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclobutanecarboxamide |
| 315 | methyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-methylpropanoate |
| 316 | (4S,5R)-5-(3,5-bis(trifluoromethyl)phenyl)-3-((2-(2-methoxy-5-(trifluoromethyl)pyridin-3-yl)-5,5-dimethylcyclohex-1-enyl)methyl)-4-methyloxazolidin-2-one |
| 317 | methyl 2-(7-(2-(((4S,5R)-5-(3,5-bis(trifluoromethyl)phenyl)-4-methyl-2-oxooxazolidin-3-yl)methyl)-4,4-dimethylcyclohex-1-enyl)benzo[d][1,3]dioxol-5-yl)acetate |
| 318 | 2-(7-(2-(((4S,5R)-5-(3,5-bis(trifluoromethyl)phenyl)-4-methyl-2-oxooxazolidin-3-yl)methyl)-4,4-dimethylcyclohex-1-enyl)benzo[d][1,3]dioxol-5-yl)-acetic acid |
| 319 | 2-(7-(2-(((4S,5R)-5-(3,5-bis(trifluoromethyl)phenyl)-4-methyl-2-oxooxazolidin-3-yl)methyl)-4,4-dimethylcyclohex-1-enyl)benzo[d][1,3]dioxol-5-yl)-N-methylacetamide |
| 320 | 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-methylpropanoic acid |
| 321 | 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N,2,2-trimethylpropanamide |
| 323 | methyl 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclopentanecarboxylate |
| 324 | 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclopentanecarboxylic acid |
| 325 | 3-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxyphenyl)-2,2-dimethylpropanoic acid |
| 326 | methyl 7-(2-(((4S,5R)-5-(3,5-bis(trifluoromethyl)phenyl)-4-methyl-2-oxooxazolidin-3-yl)methyl)-4,4-dimethylcyclohex-1-enyl)-6-methoxy-1,2,3,4-tetrahydronaphthalene-2-carboxylate |
| 327 | 7-(2-(((4S,5R)-5-(3,5-bis(trifluoromethyl)phenyl)-4-methyl-2-oxooxazolidin-3-yl)methyl)-4,4-dimethylcyclohex-1-enyl)-6-methoxy-1,2,3,4-tetrahydronaphthalene-2-carboxylic acid |
| 328 | methyl 3-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxyphenyl)-2,2-dimethylpropanoate |
| 329 | 3-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxyphenyl)-2,2-dimethylpropanamide |
| 330 | ethyl 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenethyl)cyclobutanecarboxylate |
| 331 | 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenethyl)cyclobutanecarboxylic acid |
| 332 | 3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzonitrile |
| 333 | (4S,5R)-5-(3,5-bis(trifluoromethyl)phenyl)-3-((2-(2-methoxy-5-(2H-tetrazol-5-yl)phenyl)-5,5-dimethylcyclohex-1-enyl)methyl)-4-methyloxazolidin-2-one |
| 334 | (4R,5R)-5-(3,5-bis(trifluoromethyl)phenyl)-3-((2-(4-fluoro-5-isopropyl-2-methoxyphenyl)-5,5-dimethylcyclohex-1-enyl)methyl)-4-methyloxazolidin-2-one |
| 335 | (4S,5S)-5-(3,5-bis(trifluoromethyl)phenyl)-3-((2-(4-fluoro-5-isopropyl-2-methoxyphenyl)-5,5-dimethylcyclohex-1-enyl)methyl)-4-methyloxazolidin-2-one |
| 336 | (4R,5S)-5-(3,5-bis(trifluoromethyl)phenyl)-3-((2-(4-fluoro-5-isopropyl-2-methoxyphenyl)-5,5-dimethylcyclohex-1-enyl)methyl)-4-methyloxazolidin-2-one |
| 337 | 7-(2-(((4S,5R)-5-(3,5-bis(trifluoromethyl)phenyl)-4-methyl-2-oxooxazolidin-3-yl)methyl)-4,4-dimethylcyclohex-1-enyl)-6-methoxy-1,2,3,4-tetrahydronaphthalene-2-carboxamide |
| 338 | (4S,5R)-5-(3,5-bis(trifluoromethyl)phenyl)-3-((2-(2-methoxy-5-(2-methyl-2H-tetrazol-5-yl)phenyl)-5,5-dimethylcyclohex-1-enyl)methyl)-4-methyloxazolidin-2-one |
| 339 | (4S,5R)-5-(3,5-bis(trifluoromethyl)phenyl)-3-((2-(2-methoxy-5-(1-methyl-1H-tetrazol-5-yl)phenyl)-5,5-dimethylcyclohex-1-enyl)methyl)-4-methyloxazolidin-2-one |
| 340 | (4S,5R)-5-(3,5-bis(trifluoromethyl)phenyl)-3-((2-(2-methoxy-5-(2-methyl-2(2H-tetrazol-5-yl)propyl)phenyl)-5,5-dimethylcyclohex-1-enyl)methyl)-4-methyloxazolidin-2-one |
| 341 | (4S,5R)-5-(3,5-bis(trifluoromethyl)phenyl)-3-((2-(2-methoxy-5-(2-methyl-2-(2-methyl-2H-tetrazol-5-yl)propyl)phenyl)-5,5-dimethylcyclohex-1-enyl)methyl)-4-methyloxazolidin-2-one |
| 342 | tert-butyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzamido)acetate |
| 343 | tert-butyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-N-methylbenzamido)acetate |
| 344 | (R)-methyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzamido)-3-methylbutanoate |
| 345 | (R)-methyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-N-methylbenzamido)-3-methylbutanoate |
| 346 | (R)-2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzamido)-3-methylbutanoic acid |
| 347 | methyl 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclobutanecarboxylate |
| 348 | 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-N-methylbenzamido)acetic acid |
| 349 | methyl 3-(5-(2-(((4S,5R)-5-(3,5-bis(trifluoromethyl)phenyl)-4-methyl-2-oxooxazolidin-3-yl)methyl)-4,4-dimethylcyclohex-1-enyl)-6-methoxypyridin-3-yl)-2,2-dimethylpropanoate |
| 350 | 3-(5-(2-(((4S,5R)-5-(3,5-bis(trifluoromethyl)phenyl)-4-methyl-2-oxooxazolidin-3-yl)methyl)-4,4-dimethylcyclohex-1-enyl)-6-methoxypyridin-3-yl)-2,2-dimethylpropanoic acid |
| 353 | (4S,5R)-5-(3,5-bis(trifluoromethyl)phenyl)-3-((2-(5-chloro-2-methoxyphenyl)-5,5-dimethylcyclohex-1-enyl)methyl)-4-methyloxazolidin-2-one |
| 354 | tert-butyl 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-5,6-dihydropyridine-1(2H)-carboxylate |
| 355 | (4S,5R)-5-(3,5-bis(trifluoromethyl)phenyl)-3-((2-(5-(3,6-dihydro-2H-pyran-4-yl)-2-methoxyphenyl)-5,5-dimethylcyclohex-1-enyl)methyl)-4-methyloxazolidin-2-one |
| 356 | (4S,5R)-5-(3,5-bis(trifluoromethyl)phenyl)-3-((2-(5-(hydroxymethyl)-2-methoxyphenyl)-5,5-dimethylcyclohex-1-enyl)methyl)-4-methyloxazolidin-2-one |
| 357 | methyl 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-1,2,4-oxadiazole-5-carboxylate |
| 358 | (4S,5R)-5-(3,5-bis(trifluoromethyl)phenyl)-3-((2-(2-methoxy-5-(1,2,3,6-tetrahydropyridin-4-yl)phenyl)-5,5-dimethylcyclohex-1-enyl)methyl)-4-methyloxazolidin-2-one |

| | |
|---|---|
| 359 | methyl 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-5,6-dihydropyridine-1(2H)-carboxylate |
| 360 | (S)-methyl 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)pyrrolidine-2-carboxylate |
| 361 | (R)-methyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzylamino)-3-methylbutanoate |
| 362 | 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)cyclohex-3-enecarboxylic acid |
| 363 | (R)-methyl 2-((3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)(methyl)amino)-3-methylbutanoate |
| 364 | (4S,5R)-5-(3,5-bis(trifluoromethyl)phenyl)-3-((2-(2-methoxy-5-(((R)-2-(trifluoromethyl)pyrrolidin-l-yl)methyl)phenyl)-5,5-dimethylcyclohex-1-enyl)methyl)-4-methyloxazolidin-2-one |
| 366 | (4S,5R)-5-(3,5-bis(trifluoromethyl)phenyl)-3-((2-(6-isopropyl-3-methoxypyridin-2-yl)-5,5-dimethylcyclohex-1-enyl)methyl)-4-methyloxazolidin-2-one |
| 367 | (4S,5R)-5-(3,5-bis(trifluoromethyl)phenyl)-3-((2-(5-4(S)-3-fluoropyrrolidin-1-yl)methyl)-2-methoxyphenyl)-5,5-dimethylcyclohex-1-enyl)methyl)-4-methyloxazolidin-2-one |

Specific examples of more preferred compounds of formula 1 according to the present invention include:

| | |
|---|---|
| 15 | (4S,5R)-5-(3,5-bis(trifluoromethyl)phenyl)-3-((2-(5-isopropyl-2-methoxyphenyl)-5,5-dimethylcyclohex-1-enyl)methyl)-4-methyloxazolidine-2-thione |
| 17 | (4S,5R)-5-(3,5-bis(trifluoromethyl)phenyl)-3-((2-(4-fluoro-5-isopropyl-2-methoxyphenyl)-5,5-dimethylcyclohex-1-enyl)methyl)-4-methyloxazolidine-2-thione |
| 18 | (4S,5R)-5-(3,5-bis(trifluoromethyl)phenyl)-3-((2-(2-methoxyphenyl)-5,5-dimethylcyclohex-1-enyl)methyl)-4-methyloxazolidin-2-one |
| 19 | (4S,5R)-5-(3,5-bis(trifluoromethyl)phenyl)-3-((2-(4-fluoro-5-isopropyl-2-methoxyphenyl)-5,5-dimethylcyclohex-1-enyl)methyl)-4-methyloxazolidin-2-one |
| 25 | (4S,5R)-5-(3,5-bis(trifluoromethyl)phenyl)-3-((2-(4-fluoro-5-isopropyl-2-methoxyphenyl)-5-methylcyclohex-1-enyl)methyl)-4-methyloxazolidin-2-one |
| 26 | (4S,5R)-5-(3,5-bis(trifluoromethyl)phenyl)-3-((2-(4-fluoro-5-isopropyl-2-methoxyphenyl)-5-methylcyclohex-1-enyl)methyl)-4-methyloxazolidine-2-thione |
| 27 | (4S,5R)-5-(3,5-bis(trifluoromethyl)phenyl)-3-((2-(4-fluoro-5-isopropyl-2-methoxyphenyl)cyclohex-1-enyl)methyl)-4-methyloxazolidin-2-one |
| 28 | (4S,5R)-5-(3,5-bis(trifluoromethyl)phenyl)-3-((2-(4-fluoro-5-isopropyl-2-methoxyphenyl)cyclohex-1-enyl)methyl)-4-methyloxazolidine-2-thione |
| 36 | methyl 3-(2-(((4S,5R)-5-(3,5-bis(trifluoromethyl)phenyl)-4-methyl-2-oxooxazolidin-3-yl)methyl)cyclohex-1-enyl)-4-methoxybenzoate |
| 44 | (4S,5R)-5-(3,5-bis(trifluoromethyl)phenyl)-3-((2-(5-isopropyl-2-methoxyphenyl)-4,4-dimethylcyclohex-1-enyl)methyl)-4-methyloxazolidin-2-one |
| 48 | (4S,5R)-5-(3,5-bis(trifluoromethyl)phenyl)-3-((2-(4-fluoro-5-isopropyl-2-methoxyphenyl)-5-(trifluoromethyl)cyclohex-1-enyl)methyl)-4-methyloxazolidin-2-one |
| 79 | 3-(2-(((4S,5R)-5-(3,5-bis(trifluoromethyl)phenyl)-4-methyl-2-oxooxazolidin-3-yl)methyl)cyclohex-1-enyl)-4-methoxybenzaldehyde |
| 80 | (4S,5R)-5-(3,5-bis(trifluoromethyl)phenyl)-3-((2-(5-(1-hydroxyethyl)-2-methoxyphenyl)cyclohex-1-enyl)methyl)-4-methyloxazolidin-2-one |
| 82 | (4S,5R)-5-(3,5-bis(trifluoromethyl)phenyl)-3-((2-(5-(2-hydroxypropan-2-yl)-2-methoxyphenyl)cyclohex-1-enyl)methyl)-4-methyloxazolidin-2-one |
| 86 | N-(3-(2-(((4S,5R)-5-(3,5-bis(trifluoromethyl)phenyl)-4-methyl-2-oxooxazolidin-3-yl)methyl)cyclohex-1-enyl)-4-methoxyphenyl)-N-methylisobutyramide |
| 97 | (4S,5R)-5-(3,5-bis(trifluoromethyl)phenyl)-3-((2-(2-methoxy-5-(trifluoromethyl)phenyl)-5,5-dimethylcyclohex-1-enyl)methyl)-4-methyloxazolidin-2-one |
| 101 | (4S,5R)-5-(3,5-bis(trifluoromethyl)phenyl)-3-((5-tert-butyl-2-(4-fluoro-5-isopropyl-2-methoxyphenyl)cyclohex-1-enyl)methyl)-4-methyloxazolidin-2-one |
| 103 | (4S,5R)-5-(3,5-bis(trifluoromethyl)phenyl)-3-((2-(5-(1-hydroxyethyl)-2-methoxyphenyl)-5,5-dimethylcyclohex-1-enyl)methyl)-4-methyloxazolidin-2-one |
| 104 | (4S,5R)-5-(3,5-bis(trifluoromethyl)phenyl)-3-((2-(5-(2-hydroxypropan-2-yl)-2-methoxyphenyl)-5,5-dimethylcyclohex-1-enyl)methyl)-4-methyloxazolidin-2-one |
| 107 | (4S,5R)-5-(3,5-bis(trifluoromethyl)phenyl)-3-((2-(5-isopropyl-2-methoxyphenyl)-5,5-dimethylcyclohex-1-enyl)methyl)-4-methyloxazolidin-2-one |
| 108 | (4S,5R)-5-(3,5-bis(trifluoromethyl)phenyl)-3-((2-(5-isopropyl-2-methoxyphenyl)-5-(trifluoromethyl)cyclohex-1-enyl)methyl)-4-methyloxazolidin-2-one |
| 109 | (4S,5R)-5-(3,5-bis(trifluoromethyl)phenyl)-3-((2-(4-fluoro-5-isopropyl-2-methoxyphenyl)-4,4-dimethylcyclohex-1-enyl)methyl)-4-methyloxazolidin-2-one |
| 110 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)acetamide |
| 112 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-methylacetamide |
| 115 | (4S,5R)-5-(3,5-bis(trifluoromethyl)phenyl)-3-((2-(5-tert-butyl-2-methoxyphenyl)-5,5-dimethylcyclohex-1-enyl)methyl)-4-methyloxazolidin-2-one |
| 117 | (4S,5R)-5-(3,5-bis(trifluoromethyl)phenyl)-3-((2-(2-methoxy-5-(trifluoromethoxy)phenyl)-5,5-dimethylcyclohex-1-enyl)methyl)-4-methyloxazolidin-2-one |
| 123 | (4S,5R)-5-(3,5-bis(trifluoromethyl)phenyl)-3-((5,5-difluoro-2-(4-fluoro-5-isopropyl-2-methoxyphenyl)cyclohex-1-enyl)methyl)-4-methyloxazolidin-2-one |
| 124 | methyl 3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl(methyl)carbamate |
| 128 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-methylmethanesulfonamide |
| 130 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3,3,3-trifluoro-N-methylpropanamide |
| 132 | (4S,5R)-5-(3,5-bis(trifluoromethyl)phenyl)-3-((2-(4-fluoro-2-methoxy-5-(1,1,1-trifluoropropan-2-yl)phenyl)-5,5-dimethylcyclohex-1-enyl)methyl)-4-methyloxazolidin-2-one |
| 137 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)trifluoromethanesulfonamide |
| 181 | (4S,5R)-5-(3,5-bis(trifluoromethyl)phenyl)-3-((2-(5-(1,1,1,3,3,3-hexafluoro-2-hydroxypropan-2-yl)-2-methoxyphenyl)-5,5-dimethylcyclohex-1-enyl)methyl)-4-methyloxazolidin-2-one |
| 182 | (4S,5R)-5-(3,5-bis(trifluoromethyl)phenyl)-3-((2-(5-(1,1,1,3,3,3-hexafluoro-2-methoxypropan-2-yl)-2-methoxyphenyl)-5,5-dimethylcyclohex-1-enyl)methyl)-4-methyloxazolidin-2-one |
| 184 | (4S,5R)-3-((2-(5-acetyl-4-fluoro-2-methoxyphenyl)-5,5-dimethylcyclohex-1-enyl)methyl)-5-(3,5-bis(trifluoromethyl)phenyl)-4-methyloxazolidin-2-one |
| 185 | (4S,5R)-5-(3,5-bis(trifluoromethyl)phenyl)-3-((2-(5-(4,5-dihydrooxazol-2-yl)-2-methoxyphenyl)-5,5-dimethylcyclohex-1-enyl)methyl)-4-methyloxazolidin-2-one |
| 188 | (4S,5R)-5-(3,5-bis(trifluoromethyl)phenyl)-3-((2-(5-((R)-4-isopropyl-4,5-dihydrooxazol-2-yl)-2-methoxyphenyl)-5,5-dimethylcyclohex-1-enyl)methyl)-4-methyloxazolidin-2-one |
| 189 | 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)cyclopropanecarbonitrile |
| 190 | 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)cyclopropanecarboxamide |
| 191 | (4S,5R)-5-(3,5-bis(trifluoromethyl)phenyl)-3-((2-(4-fluoro-2-methoxy-5-(2,2,2-trifluoroacetyl)phenyl)-5,5-dimethylcyclohex-1-enyl)methyl)-4-methyloxazolidin-2-one |
| 192 | (4S,5R)-5-(3,5-bis(trifluoromethyl)phenyl)-3-((2-(5-(cyclopropanecarbonyl)-4-fluoro-2-methoxyphenyl)-5,5-dimethylcyclohex-1-enyl)methyl)-4-methyloxazolidin-2-one |
| 193 | (4S,5R)-5-(3,5-bis(trifluoromethyl)phenyl)-3-((2-(2-methoxy-5-(trifluoromethyl)phenyl)-5-(trifluoromethyl)cyclohex-1-enyl)methyl)-4-methyloxazolidin-2-one |
| 194 | (4S,5R)-5-(3,5-bis(trifluoromethyl)phenyl)-3-((2-(2-methoxy-5-nitrophenyl)-5-(trifluoromethyl)cyclohex-1-enyl)methyl)-4-methyloxazolidin-2-one |

-continued

| | |
|---|---|
| 195 | (4S,5R)-3-((2-(5-amino-2-methoxyphenyl)-5-(trifluoromethyl)cyclohex-1-enyl)methyl)-5-(3,5-bis(trifluoromethyl)phenyl)-4-methyloxazolidin-2-one |
| 196 | N-(3-(2-(((4S,5R)-5-(3,5-bis(trifluoromethyl)phenyl)-4-methyl-2-oxooxazolidin-3-yl)methyl)-4-(trifluoromethyl)cyclohex-1-enyl)-4-methoxyphenyl)acetamide |
| 209 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)trifluoro-N-methylmethanesulfonamide |
| 210 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)-N-methylacetamide |
| 212 | (4S,5R)-5-(3,5-bis(trifluoromethyl)phenyl)-3-((2-(2-methoxy-5-(methyl(4-(trifluoromethyl)thiazol-2-yl)amino)phenyl)-5,5-dimethylcyclohex-1-enyl)methyl)-4-methyloxazolidin-2-one |
| 215 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxyphenyl)-N-methylacetamide |
| 222 | (4S,5R)-5-(3,5-bis(trifluoromethyl)phenyl)-3-((2-(4-fluoro-2-methoxy-5-(2,2,2-trifluoroethoxy)phenyl)-5,5-dimethylcyclohex-1-enyl)methyl)-4-methyloxazolidin-2-one |
| 223 | (4S,5R)-5-(3,5-bis(trifluoromethyl)phenyl)-3-((2-(6-methoxybenzo[d][1,3]dioxol-5-yl)-5,5-dimethylcyclohex-1-enyl)methyl)-4-methyloxazolidin-2-one |
| 227 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)-2,2,2-trifluoro-N-methylacetamide |
| 231 | (4S,5R)-5-(3,5-bis(trifluoromethyl)phenyl)-3-((4-(4-fluoro-5-isopropyl-2-methoxyphenyl)-1-methyl-1,2,5,6-tetrahydropyridin-3-yl)methyl)-4-methyloxazolidin-2-one |
| 234 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-ethyl-4-methoxyphenyl)-N-methylacetamide |
| 237 | (4S,5R)-5-(3,5-bis(trifluoromethyl)phenyl)-3-((2-(5-cyclopropyl-4-fluoro-2-methoxyphenyl)-5,5-dimethylcyclohex-1-enyl)methyl)-4-methyloxazolidin-2-one |
| 241 | (4S,5R)-5-(3,5-bis(trifluoromethyl)phenyl)-3-((2-(4-fluoro-5-isopropoxy-2-methoxyphenyl)-5,5-dimethylcyclohex-1-enyl)methyl)-4-methyloxazolidin-2-one |
| 243 | 1-((3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)(methyl)amino)-2-methyl-1-oxopropan-2-yl acetate |
| 244 | N-(3-(2-(((4S,5R)-5-(3,5-bis(trifluoromethyl)phenyl)-4-methyl-2-oxooxazolidin-3-yl)methyl)-4,4-dimethylcyclohex-1-enyl )-4-methoxyphenyl)-2-hydroxy-N,2-dimethylpropanamide |
| 245 | (4S,5R)-5-(3,5-bis(trifluoromethyl)phenyl)-3-((4-(4-fluoro-5-isopropyl-2-methoxyphenyl)-1-(trifluoromethyl)-1,2,5,6-tetrahydropyridin-3-yl)methyl)-4-methyloxazolidin-2-one |
| 249 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-methylphenyl)-N-methylacetamide |
| 251 | N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-methylphenyl)trifluoro-N-methylmethanesulfonamide |
| 262 | (4S,5R)-5-(3,5-bis(trifluoromethyl)phenyl)-3-((4-(4-fluoro-5-isopropyl-2-methoxyphenyl)-1-(trifluoromethylsulfonyl)-1,2,5,6-tetrahydropyridin-3-yl)methyl)-4-methyloxazolidin-2-one |
| 265 | (4S,5R)-5-(3,5-bis(trifluoromethyl)phenyl)-3-((4-(4-fluoro-5-isopropyl-2-methoxyphenyl)-1-isopropyl-1,2,5,6-tetrahydropyridin-3-yl)methyl)-4-methyloxazolidin-2-one |
| 268 | (4S,5R)-5-(3,5-bis(trifluoromethyl)phenyl)-3-((4-(4-fluoro-5-isopropyl-2-methoxyphenyl)-1-(2,2,2-trifluoroethyl)-1,2,5,6-tetrahydropyridin-3-yl)methyl)-4-methyloxazolidin-2-one |
| 272 | methyl 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)propanoate |
| 273 | 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)propanoic acid |
| 274 | (4S,5R)-5-(3,5-bis(trifluoromethyl)phenyl)-3-46-(4-fluoro-5-isopropyl-2-methoxyphenyl)spiro[2.5]oct-5-en-5-yl)methyl)-4-methyloxazolidin-2-one |
| 285 | methyl 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2-dimethylpropanoate |
| 286 | 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2-dimethylpropanoic acid |
| 300 | 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)propanenitrile |
| 302 | (4S,5R)-5-(3,5-bis(trifluoromethyl)phenyl)-3-((2-(4-fluoro-2-methoxy-5-(1-methylcyclopropyl)phenyl)-5,5-dimethylcyclohex-1-enyl)methyl)-4-methyloxazolidin-2-one |
| 303 | (4S,5R)-5-(3,5-bis(trifluoromethyl)phenyl)-3-46-(4-fluoro-2-methoxy-5-(1-methylcyclopropyl)phenyl)spiro[2.5]oct-5-en-5-yl)methyl)-4-methyloxazolidin-2-one |
| 308 | methyl 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3-methylbutanoate |
| 313 | 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclobutanecarboxylic acid |
| 316 | (4S,5R)-5-(3,5-bis(trifluoromethyl)phenyl)-3-((2-(2-methoxy-5-(trifluoromethyl)pyridin-3-yl)-5,5-dimethylcyclohex-1-enyl)methyl)-4-methyloxazolidin-2-one |
| 317 | methyl 2-(7-(2-(((4S,5R)-5-(3,5-bis(trifluoromethyl)phenyl)-4-methyl-2-oxooxazolidin-3-yl)methyl)-4,4-dimethylcyclohex-1-enyl)benzo[d][1,3]dioxol-5-yl)acetate |
| 321 | 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N,2,2-trimethylpropanamide |
| 323 | methyl 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclopentanecarboxylate |
| 324 | 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclopentanecarboxylic acid |
| 329 | 3-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxyphenyl)-2,2-dimethylpropanamide |
| 338 | (4S,5R)-5-(3,5-bis(trifluoromethyl)phenyl)-3-((2-(2-methoxy-5-(2-methyl-2H-tetrazol-5-yl)phenyl)-5,5-dimethylcyclohex-1-enyl)methyl)-4-methyloxazolidin-2-one |
| 340 | (4S,5R)-5-(3,5-bis(trifluoromethyl)phenyl)-3-((2-(2-methoxy-5-(2-methyl-2(2H-tetrazol-5-yl)propyl)phenyl)-5,5-dimethylcyclohex-1-enyl)methyl)-4-methyloxazolidin-2-one |
| 341 | (4S,5R)-5-(3,5-bis(trifluoromethyl)phenyl)-3-((2-(2-methoxy-5-(2-methyl-2-(2-methyl-2H-tetrazol-5-yl)propyl)phenyl)-5,5-dimethylcyclohex-1-enyl)methyl)-4-methyloxazolidin-2-one |
| 350 | 3-(5-(2-(((4S,5R)-5-(3,5-bis(trifluoromethyl)phenyl)-4-methyl-2-oxooxazolidin-3-yl)methyl)-4,4-dimethylcyclohex-1-enyl)-6-methoxypyridin-3-yl)-2,2-dimethylpropanoic acid |
| 353 | (4S,5R)-5-(3,5-bis(trifluoromethyl)phenyl)-3-((2-(5-chloro-2-methoxyphenyl)-5,5-dimethylcyclohex-1-enyl)methyl)-4-methyloxazolidin-2-one |
| 366 | (4S,5R)-5-(3,5-bis(trifluoromethyl)phenyl)-3-((2-(6-isopropyl-3-methoxypyridin-2-yl)-5,5-dimethylcyclohex-1-enyl)methyl)-4-methyloxazolidin-2-one |
| 367 | (4S,5R)-5-(3,5-bis(trifluoromethyl)phenyl)-3-((2-(5-4(S)-3-fluoropyrrolidin-1-yl)methyl)-2-methoxyphenyl)-5,5-dimethylcyclohex-1-enyl)methyl)-4-methyloxazolidin-2-one |

Preparation of Compounds

Methods for Preparing Compounds

The compounds of formula I according to the present invention can be prepared according to the methods described in various literatures (WO 2006/014357 A1). Methods for preparing the compounds of formula I will now be described in detail with reference to reaction schemes.

[Reaction Scheme 1]

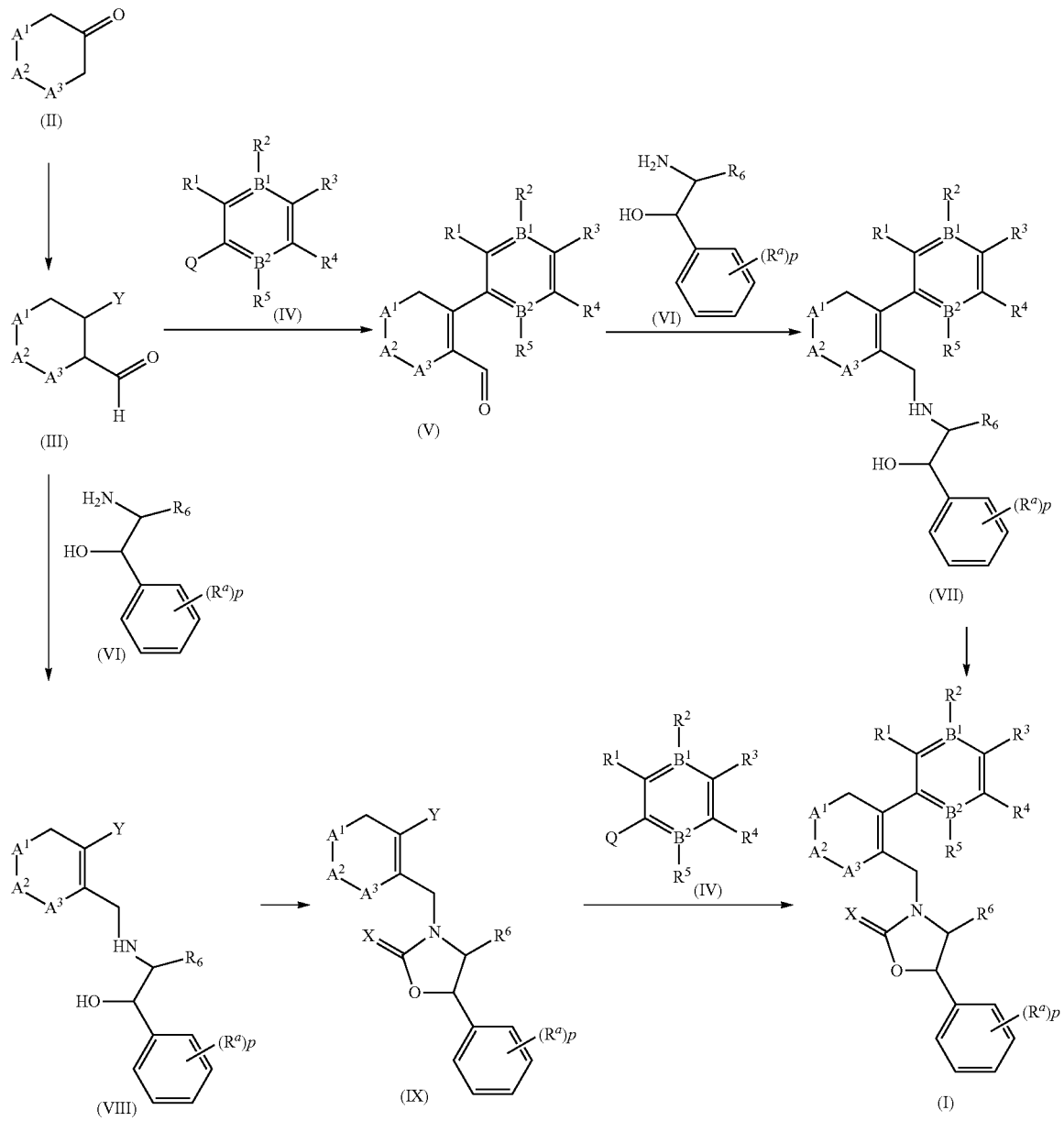

wherein $A^1$, $A^2$, $A^3$, $B^1$, $B^2$, $R^1$, $R^2$, $R^3$, $R^4$, $R^5$, $R^6$, $R^a$, p and X are as defined above; Y is a leaving group, preferably a halide group (e.g., chloride or bromide); and Q may represent —B(OH)$_2$ or

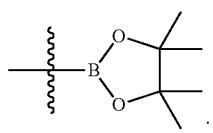

As shown in reaction scheme 1 above, the starting material compound II is allowed to react with phosphorus tribromide (PBr$_3$) or phosphorus oxychloride (POCl$_3$) in dimethylformamide (DMF), which is a Vilsmeier reaction, so as to introduce halogen into compound II.

In the reaction for preparing compound II, methylene chloride may be used as a solvent, and the reaction temperature is 0~70° C., and preferably 0~45° C.

Compound V can be prepared by subjecting compound III and compound IV to a Suzuki reaction (Morris, G. A., et al., *Tetrahedron Lett.*, 2001, 42, 2093) or an Ullmann reaction (Martin G. Banwell et al. *Org. Lett.* 2004, 6, 2741). In addition, compound IV used in the synthesis process can be prepared according to the method described in the literature (WO 2006/014357 A1, Erin F. DiMauro et al., *J. Med. Chem.* 2006, 49, 5671).

In the reaction for preparing compound V, dimethoxyethane (DME), dimethylsulfoxide (DMSO), water or the like is used as a solvent, and the reaction temperature is 80~150°

C., and preferably 80~100° C. The resulting compounds V and III may be subjected to reductive amination with amino alcohol compound VI, prepared according to the method described in the literature (WO 2006/014357 A1, Jingjun Yin et al., *J. Org. Chem.* 2006, 840), thereby synthesizing compounds VII and VIII, respectively.

The resulting compounds VII and VIII can be converted to the desired compounds I and IX, respectively, by reaction with thiophosgen or triphosgen. In addition, the resulting compound IX may also be converted to the desired compound I by a Suzuki reaction with the compound IV.

As described above, the compounds of formula I are generally prepared according to the method shown in reaction scheme 1. In addition, compounds of examples of the present invention may also be prepared according to the following reaction schemes 2, 3, 4 and 5.

[Reaction Scheme 2]

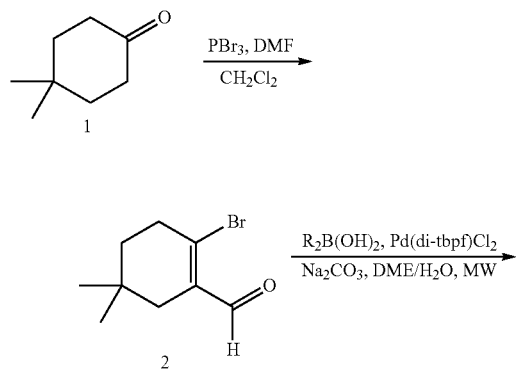

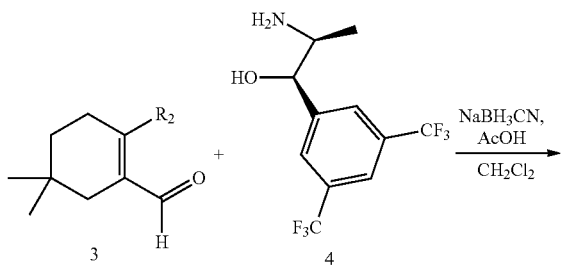

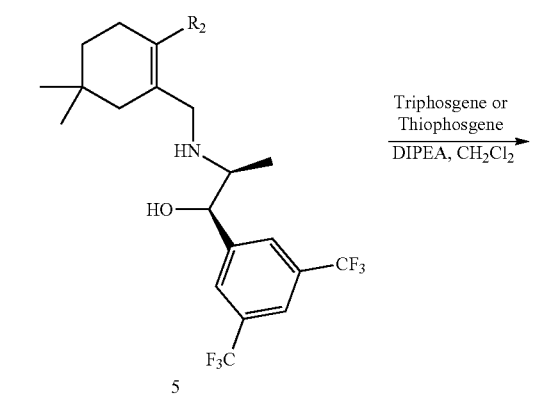

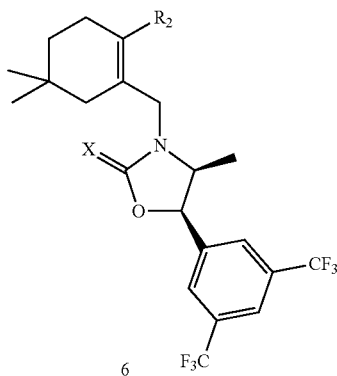

Compound 15. X = S, $R_2$ = 2-methoxy-5-isopropylbenzene
Compound 16. X = S, $R_2$ = 2-methoxybenzene
Compound 17. X = S, $R_2$ = 2-methoxy-4-fluoro-5-isopropylbenzene
Compound 18. X = O, $R_2$ = 2-methoxybenzene
Compound 36. X = O, $R_2$ = 2-methoxy-5-melhylbenzoate
Compound 41. X = O, $R_2$ = 2-methoxy-4-fluoro-5-methylbenzoate
Compound 51. X = O, $R_2$ = 4-indole
Compound 56. X = O, $R_2$ = 2-methoxy-5-dimethylbenzenamine
Compound 97. X = O, $R_2$ = 2-fluoro-5-trifluoromethylbenzene
Compound 115. X = O, $R_2$ = 2-methoxy-5-t-butylbenzene
Compound 117. X = O, $R_2$ = 2-methoxy-5-trifluoromethoxybenzene Reaction scheme 2 above shows a general process for preparing compounds 15, 16, 17, 18, 36, 41, 51, 56, 97, 115 and 117 of the present invention, and other compounds of the present invention can also be prepared according to reaction scheme 2. As shown in reaction scheme 2, dimethylformamide (DMF) and phosphorus tribromide ($PBr_3$) are added dropwise to the starting material dimethylcyclohexanone to obtain compound 2 which is then subjected to a Suzuki reaction with commercially available boronic acid derivatives in the presence of a palladium catalyst, thus synthesizing compound 3. The obtained compound 3 is converted to compound 5 by reaction with compound 4, prepared according to the method described in the literature (2006/014357 A1, Jingjun Yin et al., *J. Org. Chem.* 2006, 840). The obtained compound 5 can be converted into the desired compound 6 by reaction with thiophosgen or triphosgen.

[Reaction Scheme 3]

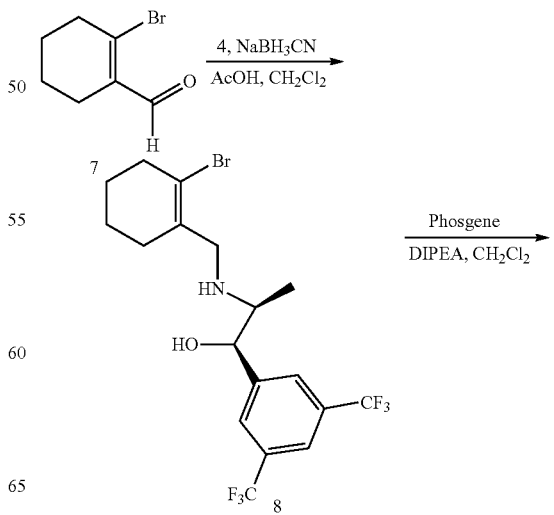

-continued

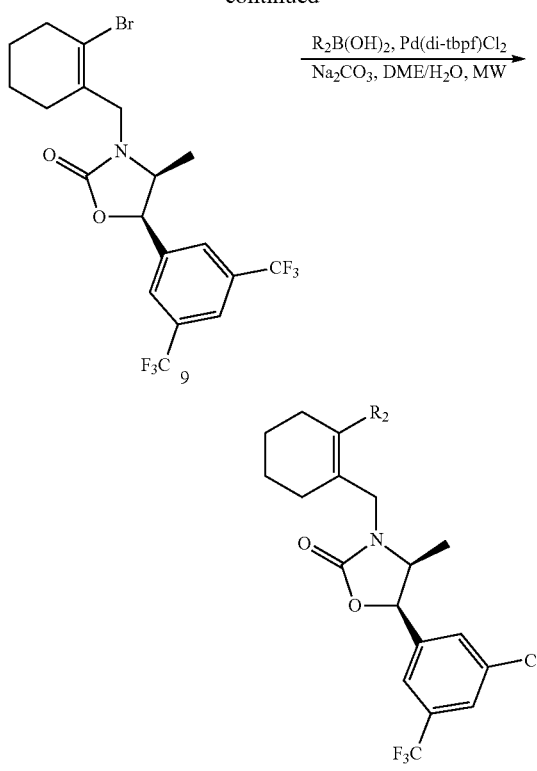

Compound 57. R$_2$ = 4-methoxy-2-benzaldehyde
Compound 60. R$_2$ = 8-quinoline
Compound 61. R$_2$ = 1-methyl-4-indazole
Compound 79. R$_2$ = 2-methoxy-5-benzaldehyde Reaction scheme 3 above shows a general process for synthesizing compounds 57, 60, 61 and 79 of the present invention, and other compounds of the present invention can also be prepared according to reaction scheme 3 above. The starting material compound 7 is allowed to react with compound 4, acetic acid and sodium cyanoborohydride to synthesize compound 8 which is then allowed to react with triphosgen, thereby preparing compound 9. The obtained compound 9 can be subjected to a Suzuki reaction (Morris, G. A., et al., *Tetrahedron Lett.*, 2001, 42, 2093) with various boronic acids, thereby preparing desired compounds.

[Reaction Scheme 4]

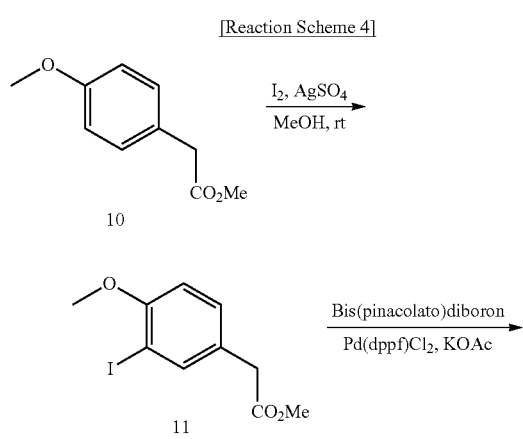

-continued

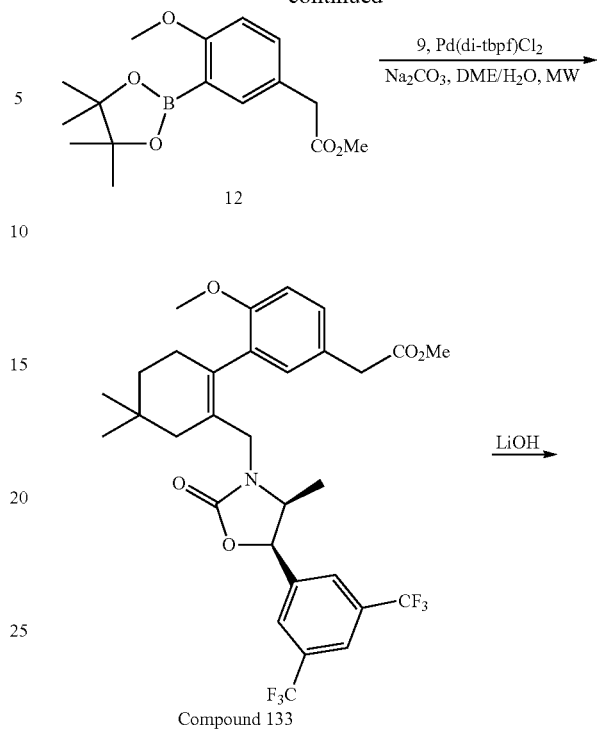

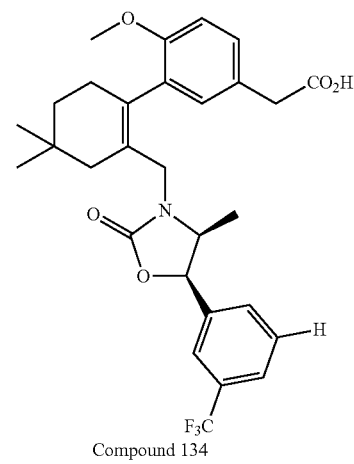

Reaction scheme 4 above shows a general process for synthesizing compounds 133 and 134 of the present invention, and other compounds of the present invention can also be prepared according to reaction scheme 4 above. As shown in reaction scheme 4, the starting material compound 10 is allowed to react with iodine (I$_2$) and silver sulfate to synthesize compound 11 which is then allowed to react with bis(pinacolato)diboron in the presence of a palladium catalyst, thus preparing compound 12. Compound 9 and boronic acid may be added dropwise to the obtained compound 12, and then subjected to a Suzuki reaction (Morris, G. A., et al., *Tetrahedron Lett.*, 2001, 42, 2093), thereby preparing compound 133. The obtained compound 133 can be converted into compound 134 by hydrolysis with lithium hydroxide (LiOH).

[Reaction Scheme 5]

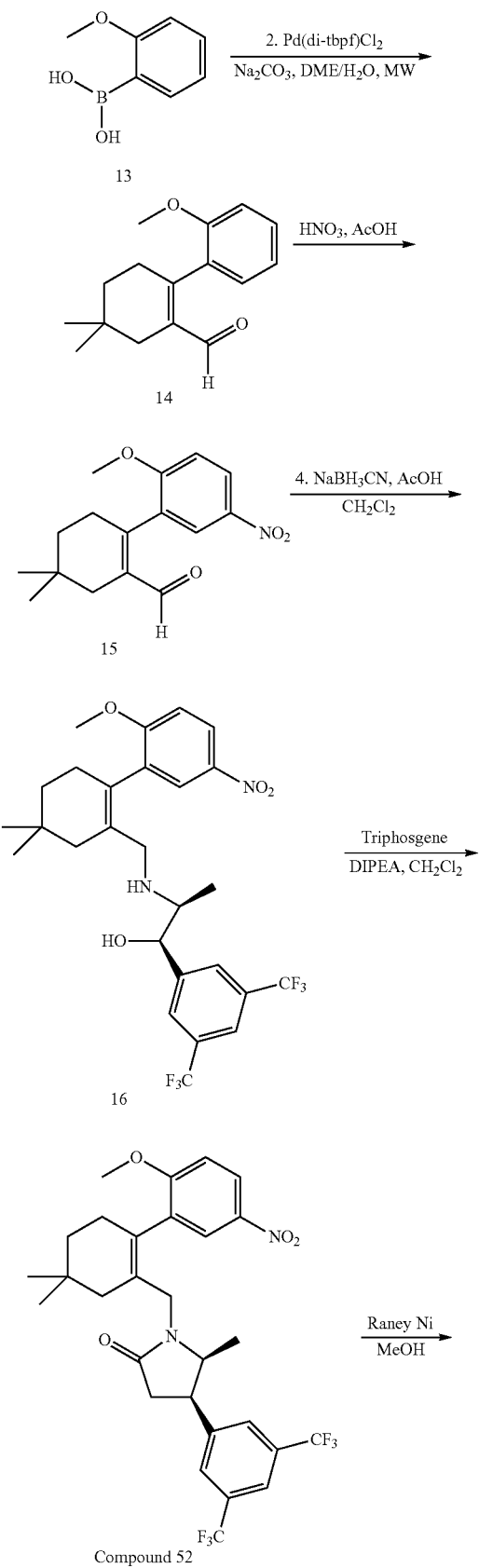

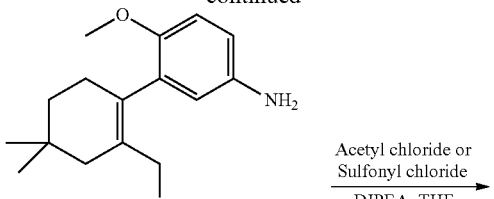

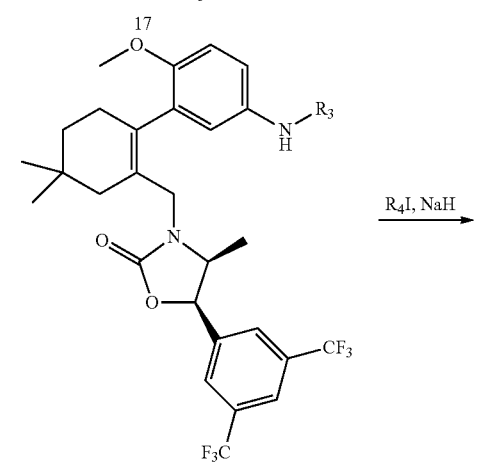

Compound 110. $R_3$ = acetyl
Compound 137. $R_3$ = trifluoromethaiesulfonyl
Compound 136. $R_3$ = cyclopropanesutfonyl
Compound 163. $R3$ = 2-bromoacetyl Compound 112. $R_3$ = acetyl, R 4= $CH_3$
Compound 128. $R_3$ = methanesulfonyl, $R_4$ = $CH_3$
Compound 138. $R_3$ = cycopropanosulfonyl, $R_4$ = $CH_3$
Compound 141. $R_3$ = trifluoromethanesulfonyl, $R_4$ = $CH_3$
Compound 177. $R_3$ = proptonyl, $R_4$ = $CH_3$ Reaction scheme 5 above shows a general process for synthesizing compounds 110, 112, 128, 136, 137, 138, 141, 163 and 177 of the present invention, and other compounds of the present invention can also be prepared according to reaction scheme 5 above. As shown in reaction scheme 5 above, the starting material boronic acid compound 13 is subjected to a Suzuki reaction (Morris, G. A., et al., *Tetrahedron Lett.*, 2001, 42, 2093) with compound 2 to prepare compound 14 which is then nitrated with nitric acid, thus synthesizing compound 15. The obtained compound 15 may be subjected to the reactions shown in reaction scheme 2, thus synthesizing compound 16 and compound 52. The obtained compound 52 may be treated with a nickel metal to reduce the nitro group thereof, and then allowed to react with various acyl chloride or sulfonyl chloride compounds, thus preparing various compounds. The resulting compounds 110, 136 and 137 may be allowed to react with iodomethane, thus obtaining compounds 112, 128, 138, 141 and 177.

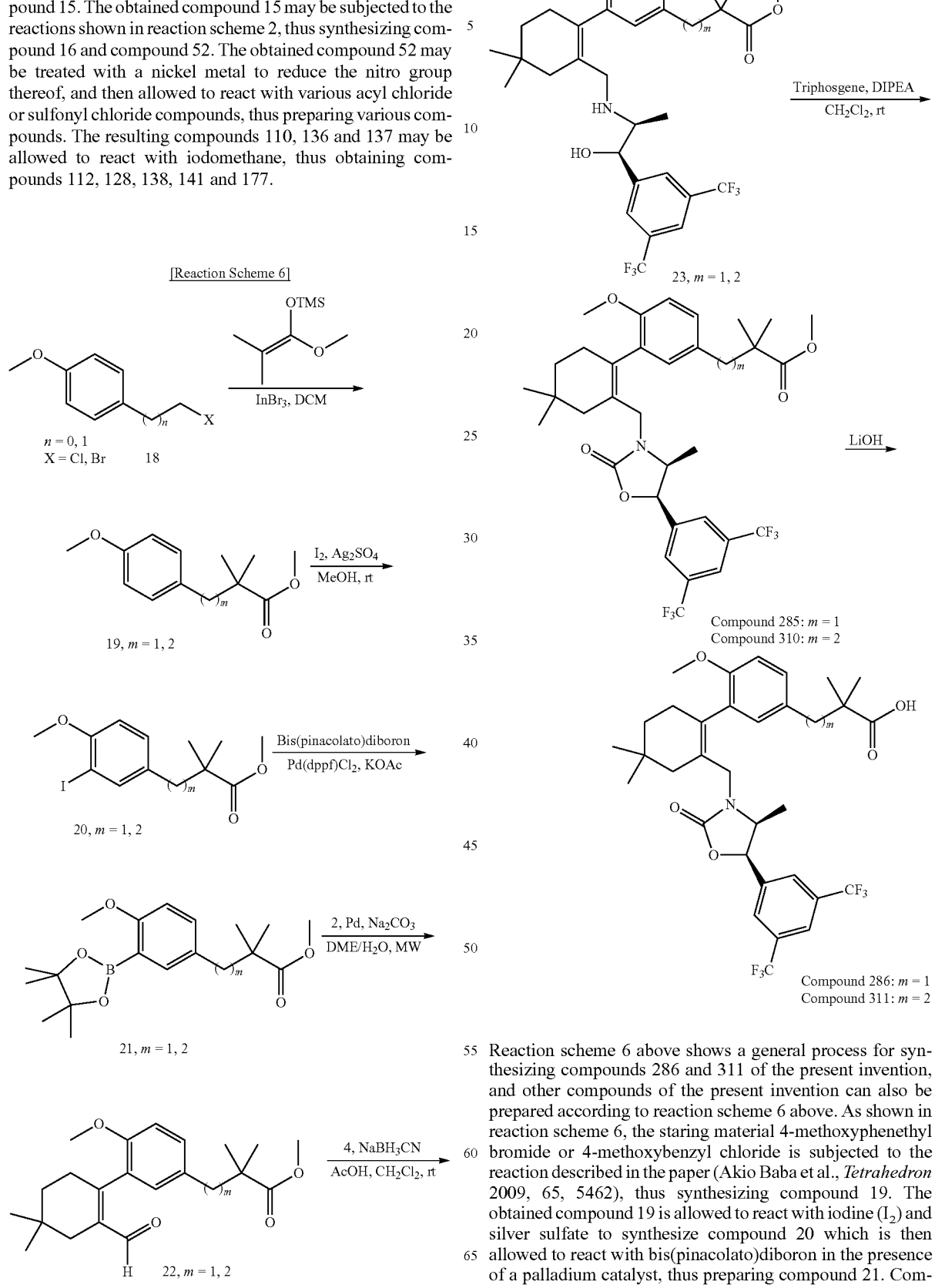

Reaction scheme 6 above shows a general process for synthesizing compounds 286 and 311 of the present invention, and other compounds of the present invention can also be prepared according to reaction scheme 6 above. As shown in reaction scheme 6, the staring material 4-methoxyphenethyl bromide or 4-methoxybenzyl chloride is subjected to the reaction described in the paper (Akio Baba et al., *Tetrahedron* 2009, 65, 5462), thus synthesizing compound 19. The obtained compound 19 is allowed to react with iodine ($I_2$) and silver sulfate to synthesize compound 20 which is then allowed to react with bis(pinacolato)diboron in the presence of a palladium catalyst, thus preparing compound 21. Compound 2 is added dropwise to the obtained compound 21, and then subjected to a Suzuki reaction (Morris, G. A., et al., *Tetrahedron Lett.*, 2001, 42, 2093), thus synthesizing compound 22. The obtained compound 22 is subjected to the reactions shown in reaction scheme 2 (reductive amination and cyclization) to synthesize compounds 285 and 310 which are then hydrolyzed with lithium hydroxide (LiOH), thus preparing the desired compounds 286 and 311.

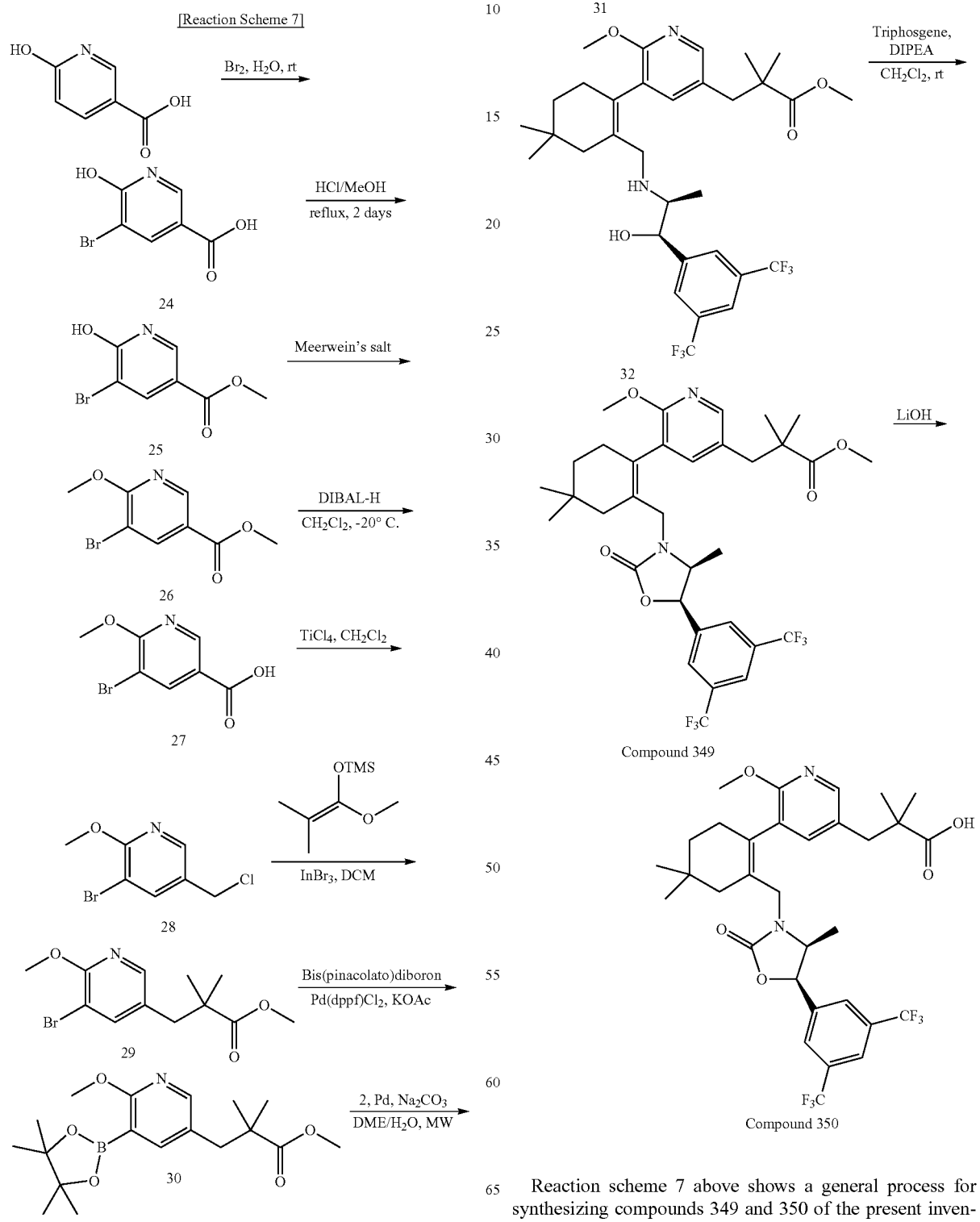

Reaction scheme 7 above shows a general process for synthesizing compounds 349 and 350 of the present invention, and other compounds of the present invention can also be prepared according to reaction scheme 7 above. As shown in reaction scheme 7, key intermediate compound 29 can be synthesized in the following manner with reference to the literature (US 2010/0081673 A1). The starting material 6-hydroxynicotinic acid is allowed to react with bromine ($Br_2$) to obtain compound 24 which is then esterified, thus synthesizing compound 25. The obtained compound 25 is allowed to be reacted with Meerwein's salt (U.S. Pat. No. 5,929,094 A1) to synthesize compound 26. The obtained compound 26 is reduced with diisobutylaluminum hydride (DIBAL-H) to obtain compound 27 which is then chlorinated with titanium chloride ($TiCl_4$), thus synthesizing compound 28. The resulting compound 28 is reacted with the reagents described in the paper (Akio Baba et al., *Tetrahedron* 2009, 65, 5462), thus synthesizing key intermediate compound 29. Then, compound 29 are subjected to the reactions shown in reaction schemes 4 and 6, thereby preparing the desired compounds 349 and 350.

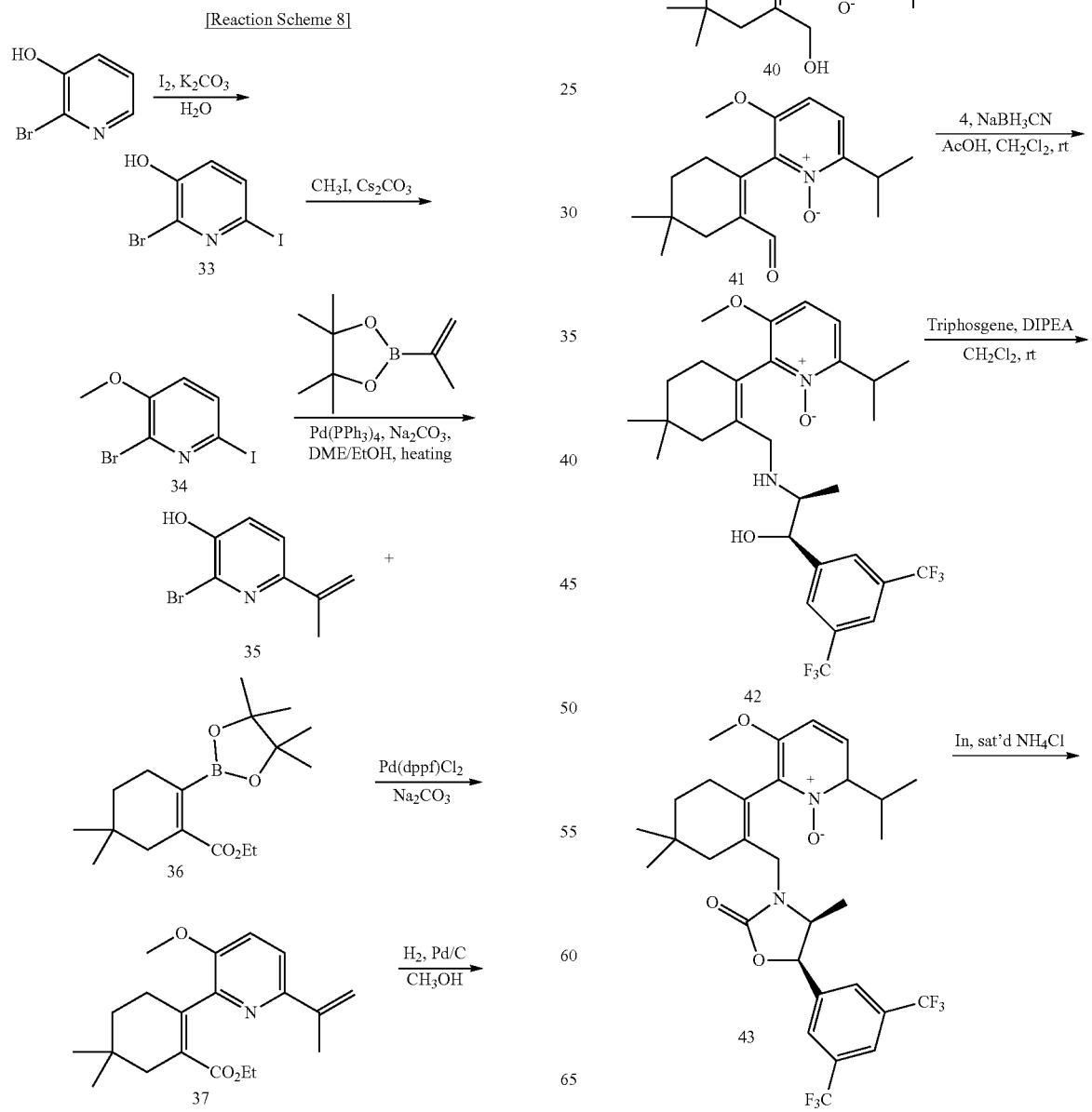

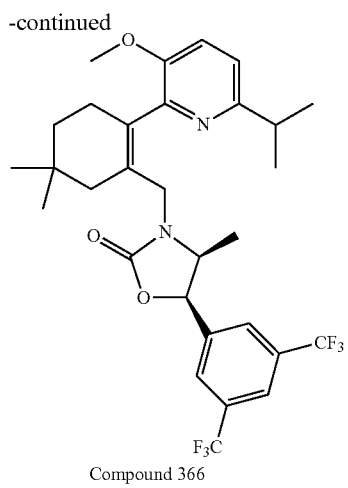

Compound 366

Reaction scheme 8 above shows a general process for synthesizing compound 366 of the present invention, and other compounds of the present invention can also be synthesized according to reaction scheme 8 above. As shown in reaction scheme 8, the starting material 2-bromo-3-pyridinol is reacted with iodine ($I_2$) to synthesize compound 33 which is then methylated, thus synthesizing compound 34. The resulting compound 34 is subjected to a Suzuki reaction (Morris, G. A., et al., *Tetrahedron Lett.*, 2001, 42, 2093) to synthesize compound 35 which is then reacted with intermediate compound 36, thus synthesizing compound 37. Then, various reactions (hydroxylation, oxidation (N-oxide)/reduction (DIBAL-H), and oxidation (Dess-Martin)) are carried out to obtain intermediate compound 41. Then, the reactions shown in reaction scheme 6 are carried out to obtain compound 43. Indium (In) and a saturated ammonium chloride aqueous solution are added dropwise to and reacted with compound 43, thus preparing compound 366.

The cycloalkenyl aryl derivatives of formula I may contain one or more asymmetric carbon atoms, and may thus occur as racemates, racemic mixtures, single enantiomers, diastereomeric mixtures, and individual diastereomers. Such isomers can be resolved using the methods of prior arts. For example, isomers of the cycloalkenyl aryl derivatives of formula I can be resolved by column chromatography or HPLC. Alternatively, any enantiomer of a compound of formula I can be obtained by stereospecific synthesis using optically pure starting materials or reagents of known configuration.

Some of the compounds of the present invention are observed as mixtures of atropisomers (rotamers) in the NMR spectra. The individual atropisomers as well as mixtures thereof are encompassed with the compounds of the present invention.

The compounds of formula I according to the present invention can be in the form of pharmaceutically acceptable salts derived from inorganic or organic acids. Preferred examples of acids which can be used to form pharmaceutically acceptable acid addition salts include hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid and toluenesulfonic acid.

Hereinafter, the present invention will be described in further detail with reference to examples, preparation examples and experimental examples. It is to be understood, however, that these examples are for illustrative purposes only and are not intended to limit the scope of the present invention.

Advantageous Effects

The present invention can provide novel cycloalkenyl aryl derivatives, isomers thereof, pharmaceutically acceptable salts thereof, hydrates thereof, or solvates thereof, and preparation methods thereof.

In addition, the present invention can provide novel cycloalkenyl aryl derivatives, which have less side effects and can effectively inhibit CETP, isomers thereof, pharmaceutically acceptable salts thereof, hydrates thereof, or solvates thereof, and preparation methods thereof.

BEST MODE

Examples

Hereinafter, the present invention will be described in further detail with reference to examples. It is to be understood, however, that these examples are illustrative purposes only and are not construed to limit the scope of the present invention.

Compound 15

(4S,5R)-5-(3,5-bis(trifluoromethyl)phenyl)-3-((2-(5-isopropyl-2-methoxyphenyl)-5,5-dimethylcyclohex-1-enyl)methyl)-4-methyloxazolidine-2-thione As shown in reaction scheme 2, intermediate 5 was synthesized. Thiophosgene (5 mL) and triethylamine (66 μl, 0.44 mmol) was added dropwise to the obtained intermediate 5 (53 mg, 0.095 mmol), and then the reaction mixture was refluxed with stirring overnight at 100° C. After the completion of the reaction, the reaction mixture was diluted with methylene chloride ($CH_2Cl_2$), washed with saturated sodium hydrogen carbonate solution and brine, dried with anhydrous magnesium sulfate, filtered, and concentrated under reduced pressure. The residue was separated by MPLC ($SiO_2$, 5% Hex/EA), thus obtaining Compound 15 (10 mg, 18%).
$^1$H NMR (400 MHz, $CDCl_3$); 1:1.5 atropisomer mixture; δ 7.77 (s, 1H), 7.65 (s, 2H), 6.98-6.95 (m, 1H), 6.72-6.62 (m, 2H), 5.63-5.60 (m, 1H), 4.50 (bd, 1H), 4.14-4.11 (m, 0.6H), 4.01-3.97 (m, 0.4H), 3.66 (s, 1H), 3.61 (s, 2H), 2.75-2.67 (m, 1H), 2.46-2.42 (bm, 1H), 2.18-2.16 (bm, 1H), 2.01-1.77 (m, 3H), 1.45-1.36 (m, 2H), 1.11-1.04 (m, 6H), 0.94-0.92 (m, 6H), 0.31 (d, 1.2H, J=6.6), 0.19 (d, 1.8H, J=6.6). MS (ESI) m/z 600 ($M^+$+H).

Compound 16

(4S,5R)-5-(3,5-bis(trifluoromethyl)phenyl)-3-((2-(2-methoxyphenyl)-5,5-dimethylcyclohex-1-enyl)methyl)-4-methyloxazolidine-2-thione Compound 16 (21 mg, 39%) as yellow solid was obtained according to the same method as the synthesis of compound 15. $^1$H NMR (400 MHz, $CDCl_3$); 1:1.7 atropisomer mixture; δ 7.77 (s, 1H), 7.65 (s, 2H), 7.15 (m, 1H), 6.89-6.71 (m, 3H), 5.62 (d, 1H, J=8.3), 4.52 (s, 0.5H), 4.48 (s, 0.5H), 4.16-3.97 (m, 1H), 3.70 (bd, 0.7H), 3.69-3.64 (bd, 3H), 3.58 (bd, 0.4H), 2.19-2.14 (bm, 1H), 2.01-1.76 (m, 3H), 1.42-1.34 (m, 2H), 0.93 (m, 6H), 0.34 (d, 1.1H, J=6.6), 0.21 (d, 1.9H, J=6.6).

Compound 17

(4S,5R)-5-(3,5-bis(trifluoromethyl)phenyl)-3-((2-(4-fluoro-5-isopropyl-2-methoxyphenyl)-5,5-dimethyl-cyclohex-1-enyl)methyl)-4-methyloxazolidine-2-thione Compound 17 (38 mg, 70%) as yellow solid was obtained according to the same method as the synthesis of compound 15.

$^1$H NMR (400 MHz, CDCl$_3$); 1:1.5 atropisomer mixture; δ 7.78 (s, 1H), 7.65 (s, 2H), 6.89-6.67 (m, 1H), 6.43 (m, 1H), 5.63 (d, 1H, J=8.4), 4.52-4.46 (m, 1H), 4.11-4.07 (m, 0.5H), 4.01-3.97 (m, 0.4H), 3.66 (bd, 0.6H), 3.65 (s, 1H), 3.59 (s, 2H), 3.56 (bd, 0.4H), 3.05-2.99 (m, 1H), 2.20-2.00 (bm, 1H), 1.91-1.77 (m, 2H), 1.42-1.37 (m, 2H), 1.12 (d, 3H, J=6.9), 1.08 (d, 1.5H, J=6.9), 1.02 (d, 1.3H, J=6.9), 0.93 (m, 6H), 0.34 (d, 1.2H, J=6.6), 0.24 (d, 1.8H, J=6.6). MS (ESI) m/z 618 (M$^+$+H).

Compound 18

(4S,5R)-5-(3,5-bis(trifluoromethyl)phenyl)-3-((2-(2-methoxyphenyl)-5,5-dimethylcyclohex-1-enyl)methyl)-4-methyloxazolidin-2-one As shown in reaction scheme 2, intermediate 5 was synthesized. The obtained intermediate 5 (43 mg, 0.083 mmol) was dissolved in methylene chloride (3 mL). Triphosgene (13 mg, 0.04 mmol) and diisopropylethylamine (0.09 mL, 0.49 mmol) were added dropwise to the obtained reaction mixture, and then stirred at room temperature for 1 hour. After the completion of the reaction, the reaction mixture was diluted with ethyl acetate, washed with brine, dried with anhydrous magnesium sulfate, filtered, and concentrated under reduced pressure. The residue was separated by column chromatography, thus obtaining Compound 18 (36 mg, 80%) as colorless oil.

$^1$H NMR (400 MHz, CDCl$_3$); 1:1.5 atropisomer mixture; δ 7.74 (s, 1H), 7.62 (s, 2H), 7.14-7.09 (m, 1H), 6.89-6.71 (m, 3H), 5.50-5.46 (m, 1H), 3.92-3.79 (m, 2H), 3.66 (s, 1.3H), 3.63 (s, 1.8H), 3.48 (bd, 0.6H), 3.33 (bd, 0.4H), 2.20-2.00 (m, 1H), 2.00-1.81 (m, 3H), 1.41-1.35 (m, 2H), 0.94 (d, 3H, J=6), 0.91 (s, 3H), 0.31 (d, 1.2H, J=6.6), 0.19 (d, 1.8H, J=6.5). MS (ESI) m/z 542 (M$^+$+H).

Compound 19

(4S,5R)-5-(3,5-bis(trifluoromethyl)phenyl)-3-((2-(4-fluoro-5-isopropyl-2-methoxyphenyl)-5,5-dimethyl-cyclohex-1-enyl)methyl)-4-methyloxazolidin-2-one Compound 19 (37 mg, 100%) as white solid was obtained according to the same method as the synthesis of compound 18.

$^1$H NMR (400 MHz, CDCl$_3$); 1:1.2 atropisomer mixture; δ 7.75 (s, 1H), 7.62 (s, 2H), 6.68 (dd, 1H, J=8.7, 10.9), 6.42 (dd, 1H, J=12, 17), 5.50 (t, 1H, J=6.8), 3.91-3.77 (m, 2H), 3.62 (s, 1.4H), 3.59 (s, 1.7H), 3.44 (bd, 0.6H), 3.31 (bd, 0.4H), 3.09-2.97 (m, 1H), 2.39-2.34 (bm, 0.5H), 2.12-2.01 (bm, 1H), 1.95-1.90 (bm, 0.6H), 1.82-1.80 (m, 2H), 1.43-1.32 (m, 2H), 1.11-1.01 (m, 6H), 0.94 (s, 3H), 0.90 (d, 3H, J=6.6), 0.31 (d, 1.4H, J=6.5), 0.22 (d, 1.6H, J=6.5). MS (ESI) m/z 602.0 (M$^+$+H)

Compound 25

4S,5R)-5-(3,5-bis(trifluoromethyl)phenyl)-3-((2-(4-fluoro-5-isopropyl-2-methoxyphenyl)-5-methylcy-clohex-1-enyl)methyl)-4-methyloxazolidin-2-one Compound 25 (33 mg, 87%) as white solid was obtained according to the same method as the synthesis of compound 18.

$^1$H NMR (400 MHz, CDCl$_3$); 1:1 atropisomer mixture; δ 7.83 (s, 1H), 7.71 (s, 2H), 6.79-6.73 (m, 1H), 6.55-6.47 (m, 1H), 5.62-5.56 (m, 1H), 3.98-3.85 (m, 2H), 3.70 (s, 1.4H), 3.67 (d, 1.6H, J=3.9), 3.59-3.35 (m, 1H), 3.13-3.07 (m, 1H), 2.25-2.02 (m, 2H), 1.82-1.71 (m, 3H), 1.35-1.28 (m, 1H), 1.19-1.09 (m, 6H), 1.04-1.02 (m, 3H), 0.39 (dd, 1.38H, J=1.7, 6.5), 0.34 (d, 0.79H, J=6.5), 0.30 (d, 0.82H, J=6.5).

Compound 26

(4S,5R)-5-(3,5-bis(trifluoromethyl)phenyl)-3-((2-(4-fluoro-5-isopropyl-2-methoxyphenyl)-5-methylcy-clohex-1-enyl)methyl)-4-methyloxazolidine-2-thione Compound 26 (22 mg, 73%) as yellow solid was obtained according to the same method as the synthesis of compound 15.

$^1$H NMR (400 MHz, CDCl$_3$); atropisomer mixture; δ 7.88 (s, 1H), 7.76 (s, 2H), 6.82-6.78 (m, 1H), 6.59-6.49 (m, 1H), 5.78-5.73 (m, 1H), 4.75-4.25 (m, 1H), 4.40-4.07 (m, 1H), 3.82 (d, 0.3H), 3.75 (s, 1.5H), 3.71-3.58 (m, 0.7H), 3.69 (d, 1.5H, J=4.1), 3.15-3.10 (m, 1H), 2.60-2.05 (bm, 3H), 1.85-1.77 (bm, 3H), 1.43-1.33 (m, 1H), 1.19-1.08 (m, 6H), 1.06 (d, 3H, J=4.4), 0.46 (m, 1.1H), 0.40 (d, 0.7H, J=6.6), 0.34 (d, 0.8H, J=6.6).

Compound 27

(4S,5R)-5-(3,5-bis(trifluoromethyl)phenyl)-3-((2-(4-fluoro-5-isopropyl-2-methoxyphenyl)cyclohex-1-enyl)methyl)-4-methyloxazolidin-2-one Compound 27 (91 mg, 93%) as colorless oil was obtained according to the same method as the synthesis of compound 18.

$^1$H NMR (400 MHz, CDCl$_3$); 1:1.1 atropisomer mixture; δ 7.86 (s, 1H), 7.73 (s, 2H), 6.80 (dd, 1H, J=11.6, 8.7), 6.54 (dd, 1H, J=16.9, 12.2), 5.61 (d, 1H, J=8.1), 4.01-3.87 (m, 2H), 3.73 (s, 1.4H), 3.70 (s, 1.6H), 3.54 (d, 0.6H, J=14.5), 3.43 (d, 0.4H, J=14.9), 3.17-3.08 (m, 1H), 2.43-1.99 (bm, 4H), 1.81-1.73 (bm, 4H), 1.24-1.18 (m, 5H), 1.14 (d, 1H, J=6.9), 0.42 (d, 1.4H, J=6.5), 0.35 (d, 1.6H, J=6.5). MS (ESI) m/z 574 (M$^+$+H).

Compound 28

(4S,5R)-5-(3,5-bis(trifluoromethyl)phenyl)-3-((2-(4-fluoro-5-isopropyl-2-methoxyphenyl)cyclohex-1-enyl)methyl)-4-methyloxazolidine-2-thione Compound 28 (75 mg, 82%) as yellow oil was obtained according to the same method as the synthesis of compound 15.

$^1$H NMR (400 MHz, CDCl$_3$); 1:1.3 atropisomer mixture; δ 7.87 (s, 1H), 7.76 (s, 2H), 6.81-6.54 (t, 1H, J=8.8), 6.54 (dd, 1H, J=12.2, 21.1), 5.77 (t, 1H, J=8.7), 4.64-4.56 (bm, 1H), 4.22-4.08 (m, 1H), 3.78-3.68 (m, 1H), 3.75 (s, 1.23H), 3.69 (s, 1.64H), 3.17-3.09 (m, 1H), 2.44-2.00 (bm, 4H), 1.79-1.71 (bm, 4H), 1.31-1.12 (m, 6H), 0.46 (d, 1.3H, J=6.6), 0.38 (d, 1.7H, J=6.6). MS (ESI) m/z 590 (M$^+$+H).

Compound 29

(4S,5R,Z)-5-(3,5-bis(trifluoromethyl)phenyl)-3-((2-(4-fluoro-5-isopropyl-2-methoxyphenyl)cyclohept-1-enyl)methyl)-4-methyloxazolidin-2-one Compound 29 (99 mg, 62%) as white solid was obtained according to the same method as the synthesis of compound 18.
$^1$H NMR (400 MHz, CDCl$_3$); 1:1.7 atropisomer mixture; δ 7.84 (s, 1H), 7.72 (s, 2H), 6.75 (2d, 1H, J=8.6), 6.52 (2d, 1H, J=12.2), 5.60 (dd, 1H, J=8.1, 12.5), 4.04-3.87 (m, 2H), 3.72 (s, 1H), 3.69 (s, 2H), 3.47 (dd, 1H, J=14.6), 3.15-3.05 (m, 1H), 2.47-2.24 (m, 4H), 1.84-1.80 (m, 2H), 1.72-1.48 (m, 4H), 1.21-1.11 (m, 6H), 0.40 (d, 1.1H, J=6.5), 0.27 (d, 1.9H, J=6.5). MS (ESI) m/z 588 (M$^+$+H).

Compound 30

(4S,5R)-5-(3,5-bis(trifluoromethyl)phenyl)-3-((4-(4-fluoro-5-isopropyl-2-methoxyphenyl)-5,6-dihydro-2H-pyran-)methyl)-4-methyloxazolidin-2-one Compound 30 (35 mg, 61%) as colorless oil was obtained according to the same method as the synthesis of compound 18.
$^1$H NMR (400 MHz, CDCl$_3$); atropisomer mixture; δ 7.86 (s, 1H), 7.71 (s, 2H), 6.56-6.89 (m, 1H), 6.53-6.61 (m, 1H), 5.60 (d, J=8.0, 1H), 4.15 (s, 2H), 3.84-4.03 (m, 4H), 3.76 (s, 3H), 3.45-3.63 (m, 1H), 3.12-3.17 (m, 1H), 2.12-2.66 (m, 2H), 1.21-1.28 (m, 6H), 0.38-0.39 (m, 3H). MS (ESI) m/z 620 (M$^+$+H).

Compound 31

(4S,5R)-5-(3,5-bis(trifluoromethyl)phenyl)-3-((2-(4-fluoro-5-isopropyl-2-methoxyphenyl)cyclopent-1-enyl)methyl)-4-methyloxazolidin-2-one Compound 31 (0.13 g, 81%) as white solid was obtained according to the same method as the synthesis of compound 18. $^1$H NMR (400 MHz, CDCl$_3$); atropisomer mixture; δ 7.86 (s, 1H), 7.71 (s, 2H), 6.88 (d, J=8.7, 1H), 6.57 (d, J=12.2, 1H), 5.46 (d, J=8.0, 1H), 4.20 (d, J=15.0, 1H), 3.76-3.95 (m, 1H), 3.65 (s, 3H), 3.11-3.17 (m, 1H), 2.53-2.80 (m, 4H), 1.21-1.28 (m, 6H), 0.40 (m, 3H). MS (ESI) m/z 604 (M$^+$+45).

Compound 32

(4S,5R)-5-(3,5-bis(trifluoromethyl)phenyl)-3-((2-(5-isopropyl-2-methoxyphenyl)cyclopent-1-enyl)methyl)-4-methyloxazolidin-2-one Compound 32 (0.22 g, 89%) as white solid was obtained according to the same method as the synthesis of compound 18.
$^1$H NMR (400 MHz, CDCl$_3$) δ 7.85 (s, 1H), 7.69 (s, 2H), 7.08-7.10 (m, 1H), 6.90-6.91 (m, 1H), 6.81 (d, J=8.4, 1H), 5.36 (d, J=8.1, 1H), 4.23 (d, J=14.8, 1H), 3.87-3.94 (m, 1H), 3.68 (m, 3H), 2.54-2.87 (m, 5H), 1.97-2.05 (m, 2H), 1.20-1.22 (m, 6H), 0.40 (m, 3H). MS (ESI) m/z 587 (M$^+$+H).

Compound 34

3-(2-(((4S,5R)-5-(3,5-bis(trifluoromethyl)phenyl)-4-methyl-2-oxooxazolidin-3-yl)methyl)cyclohex-1-enyl)-4-methoxybenzoic acid Compound 36 (20 mg, 0.035 mmol) was dissolved in tetrahydropuran/water (3 mL, volume/volume 1:1). Lithium hydroxide (an excess amount) was added dropwise to the obtained solution, and then the reaction mixture was refluxed with stirring at room temperature for 2 hours. After the completion of the reaction, the reaction mixture was diluted with ethyl acetate, washed with water and brine, dried with anhydrous magnesium sulfate, filtered, and concentrated under reduced pressure, thus obtaining Compound 34 (16 mg, 60%) as white solid.
$^1$H NMR (400 MHz, benzene-d$_6$); 1:1 atropisomer mixture; δ 8.19-8.14 (m, 1H), 8.03-8.01 (m, 1H), 7.63 (s, 1H), 7.41-7.15 (m, 2H), 6.39-6.35 (m, 1H), 4.78-4.76 (d, J=8.0, 0.5H), 4.72-4.70 (d, J=8.0, 0.5H), 4.19-4.16 (d, J=13.6, 0.5H), 4.04-4.00 (d, J=13.6, 0.5H), 3.49-3.31 (m, 2H), 3.14 (s, 1.5H), 3.11 (s, 1.5H), 2.38-1.98 (m, 4H), 1.67-1.56 (m, 5H),(−)0.09-(−) 0.11 (d, J=6.5, 1.5H),(−)0.15-(−)0.17 (d, J=6.5, 1.5H). MS (ESI) m/z 558 (M$^+$+H).

Compound 36 methyl 3-(2-(((4S,5R)-5-(3,5-bis(trifluoromethyl)phenyl)-4-methyl-2-oxooxazolidin-3-yl)methyl)cyclohex-1-enyl)-4-methoxybenzoate Compound 36 (40 mg, 63%) as white solid was obtained according to the same method as the synthesis of compound 18. $^1$H NMR (400 MHz, benzene-d$_6$); 1:1 atropisomer mixture; δ 8.11-8.05 (m, 1H), 7.96-7.91 (d, J=2.2, 0.5H), 7.95-7.94 (d, J=2.2, 0.5H), 7.62 (s, 1H), 7.38-7.36 (d, J=6.4, 1H), 6.41-6.35 (dd, J=8.6, 8.6, 1H), 4.76-4.74 (d, J=8.0, 0.5H), 4.70-4.68 (d, J=8.0, 0.5H), 4.20-4.16 (d, J=15.6, 0.5H), 4.01-3.98 (d, J=15.6, 0.5H), 3.58 (s, 1.5H), 3.52 (s, 1.5H), 3.43-3.30 (m, 3H), 3.16 (s, 1.5H), 3.12 (s, 1.5H), 2.16-2.07 (m, 3H), 1.67-1.55 (m, 4H), (−)0.12-(−)0.13 (d, J=6.5, 1.5H), (−)0.17-(−)0.19 (d, J=6.5, 1.5H). MS (ESI) m/z 573 (M$^+$+H).

Compound 37

3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzoic acid Compound 37 (19 mg, 80%) as white solid was obtained according to the same method as the synthesis of compound 34.
$^1$H NMR (400 MHz, benzene-d$_6$); 1:1 atropisomer mixture; δ 8.19-8.14 (m, 1H), 8.03-8.01 (m, 1H), 7.63 (s, 1H), 7.41-7.15 (m, 2H), 6.39-6.35 (m, 1H), 4.83-4.81 (d, J=8.4, 0.5H), 4.77-4.75 (d, J=8.4, 0.5H), 4.17-4.13 (d, J=15.2, 0.5H), 4.00-3.96 (d, J=15.2, 0.5H), 3.49-3.31 (m, 2H), 3.14 (s, 1.5H), 3.11 (s, 1.5H), 2.42-1.90 (m, 3H), 1.46-1.23 (m, 4H), 1.06-0.83 (m, 6H), (−)0.06-(−)0.08 (d, J=6.5, 1.5H), (−)0.13-(−)0.15 (d, J=6.5, 1.5H). MS (ESI) m/z 586 (M$^+$+H).

Compound 41 methyl 3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzoate Compound 41 (45 mg, 70%) as white solid was obtained according to the same method as the synthesis of compound 18. $^1$H NMR (400 MHz, benzene-d$_6$); 1:1 atropisomer mixture; δ 8.11-8.05 (m, 1H), 7.96-7.91 (d, 0.5H), 7.95-7.94 (d, 0.5H), 7.62 (s, 1H), 7.38-7.36 (d, 1H), 6.41-6.35 (dd, J=8.6, 8.6, 1H), 4.80-4.78 (d, J=8.0, 0.5H), 4.76-4.74 (d, J=8.0, 0.5H), 4.16-4.13 (d, J=15.0, 0.5H), 3.98-3.94 (d, J=15.0, 0.5H), 3.58 (s, 1.5H), 3.52 (s, 1.5H), 3.43-3.30 (m, 3H), 3.16 (s, 1.5H), 3.12 (s, 1.5H), 2.04-1.93 (m, 3H), 1.42-1.22 (m, 4H), 1.02-0.86 (m, 6H), (−)0.09-(−)0.10 (d, J=6.5, 1.5H), (−)0.16-(−)0.18 (d, J=6.5, 1.5H). MS (ESI) m/z 600 (M$^+$+H).

Compound 42

(4S,5R,Z)-5-(3,5-bis(trifluoromethyl)phenyl)-3-((2-(5-isopropyl-2-methoxyphenyl)cyclohept-1-enyl)methyl)-4-methyloxazolidin-2-one

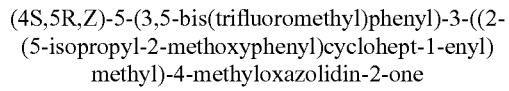

Compound 42 (0.11 g, 75%) as white solid was obtained according to the same method as the synthesis of compound 18. $^1$H NMR (400 MHz, CDCl$_3$); 1:1.9 atropisomer mixture; δ 7.84 (s, 1H), 7.73 (s, 2H), 7.04 (dd, 1H, J=8.3, 2.0), 6.81-6.71 (m, 2H), 5.58 (2d, 1H, J=8.0), 4.05-3.90 (m, 2H), 3.73 (d, 3H, J=11.3), 3.51 (2d, 1H, J=14.2), 2.85-2.76 (m, 1H), 2.52-2.27 (m, 4H), 1.85-1.82 (m, 2H), 1.71-1.51 (m, 4H), 1.20-1.14 (m, 6H), 0.38 (d, 1H, J=6.5), 0.23 (d, 1.9H, J=6.5). MS (ESI) m/z 574 (M$^+$+H).

Compound 43

(4S,5R)-5-(3,5-bis(trifluoromethyl)phenyl)-3-((5-ethyl-2-(4-fluoro-5-isopropyl-2-methoxyphenyl)cyclohex-1-enyl)methyl)-4-methyloxazolidin-2-one

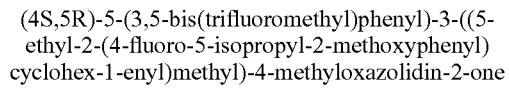

Compound 43 (0.12 g, 80%) as white solid was obtained according to the same method as the synthesis of compound 18. $^1$H NMR (400 MHz, CDCl$_3$); atropisomer mixture; δ 7.86 (s, 1H), 7.74 (s, 2H), 6.76-6.81 (m, 1H), 6.49-6.58 (m, 1H), 3.92-4.14 (m, 2H), 3.69-3.75 (m, 3H), 3.37-3.59 (m, 1H), 3.10-3.15 (m, 1H), 1.82-2.22 (m, 4H), 1.40-1.43 (m, 2H), 0.87-1.00 (m, 6H), 0.40 (m, 3H). MS (ESI) m/z 647 (M$^+$+H).

Compound 44

(4S,5R)-5-(3,5-bis(trifluoromethyl)phenyl)-3-((2-(5-isopropyl-2-methoxyphenyl)-4,4-dimethylcyclohex-1-enyl)methyl)-4-methyloxazolidin-2-one

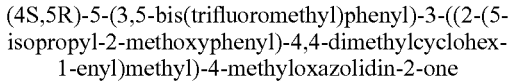

Compound 44 (2 mg, 4%) as colorless oil was obtained according to the same method as the synthesis of compound 18.

$^1$H NMR (400 MHz, CDCl$_3$); 1:1.3 atropisomer mixture; δ 7.81 (s, 1H), 7.68 (s, 2H), 7.03-7.00 (m, 1H), 6.76-6.69 (m, 2H), 5.56 (d, 1H, J=8.2), 3.96-3.83 (m, 2H), 3.69 (d, 3H, J=11.1), 3.51 (2d, 1H, J=14.6, 14.7), 2.61-2.74 (m, 1H), 2.18-2.12 (m, 2H), 1.98-1.82 (m, 2H), 1.50-1.45 (m, 5H), 1.18-1.11 (m, 6H), 0.99-0.94 (m, 6H), 0.37 (d, 1.3H, J=6.6), 0.28 (d, 1.7H, J=6.5). MS (ESI) m/z 584 (M$^+$+H).

Compound 46

(4S,5R)-5-(3,5-bis(trifluoromethyl)phenyl)-3-((2-(5-(hydroxymethyl)-2-methoxyphenyl)cyclohex-1-enyl)methyl)-4-methyloxazolidin-2-one

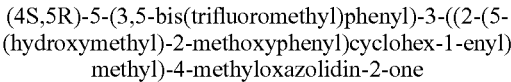

Compound 36 (30 mg, 0.052 mmol) was dissolved in anhydrous tetrahydropuran (5 mL). Lithium hydroxide (5 mg, 0.08 mmol) was added dropwise to the obtained solution at −78° C., and then stirred at room temperature for 5 hours. After the completion of the reaction, the reaction was quenched with 1M HCl (hydrochloride) solution. The reaction mixture was diluted with ethyl acetate, washed with water and brine, dried with anhydrous magnesium sulfate, filtered, and concentrated under reduced pressure, thus obtaining Compound 46 (20 mg, 60%) as white solid.

$^1$H NMR (400 MHz, benzene-d$_6$); 1:1 atropisomer mixture; δ 7.62 (s, 1H), 7.40-7.38 (d, J=10.7, 2H), 7.10-6.96 (m, 2H), 6.51-6.45 (m, 1H), 4.73-4.71 (d, J=7.9, 1H), 4.40-4.36 (m, 2H), 4.21-4.15 (m, 1H), 3.49-3.41 (m, 2H), 2.54-2.39 (m, 1H), 2.18-2.05 (m, 3H), 1.73-1.52 (m, 5H), −0.07-(−)0.08 (d, J=6.5, 1.5H), (−)0.16-(−)0.18 (d, J=6.5, 1.5H). MS (ESI) m/z 544 (M$^+$+H).

Compound 47

(4S,5R)-5-(3,5-bis(trifluoromethyl)phenyl)-3-((2-(2-methoxy-5-(methoxymethyl)phenyl)cyclohex-1-enyl)methyl)-4-methyloxazolidin-2-one

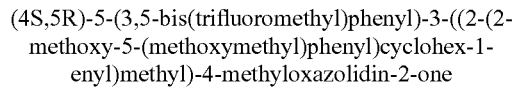

Compound 46 (6.8 mg, 0.013 mmol) was dissolved in anhydrous tetrahydropuran (2 mL). Sodium hydride (1 mg, 0.03 mmol) was added dropwise to the obtained solution at 0° C., and then stirred at room temperature for 30 minutes. Iodomethane (an excess amount) was added dropwise slowly to the reaction mixture at 0° C., and then stirred at room temperature for 3 hours. After the completion of the reaction, the reaction mixture was diluted with ethyl acetate, washed with brine, dried with anhydrous magnesium sulfate, filtered, and concentrated under reduced pressure. The residue was separated by column chromatography, thus obtaining Compound 47 (5 mg, 97%) as white solid.

$^1$H NMR (400 MHz, benzene-d$_6$); 1:1 atropisomer mixture; δ 7.61 (s, 1H), 7.39-7.38 (m, 2H), 7.13-7.10 (m, 0.5H), 7.06-7.04 (m, 1H), 6.99-6.98 (m, 0.5H), 6.51-6.44 (m, 1H), 4.75-4.68 (dd, J=7.9, 7.9, 1H), 4.22-4.13 (m, 3H), 3.53-3.44 (m, 2H), 3.25 (s, 1.5H), 3.23 (s, 1.5H), 3.19 (s, 1.5H), 3.10 (s, 1.5H), 2.51-2.47 (m, 1H), 2.22-2.09 (m, 3H), 1.71-1.61 (m, 4H), (−)0.07-(−)0.09 (d, J=6.5, 1.5H), (−)0.18-(−)0.20 (d, J=6.5, 1.5H). MS (ESI) m/z 558 (M$^+$+H).

Compound 48

(4S,5R)-5-(3,5-bis(trifluoromethyl)phenyl)-3-((2-(4-fluoro-5-isopropyl-2-methoxyphenyl)-5-(trifluoromethyl)cyclohex-1-enyl)methyl)-4-methyloxazolidin-2-one

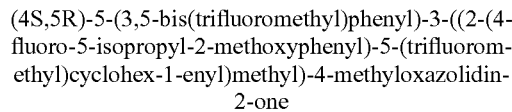

Compound 48 (0.2 g, 79.5%) as colorless oil was obtained according to the same method as the synthesis of compound 18.

$^1$H NMR (400 MHz, CDCl$_3$); atropisomer mixture; δ 7.76 (s, 1H), 7.63-7.61 (m, 2H), 7.15-6.64 (m, 1H), 6.49-6.40 (m, 1H), 5.57-5.47 (m, 1H), 3.91-3.77 (m, 2H), 3.63-3.59 (m, 3H), 3.56-3.29 (m, 1H), 3.05-3.00 (m, 1H), 2.35-1.97 (m, 6H), 1.80-1.50 (m, 1H), 1.15-1.00 (m, 6H), 0.34-0.21 (ddd, J=6.5, 3H). MS (ESI) m/z 642 (M$^+$+H).

Compound 49

(4S,5R)-5-(3,5-bis(trifluoromethyl)phenyl)-3-((2-(3'-chloro-4,6'-dimethoxybiphenyl-3-yl)cyclohex-1-enyl)methyl)-4-methyloxazolidin-2-one

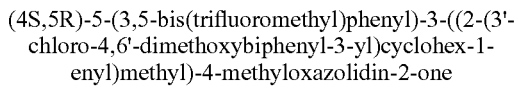

Compound 49 (2 mg, 33%) as a colorless oil was obtained according to the same method as the synthesis of compound 18.

$^1$H NMR (400 MHz, CDCl$_3$); 1:1.5 atropisomer mixture; δ 7.82 (s, 1H), 7.70 (s, 2H), 7.37-7.32 (m, 1H), 7.22-7.11 (m, 3H), 6.90-6.81 (m, 2H), 4.01-3.87 (m, 2H), 3.78-3.70 (m, 6H), 3.68-3.50 (m, 1H), 2.28-2.02 (m, 4H), 1.79-1.72 (m, 4H), 0.41 (d, 1.2H, J=6.5), 0.34 (d, 1.8H, J=6.5). MS (ESI) m/z 654 (M$^+$+H).

Compound 50

(4S,5R)-5-(3,5-bis(trifluoromethyl)phenyl)-3-((2-(5-chloro-2-methoxyphenyl)cyclohex-1-enyl)methyl)-4-methyloxazolidin-2-one

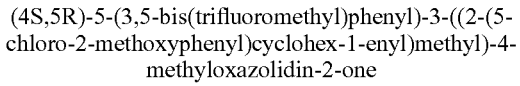

Compound 50 (84 mg, 94%) as white solid was obtained according to the same method as the synthesis of compound 18.

¹H NMR (400 MHz, CDCl₃); 1:1.1 atropisomer mixture; δ 7.83 (s, 1H), 7.73 (d, 2H, J=4.9), 7.17-7.13 (m, 1H), 6.95 (t, 1H, J=2.4), 6.76 (dd, 1H, J=8.8, 16.3), 5.59 (2d, 1H, J=8.0), 3.98-3.88 (m, 2H), 3.73 (d, 3H, J=11.8), 3.47 (2d, 1H, J=14.7), 2.38-2.02 (m, 4H), 1.77-1.67 (m, 4H), 0.45 (d, 1.4H, J=6.5), 0.36 (d, 1.6H, J=6.5). MS (ESI) m/z 548 (M⁺+H).
Compound 51

(4S,5R)-3-((2-(1H-indol-4-yl)-5,5-dimethylcyclohex-1-enyl)methyl)-5-(3,5-bis(trifluoromethyl)phenyl)-4-methyloxazolidin-2-one Compound 51 (95 mg, 38%) as colorless oil was obtained according to the same method as the synthesis of compound 18.
¹H NMR (400 MHz, CDCl₃); atropisomer mixture; δ 8.29 (bs, 1H), 7.80 (d, 1H, J=7.4), 7.65 (d, 2H, J=17), 7.26 (d, 1H, J=8), 7.18-7.07 (m, 2H), 6.84 (dd, 1H, J=17.7), 6.36-6.29 (bm, 1H), 5.48 (t, 1H, J=8.0), 4.00-3.43 (m, 3H), 2.65-2.24 (m, 2H), 2.02-1.94 (m, 2H), 1.07 (t, 6H, J=13), 0.25 (2d, 3H, J=6.5).
Compound 52

(4S,5R)-5-(3,5-bis(trifluoromethyl)phenyl)-3-((2-(2-methoxy-5-nitrophenyl)-5,5-dimethylcyclohex-1-enyl)methyl)-4-methyloxazolidin-2-one As shown in reaction scheme 5, intermediate 16 was reacted with triphosgene, thus obtaining Compound 52 (0.13 g, 62%) as yellow oil. ¹H NMR (400 MHz, CDCl₃); 1:1 atropisomer mixture; δ 8.16-8.20 (m, 1H), 7.90-7.92 (m, 1H), 7.87 (s, 1H), 7.74 (d, J=8.0, 1H), 6.95 (t, J=9.2, 1H), 5.67 (d, J=8.3, 0.51H), 5.58 (d, J=8.1, 0.43H), 3.91-4.04 (m, 2H), 3.54 (d, J=13.9, 0.45H), 3.32 (d, J=15.0, 0.54H), 2.10-2.27 (m, 2H), 1.89-2.00 (m, 2H), 1.49-1.54 (m, 2H), 1.03-1.10 (m, 6H), 0.42-0.48 (m, 3H). MS (ESI) m/z 633 (M+45)⁻.
Compound 55

(4S,5R)-5-(3,5-bis(trifluoromethyl)phenyl)-3-((4-(2-methoxyphenyl)-5,6-dihydro-2H-pyran-3-yl)methyl)-4-methyloxazolidin-2-one Compound 55 (0.8 g, 99%) as yellow oil was obtained according to the same method as the synthesis of compound 18.
¹H NMR (400 MHz, CDCl₃); atropisomer mixture; δ 7.86 (s, 1H), 7.71 (s, 2H), 7.27-7.29 (m, 1H), 6.86-7.05 (m, 3H), 5.58 (d, J=8.0, 1H), 4.26 (s, 2H), 3.86-4.15 (m, 4H), 3.86 (m, 3H), 3.65 (d, J=15.2, 0.58H), 3.49 (d, J=15.9, 0.42H), 2.13-2.71 (m, 2H), 0.4 (d, J=6.4, 1.3H), 0.28 (d, J=6.5, 1.3H). MS (ESI) m/z 560 (M+45)⁻.
Compound 56

(4S,5R)-5-(3,5-bis(trifluoromethyl)phenyl)-3-((2-(5-(dimethylamino)-2-methoxyphenyl)-5,5-dimethylcyclohex-1-enyl)methyl)-4-methyloxazolidin-2-one Compound 56 (50 mg, 62%) as colorless oil was obtained according to the same method as the synthesis of compound 18.
¹H NMR (400 MHz, CDCl₃); 1:2 atropisomer mixture; δ 7.85 (s, 1H), 7.73 (m, 2H), 6.81 (d, J=8.9, 0.35H), 6.74 (d, J=8.9, 0.65H), 6.60-6.66 (m, 1H), 6.44 (d, J=3.0, 0.35H), 6.41 (d, J=3.1, 0.65H), 5.57-5.59 (m, 1H), 3.89-4.08 (m, 2H), 3.67-3.70 (m, 3H), 3.51-3.67 (m, 1H), 2.81-2.86 (m, 6H), 2.06-2.51 (m, 2H) 1.93 (s, 2H), 1.43-1.55 (m, 2H), 1.01-1.05 (m, 6H), 0.47 (d, J=0.6, 1H), 0.32 (d, J=6.5, 2H). MS (ESI) m/z 630 (M+45)⁻.
Compound 57

2-(2-(((4S,5R)-5-(3,5-bis(trifluoromethyl)phenyl)-4-methyl-2-oxooxazolidin-3-yl)methyl)cyclohex-1-enyl)-5-methoxybenzaldehyde As shown in reaction scheme 3, intermediate 9 was synthesized. The obtained intermediate 9 (0.13 g, 0.20 mmol) was subjected to a Suzuki reaction with boronic acid (58 mg, 0.33 mmol), thus obtaining Compound 57 (0.11 g, 75%) as brown oil.
¹H NMR (400 MHz, CDCl₃); atropisomer mixture; δ 10.05 (s, 0.49H), 10.00 (s, 0.47H), 7.86 (s, 1H), 7.73 (s, 2H), 7.37-7.42 (m, 1H), 7.70-7.17 (m, 2H), 5.62-5.64 (m, 1H), 3.83-4.03 (m, 2H), 3.86 (d, J=3.0, 3H), 2.15-2.39 (m, 4H), 1.72-1.88 (m, 4H), 3.82 (d, J=3.4, 3H), 2.03-2.38 (m, 4H), 1.75 (d, J=3.8, 4H), 0.37-0.42 (m, 3H). MS (ESI) m/z 542 (M⁺+H).
Compound 58

(4S,5R)-5-(3,5-bis(trifluoromethyl)phenyl)-3-((2-(2-(hydroxymethyl)-4-methoxyphenyl)cyclohex-1-enyl)methyl)-4-methyloxazolidin-2-one Compound 57 (94 mg, 0.17 mmol) was dissolved in methanol (2 mL). Sodium borohydride (10 mg, 0.19 mmol) was added dropwise slowly to the obtained solution at room temperature, and then stirred at room temperature for 2 hours. After the completion of the reaction, the reaction was quenched with saturated ammonium solution. The reaction mixture was diluted with ethyl acetate, washed with brine, dried with sodium sulfate anhydrous, filtered, and concentrated under reduced pressure. The residue was separated by column chromatography, thus obtaining Compound 58 (85 mg, 90%) as colorless oil.
¹H NMR (400 MHz, CDCl₃); atropisomer mixture; δ 7.87 (s, 1H), 7.74 (d, J=12.0, 2H), 6.75-7.08 (m, 3H), 5.47-5.68 (m, 1H), 4.53-4.57 (m, 2H), 3.87-4.03 (m, 2H), 3.82 (d, J=5.4, 3H), 3.62 (d, J=15.1, 0.37H), 3.31 (d, J=14.7, 0.61H), 2.09-2.21 (m, 4H), 1.73-1.77 (m, 4H), 0.46-0.57 (m, 3H). MS (ESI) m/z 544 (M⁺+H).
Compound 59

(4S,5R)-5-(3,5-bis(trifluoromethyl)phenyl)-3-((2-(4-methoxy-2-(methoxymethyl)phenyl)cyclohex-1-enyl)methyl)-4-methyloxazolidin-2-one Compound 59 (85 mg, 90%) as yellow oil was obtained according to the same method as the synthesis of compound 47.
¹H NMR (400 MHz, CDCl₃); 1:1.9 atropisomer mixture; δ 7.86 (s, 1H), 7.75 (d, J=5.9, 2H), 6.75-7.00 (m, 3H), 5.65 (d, J=8.0, 0.63H), 5.58 (d, J=8.0, 0.31H), 4.28 (d, J=5.6, 0.67H), 4.25 (d, J=3.9, 1.15H), 3.83-4.00 (m, 2H), 3.80-3.81 (m, 3H), 3.78 (d, J=12.7, 0.32H), 3.40-3.42 (m, 3H), 3.34 (d, J=14.7, 4H), 2.05-2.25 (m, 4H), 1.70-1.76 (m, 4H), 0.54 (d, J=6.5, 0.95H), 0.40 (d, J=6.5, 1.9H). MS (ESI) m/z 558 (M⁺+H).
Compound 60

(4S,5R)-5-(3,5-bis(trifluoromethyl)phenyl)-4-methyl-3-((2-(quinolin-8-yl)cyclohex-1-enyl)methyl)oxazolidin-2-one Compound 60 (8 mg, 22%) as yellow oil was obtained according to the same method as the synthesis of compound 57.

¹H NMR (400 MHz, CDCl₃); 1:2 atropisomer mixture; δ 8.94-8.86 (m, 1H), 8.17-8.10 (m, 1H), 7.90 (bd, 1H, J=14), 7.75-7.72 (m, 1H), 7.67-7.62 (bm, 2H), 7.44-7.31 (m, 3H), 3.52-3.34 (m, 1H), 4.13-3.98 (m, 2H), 3.52-3.34 (m, 1H), 2.85-2.60 (m, 1H), 2.40-2.15 (m, 3H), 1.85-1.62 (m, 4H), 0.46 (d, 1H, J=6.6), (–)0.34 (d, 2H, J=6.4). MS (ESI) m/z 535 (M⁺+H).

Compound 61

(4S,5R)-5-(3,5-bis(trifluoromethyl)phenyl)-4-methyl-3-((2-(1-methyl-1H-indazol-4-yl)cyclohex-1-enyl)methyl)oxazolidin-2-one Compound 61 (16 mg, 46%) as yellow oil was obtained according to the same method as the synthesis of compound 57.

¹H NMR (400 MHz, CDCl₃); atropisomer mixture; δ 7.80 (d, 2H, J=11), 7.66 (s, 2H), 7.34-7.25 (m, 2H), 6.82 (d, 1H, J=6.7), 5.53 (d, 1H, J=15), 3.86 (bs, 1H), 3.8-3.4 (bm, 1H), 2.6-2.18 (brm, 2H), 2.15 (s, 2H), 1.76 (bs, 4H), 0.38-0.11 (brm, 3H).

Compound 62

(4S,5R)-5-(3,5-bis(trifluoromethyl)phenyl)-3-((2-(5-(3-isopropyl-1,2,4-oxadiazol-5-yl)-2-methoxyphenyl)cyclohex-1-enyl)methyl)-4-methyloxazolidin-2-one Hydroxyisobutylamidine (9 mg, 0.08 mol) was dissolved in tetrahydrofuran (0.5 mL). Sodium hydride (8 mg, 0.17 mmol) was added dropwise to the obtained solution at room temperature, and stirred at 50° C. for 2 hours. Compound 36 (25 mg, 0.044 mmol) was added dropwise to the solution, and was refluxed with stirring at 90° C. overnight. After the completion of the reaction, the reaction mixture was diluted with ethyl acetate, washed with brine, dried with anhydrous magnesium sulfate, filtered, and concentrated under reduced pressure. The residue was separated by column chromatography, thus obtaining Compound 62 (17 mg, 63%) as white solid.

¹H NMR (400 MHz, CDCl₃); atropisomer mixture; δ 8.03-8.00 (m, 1H), 7.85 (s, 1H), 7.78-7.73 (m, 3H), 6.98 (dd, 1H, J=11.9, 8.7), 5.63 (m, 1H), 4.05-3.97 (m, 2H), 3.87 (d, 3H, J=12.4), 3.48 (m, 1H), 3.17-3.05 (m, 1H), 2.25-2.05 (bm, 4H), 1.83-1.75 (bm, 4H), 1.40-1.25 (m, 6H), 0.44-0.39 (m, 3H). MS (ESI) m/z 624 (M⁺+H).

Compound 63

(4S,5R)-5-(3,5-bis(trifluoromethyl)phenyl)-3-((2-(4-fluoro-2-hydroxy-5-isopropylphenyl)-5,5-dimethylcyclohex-1-enyl)methyl)-4-methyloxazolidin-2-one Compound 19 (21 mg, 0.035 mmol) was dissolved in methylene chloride (1 mL). Boron tribromide (0.07 mL, 0.07 mmol) was added dropwise slowly to the obtained solution at −78° C., and stirred at room temperature for 3 hours. After the completion of the reaction, the reaction was quenched with saturated sodium carbonate solution. The reaction mixture was extracted with methylene chloride, washed with water and brine, dried with anhydrous magnesium sulfate, filtered, and concentrated under reduced pressure. The residue was separated by column chromatography, thus obtaining Compound 63 (5 mg, 25%) as colorless oil.

¹H NMR (400 MHz, CDCl₃); 1:1.6 atropisomer mixture; δ 7.89 (d, J=7.4, 1H), 7.74 (s, 2H), 6.72-6.75 (m, 1H), 6.57-6.64 (m, 1H), 6.04-6.06 (m, 1H), 5.72 (d, J=8.0, 0.61H), 5.62 (d, J=8.3, 0.37H), 3.98-4.06 (m, 1.65H), 3.75 (d, J=14.7, 0.39H), 3.60 (s, 0.38H), 3.37 (d, J=14.8, 0.61H), 3.10-3.15 (m, 1H), 1.48-2.26 (m, 6H), 0.67 (d, J=6.5, 1.18H), 0.50 (d, J=6.6, 1.94H). MS (ESI) m/z 588 (M⁺+H).

Compound 64

(4S,5R)-5-(3,5-bis(trifluoromethyl)phenyl)-3-((2-(4-fluoro-2-hydroxy-5-isopropylphenyl)-5-methylcyclohex-1-enyl)methyl)-4-methyloxazolidin-2-one Compound 64 (24 mg, 52%) as colorless oil was obtained according to the same method as the synthesis of compound 63.

¹H NMR (400 MHz, CDCl₃); atropisomer mixture; δ 7.89 (d, J=5.4, 1H), 7.74 (s, 2H), 6.72-6.78 (m, 1H), 6.56-6.64 (m, 1H), 5.65-5.75 (m, 0.8H), 3.94-4.06 (m, 1.46H), 3.69 (m, 0.73H), 3.37 (d, J=14.8, 0.5H), 3.10-3.13 (m, 1H), 1.29-2.28 (m, 7H), 1.04-1.28 (m, 6H), 0.89 (t, J=6.7, 1H), 0.67 (t, J=6.7, 0.99H), 0.47-0.52 (m, 1.5H). MS (ESI) m/z 574 (M⁺+H).

Compound 65

(4S,5R)-5-(3,5-bis(trifluoromethyl)phenyl)-3-((2-(4-fluoro-2-hydroxy-5-isopropylphenyl)-5-(trifluoromethyl)cyclohex-1-enyl)methyl)-4-methyloxazolidin-2-one Compound 65 (15 mg, 60%) as colorless oil was obtained according to the same method as the synthesis of compound 63.

¹H NMR (400 MHz, CDCl₃); atropisomer mixture; δ 7.89 (s, 1H), 7.75 (d, J=9.3, 2H), 6.57-6.78 (m, 3H), 5.66-5.86 (m, 1H), 3.96-4.10 (m, 2H), 3.41-3.73 (m, 1H), 2.10-2.48 (m, 6H), 1.75 (m, 1H), 1.15-1.20 (m, 1H), 0.55-0.69 (m, 3H). MS (ESI) m/z 628 (M⁺+H).

Compound 66

(4S,5R)-5-(3,5-bis(trifluoromethyl)phenyl)-3-((2-(2-methoxy-5-morpholinophenyl)cyclohex-1-enyl)methyl)-4-methyloxazolidin-2-one Compound 50 (40.0 mg, 0.073 mmol), palladium acetate (0.8 mg, 0.0037 mmol), biphenyl ligand (2.2 mg, 0.007 mmol), sodium tert-butoxide (10.5 mg, 0.11 mmol) and morpholine (10.9 mg, 0.13 mmol) were dissolved in toluene (1.0 mL). The obtained solution was refluxed in microwave-reactor with stirring at 100° C. for 20 minutes. After the completion of the reaction, the reaction mixture was diluted with ethyl acetate, washed with water and brine, dried with anhydrous magnesium sulfate, filtered, and concentrated under reduced pressure. The residue was separated by MPLC (4 g silica, 4:1=hexane: EtOAc), thus obtaining Compound 66 (12.8 mg, 29%) as brown solid.

¹H NMR (400 MHz, CDCl₃); atropisomer mixture; δ 7.87-7.73 (m, 3H), 6.84-6.60 (m, 3H), 5.62, 5.57 (2d, 1H, J=8.0), 4.05-3.81 (m, 7H), 3.74, 3.70 (2s, 3H), 3.07-2.99 (m, 4H), 2.25-2.03 (m, 4H), 1.84-1.74 (m, 4H), 0.48, 0.34 (2s, 3H). MS(ESI): 599 (M⁺).

Compound 67

3-(2-(((4S,5R)-5-(3,5-bis(trifluoromethyl)phenyl)-4-methyl-2-oxooxazolidin-3-yl)methyl)cyclohex-1-enyl)-4-methoxy-N-methylbenzamide Compound 34 (20 mg, 0.036 mmol), methylamine (13.5 μl, 0.02 mmol) and 1-hydroxybenzotriazole (5.6 mg, 0.04 mmol) were dissolved in methylene chloride (0.5 mL). 1-Ethyl-3-(3-dimethylpropyl)carbodiimide (7.9 mg, 0.04 mmol) was added dropwise to the obtained solution at 0° C., and stirred at room temperature overnight. After the completion of the reaction, the reaction mixture was neutralized with saturated sodium hydrogen carbonate solution. The reaction mixture was extracted with methylene chloride, washed with water and brine, dried with anhydrous magnesium sulfate, filtered, and concentrated under reduced pressure. The residue was separated by MPLC (silica, 1%~3% DCM/MeOH, thus obtaining Compound 67 (3 mg, 15%) as colorless oil.

$^1$H NMR (400 MHz, CDCl$_3$); atropisomer mixture; δ 7.86 (d, 1H, J=5.0), 7.75-7.57 (m, 3H), 7.54-7.48 (m, 1H), 6.89 (dd, 1H, J=8.6, 6.5), 6.30-6.16 (m, 1H), 5.54 (m, 1H), 4.07-3.93 (m, 2H), 3.85 (d, 3H, J=16.0), 3.48-3.36 (m, 1H), 2.99 (dd, 3H, J=15.5, 4.8), 2.40-2.01 (bm, 4H), 1.84-1.75 (bm, 4H), 0.45 (t, 3H, J=6.9).

Compound 68

3-(2-(((4S,5R)-5-(3,5-bis(trifluoromethyl)phenyl)-4-methyl-2-oxooxazolidin-3-yl)methyl)cyclohex-1-enyl)-N-ethyl-4-methoxybenzamide Compound 68 (11 mg, 61%) as yellow solid was obtained according to the same method as the synthesis of compound 67.

$^1$H NMR (400 MHz, CDCl$_3$); atropisomer mixture; δ 7.86 (d, 1H, J=4.8), 7.75-7.58 (m, 3H), 7.51 (m, 1H), 6.89 (dd, 1H, J=8.5, 6.4), 6.27-6.12 (m, 1H), 5.54 (m, 1H), 4.07-4.02 (m, 2H), 3.83 (d, 3H, J=15.6), 3.52-3.37 (m, 3H), 2.17-2.05 (bm, 4H), 1.82-1.62 (bm, 4H), 1.28-1.20 (m, 2H), 0.47-0.43 (m, 3H).

Compound 69

3-(2-(((4S,5R)-5-(3,5-bis(trifluoromethyl)phenyl)-4-methyl-2-oxooxazolidin-3-yl)methyl)cyclohex-1-enyl)-4-methoxy-N-(2,2,2-trifluoroethyl)benzamide Compound 69 (23 mg, 100%) as yellow oil was obtained according to the same method as the synthesis of compound 67.

$^1$H NMR (400 MHz, CDCl$_3$); atropisomer mixture; δ 7.87 (d, 1H, J=6.8), 7.73 (d, 2H, J=18.8), 7.67 (dd, 1H, J=8.5, 2.4), 7.58 (dd, 1H, J=8.3, 2.4), 6.93 (t, 1H, J=8.8), 6.88-6.55 (m, 1H), 5.65-5.42 (m, 1H), 4.24-3.94 (m, 4H), 3.85 (d, 3H, J=18.3), 3.39 (dd, 1H, J=18.0, 15.3), 2.42-2.05 (bm, 4H), 1.83-1.76 (bm, 4H), 0.51-0.46 (m, 3H). MS (ESI) m/z 639 (M$^+$+H).

Compound 70

3-(2-(((4S,5R)-5-(3,5-bis(trifluoromethyl)phenyl)-4-methyl-2-oxooxazolidin-3-yl)methyl)cyclohex-1-enyl)-N-isopropyl-4-methoxybenzamide Compound 70 (24 mg, 100%) as yellow solid was obtained according to the same method as the synthesis of compound 67.

$^1$H NMR (400 MHz, CDCl$_3$); atropisomer mixture; δ 7.86 (d, 1H, J=4.0), 7.74 (d, 2H, J=9.4), 7.71-7.56 (m, 1H), 7.48 (m, 1H), 6.88 (m, 1H), 6.00 (m, 1H), 5.55 (m, 1H), 4.30-4.20 (m, 1H), 4.07-3.93 (m, 2H), 3.83 (d, 3H, J=15.6), 3.43 (q, 1H, J=15.0), 2.30-2.04 (bm, 4H), 1.82-1.74 (bm, 4H), 1.28-1.22 (m, 6H), 0.45 (dd, 3H, J=12.9, 6.5). MS (ESI) m/z 599 (M$^+$+H).

Compound 71

N-(3-(2-(((4S,5R)-5-(3,5-bis(trifluoromethyl)phenyl)-4-methyl-2-oxooxazolidin-3-yl)methyl)cyclohex-1-enyl)-4-methoxyphenyl)acetamide As shown in reaction scheme 5, (4S,5R)-3-((2-(5-amico-2-methoxyphenyl)cyclohex-1-enyl)methyl)-5-(3,5-bis(trifluoromethyl)phenyl)-4-oxooxazolidin-2-one (29 mg, 0.05 mmol) and diisopropylamine (0.01 mL, 0.08 mmol) were dissolved in tetrahydropuran (1 mL). Acetyl chloride (5 μl, 0.08 mmol) was added dropwise slowly to the obtained solution at room temperature, and stirred at room temperature for 2 hours. After the completion of the reaction, the reaction was quenched with saturated ammonium solution. The reaction mixture was extracted with ethyl acetate, dried with anhydrous magnesium sulfate, filtered, and concentrated under reduced pressure. The residue was separated by MPLC (12 g silica, 2:1=Hexane:EtOAc), thus obtaining Compound 71 (21 mg, 68%) as colorless oil.

$^1$H NMR (400 MHz, CDCl$_3$); 1:1 atropisomer mixture; δ 7.84 (d, J=9.8, 2H), 7.79 (s, 1H), 6.77-7.33 (m, 3H), 5.62 (d, J=7.9, 0.5H), 5.52 (d, J=8.0, 0.5H) 4.06-4.16 (m, 2H), 3.98 (t, J=15.0, 1H), 3.76 (d, J=7.8, 3H), 3.58 (d, J=14.9, 0.5H), 3.38 (d, J=14.8, 0.5H), 1.71-2.39 (m, 8H), 2.14 (d, J=15.9, 3H), 0.44 (d, J=6.5, 1.5H), 0.32 (d, J=6.4, 1.5H). MS (ESI) m/z 571 (M$^+$+H).

Compound 72

N-(3-(2-(((4S,5R)-5-(3,5-bis(trifluoromethyl)phenyl)-4-methyl-2-oxooxazolidin-3-yl)methyl)cyclohex-1-enyl)-4-methoxyphenyl)isobutyramide Compound 72 (24 mg, 79%) as colorless oil was obtained according to the same method as the synthesis of compound 71.

$^1$H NMR (400 MHz, CDCl$_3$); 1:1.1 atropisomer mixture; δ 7.84 (s, 1H), 7.78 (s, 2H), 7.58 (d, J=2.6, 0.5H), 7.25-7.27 (m, 0.5H), 7.22 (s, 0.5H), 7.13 (s, 0.5H), 7.03 (dd, J=8.6, 2.7, 0.5H), 6.80 (t, J=8.3, 1H), 5.63 (d, J=8.0, 0.44H), 5.51 (d, J=8.0, 0.54H), 4.04-4.15 (m, 2H), 3.76 (d, J=4.1, 3H), 3.54 (d, J=14.8, 0.6H), 3.41 (d, J=14.8, 0.4H), 2.44-2.53 (m, 1H), 1.71-2.34 (m, 4H), 1.15-1.30 (m, 6H), 0.44 (d, J=6.5, 1.6H), 0.36 (d, J=6.4, 1.4H). (ESI) m/z 599 (M$^+$+H).

Compound 76

(4S,5R)-5-(3,5-bis(trifluoromethyl)phenyl)-3-((2-(5-(3-cyclopropyl-1,2,4-oxadiazol-5-yl)-2-methoxyphenyl)cyclohex-1-enyl)methyl)-4-methyloxazolidin-2-one Compound 76 (14 mg, 52%) as yellow oil was obtained according to the same method as the synthesis of compound 62.

$^1$H NMR (400 MHz, CDCl$_3$); atropisomer mixture; δ 7.99-7.96 (m, 1H), 7.86 (s, 1H), 7.75-7.72 (m, 3H), 6.97 (dd, 1H, J=8.7, 11.7), 5.62 (2d, 1H, J=8.0, 8.0), 4.04-3.97 (m, 2H), 3.86 (d, 3H, J=12.3), 3.47 (2d, 1H, J=14.8, 14.9), 2.24-2.05 (m, 5H), 1.76-1.75 (m, 4H), 1.60-1.58 (m, 2H), 1.16-0.97 (m, 2H), 0.42-0.39 (m, 3H).

Compound 79

3-(2-(((4S,5R)-5-(3,5-bis(trifluoromethyl)phenyl)-4-methyl-2-oxooxazolidin-3-yl)methyl)cyclohex-1-enyl)-4-methoxybenzaldehyde As shown in reaction scheme 4, a pinacolato compound was synthesized, and then subjected to a Suzuki reaction with Compound 9, thus obtaining Compound 79 (65 mg, 35%) as colorless oil.

$^1$H NMR (400 MHz, CDCl$_3$); atropisomer mixture; δ 9.86 (s, 1H), 9.81 (s, 1H), 7.83 (s, 1H), 7.82-7.71 (m, 3H), 7.56-7.53 (dd, 1H), 7.00-6.95 (dd, 1H), 5.64-5.54 (dd, 1H), 4.00-3.92 (m, 1H), 3.87 (s, 1.5H), 3.84 (s, 1.5H), 3.52-3.49 (d, 0.5H), 3.35-3.31 (d, 0.5H), 2.20-2.19 (m, 1H), 1.80-1.72 (m, 5H), 0.40-0.37 (m, 3H). MS (ESI) m/z 406 (M⁺+H).

Compound 80

(4S,5R)-5-(3,5-bis(trifluoromethyl)phenyl)-3-((2-(5-(1-hydroxyethyl)-2-methoxyphenyl)cyclohex-1-enyl)methyl)-4-methyloxazolidin-2-one Compound 79 (65 mg, 0.117 mmol) was dissolved in tetrahydropuran (3 mL). Methylmagnesium chloride (56 μL, 0.17 mmol) was added dropwise to the obtained solution at 0° C., and stirred at room temperature for 2 hours. After the completion of the reaction, the reaction mixture was diluted with methylene chloride, washed with water and brine, dried with anhydrous magnesium sulfate, filtered, and concentrated under reduced pressure. The residue was separated by column chromatography (silica gel; Hexane/EtOAC=6:1~3:1), thus obtaining Compound 80 (88 mg, 98%) as colorless oil.

¹H NMR (400 MHz, CDCl₃); 1:1 atropisomer mixture; δ 7.83 (s, 1H), 7.73-7.69 (m, 2H), 7.21-7.17 (m, 1H), 7.07 (m, 0.5H), 7.00-6.97 (m, 0.5H), 6.85-6.78 (dd, 1H), 5.59-5.56 (m, 0.5H), 5.50-5.44 (dd, 0.5H), 4.83-4.79 (m, 1H), 4.11-3.94 (m, 2H), 3.78-3.77 (d, 1.5H), 3.72 (s, 1.5H), 3.55-3.39 (m, 1H), 2.17-2.20 (m, 4H), 1.71 (brs, 4H), 1.46-1.39 (m, 3H), 0.43-0.33 (m, 3H). MS (ESI) m/z 557 (M⁺+H).

Compound 81

(4S,5R)-3-((2-(5-acetyl-2-methoxyphenyl)cyclohex-1-enyl)methyl)-5-(3,5-bis(trifluoromethyl)phenyl)-4-methyloxazolidin-2-one Compound 80 (88 mg, 0.158 mmol) was dissolved in methylene chloride (2 mL). Dess-Martin periodinane (0.17 mg, 0.35 mmol) was added dropwise to the obtained solution at room temperature, and stirred at room temperature for 1 hour. After the completion of the reaction, the reaction mixture was diluted with ethyl acetate, washed with brine, dried with anhydrous magnesium sulfate, filtered, and concentrated under reduced pressure. The residue was separated by column chromatography (silica gel; hexane/EtOAC=5:1~3:1), thus obtaining Compound 81 (45 mg, 90%) as colorless oil.

¹H NMR (400 MHz, CDCl₃); atropisomer mixture; δ 7.84 (m, 0.5H), 7.78 (m, 0.5H), 7.75-7.72 (m, 0.5H), 7.64-7.58 (m, 1.5H), 7.43-7.41 (m, 2H), 6.42-6.39 (m, 1H), 4.83-4.17 (m, 1H), 4.17-4.02 (dd, 1H), 3.45-3.24 (m, 2H), 3.23 (s, 1.5H), 3.19 (s, 1.5H), 2.41-1.99 (m, 4H), 2.27 (s, 1.5H), 2.23 (s, 1.5H), 1.69-1.57 (m, 4H), (−)0.07-(−)0.12 (m, 3H). MS (ESI) m/z 556 (M⁺+H).

Compound 82

(4S,5R)-5-(3,5-bis(trifluoromethyl)phenyl)-3-((2-(5-(2-hydroxypropan-2-yl)-2-methoxyphenyl)cyclohex-1-enyl)methyl)-4-methyloxazolidin-2-one Compound 82 (8.2 mg, 36%) as yellow oil was obtained according to the same method as the synthesis of compound 80.

¹H NMR (400 MHz, CDCl₃); 1:1 atropisomer mixture; δ 7.62-7.61 (m, 1H), 7.40-7.29 (m, 3H), 7.291-7.18 (m, 1H), 6.53-6.49 (m, 1H), 4.74-4.69 (m, 1H), 4.28-4.19 (m, 1H), 3.56-3.33 (m, 2H), 3.30 (s, 1.5H), 3.26 (s, 1.5H), 2.54-2.10 (m, 4H), 1.74-1.65 (m, 4H), 1.42-1.37 (m, 6H), (−)0.07-(−)0.16 (m, 3H). MS (ESI) m/z 572 (M⁺+H).

Compound 83

(4S,5R)-5-(3,5-bis(trifluoromethyl)phenyl)-4-methyl-3-((2-(2-(trifluoromethoxy)phenyl)cyclohex-1-enyl)methyl)oxazolidin-2-one Compound 83 (96 mg, 95%) as colorless oil was obtained according to the same method as the synthesis of compound 18.

¹H NMR (400 MHz, CDCl₃); atropisomer mixture; δ 7.86 (s, 1H), 7.75 (s, 2H), 7.33-7.22 (m, 3H), 7.17-7.14 (m, 1H), 5.64 (dd, J=4.4, 8.0, 1H), 4.04-3.88 (m, 2H), 3.54, 3.42 (2d, J=15.0, 1H), 2.36-2.04 (m, 4H), 1.81-1.73 (m, 4H), 0.49, 0.43 (2d, J=6.5, 3H). MS (ESI) m/z 568 (M⁺+H).

Compound 84

(4S,5R)-5-(3,5-bis(trifluoromethyl)phenyl)-3-((2-(2-fluoro-5-(trifluoromethyl)phenyl)cyclohex-1-enyl)methyl)-4-methyloxazolidin-2-one Compound 84 (0.14 g, 79%) as colorless oil was obtained according to the same method as the synthesis of compound 18.

¹H NMR (400 MHz, CDCl₃); atropisomer mixture; δ 7.87 (s, 1H), 7.75 (s, 2H), 7.55-7.54 (m, 1H), 7.40-7.38 (m, 1H), 7.21-7.14 (m, 1H), 5.64 (d, J=7.9, 1H), 4.15-3.92 (m, 2H), 3.51-3.47 (m, 1H), 2.39-2.20 (m, 4H), 1.78 (bs, 4H), 0.46 (d, J=6.5, 3H). MS (ESI) m/z 570 (M⁺+H).

Compound 85

1-(3-(2-(((4S,5R)-5-(3,5-bis(trifluoromethyl)phenyl)-4-methyl-2-oxooxazolidin-3-yl)methyl)cyclohex-1-enyl)-4-methoxyphenyl)ethyl acetate Compound 80 (65.0 mg, 0.117 mmol) was dissolved in tetrahydropuran (2 mL). Methylmagnesium chloride (56 μL, 0.16 mmol) was added dropwise to the obtained solution at 0° C., and stirred at room temperature for 5 hours. After the completion of the reaction, ethyl acetate was added dropwise to the reaction mixture. And then, the reaction mixture was washed with water and brine, and concentrated under reduced pressure. The residue was separated by MPLC (15% Hexane/EtOAc), thus obtaining Compound 85 (30 mg, 70%) as white foam.

¹H NMR (400 MHz, CDCl₃); atropisomer mixture; δ 7.82 (s, 1H), 7.73 (d, J=7.3, 1H), 7.25-7.17 (m, 1H), 6.99-6.93 (m, 1H), 6.84-6.77 (m, 1H), 5.82-5.71 (m, 1H), 5.60-5.55 (m, 1H), 3.99-3.87 (m, 2H), 3.75 (s, 1.5H), 3.72 (d, J=9.4, 1.5H), 3.58-3.39 (m, 1H), 2.41-1.63 (m, 11H), 1.49-1.42 (m, 3H), 0.40-0.31 (m, 3H). MS (ESI) m/z 540.0 (M⁺+H-OAc).

Compound 86

N-(3-(2-(((4S,5R)-5-(3,5-bis(trifluoromethyl)phenyl)-4-methyl-2-oxooxazolidin-3-yl)methyl)cyclohex-1-enyl)-4-methoxyphenyl)-N-methylisobutyramide Compound 86 (5 mg, 35%) as colorless oil was obtained according to the same method as the synthesis of compound 47.

¹H NMR (400 MHz, CDCl₃); 1:1.1 atropisomer mixture; δ 7.87 (s, 1H), 7.75 (d, J=7.2, 2H), 7.06-6.84 (m, 3H), 5.65-5.60 (m, 1H), 4.06-3.89 (m, 2H), 3.80 (d, J=13.7, 3H), 3.54-3.44 (m, 1H), 3.18 (d, J=24.4, 3H), 2.50-2.42 (m, 1H), 2.27-1.75 (m, 4H), 1.03-0.83 (m, 6H), 0.48 (d, J=6.5, 1.4H), 0.39 (d, J=6.4, 1.6H). MS (ESI) m/z 613 (M⁺+H).

Compound 87

3-(2-((((4S,5R)-5-(3,5-bis(trifluoromethyl)phenyl)-4-methyl-2-oxooxazolidin-3-yl)methyl)cyclohex-1-enyl)-N-isopropyl-4-methoxy-N-methylbenzamide

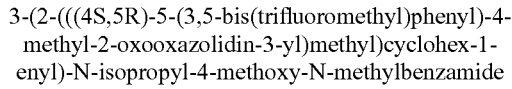

Compound 87 (11 mg, 79%) as yellow solid was obtained according to the same method as the synthesis of compound 47.

$^1$H NMR (400 MHz, CDCl$_3$); atropisomer mixture; δ 7.85 (s, 1H), 7.77 (d, J=6.7, 2H), 7.29-7.25 (m, 1H), 7.12, 7.07 (2d, J=2.0, 1H), 6.86 (dd, J=7.1, 8.4, 1H), 5.63-5.49 (m, 1H), 4.04-3.92 (m, 2H), 3.81 (d, J=9.4, 3H), 3.53, 3.41 (2d, J=15.0, 1H), 2.88-2.85 (m, 3H), 2.25-2.05 (m, 4H), 1.74 (bs, 4H), 1.20-1.15 (m, 6H), 0.44 (dd, J=6.5, 15.2, 3H). MS (ESI) m/z 613 (M$^+$+H).

Compound 96

(4S,5R)-5-(3,5-bis(trifluoromethyl)phenyl)-3-((2-(2-methoxy-5-(trifluoromethyl)phenyl)-5-methylcyclohex-1-enyl)methyl)-4-methyloxazolidin-2-one

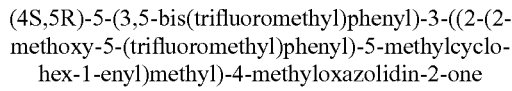

Compound 96 (57 mg, 69%) as colorless oil was obtained according to the same method as the synthesis of compound 18.

$^1$H NMR (400 MHz, CDCl$_3$); atropisomer mixture; δ 7.87 (s, 1H,), 7.75-7.73 (m, 2H), 7.52-7.49 (m, 1H), 7.25-7.23 (m, 1H), 6.96-6.90 (m, 1H), 5.67, 5.65, 5.61, 5.49 (4d, J=7.8, 7.9, 8.1, 8.2, 1H), 4.05-3.89 (m, 2H), 4.05-3.89 (m, 2H), 3.84, 3.82, 3.80 (3s, 3H), 3.55, 3.47, 3.38, 3.32 (4d, J=15.0, 14.8, 14.9, 14.9, 1H), 2.29-2.19 (m, 3H), 1.87-1.71 (m, 3H), 1.45-1.26 (m, 1H), 1.08-1.06 (m, 3H), 0.42-0.37 (m, 3H). MS (ESI) m/z 596 (M$^+$+H).

Compound 97

(4S,5R)-5-(3,5-bis(trifluoromethyl)phenyl)-3-((2-(2-methoxy-5-(trifluoromethyl)phenyl)-5,5-dimethylcyclohex-1-enyl)methyl)-4-methyloxazolidin-2-one

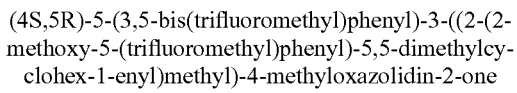

Compound 97 (77.8 mg, 75%) as colorless oil was obtained according to the same method as the synthesis of compound 18.

$^1$H NMR (400 MHz, CDCl$_3$); 1:1 atropisomer mixture; δ 7.87 (s, 1H,), 7.75, 7.73 (2s, 2H), 7.51 (dm, 1H), 7.23 (d, 1H), 6.94 (d, J=8.7, 0.5H), 6.91 (d, J=8.7, 0.5H), 5.65 (d, J=8.1, 0.5H), 5.55 (d, J=8.2, 0.5H), 3.99-3.89 (m, 2H), 3.50 (d, J=14.9, 0.5H), 3.33 (d, J=15.0, 0.5H), 3.84 (s, 1.5H), 3.81 (s, 1.5H), 2.49-2.15 (m, 2H), 1.99-1.88 (m, 2H), 1.55-1.43 (m, 2H), 1.06, 1.02 (2s, 6H$_3$), 0.40 (d, J=6.6, 1.5H), 0.37 (d, J=6.5, 1.5H). MS (ESI) m/z 610 (M$^+$+H).

Compound 101

(4S,5R)-5-(3,5-bis(trifluoromethyl)phenyl)-3-((5-tert-butyl-2-(4-fluoro-5-isopropyl-2-methoxyphenyl)cyclohex-1-enyl)methyl)-4-methyloxazolidin-2-one

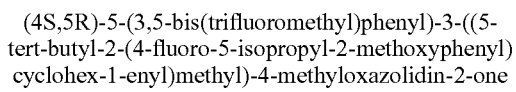

Compound 101 (0.31 g, 89%) as yellow solid was obtained according to the same method as the synthesis of compound 18.

$^1$H NMR (400 MHz, CDCl$_3$); atropisomer mixture; δ 7.90-7.73 (m, 3H), 6.81-6.75 (m, 1H), 6.58-6.49 (m, 1H), 5.65-5.55 (m, 1H), 4.14-3.91 (m, 2H), 3.74-3.69 (m, 3H), 3.65-3.40 (m, 1H), 3.20-3.10 (m, 1H), 2.58-2.12 (m, 4H), 1.91-1.87 (m, 3H), 1.22-1.18 (m, 6H), 0.95 (d, J=2.6, 9H), 0.41-0.28 (m, 3H). MS (ESI) m/z 630 (M$^+$+H).

Compound 103

(4S,5R)-5-(3,5-bis(trifluoromethyl)phenyl)-3-((2-(5-(1-hydroxyethyl)-2-methoxyphenyl)-5,5-dimethylcyclohex-1-enyl)methyl)-4-methyloxazolidin-2-one

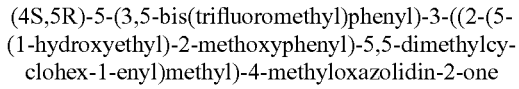

Compound 103 (65 mg, 73%) as colorless oil was obtained according to the same method as the synthesis of compound 80.

$^1$H NMR (400 MHz, CDCl$_3$); 1:1 atropisomer mixture; δ 7.84 (s, 1H), 7.71 (m, 2H), 7.21-7.06 (m, 1H), 7.05-6.98 (m, 0.5H), 6.97-6.85 (m, 0.5H), 6.83-6.78 (m, 1H), 5.59-5.30 (m, 1H), 4.85-4.78 (m, 1H), 4.04-3.92 (m, 2H), 3.78-3.72 (m, 3H), 3.55-3.49 (m, 1H), 3.41-3.33 (m, 1H), 2.43-1.90 (m, 6H), 147-1.41 (m, 6H), 1.04-1.01 (m, 3H), 0.42-0.30 (m, 3H). MS (ESI) m/z 568.0 (M-OH).

Compound 104

(4S,5R)-5-(3,5-bis(trifluoromethyl)phenyl)-3-((2-(5-(2-hydroxypropan-2-yl)-2-methoxyphenyl)-5,5-dimethylcyclohex-1-enyl)methyl)-4-methyloxazolidin-2-one

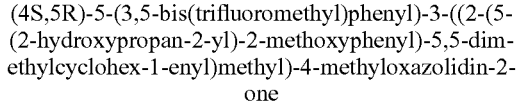

Compound 104 (6 mg, 53%) as colorless oil was obtained according to the same method as the synthesis of compound 80.

$^1$H NMR (400 MHz, CDCl$_3$); 1:1 atropisomer mixture; δ 7.84 (s, 1H), 7.71 (d, J=8.3, 2H), 7.33-7.30 (m, 1H), 7.18-7.17 (m, 0.5H), 7.078-7.072 (m, 0.5H), 6.82 (d, J=8.5, 0.5H), 6.77 (d, J=8.5, 0.5H), 5.57 (d, J=8.1, 0.5H), 5.48 (d, J=8.1, 0.5H), 4.05-3.90 (m, 2H), 3.77 (s, 1.5H), 3.72 (s, 1.5H), 3.53 (d, J=14.5, 0.5H), 3.38 (d, J=14.5, 0.5H), 2.60-1.70 (m, 6H), 1.55-1.1.51 (m,6H), 1.04-1.00 (m, 6H), 0.40 (d, J=6.6, 1.5H), 0.30 (d, J=6.6, 1.5H). MS (ESI) m/z 583 (M$^+$−OH).

Compound 107

(4S,5R)-5-(3,5-bis(trifluoromethyl)phenyl)-3-((2-(5-isopropyl-2-methoxyphenyl)-5,5-dimethylcyclohex-1-enyl)methyl)-4-methyloxazolidin-2-one

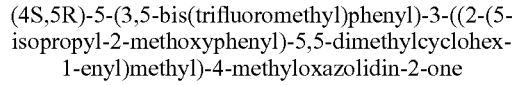

Compound 107 (34 mg, 48%) as colorless oil was obtained according to the same method as the synthesis of compound 18.

$^1$H NMR (400 MHz, CDCl$_3$); atropisomer mixture; δ 7.84 (s, 1H), 7.72 (s, 2H), 7.06 (dd, J=8.4, 2.2, 1H), 6.82-6.72 (m, 2H), 5.60-5.57 (m, 1H), 4.01-3.89 (m, 2H), 3.73, 3.70 (2s, 3H), 3.58, 3.44 (2d, J=14.6, 1H), 2.86-2.75 (m, 1H), 2.53-1.86 (m, 4H), 1.54-1.42 (m, 2H), 1.20-1.14 (m, 6H), 1.06-1.01 (m, 6H), 0.38, 0.28 (2d, J=6.5, 3H). MS (ESI) m/z 584 (M$^+$+H).

Compound 108

(4S,5R)-5-(3,5-bis(trifluoromethyl)phenyl)-3-((2-(5-isopropyl-2-methoxyphenyl)-5-(trifluoromethyl)cyclohex-1-enyl)methyl)-4-methyloxazolidin-2-one

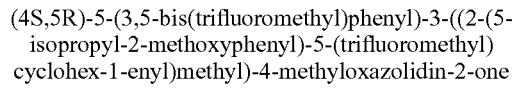

Compound 108 (80 mg, 55%) as yellow oil was obtained according to the same method as the synthesis of compound 18.

$^1$H NMR (400 MHz, CDCl$_3$); 1:1 atropisomer mixture; δ 7.63 (m, 1H), 7.43-7.32 (m, 2H), 7.04-6.95 (m, 1H), 6.85-6.78 (m, 1H), 6.57-6.45 (m, 1H), 4.77-4.72 (m, 1H), 4.24-4.15 (m, 0.5H), 4.03-3.93 (m, 0.5H), 3.68-3.62 (m, 0.5H), 3.51-3.43 (m, 1.5H), 3.35-3.28 (m, 1.5H), 3.27-3.19 (m, 1.5H), 2.84-2.63 (m, 1H), 2.54-2.38 (m, 2H), 2.33-2.10 (m, 2H), 1.99-1.65 (m, 2H), 1.53-1.39 (m, 1H), 1.24-1.11 (m, 6H), (−)0.01-(−)0.27 (m, 3H). MS (ESI) m/z 625 (M$^+$+H).

Compound 109

(4S,5R)-5-(3,5-bis(trifluoromethyl)phenyl)-3-((2-(4-fluoro-5-isopropyl-2-methoxyphenyl)-4,4-dimethyl-cyclohex-1-enyl)methyl)-4-methyloxazolidin-2-one Compound 109 (87 mg, 93%) as white solid foam was obtained according to the same method as the synthesis of compound 18.

$^1$H NMR (400 MHz, CDCl$_3$); atropisomer mixture; δ 7.85 (s, 1H), 7.72 (s, 2H), 6.76 (dd, J=8.7, 3.6, 1H), 6.54, 6.50 (2d, J=12.2, 1H), 5.61 (d, J=8.1, 1H), 3.98-3.87 (m, 2H), 3.70 (d, J=11.7, 3H), 3.55, 3.46 (2d, J=14.7, 1H), 3.15-3.07 (m, 1H), 2.21-2.11 (m, 2H), 1.95-1.81 (m, 2H), 1.53-1.46 (m, 2H), 1.20-1.12 (m, 6H), 1.00-0.86 (m, 6H), 0.42, 0.35 (2d, J=6.5, 3H). MS (ESI) m/z 602 (M$^+$+H).

Compound 110

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)acetamide As shown in reaction scheme 5, intermediate 17 was synthesized. Intermediate 17 (48.0 mg, 0.078 mmol) and diisopropylamine (30.0 μl, 0.17 mmol) were dissolved in methylene chloride (1.5 mL). Acetyl chloride (12.3 μl, 0.17 mmol) was added dropwise slowly to the obtained solution at room temperature, and stirred at room temperature for 2 hours. After the completion of the reaction, the reaction was quenched with saturated ammonium solution. The reaction mixture was extracted with ethyl acetate, dried with anhydrous magnesium sulfate, filtered, and concentrated under reduced pressure. The residue was separated by MPLC (4 g silica, 4:1=hexane/EtOAc), thus obtaining Compound 110 (21.6 mg, 42%) as white solid foam.

$^1$H NMR (400 MHz, CDCl$_3$); 1:1 atropisomer mixture; δ 7.85, 7.84 (2s, 1H), 7.82, 7.77 (2s, 2H), 7.49 (d, J=2.7, 0.5H), 7.35 (dd, J=8.8, 2.7, 0.5H), 7.13 (d, J=2.7, 0.5H), 7.12, 7.06 (2brs, 1H), 7.02 (dd, J=8.8, 2.7, 1H), 6.82-6.78 (m, 1H), 5.61, 5.52 (2d, J=8.0, 1H), 4.14-3.92 (m, 2H), 3.76, 3.74 (2s, 3H), 3.57, 3.39 (2d, J=14.8, 1H), 2.49-2.21 (m, 2H), 2.16-2.12 (2s, 3H$_3$), 1.96-1.92 (br m, 2H), 1.54-1.41 (m, 2H), 1.04, 1.03, 1.02, 1.00 (4s, 0.41, 0.40, 0.35, 0.33 (4s, 3H, CH$_3$, 6H). MS (ESI) m/z 600 (M$^+$+H).

Compound 111

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)isobutyramide Compound 111 (38.8 mg, 72%) as yellow solid foam was obtained according to the same method as the synthesis of compound 110.

$^1$H NMR (400 MHz, CDCl$_3$); 1:1 atropisomer mixture; δ 7.85 (s, 1H), 7.79, 7.77 (2s, 2H), 7.56 (d, J=2.7, 0.5H), 7.32 (dd, J=8.8, 2.7, 0.5H), 7.22 (d, J=2.7, 0.5H), 7.08 (brs, 0.5H), 7.04 (dd, J=8.8, 2.7, 0.5H), 7.02 (brs, 0.5H), 6.82-6.78 (m, 1H), 5.62, 5.51 (2s, 3H), 3.54, 3.41 (2d, J=14.8, 1H), 2.52-2.08 (m, 3H), 1.94-1.92 (br m, 2H), 1.54-1.41 (m, 2H), 1.24-1.18 (m, 6H), 1.04, 1.03, 1.02, 1.00 (4s, 6H), 0.41, 0.40, 0.38, 0.37 (4s, 3H). MS (ESI) m/z 627 (M$^+$+H).

Compound 112

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-methylacetamide Compound 110 (18 mg, 0.03 mmol) was dissolved in anhydrous tetrahydropuran (1 mL). Sodium hydride (4 mg, 0.09 mmol) was added dropwise to the obtained solution at 0° C., and stirred at room temperature for 30 minutes. Iodomethane (9.4 μl, 0.15 mmol) was added dropwise slowly to the reaction mixture at 0° C., and then stirred at room temperature for 3 hours. After the completion of the reaction, the reaction mixture was diluted with ethyl acetate, washed with brine, dried with anhydrous magnesium sulfate, filtered, and concentrated under reduced pressure. The residue was separated by column chromatography, thus obtaining Compound 112 (14 mg, 76%) as white solid foam.

$^1$H NMR (400 MHz, CDCl$_3$); atropisomer mixture; δ 7.88 (s, 1H), 7.74 (s, 2H), 7.08-7.05 (m, 1H), 6.90-6.82 (m, 2H), 5.64 (d, J=7.9, 1H), 4.05-3.91 (m, 2H), 3.81, 3.78 (2s, 3H), 3.53, 3.43 (2d, J=14.8, 1H), 3.23, 3.17 (2s, 3H), 2.54-2.19 (m, 2H), 1.85, 1.82 (2s, 3H), 1.57-1.43 (m, 2H), 1.07, 1.05, 1.03, 1.02 (4s, 6H), 0.48, 0.46, 0.36, 0.35 (4s, 3H). MS (ESI) m/z 613 (M$^+$+H).

Compound 113

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-methylisobutyramide Compound 113 (28 mg, 86%) as yellow foam was obtained according to the same method as the synthesis of compound 112.

$^1$H NMR (400 MHz, CDCl$_3$); atropisomer mixture; δ 7.88 (s, 1H), 7.75 (s, 2H), 7.07 (m, 1H), 6.90-6.82 (m, 2H), 5.63 (d, J=8.1, 1H), 4.06-3.92 (m, 2H), 3.81, 3.78 (2s, 3H), 3.53, 3.43 (2d, J=14.8, 1H), 3.21, 3.15 (2s, 3H), 2.52-2.15 (m, 3H), 1.99-1.87 (m, 2H), 1.56-1.40 (m, 2H), 1.06-0.94 (m, 12H), 0.47, 0.45, 0.37, 0.35 (4s, 3H). MS (ESI) m/z 641 (M$^+$+H).

Compound 114

(4S,5R)-5-(3,5-bis(trifluoromethyl)phenyl)-3-((2-(2-(methoxymethyl)-4-(trifluoromethyl)phenyl)-5,5-dimethylcyclohex-1-enyl)methyl)-4-methyloxazolidin-2-one Compound 9 was subjected to a Suzuki reaction with 6-(trifluoromethyl)benzo[c][1,2]oxaborol-1(3H)-ol, and then, the obtained intermediate compound was used as the same method as the synthesis of Compound 47, to obtain Compound 114 (60 mg, 74%) as white solid.

$^1$H NMR (400 MHz, CDCl$_3$); atropisomer mixture; δ 7.86 (s, 1H), 7.73 (s, 3H), 7.55-7.47 (m, 1H), 7.13 (d, J=7.8, 1H), 5.64, 5.57 (2d, J=8.1, 1H), 4.36-4.26 (m, 2H), 4.01-3.81 (m, 2H), 3.71-3.21 (m, 1H), 3.43 (d, J=4.1, 3H), 2.23-2.18 (m, 2H), 1.99-1.90 (m, 2H), 1.55-1.46 (m, 2H), 1.07-0.87 (m, 6H), 0.55, 0.38 (2d, J=6.5, 3H). MS (ESI) m/z 624 (M$^+$+H).

Compound 115

(4S,5R)-5-(3,5-bis(trifluoromethyl)phenyl)-3-((2-(5-tert-butyl-2-methoxyphenyl)-5,5-dimethylcyclohex-1-enyl)methyl)-4-methyloxazolidin-2-one Compound 115 (9 mg, 39%) as a gray solid was obtained according to the same method as the synthesis of compound 18.

¹H NMR (400 MHz, CDCl₃); atropisomer mixture; δ 7.84 (s, 1H), 7.71 (s, 2H), 7.22-7.19 (m, 1H), 6.95 (dd, J=12.6, 2.5, 1H), 6.80-6.72 (m, 1H), 5.60-5.54 (m, 1H), 4.00-3.86 (m, 2H), 3.73 (d, J=9.9, 3H), 3.57, 3.43 (2d, J=14.7, 1H), 2.55-2.04 (m, 2H), 1.93-1.91 (m, 2H), 1.52-1.42 (m, 2H), 1.28-1.23 (m, 9H), 1.04-1.00 (m, 6H), 0.36, 0.26 (2d, J=6.5, 3H). MS (ESI) m/z 598 (M⁺+H).

Compound 116

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)-N-(2,2,2)acetamide 3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzaldehyde (32 mg, 0.06 mmol), which is a starting material, and 2,2,2-trifluoroethane amine (5.4 µl, 0.067 mmol) were dissolved in methylene chloride (2 mL). The obtained solution was stirred at room temperature overnight. Sodium cyanoborohydride (4 mg, 0.056 mmol) and acetic acid (3.2 µl, 0.06 mmol) were added dropwise to the solution, and stirred at room temperature for 1 hour. After the completion of the reaction, the reaction mixture was neutralized with saturated sodium hydrogen carbonate solution, extracted with methylene chloride, washed with water and brine, dried with anhydrous magnesium sulfate, filtered, and concentrated under reduced pressure. The obtained intermediate compound (39 mg, 0.06 mmol) was dissolved in methylene chloride (2 mL). Diisopropylethylamine (26 µl, 0.15 mmol) and acetyl chloride (4.6 µl, 0.06 mmol) were added dropwise carefully to the obtained solution, and stirred at room temperature for 2 hours. The reaction was quenched with water. The reaction mixture was extracted with methylene chloride, washed with brine, dried with anhydrous magnesium sulfate, filtered, and concentrated under reduced pressure. The residue was separated by MPLC (silica, 20~50% Hexane/EtOAc), thus obtaining Compound 116 (25 mg, 61%) as colorless oil.

¹H NMR (400 MHz, CDCl₃); atropisomer mixture; δ 7.85 (s, 1H), 7.72 (d, J=12.2, 2H), 7.08-6.98 (m, 1H), 6.88-6.75 (m, 2H), 5.62-5.54 (m, 1H), 4.67-4.53 (m, 2H), 4.03-3.90 (m, 4H), 3.78-3.69 (m, 3H), 3.50-3.31 (m, 1H), 2.21-2.15 (m, 2H), 2.04 (s, 3H), 1.92-1.88 (m, 2H), 1.52-1.45 (m, 2H), 1.05-1.00 (m, 6H), 0.43, 0.34 (dt, J=5.9, 6.5, 3H). MS (ESI) m/z 695 (M⁺+H).

Compound 117

(4S,5R)-5-(3,5-bis(trifluoromethyl)phenyl)-3-((2-(2-methoxy-5-(trifluoromethoxy)phenyl)-5,5-dimethylcyclohex-1-enyl)methyl)-4-methyloxazolidin-2-one Compound 117 (27.8 mg, 67%) as colorless oil was obtained according to the same method as the synthesis of compound 18.

¹H NMR (400 MHz, CDCl₃); atropisomer mixture; δ 7.87 (s, 1H), 7.74 (s, 2H), 7.11-7.08 (m, 1H), 6.89-6.81 (m, 2H), 4.01-3.89 (m, 2H), 3.79, 3.77 (2s, 3H), 3.56, 3.39 (2d, J=14.8, 1H), 2.50-2.04 (m, 2H), 1.99-1.89 (m, 2H), 1.54-1.45 (m, 2H), 1.05, 1.05, 1.02, 1.019 (4s, 6H), 0.40, 0.39, 0.37, 0.35 (4s, 3H). MS (ESI) m/z 626 (M⁺+H).

Compound 118

N-acetyl-N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)acetamide Compound 118 (0.15 g, 79%) as yellow solid was obtained according to the same method as the synthesis of compound 71.

MS (ESI) m/z 641 (M⁺+H).

Compound 120

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2,2-trifluoro-N-methylacetamide As shown in reaction scheme 5, intermediate 17 was synthesized. Intermediate 17 (0.16 g, 0.29 mmol), a starting material, was reacted with di-tert-butyl carboxylate. The obtained intermediate compound was subjected to methylation, and then subjected to deprotection using hydrogen chloride, thus obtaining (4S,5R)-5-(bis(trifluoromethyl)phenyl)-3-((2-(2-methoxy-5-(methylamino)phenyl)-5,5-dimethylcyclohex-1-enyl)methyl)-4-methyloxooxazolidin-2-one. The obtained compound (40 mg, 0.07 mmol), a starting material, was dissolved in methylene chloride (1.5 mL). Trifluoroacetic anhydride (TFAA) (20 µl, 0.14 mmol) was added dropwise to the obtained solution at room temperature diisopropylamine (37 µl, 0.21 mmol), and stirred at room temperature for 2 hours. After the completion of the reaction, the reaction was quenched with water. The reaction mixture was extracted with ethyl acetate, washed with brine, dried with anhydrous magnesium sulfate, filtered, and concentrated under reduced pressure. The residue was separated by Prep TLC (silica, 25% hexane/EtOAc), thus obtaining Compound 120 (37 mg, 80%) as yellow oil.

¹H NMR (400 MHz, CDCl₃); atropisomer mixture; δ 7.85 (s, 1H), 7.72 (s, 2H), 7.12-7.09 (m, 1H), 6.89-6.83 (m, 2H), 5.61 (d, J=8.0, 1H), 4.01-3.84 (m, 2H), 3.81, 3.78 (2s, 3H), 3.54-3.42 (m, 1H), 3.32 (s, 1.8H), 3.27 (s, 1.2H), 2.50-1.90 (m, 4H), 1.53-1.42 (m, 2H), 1.38, 1.29 (2d, J=6.5, 3H), 1.04-0.99 (m, 6H).

Compound 121

(4S,5R)-5-(3,5-bis(trifluoromethyl)phenyl)-3-((2-(2-methoxy-5-(2-oxopyrrolidin-1-yl)phenyl)-5,5-dimethylcyclohex-1-enyl)methyl)-4-methyloxazolidin-2-one As shown in reaction scheme 4, 3-iodo-4-methoxyaniline, a starting material, was subjected to acylation using acyl chloride and then reacted with sodium methoxide, a base, to synthesize a compound forming a ring. The obtained compound was reacted with bis(pinacolato)diborane to synthesize a pinacolato intermediate compound. The obtained pinacolato compound (0.05 g, 0.16 mmol) was subjected to a Suzuki reaction with Compound 9 (0.09 g, 0.138 mmol), thus obtaining Compound 121 (29 mg, 30%) as brown oil.

¹H NMR (400 MHz, CDCl₃); atropisomer mixture; δ 7.84 (d, J=7.4, 2H), 7.77 (m, 1H), 7.09-7.60 (m, 2H), 6.84 (t, J=1.0, 1H), 5.62 (d, J=7.9, 0.5H), 5.52 (d, J=8.0, 0.5H) 3.70-4.12 (m, 4H), 3.80-3.82 (m, 3H), 2.12-2.60 (m, 6H), 2.05-2.11 (m, 2H), 1.45-2.11 (m, 2H), 1.01-1.04 (m, 6H), 0.31-0.42 (m, 3H). MS (ESI) m/z 626 (M⁺+H).

Compound 122

(4S,5R)-5-(3,5-bis(trifluoromethyl)phenyl)-3-((2-(2-methoxy-5-(2-oxopiperidin-1-yl)phenyl)-5,5-dimethylcyclohex-1-enyl)methyl)-4-methyloxazolidin-2-one Compound 122 (18 mg, 21%) as brown oil was obtained according to the same method as the synthesis of compound 121.

¹H NMR (400 MHz, CDCl₃); atropisomer mixture; δ 7.83 (s, 1H), 7.81 (s, 2H), 6.82-7.17 (m, 3H), 5.58 (d, J=8.0, 0.5H), 5.47 (d, J=7.9, 0.5H), 3.95-4.02 (m, 2H), 3.78 (d, J=4.6, 3H), 3.44-3.75 (m, 3H), 2.50-2.55 (m, 2H), 2.05-2.15 (m, 2H), 1.91-1.96 (m, 6H), 1.43-1.49 (m, 2H), 0.99-1.03 (m, 6H), 0.37-0.42 (m, 3H). MS (ESI) m/z 640 (M⁺+H).

Compound 123

(4S,5R)-5-(3,5-bis(trifluoromethyl)phenyl)-3-((5,5-difluoro-2-(4-fluoro-5-isopropyl-2-methoxyphenyl)cyclohex-1-enyl)methyl)-4-methyloxazolidin-2-one Compound 123 (45 mg, 58%) as white solid was obtained according to the same method as the synthesis of compound 18.

¹H NMR (400 MHz, CDCl₃); 1:1 atropisomer mixture; δ 7.85 (s, 1H), 7.72 (s, 2H), 6.81-6.77 (m, 1H), 6.59-6.51 (m, 1H), 5.65-5.62 (m, 1H), 3.99-3.86 (m, 3H), 3.73 (s, 1.5H), 3.70 (s, 1.5H), 3.57 (d, J=14.8, 1H), 3.46 (d, J=14.8, 1H), 3.15-3.09 (m, 1H), 2.70-2.47 (m, 6H), 1.32-1.13 (m, 6H), 0.40 (d, J=6.5, 1.5H), 0.33 (d, J=6.5, 1.5H).

Compound 124 methyl 3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl(methyl)carbamate Compound 124 (18 mg, 55%) as yellow oil was obtained according to the same method as the synthesis of compound 120.

¹H NMR (400 MHz, CDCl₃); atropisomer mixture; δ 7.84 (s, 1H), 7.75 (s, 2H), 7.07-7.03 (m, 1H), 7.00-6.83 (m, 1H), 6.84-6.77 (m, 1H), 5.60-5.51 (m, 1H), 4.00-3.90 (m, 2H), 3.76 (d, J=5.4, 3H), 3.68-3.57 (m, 3H), 3.55-3.42 (m, 1H), 3.34, 3.25 (2s, 3H), 2.40-2.04 (m, 2H), 1.92-1.88 (m, 2H), 1.52-1.41 (m, 2H), 1.03-1.00 (m, 6H), 0.41, 0.36 (2d, J=6.0, 3H).

Compound 128

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-methylmethanesulfonamide Compound 128 (30 mg, 59%) as colorless oil was obtained according to the same method as the synthesis of compound 112.

¹H NMR (400 MHz, CDCl₃); atropisomer mixture; δ 7.86 (d, J=3.8, 1H), 7.76 (d, J=10.2, 2H), 7.02-7.24 (m, 2H), 6.83-6.88 (m, 1H), 5.58 (t, J=9.6, 1H), 3.92-4.02 (m, 2H), 3.82 (d, J=1.0, 3H), 3.38-3.57 (m, 1H), 3.28 (d, J=13.8, 3H), 2.81 (d, J=28.0, 3H), 2.10-2.47 (m, 2H), 1.94-2.02 (m, 2H), 1.44-1.51 (m, 2H), 1.02-1.06 (m, 6H), 1.36-1.48 (m, 3H). MS (ESI) m/z 650 (M⁺+H).

Compound 130

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3,3,3-trifluoro-N-methylpropanamide Compound 130 (17 mg, 43%) as yellow oil was obtained according to the same method as the synthesis of compound 120.

¹H NMR (400 MHz, CDCl₃); atropisomer mixture; δ 7.86 (s, 1H), 7.72 (d, J=5.0, 2H), 7.07-7.03 (m, 1H), 6.92-6.83 (m, 2H), 5.61 (t, J=8.0, 1H), 4.05-3.91 (m, 2H), 3.82, 3.78 (2s, 3H), 3.51-3.35 (m, 1H), 3.26, 3.19 (2s, 3H), 2.98-2.88 (m, 2H), 2.48-1.97 (m, 2H), 1.93-1.86 (m, 2H), 1.55-1.44 (m, 2H), 1.03-0.97 (m, 6H), 0.47, 0.39 (2d, J=6.0, 3H). MS (ESI) m/z 681, 682 (M⁺+1, M⁺+2).

Compound 132

(4S,5R)-5-(3,5-bis(trifluoromethyl)phenyl)-3-((2-(4-fluoro-2-methoxy-5-(1,1,1-trifluoropropan-2-yl)phenyl)-5,5-dimethylcyclohex-1-enyl)methyl)-4-methyloxazolidin-2-one 2-Fluoro-4-methoxyacetophenone, a starting material, was subjected to several synthesis processes to obtain a pinacolato compound. The obtained pinacolato compound was subjected to a Suzuki reaction with Compound 2, thus synthesizing an aldehyde compound. The obtained aldehyde compound was reacted with Compound 4 to synthesize an amino alcohol compound, as an intermediate compound. The obtained amino alcohol compound was reacted with triphosgene, thus obtaining Compound 132 (24 mg, 68%) as colorless oil.

¹H NMR (400 MHz, CDCl₃); atropisomer mixture; δ 7.86 (s, 1H), 7.73 (s, 2H), 6.94-6.96 (m, 1H), 6.57-6.64 (m, 2H), 5.53-5.62 (m, 1H), 3.80-3.99 (m, 2H), 3.77-3.78 (m, 3H), 3.75-3.80 (m, 1H), 1.20-2.50 (m, 6H), 1.45-1.52 (m, 3H), 1.00-1.05 (m, 6H), 0.30-0.43 (m, 3H). MS (ESI) m/z 657 (M⁺+H).

Compound 133

Methyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)acetate As shown in reaction scheme 4, pinacolato compound was synthesized. The obtained pinacolato compound (0.1 g, 0.33 mmol), Compound 9 (0.17 g, 0.167 mmol), palladium catalyst (10 mg, 0.02 mmol) and sodium carbonate (70 mg, 0.65 mmol) were dissolved in dimethoxyethane/water (5 mL). The obtained solution was refluxed with stirring in microvessel at 120° C. for 15 minutes. After the completion of the reaction, the reaction was quenched with saturated ammonium chloride solution. The reaction product was extracted with ethyl acetate, washed with brine, dried with anhydrous magnesium sulfate, filtered, and concentrated under reduced pressure. The residue was separated by MPLC (12 g silica, 1:1=Hexane/EtOAc), thus obtaining Compound 133 (91 mg, 45%) as brown oil.

¹H NMR (400 MHz, CDCl₃); 1:1 atropisomer mixture; δ 7.85 (s, 1H), 7.76 (d, J=7.0, 2H), 7.09-7.13 (m, 1H), 6.76-6.93 (m, 2H), 5.61 (d, J=8.1, 0.5H), 5.55 (d, J=8.0, 0.5H), 3.90-4.03 (m, 2H), 3.75 (d, J=7.3, 3H), 3.64 (d, J=38.0, 3H), 3.41-3.68 (m, 2H), 3.41-3.68 (m, 1H), 2.04-2.53 (m, 2H), 1.89-1.98 (m, 2H), 1.42-1.54 (m, 2H), 1.01-1.04 (m, 6H), 0.33-0.37 (m, 3H). MS (ESI) m/z 615 (M⁺+H).

Compound 134

2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)acetic acid Compound 133 (0.08 g, 0.13 mmol) was dissolved in dioxan/water (5 mL V/V 2:1). Lithium hydroxide (0.06 g, 1.32 mmol) was added dropwise to the obtained solution at room temperature, and stirred at room temperature for 6 hours. After the completion of the reaction, the reaction was quenched with saturated ammonium solution. The reaction mixture was extracted with ethyl acetate, washed with brine, dried with anhydrous magnesium sulfate, filtered, and concentrated under reduced pressure. The residue was separated by MPLC (12 g silica, 1:1=Hexane/EtOAc), thus obtaining Compound 134 (60 mg, 76%) as brown oil.

$^1$H NMR (400 MHz, CDCl$_3$); 1:1.3 atropisomer mixture; δ 7.85 (s, 1H), 7.74 (d, J=5.4, 2H), 7.09-7.13 (m, 1H), 6.77-6.91 (m, 2H), 5.58 (t, J=7.7, 1H), 3.92-4.02 (m, 2H), 3.70-3.76 (m, 3H), 3.41-3.60 (m, 2H), 3.41-3.60 (m, 1H), 2.17-2.50 (m, 2H), 1.88-1.97 (m, 2H), 1.41-1.54 (m, 2H), 1.04-1.07 (m, 6H), 0.41 (d, J=6.5, 1.3H), 0.33 (d, J=6.5, 1.7H). MS (ESI) m/z 601 (M$^+$+H).

Compound 136

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)cyclopropanesulfonamide Compound 136

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)cyclopropanesulfonamide Compound 136 (37 mg, 63%) as yellow solid was obtained according to the same method as the synthesis of compound 110.

$^1$H NMR (400 MHz, CDCl$_3$); atropisomer mixture; δ 7.84 (s, 1H), 7.74 (d, J=6.4, 2H), 7.16, 7.08 (2dd, J=8.7, 2.7, 1H), 7.04, 6.94 (2d, J=2.7, 1H), 6.83-6.78 (m, 1H), 6.35-6.28 (m, 1H), 5.59 (dd, J=4.5, 8.0, 1H), 4.04-3.92 (m, 2H), 3.76, 3.74 (2s, 3H), 3.54, 3.39 (2d, J=14.0, 1H), 2.46-2.01 (m, 3H), 1.92 (bs, 2H), 1.53-1.43 (m, 2H), 1.12-1.06 (m, 2H), 1.06-1.03 (m, 6H), 1.02-0.82 (m, 2H), 0.43, 0.38 (2d, J=6.5, 3H).

Compound 137

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)trifluoromethanesulfonamide Compound 137 (43 mg, 98%) as white solid was obtained according to the same method as the synthesis of compound 110.

$^1$H NMR (400 MHz, CDCl$_3$); atropisomer mixture; δ 7.85 (s, 1H), 7.72 (d, J=4.9, 2H), 7.29-7.25 (m, 1H), 7.21-6.99 (m, 1H), 6.96-6.81 (m, 1H), 5.63-5.51 (m, 1H), 3.98-3.87 (m, 2H), 3.84 (d, J=5.2, 2H), 3.77 (d, J=8.3, 1H), 3.56, 3.37 (2d, J=15.0, 1H), 2.46-1.99 (m, 2H), 1.95-1.91 (m, 2H), 1.55-1.40 (m, 2H), 1.04-0.95 (m, 6H), 0.37-0.33 (m, 3H). MS (ESI) m/z 689 (M$^+$+H).

Compound 138

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-methylcyclopropanesulfonamide Compound 138 (21 mg, 66%) as yellow solid was obtained according to the same method as the synthesis of compound 112.

$^1$H NMR (400 MHz, CDCl$_3$); atropisomer mixture; δ 7.84 (s, 1H), 7.75 (d, J=4.6, 2H), 7.27-7.20 (m, 1H), 7.10, 7.04 (2d, J=2.7, 1H), 6.83 (dd, J=12.1, 8.8, 1H), 5.57 (dd, J=14.9, 8.0, 1H), 4.01-3.91 (m, 2H), 3.77 (d, J=7.1, 3H), 3.56, 3.41 (2d, J=14.6, 1H), 3.30, 3.25 (2s, 3H), 2.47-2.22 (m, 3H), 1.92 (bm, 2H), 1.51-1.44 (m, 2H), 1.11-0.84 (m, 4H), 1.02-1.00 (m, 6H), 0.39 (dd, J=6.5, 2.4, 3H). MS (ESI) m/z 675 (M$^+$+H).

Compound 140

1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3-methylthiourea As shown in reaction scheme 5, intermediate 17 was synthesized. Intermediate 17 (30 mg, 0.049 mmol) was dissolved in ethanol. Isothiocyanato methane (an excess amount) was added dropwise to the obtained solution, and then refluxed with stirring. After the completion of the reaction, the reaction mixture was extracted with ethyl acetate, washed with brine, dried with anhydrous magnesium sulfate, filtered, and concentrated under reduced pressure. The residue was separated by MPLC (12 g silica, 15%~35%=hexane/EtOAc), thus obtaining Compound 140 (20 mg, 59%) as white solid.

$^1$H NMR (400 MHz, CDCl$_3$); 1:2 atropisomer mixture; δ 7.86 (s, 1H), 7.75 (s, 1H), 7.72 (s, 1H), 7.08-6.96 (m, 1H), 6.92-6.87 (m, 2H), 5.63 (m, 0.5H), 5.42-5.40 (m, 0.5H), 4.32-4.29 (m, 0.5H), 4.18-4.10 (m, 1H), 3.96-3.92 (m, 0.5H), 3.87 (s, 2H), 3.76 (s, 1H), 3.18-3.10 (m, 3H), 2.45-2.39 (m, 1H), 2.2.08-1.87 (m, 2H), 1.80-1.71 (m, 3H), 1.03-1.00 (m, 6H), 0.62-0.60 (d, J=6.4, 2H), 0.52-0.51 (d, J=6.4, 1H). MS(ESI) 630 (M+H)$^+$.

Compound 141

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)trifluoro-N-methylmethanesulfonamide Compound 141 (23 mg, 62%) as colorless oil was obtained according to the same method as the synthesis of compound 112.

$^1$H NMR (400 MHz, CDCl$_3$); atropisomer mixture; δ 7.84 (s, 1H), 7.73 (d, J=4.1, 2H), 7.24-7.17 (m, 1H), 7.03, 6.99 (2d, J=2.7, 1H), 6.86 (dd, J=13.4, 8.8, 1H), 5.58, 5.52 (2d, J=8.0, 1H), 3.97-3.81 (m, 2H), 3.79 (d, J=7.0, 3H), 3.56 (d, J=15.0, 0.5H), 3.42 (d, J=15.3, 3H), 3.36 (d, J=14.9, 0.5H), 2.46-2.04 (m, 2H), 1.99-1.94 (m, 2H), 1.55-1.42 (m, 2H), 1.02 (d, J=11.6, 6H), 0.37, 0.32 (2d, J=6.5, 3H). MS (ESI) m/z 703 (M$^+$+H).

Compound 142

(4S,5R)-5-(3,5-bis(trifluoromethyl)phenyl)-3-((2-(2-methoxy-5-(2-oxoimidazolidin-1-yl)phenyl)-5,5-dimethylcyclohex-1-enyl)methyl)-4-methyloxazolidin-2-one As shown in reaction scheme 5, intermediate 17 was synthesized. Intermediate 17 (50 mg, 0.081 mmol) was reacted with 2-bromoethane amine (20 mg, 0.10 mmol) to synthesize an intermediate compound. The obtained intermediate compound (0.1 g, 0.167 mmol), diisopropylethylamine (43 μL, 0.25 mmol) and triphosgene (25 mg, 0.08 mmol) were dissolved in methylene chloride (3 mL). The obtained solution was stirred at room temperature. After the completion of the reaction, the reaction was quenched with saturated ammonium solution. The reaction mixture was extracted with ethyl acetate, washed with brine, dried with anhydrous magnesium sulfate, filtered, and concentrated under reduced pressure. The residue was separated by MPLC (12 g silica, 10%~20%=hexane/EtOAc), thus obtaining Compound 142 (61.6 mg, 59%) as white solid.

$^1$H NMR (400 MHz, CDCl$_3$); atropisomer mixture; δ 7.83 (s, 1H), 7.73 (s, 2H), 7.54-7.53 (m, 0.5H), 7.32-7.25 (m, 0.5H), 7.10-7.07 (m, 0.5H), 6.88-6.83 (m, 1H), 5.59-5.51 (dd, J=8.2, 23.7, 1H), 5.50-5.48 (d, J=7.9, 0.5H), 4.09-3.86 (m, 2H), 3.74-3.67 (m, 3H), 3.57-3.53 (d, J=14.7, 0.5H), 3.41-3.37 (d, J=4.7, 0.5H), 2.45-2.41 (m, 0.5H), 2.24-2.22 (m, 1H), 2.17-2.13 (m, 0.5H), 1.93-1.91 (m, 3H), 1.61 (brs, 2H), 1.51-1.41 (m, 3H), 1.02-1.00 (m, 6H), 0.39-0.35 (m, 3H). MS (ESI) m/z 626 (M$^+$+H).

Compound 143

(4S,5R)-5-(3,5-bis(trifluoromethyl)phenyl)-3-((2-(2-methoxy-5-(2-oxooxazolidin-3-yl)phenyl)-5,5-dimethylcyclohex-1-enyl)methyl)-4-methyloxazolidin-2-one Compound 143 (10 mg, 32%) as white solid was obtained according to the same method as the synthesis of compound 142.

$^1$H NMR (400 MHz, CDCl$_3$); 1:1 atropisomer mixture; δ 7.83 (s, 1H), 7.77-7.72 (m, 2H), 7.29 (m, 0.5H), 7.17-7.16 (m, 0.5H), 7.14-7.07 (m, 0.5H), 6.97-6.94 (0.5H), 6.80-6.75 (m, 1H), 6.49-6.44 (m, 1H), 5.61-5.59 (d, J=7.9, 0.5H), 5.50-5.48 (d, J=7.9, 0.5H), 4.09-3.86 (m, 2H), 3.74-3.67 (m, 3H), 3.57-3.53 (d, J=14.7, 0.5H), 3.41-3.37 (d, J=14.7, 0.5H), 2.45-2.41 (m, 0.5H), 2.24-2.22 (m, 1H), 2.17-2.13 (m, 0.5H), 1.93-1.91 (m, 3H), 1.61 (brs, 2H), 1.51-1.41 (m, 3H), 1.02-1.00 (m, 6H), 0.39-0.35 (m, 3H). MS (ESI) m/z 627 (M$^+$+H).

Compound 144

(4S,5R)-3-((2-(2-amino-5-isopropylphenyl)-5,5-dimethylcyclohex-1-enyl)methyl)-5-(3,5-bis(trifluoromethyl)phenyl)-4-methyloxazolidin-2-one Compound 144 (54 mg, 50%) as brown oil was obtained according to the same method as the synthesis of compound 132.

$^1$H NMR (400 MHz, CDCl$_3$); 1:2 atropisomer mixture; δ 7.86 (s, 1H), 7.73 (s, 2H), 6.63-6.96 (m, 3H), 5.63 (d, J=8.0, 0.68H), 5.54 (d, J=8.1, 0.32H), 3.71-4.04 (m, 2H), 3.49 (d, J=14.6, 1H), 2.70-2.81 (m, 1H), 2.21-2.31 (m, 2H), 1.90-2.05 (m, 2H), 1.48-1.55 (m, 2H), 1.10-1.31 (m, 6H), 1.04-1.09 (m, 6H), 0.57 (d, J=6.5, 1H), 0.33 (d, J=6.5, 2H). MS (ESI) m/z 569 (M$^+$+H).

Compound 145

N-(2-(2-(((4S,5R)-5-(3,5-bis(trifluoromethyl)phenyl)-4-methyl-2-oxooxazolidin-3-yl)methyl)-4,4-dimethylcyclohex-1-enyl)-4-isopropylphenyl)-N-methylacetamide According to the same method as the synthesis of compound 110, compound 166 was synthesized and then reacted with iodomethane to obtain Compound 145 (10 mg, 45%) as yellow oil.

$^1$H NMR (400 MHz, CDCl$_3$); atropisomer mixture; δ 7.90 (s, 1H), 7.79 (d, J=15.0, 2H), 6.90-7.20 (m, 3H), 5.70-5.73 (m, 1H), 3.94-4.13 (m, 2H), 3.13-3.41 (m, 1H), 2.87-3.24 (m, 3H), 2.82-3.00 (m, 1H), 1.62-2.30 (m, 4H), 1.44-1.49 (m, 2H), 1.17-1.29 (m, 6H), 1.00-1.29 (m, 6H), 0.42-0.72 (m, 3H). MS (ESI) m/z 625 (M$^+$+H).

Compound 146

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-1,1-dimethylurea Compound 146 (21 mg, 55%) as colorless oil was obtained according to the same method as the synthesis of compound 110.

$^1$H NMR (400 MHz, CDCl$_3$); atropisomer mixture; δ 7.82 (s, 1H), 7.79 (d, J=6.2, 2H), 7.77-7.11 (m, 1H), 7.09-6.92 (m, 1H), 6.76 (t, J=9.0, 1H), 6.14 (d, J=14.4, 1H), 5.59, 5.44 (2d, J=7.9, 1H), 4.05-3.91 (m, 2H), 3.73 (s, 3H), 3.52-3.41 (m, 1H), 3.00 (d, J=15.4, 6H), 2.42-2.09 (m, 2H), 1.93-1.89 (m, 2H), 1.50-1.41 (m, 2H), 1.01-0.99 (m, 6H), 0.40, 0.36 (2d, J=6.5, 3H). MS (ESI) m/z 628 (M$^+$+H).

Compound 147

(4S,5R)-5-(3,5-bis(trifluoromethyl)phenyl)-3-((2-(2-methoxy-5-(methylthio)phenyl)-5,5-dimethylcyclohex-1-enyl)methyl)-4-methyloxazolidin-2-one As shown in reaction scheme 5, intermediate 17 was synthesized. Intermediate 17 (50 mg, 0.076 mmol), a starting material, was dissolved in chloroform (1.5 mL). Dimethyl sulfide (10 μl, 0.11 mmol) and tert-butyl nitrile (18 μl, 0.15 mmol) were added dropwise to the obtained solution at room temperature, stirred at room temperature for 30 minutes, and then refluxed with stirring and heating for 3 hours. After the completion of the reaction, the reaction mixture was cooled down to room temperature, diluted with n-hexane, and immediately purified by column chromatography (silica, 20% Hexane/EtOAc), thus obtaining Compound 147 (9 mg, 21%) as yellow oil.

(ESI) m/z (586.2 neg. (M$^+$−H).

Compound 148

(4S,5R)-5-(3,5-bis(trifluoromethyl)phenyl)-3-((5,5-dimethyl-2-(2-(methylthio)-5-(trifluoromethoxy)phenyl)cyclohex-1-enyl)methyl)-4-methyloxazolidin-2-one Compound 148 (25 mg, 50%) as yellow solid was obtained according to the same method as the synthesis of compound 57.

$^1$H NMR (400 MHz, CDCl$_3$); atropisomer mixture; δ 7.85 (s, 1H), 7.73 (s, 2H), 7.12-7.10 (m, 2H), 6.85-6.83 (m, 1H), 5.64, 5.61 (2d, J=8.0, 1H), 4.10-4.05 (m, 1H), 3.91-3.83 (m, 1H), 3.54, 3.28 (2d, J=15.0, 1H), 2.60-2.00 (m, 2H), 2.41 (s, 3H), 1.94 (bm, 2H), 1.56-1.46 (m, 2H), 1.08-1.03 (m, 6H), 0.50, 0.37 (2d, J=6.5, 3H).

Compound 151

(E)-1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-cyano-3-methylguanidine As shown in reaction scheme 5, intermediate 17 was synthesized. Intermediate 17 (70 mg, 0.113 mmol), a starting material, was reacted with diphenyl cyanocarboimidate to synthesize an intermediate compound. The obtained intermediate compound (70 mg, 0.1 mmol) and methylamine (13 mg, 0.2 mmol) were dissolved in acetonitrile (3 mL). The obtained solution was refluxed with stirring at 80° C. After the completion of the reaction, the reaction mixture was diluted with methylene chloride, washed with brine, dried with anhydrous magnesium sulfate, filtered, and concentrated under reduced pressure. The residue was separated by MPLC (12 g silica, 25%~35%=Hexane/EtOAc), thus obtaining Compound 151 (30 mg, 47%) as white solid.

$^1$H NMR (400 MHz, CDCl$_3$); 1:2 atropisomer mixture; δ 7.85 (s, 1H), 7.73 (s, 1H), 7.67 (s, 1H), 7.09-7.05 (m, 1H), 6.95-6.87 (m, 2H), 5.40-5.38 (m, 1H), 4.36-4.32 (m, 0.5H), 4.22-4.18 (m, 1H), 3.94-3.91 (m, 0.5H), 3.88 (s, 2H), 3.76 (s, 1H), 3.08-3.05 (m, 1H), 2.84-2.80 (m, 3H), 2.50-2.37 (m, 1H), 2.08-1.91 (m, 3H), 1.69 (brs, 2H), 1.56-1.42 (m, 2H), 1.03-0.97 (m, 6H), 0.64-0.62 (d, J=6.6, 2H), 0.57-0.56 (d, J=6.5, 1H). MS (ESI) 638 (M+H)$^+$.

Compound 149

(Z)-3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-cyano-1,1-dimethylguanidine Compound 149 (20 mg, 51%) as white solid was obtained according to the same method as the synthesis of compound 151.

$^1$H NMR (400 MHz, CDCl$_3$); 1:1 atropisomer mixture; δ 7.85 (s, 1H), 7.74-7.72 (m, 2H), 6.95-6.91 (m, 1H), 6.84-6.75 (m, 1H), 6.70-6.68 (m, 1H), 5.61-5.55 (dd, J=8.1, 17.2, 1H), 4.07-3.92 (m, 2H), 3.88 (s, 1.5H), 3.76 (s, 1.5H), 3.63-3.59 (d, J=14.6, 0.5H), 3.51-3.47 (d, J=14.6, 0.5H), 2.95-2.92 (m, 6H), 2.45-2.22 (m, 2H), 1.92 (s, 2H), 1.65 (brs, 2H), 1.49-1.43 (m, 1H), 1.03-0.94 (m, 6H), 0.52-0.50 (d, J=6.5, 1.5H), 0.42-0.41 (d, J=6.5, 1.5H). MS (ESI) m/z 652 (M$^+$+H).

Compound 153

(E)-1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-cyano-1,3,3-trimethylguanidine Compound 153 (5 mg, 25%) as white solid was obtained according to the same method as the synthesis of compound 47.

$^1$H NMR (400 MHz, CDCl$_3$); 1:1 atropisomer mixture; δ 7.85 (s, 1H), 7.74-7.72 (m, 2H), 6.89-6.79 (m, 2H), 6.67-6.62 (m, 1H), 5.63-5.58 (m, 1H), 4.04-3.89 (m, 2H), 3.76-3.73 (m, 3H), 3.55-3.43 (m, 1H), 3.37-3.31 (m, 3H), 2.81-2.79 (m, 6H), 2.40-2.20 (m, 1H), 1.99 (s, 2H), 1.53-1.49 (m, 4H), 1.04-0.96 (m, 6H), 0.49-0.48 (d, J=6.5, 1.5H), 0.39-0.37 (d, J=6.5, 1.5H). MS (ESI) m/z 666 (M$^+$+H).

Compound 156

(Z)-methyl N-3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl-N'-methylcarbamimidothioate Compound 156 (16 mg, 64%) as colorless oil was obtained according to the same method as the synthesis of compound 47.

$^1$H NMR (400 MHz, CDCl$_3$); atropisomer mixture; δ 7.85 (s, 1H), 7.72 (d, J=9.1, 2H), 7.11-7.08 (m, 1H), 6.90-6.83 (m, 2H), 5.60, 5.53 (2d, J=8.0, 1H), 4.64-4.63 (m, 0.5H), 4.29-4.27 (m, 0.5H), 4.19-3.95 (m, 2H), 3.82, 3.75 (2s, 3H), 3.45, 3.21 (2d, J=15.0, 1H), 3.21, 3.16 (2s, 3H), 2.71 (dd, J=14.7, 4.7, 3H), 2.45-2.0 (m, 2H), 1.92 (s, 2H), 1.51-1.46 (m, 2H), 1.04-1.00 (m, 6H), 0.53, 0.41 (2 d, J=6.6 Hz, 3H).

Compound 157

1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-1,3,3-trimethylurea Compound 157 (8 mg, 44%) as colorless oil was obtained according to the same method as the synthesis of compound 112.

$^1$H NMR (400 MHz, CDCl$_3$); atropisomer mixture; δ 7.85 (s, 1H), 7.73 (s, 2H), 6.95-6.91 (m, 1H), 6.79, 6.77 (dd, J=8.8, 1H), 6.72 (dd, J=13.0, 2.7, 1H), 5.61 (dd, J=4.4, 8.0, 1H), 4.02-3.89 (m, 2H), 3.74 (d, J=8.9, 3H), 3.53, 3.44 (2d, J=14.0, 1H), 3.13, 3.06 (2s, 3H), 2.65 (d, J=12.3, 6H), 2.50-2.00 (m, 2H), 2.07-2.04 (m, 2H), 1.50-1.45 (m, 2H), 1.04-0.99 (m, 6H), 0.43, 0.33 (2d, J=6.5, 3H). MS (ESI) m/z 642 (M$^+$+H).

Compound 159 methyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)propanoate Compound 159 (30 mg, 32%) as brown oil was obtained according to the same method as the synthesis of compound 133.

$^1$H NMR (400 MHz, CDCl$_3$); atropisomer mixture; δ 7.85 (s, 1H), 7.73-7.75 (m, 2H), 7.13-7.16 (m, 1H), 6.77-6.96 (m, 2H), 5.31-5.61 (m, 1H), 3.89-4.00 (m, 2H), 3.73-3.75 (m, 3H), 3.53-3.68 (m, 3H), 3.53-3.68 (m, 1H), 3.37-3.68 (m, 1H), 1.94-2.47 (m, 6H), 1.44-1.59 (m, 3H), 1.01-1.25 (m, 6H), 0.27-0.38 (m, 3H). MS (ESI) m/z 628 (M$^+$+H).

Compound 160

(4S,5R)-5-(3,5-bis(trifluoromethyl)phenyl)-3-((2-(2-methoxy-5-(1,1,1-trifluoropropan-2-ylamino)phenyl)-5,5-dimethylcyclohex-1-enyl)methyl)-4-methyloxazolidin-2-one According to the same method as the synthesis of Compound 133, 3-iodo-4-methoxyaniline, a starting material, was subjected to several synthesis processes to obtain a pinacolato compound. The obtained pinacolato compound was reacted with Compound 4 to synthesize an amino alcohol compound, which is an intermediate compound. The obtained amino alcohol compound was reacted with triphosgene, thus obtaining Compound 160 (72 mg, 38%) as brown oil.

$^1$H NMR (400 MHz, CDCl$_3$); atropisomer mixture; δ 7.85 (s, 1H), 7.73 (m, 2H), 6.67-6.77 (m, 1H), 6.52-6.56 (m, 1H), 6.33-6.36 (m, 1H), 5.57-5.60 (m, 1H), 4.00-4.04 (m, 1H), 3.84-3.99 (m, 2H), 3.69 (d, J=8.2, 3H), 3.46-3.64 (m, 1H), 3.34 (br s, 1H), 1.43-2.50 (m, 6H), 1.33-1.41 (m, 3H), 0.97-1.04 (m, 6H), 0.32-0.46 (m, 3H), 1.01-1.04 (m, 6H), 0.33-0.37 (m, 3H). MS (ESI) m/z 653 (M$^+$+H).

Compound 161

(4S,5R)-5-(3,5-bis(trifluoromethyl)phenyl)-3-((2-(2-methoxy-5-(methyl(1,1,1-trifluoropropan-2-yl)amino)phenyl)-5,5-dimethylcyclohex-1-enyl)methyl)-4-methyloxazolidin-2-one Compound 161 (25 mg, 54%) as yellow oil was obtained according to the same method as the synthesis of compound 112.

$^1$H NMR (400 MHz, CDCl$_3$); 1:1 atropisomer mixture; δ 7.86 (s, 1H), 7.73 (s, 2H), 6.69-6.81 (m, 2H), 6.48-6.52 (m, 1H), 5.56-5.60 (m, 1H), 4.10-4.14 (m, 1H), 3.90-4.02 (m, 2H), 3.69-3.72 (m, 3H), 3.43-3.69 (m, 1H), 2.80 (d, J=15.6, 3H), 2.05-2.48 (m, 2H), 1.93 (s, 2H), 1.47-1.55 (m, 2H), 1.34-1.48 (m, 3H), 1.01-1.05 (m, 6H), 0.31-0.45 (m, 3H). MS (ESI) m/z 666 (M$^+$+H).

Compound 162

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2,2-trifluoroacetamide Compound 162 (0.21 mg, 92%) as yellow foam was obtained according to the same method as the synthesis of compound 18.

MS (ESI) m/z 653 (M$^+$+H).

Compound 163

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-bromoacetamide Compound 163 (44 mg, 100%) as yellow oil was obtained according to the same method as the synthesis of compound 110.

$^1$H NMR (400 MHz, CDCl$_3$); atropisomer mixture; δ 8.11, 8.04 (2S, 1H), 7.84 (d, J=5.5, 1H), 7.79, 7.74 (2S, 1H), 7.43-7.36 (m, 1H), 7.15-7.09 (m, 1H), 6.82 (t, J=9.1, 1H), 5.60, 5.52 (2d, J=8.0, 1H), 4.08-3.90 (m, 4H), 3.75 (d, J=7.3, 3H), 3.57, 3.38 (2d, J=14.7, 1H), 2.24-2.03 (m, 2H), 1.93 (d, J=11.2, 2H), 1.51-1.41 (m, 2H), 1.01 (dd, J=10.0, 4.4, 6H), 0.39, 0.34 (2d, J=6.5, 3H). MS (ESI) m/z 676.0, 679.0 (M$^+$-1, M$^+$+2).

Compound 166

N-(2-(2-(((4S,5R)-5-(3,5-bis(trifluoromethyl)phenyl)-4-methyl-2-oxooxazolidin-3-yl)methyl)-4,4-dimethylcyclohex-1-enyl)-4-isopropylphenyl)acetamide Compound 166 (25 mg, 44%) as colorless oil was obtained according to the same method as the synthesis of compound 110.

$^1$H NMR (400 MHz, CDCl$_3$); 1:1.2 atropisomer mixture; δ 7.88 (s, 1H), 7.78 (s, 2H), 6.98-7.25 (m, 3H), 5.64-5.67 (m, 1H), 3.77-4.02 (m, 2H), 3.41-3.49 (m, 1H), 2.86-2.98 (m, 1H), 2.52 (s, 1H), 2.47 (s, 2H), 2.14-2.22 (m, 2H), 1.83-1.99 (m, 2H), 1.41-1.50 (m, 2H), 1.22-1.31 (m, 6H), 0.90-1.03 (m, 6H), 0.71 (d, J=6.4, 1H), 0.57 (d, J=6.5, 2H). MS (ESI) m/z 611 (M$^+$+H).

Compound 167

(4S,5R)-5-(3,5-bis(trifluoromethyl)phenyl)-3-((2-(5-isopropyl-2-(methylamino)phenyl)-5,5-dimethylcyclohex-1-enyl)methyl)-4-methyloxazolidin-2-one Compound 167 (13 mg, 11%) as colorless oil was obtained according to the same method as the synthesis of compound 47.

$^1$H NMR (400 MHz, CDCl$_3$); 1:1 atropisomer mixture; δ 7.87 (d, J=5.2, 1H), 7.72 (d, J=7.4, 2H), 7.00-7.07 (m, 1H), 6.54-6.70 (m, 2H), 5.63 (d, J=8.1, 0.5H), 5.49 (d, J=8.2, 0.5H), 3.98 (d, J=14.7, 0.5H), 3.83-3.92 (m, 1H), 3.71-3.73 (m, 1H), 3.42 (d, J=14.6, 0.5H), 2.81 (d, J=8.4, 3H), 2.72-2.78 (m, 1H), 2.18-2.29 (m, 2H), 1.87-1.98 (m, 2H), 1.47-1.54 (m, 2H), 0.74-1.35 (m, 15H), 0.55 (d, J=6.5, 1.7H), 0.32 (d, J=6.5, 1.3H). MS (ESI) m/z 583 (M$^+$+H).

Compound 168

(4S,5R)-5-(3,5-bis(trifluoromethyl)phenyl)-3-((2-(2-(dimethylamino)-5-isopropylphenyl)-5,5-dimethylcyclohex-1-enyl)methyl)-4-methyloxazolidin-2-one Compound 144 (34 mg, 0.06 mmol), paraformaldehyde (1 mL) and sodium cyanoborohydride (7 mg, 0.12 mmol) were dissolved in acetonitrile (2 mL). Acetic acid (7.4 µl, 0.12 mmol) was added dropwise slowly to the obtained solution at room temperature, and stirred at room temperature for 2 hours. After the completion of the reaction, the reaction mixture was diluted with ethyl acetate, washed with brine, dried with anhydrous magnesium sulfate, filtered, and concentrated under reduced pressure. The residue was separated by MPLC (12 g silica, 4:1=Hexane/EtOAc), thus obtaining Compound 168 (30 mg, 85%) as colorless oil.

$^1$H NMR (400 MHz, CDCl$_3$); 1:3.2 atropisomer mixture; δ 7.84 (s, 1H), 7.73 (s, 2H), 6.99-7.02 (m, 1H), 6.80-6.86 (m, 2H), 5.59-5.61 (m, 1H), 3.40-3.82 (m, 3H), 2.75-2.78 (m, 1H), 2.67 (d, J=10.2, 3H), 2.15-2.25 (m, 2H), 1.88-2.05 (m, 2H), 1.52-1.56 (m, 2H), 1.27-1.33 (m, 6H), 1.12-1.19 (m, 6H), 1.04-1.07 (m, 6H), 0.61 (d, J=6.6, 0.7H), 0.16 (d, J=6.5, 2.3H). MS (ESI) m/z 597 (M$^+$+H).

Compound 170

(4S,5R)-5-(3,5-bis(trifluoromethyl)phenyl)-3-((2-(2-methoxy-5-(2,2,2-trifluoroacetyl)phenyl)-5,5-dimethylcyclohex-1-enyl)methyl)-4-methyloxazolidin-2-one (3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzaldehyde (0.18 g, 0.32 mmol), a starting material, was dissolved in dimethoxyethane (5.0 mL). Cesium fluoride (5 mg, 0.03 mmol) and trimethylsilyl trifluoride (0.05 mL, 0.36 mmol) were added dropwise slowly to the obtained solution at room temperature, and stirred at room temperature for 2 hours. After the completion of the reaction, the reaction was quenched with 1M HCl (hydrochloride) solution. The reaction mixture was diluted with ethyl acetate, washed with brine, dried with anhydrous magnesium sulfate, filtered, and concentrated under reduced pressure. The residue was separated by MPLC (12 g silica, 4:1=Hexane/EtOAc), thus obtaining an intermediate compound (0.14 g, 68%) as colorless oil. The obtained intermediate compound (0.14 g, 0.22 mmol) and Dess-Martin periodinane (0.14 mg, 0.33 mmol) were dissolved in methylene chloride (5.0 mL), and stirred at room temperature for 2 hours. After the completion of the reaction, the reaction was quenched with water. The reaction mixture was extracted with methylene chloride. The obtained organic layer was dried with anhydrous sodium sulfate, filtered, and concentrated under reduced pressure. The residue was separated by MPLC (12 g silica, 3:1=hexane/EtOAc), thus obtaining Compound 170 (0.1 g, 70%), which is an intermediate compound, as colorless oil.

$^1$H NMR (400 MHz, CDCl$_3$); 1:1.2 atropisomer mixture; δ 8.03 (d, J=7.6, 1H), 7.87 (s, 1H), 7.73 (d, J=7.5, 3H), 6.99 (t, J=9.0, 1H), 5.66 (d, J=7.6, 0.55H), 5.55 (d, J=7.9, 0.45H), 3.91-4.03 (m, 3H), 3.90 (d, J=10.4, 3H), 3.54 (d, J=15.0, 0.45H), 3.31 (d, J=14.8, 0.55H), 2.21-2.26 (m, 2H), 1.52-1.53 (m, 2H), 1.48-1.51 (m, 2H), 1.02-1.06 (m, 6H), 0.39-0.43 (m, 3H). MS (ESI) m/z 638 (M$^+$+H).

Compound 171

(4S,5R)-5-(3,5-bis(trifluoromethyl)phenyl)-3-((2-(2-methoxy-5-(perfluoroprop-1-en-2-yl)phenyl)-5,5-dimethylcyclohex-1-enyl)methyl)-4-methyloxazolidin-2-one

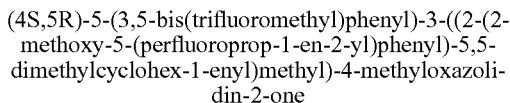

Compound 170 (0.1 g, 0.149 mmol) was dissolved in dimethylformamide (5 mL). Triphenylphosphine (0.08 g, 0.3 mmol) and sodium chlorodifluoroacetate (0.05 g, 0.3 mmol) were added dropwise in sequence to the obtained solution at room temperature, and then refluxed with stirring at 135° C. for 6 hours. After the completion of the reaction, the reaction was quenched with water. The reaction mixture was extracted with ethyl acetate. The obtained organic layer was dried with anhydrous sodium sulfate, filtered, and concentrated under reduced pressure. The residue was separated by MPLC (4 g silica, 3:1=hexane/EtOAc), thus obtaining the intermediate Compound 171 (17 mg, 20%) as colorless oil.

$^1$H NMR (400 MHz, CDCl$_3$); atropisomer mixture; δ 7.86 (s, 1H), 7.72 (s, 2H), 7.18-7.22 (m, 1H), 6.86-6.96 (m, 2H), 5.55-5.62 (m, 1H), 3.84-3.99 (m, 2H), 3.80 (d, J=8.6, 3H), 3.58 (d, J=12.2, 0.5H), 3.39 (d, J=14.9, 0.5H), 2.08-2.51 (m, 2H), 1.88 (s, 2H), 1.49-1.55 (m, 6H), 1.01-1.05 (m, 6H), 0.31-0.34 (m, 3H). MS (ESI) m/z 672 (M$^+$+H).

Compound 172

(4S,5R)-5-(3,5-bis(trifluoromethyl)phenyl)-3-((2-(5-(1,1,1,3,3,3-hexafluoropropan-2-yl)-2-methoxyphenyl)-5,5-dimethylcyclohex-1-enyl)methyl)-4-methyloxazolidin-2-one

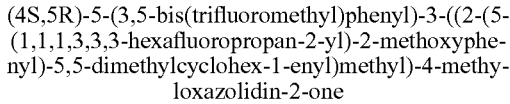

Compound 172 (14 mg, 14%) as yellow oil was obtained according to the same method as the synthesis of compound 171.

$^1$H NMR (400 MHz, CDCl$_3$); 1:1 atropisomer mixture; δ 7.86 (s, 1H), 7.72 (s, 2H), 7.24-7.31 (m, 1H), 7.01-7.06 (m, 1H), 6.87-6.92 (m, 1H), 5.55-5.63 (m, 1H), 3.83-4.03 (m, 2H), 3.83-4.03 (m, 1H), 3.80 (d, J=7.2, 3H), 3.55 (d, J=14.7, 0.5H), 3.37 (d, J=14.8, 0.5H), 2.21-2.53 (m, 2H), 1.89-1.99 (m, 2H), 1.44-1.52 (m, 2H), 1.04 (d, J=13.4, 6H), 0.27-0.33 (m, 3H). MS (ESI) m/z 692 (M$^+$+H).

Compound 173 tert-butyl 3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl(isopropyl)carbamate

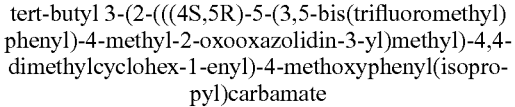

Compound 173 (50 mg, 56%) as colorless oil was obtained according to the same method as the synthesis of compound 112.

$^1$H NMR (400 MHz, CDCl$_3$); 1:1.2 atropisomer mixture; δ 7.84 (s, 1H), 7.72 (s, 2H), 6.92-6.90 (m, 1H), 6.81-6.74 (m, 1H), 6.68-6.66 (m, 1H), 5.62-5.56 (m, 1H), 4.47 (brs, 1H), 3.99-3.90 (m, 2H), 3.89-3.87 (m, 3H), 3.60-3.48 (m, 1H), 2.54-2.49 (m, 1H), 2.24-2.02 (m, 1H), 1.92 (s, 2H), 1.53-1.42 (m, 2H), 1.33-1.21 (m, 9H), 1.19-1.00 (m, 12H), 0.46 (d, J=6.6, 1H), 0.27 (d, J=6.3, 2H). MS (ESI) m/z 699 (M$^+$+H).

Compound 174 tert-butyl 3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl(ethyl)carbamate

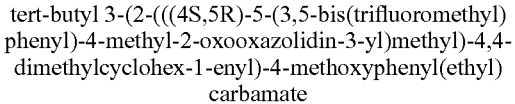

Compound 174 (45 mg, 52%) as colorless oil was obtained according to the same method as the synthesis of compound 112.

$^1$H NMR (400 MHz, CDCl$_3$); atropisomer mixture; δ 7.84 (s, 1H), 7.79 (s, 2H), 6.95 (s, 1H), 6.81 (m, 2H), 5.57 (m, 1H), 3.99-3.85 (m, 2H), 3.75-3.74 (m, 3H), 3.63-3.41 (m, 3H), 2.47-1.86 (m, 4H), 1.58-1.23 (m, 11H), 1.16-0.88 (m, 9H), 0.44-0.22 (m, 4H). MS (ESI) m/z 684 (M$^+$+H).

Compound 177

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-ethylacetamide

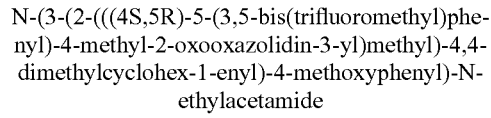

Compound 177 (15 mg, 79%) as colorless oil was obtained according to the same method as the synthesis of compound 112.

$^1$H NMR (400 MHz, CDCl$_3$); 1:1.3 atropisomer mixture; δ 7.85 (s, 1H), 7.72 (s, 2H), 7.03-7.01 (m, 1H), 6.99-6.77 (m, 2H), 5.62-5.60 (d, J=8.0, 1H), 4.06-3.87 (m, 2H), 3.79 (s, 1.2H), 3.76 (s, 1.8H), 3.74-3.61 (m, 2H), 3.54-3.34 (m, 1H), 2.51-2.47 (m, 0.5H), 2.29-2.08 (m, 1.5H), 2.06-2.01 (m, 1H), 1.93-1.79 (m, 3H), 1.79 (s, 1.5H), 1.75 (s, 1.5H), 1.55-1.43 (m, 2H), 1.17-0.92 (m, 6H), 0.46-0.44 (d, J=6.2, 1.3H), 0.34-0.32 (d, J=6.2, 1.7H). MS (ESI) m/z 627 (M$^+$+H).

Compound 178

(4S,5R,Z)-5-(3,5-bis(trifluoromethyl)phenyl)-3-((2-(2-methoxy-5-(2,2,2-trifluoro-1-(methoxyimino)ethyl)phenyl)-5,5-dimethylcyclohex-1-enyl)methyl)-4-methyloxazolidin-2-one

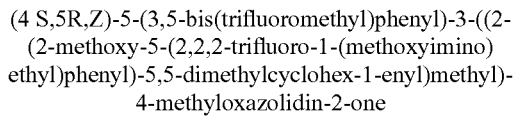

Compound 170 (0.1 g, 0.157 mmol) and methylamine (26 mg, 0.31 mmol) were dissolved in methanol (5 mL). Pyridine (25 µl, 0.31 mmol) was added dropwise slowly to the obtained solution at room temperature, and stirred at 60° C. for 12 hours. After the completion of the reaction, the reaction was quenched with water. The reaction mixture was extracted with methylene chloride. The obtained organic layer was dried with anhydrous sodium sulfate, filtered, and concentrated under reduced pressure. The residue was separated by MPLC (12 g silica, 3:1=hexane/EtOAc), thus obtaining Compound 178 (35 mg, 30%), which is an intermediate compound, as colorless oil.

$^1$H NMR (400 MHz, CDCl$_3$); 1:3.2 atropisomer mixture; δ 7.84 (s, 1H), 7.73 (s, 2H), 6.99-7.02 (m, 1H), 6.80-6.86 (m, 2H), 5.59-5.61 (m, 1H), 3.40-3.82 (m, 3H), 2.75-2.78 (m, 1H), 2.67 (d, J=10.2, 3H), 2.15-2.25 (m, 2H), 1.88-2.05 (m, 2H), 1.52-1.56 (m, 2H), 1.27-1.33 (m, 6H), 1.12-1.19 (m, 6H), 1.04-1.07 (m, 6H), 0.61 (d, J=6.6, 0.7H), 0.16 (d, J=6.5, 2.3H). MS (ESI) m/z 685 (M$^+$+H).

Compound 179

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-(2-hydroxy-2-methylpropyl)acetamide

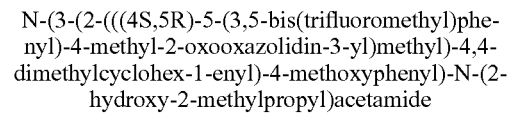

As the same method as the synthesis of Compound 112, except using isobutylene oxide instead of iodomethane, Compound 179 (10 mg, 50%) as colorless oil was obtained.

$^1$H NMR (400 MHz, CDCl$_3$); atropisomer mixture; δ 7.88 (s, 1H), 7.82-7.78 (m, 1H), 7.48-7.45 (m, 0.5H), 7.24-7.23 (m, 0.5H), 7.17-7.00 (m, 2H), 6.82-6.79 (m, 1H), 4.99-4.98 (d, J=5.5, 1H), 3.93-3.41 (m, 7H), 2.38-2.32 (m, 1H), 2.17-2.15 (m, 3H), 1.97-1.83 (m, 3H), 1.50-1.42 (m, 2H), 1.38-1.22 (m, 6H), 1.15-1.05 (m, 3H), 0.89-0.86 (m, 3H), 0.69-0.61 (m, 3H). MS (ESI) 671 (M$^+$+H).

Compound 180

(4S,5R)-5-(3,5-bis(trifluoromethyl)phenyl)-3-((2-(5-(3,3-difluoroazetidine-1-carbonyl)-2-methoxyphenyl)cyclohex-1-enyl)methyl)-4-methyloxazolidin-2-one Compound 180 (17 mg, 77%) as colorless oil was obtained according to the same method as the synthesis of compound 67.

$^1$H NMR (400 MHz, CDCl$_3$); atropisomer mixture; δ 7.84 (s, 1H), 7.73 (s, 2H), 7.55-7.44 (m, 1H), 7.43-7.33 (m, 1H), 6.88 (dd, J=8.6, 3.9, 1H), 5.60, 5.53 (2d, J=8.0, 1H), 4.55-4.47 (m, 4H), 4.01-3.93 (m, 2H), 3.83, 3.80 (2s, 3H), 3.48, 3.35 (2d, J=14.9, 1H), 2.39-2.01 (m, 4H), 1.80-1.73 (m, 4H), 0.42 (dd, J=15.7, 6.5, 3H). MS (ESI) m/z 633, 634 (M$^+$+H, M$^+$+2).

Compound 181

(4S,5R)-5-(3,5-bis(trifluoromethyl)phenyl)-3-((2-(5-(1,1,1,3,3,3-hexafluoro-2-hydroxypropan-2-yl)-2-methoxyphenyl)-5,5-dimethylcyclohex-1-enyl)methyl)-4-methyloxazolidin-2-one Compound 181 (37 mg, 72%) as white solid was obtained according to the same method as the synthesis of compound 170.

$^1$H NMR (400 MHz, CDCl$_3$); 1:3.2 atropisomer mixture; δ 7.84 (s, 1H), 7.73 (s, 2H), 6.99-7.02 (m, 1H), 6.80-6.86 (m, 2H), 5.59-5.61 (m, 1H), 3.40-3.82 (m, 3H), 2.75-2.78 (m, 1H), 2.67 (d, J=10.2, 3H), 2.15-2.25 (m, 2H), 1.88-2.05 (m, 2H), 1.52-1.56 (m, 2H), 1.27-1.33 (m, 6H), 1.12-1.19 (m, 6H), 1.04-1.07 (m, 6H), 0.61 (d, J=6.6, 0.7H), 0.16 (d, J=6.5, 2.3H). MS (ESI) m/z 708 (M$^+$+H).

Compound 182

(4S,5R)-5-(3,5-bis(trifluoromethyl)phenyl)-3-((2-(5-(1,1,1,3,3,3-hexafluoro-2-methoxypropan-2-yl)-2-methoxyphenyl)-5,5-dimethylcyclohex-1-enyl)methyl)-4-methyloxazolidin-2-one Compound 182 (12 mg, 47%) as white solid was obtained according to the same method as the synthesis of compound 47.

$^1$H NMR (400 MHz, CDCl$_3$); 1:3.2 atropisomer mixture; δ 7.84 (s, 1H), 7.73 (s, 2H), 6.99-7.02 (m, 1H), 6.80-6.86 (m, 2H), 5.59-5.61 (m, 1H), 3.40-3.82 (m, 3H), 2.75-2.78 (m, 1H), 2.67 (d, J=10.2, 3H), 2.15-2.25 (m, 2H), 1.88-2.05 (m, 2H), 1.52-1.56 (m, 2H), 1.27-1.33 (m, 6H), 1.12-1.19 (m, 6H), 1.04-1.07 (m, 6H), 0.61 (d, J=6.6, 0.7H), 0.16 (d, J=6.5, 2.3H). MS (ESI) m/z 722 (M$^+$+H).

Compound 183

(4S,5R)-5-(3,5-bis(trifluoromethyl)phenyl)-3-((2-(5-((2-hydroxy-2-methylpropyl)(methyl)amino)-2-methoxyphenyl)-5,5-dimethylcyclohex-1-enyl)methyl)-4-methyloxazolidin-2-one Compound 183 (8 mg, 24%) as yellow oil was obtained according to the same method as the synthesis of compound 120.

$^1$H NMR (400 MHz, CDCl$_3$); atropisomer mixture; δ 7.88 (s, 1H), 7.78 (s, 2H), 6.76-6.72 (m, 1H), 6.52-6.49 (m, 1H), 6.24 (dd, J=10.1, 2.9, 1H), 4.99-4.97 (m, 1H), 3.94-3.83 (m, 1H), 3.67-3.61 (2s, 3H), 3.70-3.53 (m, 2H), 2.79, 2.77 (2s, 3H), 2.39-1.91 (m, 4H), 1.86, 1.81 (2s, 1H), 1.60-1.52 (m, 2H), 1.53, 1.49 (2s, 1H), 1.47-1.25 (m, 6H), 1.04-0.97 (m, 6H), 0.79, 0.55 (2s, 3H).

Compound 184

(4S,5R)-3-((2-(5-acetyl-4-fluoro-2-methoxyphenyl)-5,5-dimethylcyclohex-1-enyl)methyl)-5-(3,5-bis(trifluoromethyl)phenyl)-4-methyloxazolidin-2-one As shown in reaction scheme 4, Compound 12 was synthesized. The obtained Compound 12 (0.24 g, 0.83 mmol) was subjected to a Suzuki reaction with Compound 9 (0.39 g, 0.756 mmol) to obtain Compound 184 (0.11 g, 25%) as brown oil.

MS (ESI) m/z 602 (M$^+$+H).

Compound 185

(4S,5R)-5-(3,5-bis(trifluoromethyl)phenyl)-3-((2-(5-(4,5-dihydrooxazol-2-yl)-2-methoxyphenyl)-5,5-dimethylcyclohex-1-enyl)methyl)-4-methyloxazolidin-2-one (3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzaldehyde (35 mg, 0.06 mmol), a starting material, was dissolved in tert-butyl alcohol (2 mL). Ethanolamine (4 μl, 0.07 mmol) was added dropwise to the obtained solution at room temperature, and stirred for 30 minutes at room temperature. Potassium carbonate (25 mg, 0.18 mmol) and iodine (31 mg, 0.12 mmol) were added dropwise to the obtained reaction mixture. The obtained reaction mixture was refluxed with stirring at 70° C. overnight. After the completion of the reaction, saturated sodium thiosulfate solution was added dropwise to the reaction mixture, to quench the reaction. The reaction mixture was extracted with ethyl acetate. The obtained organic layer was dried with anhydrous magnesium sulfate, filtered, and concentrated under reduced pressure. The residue was separated by column chromatography, thus obtaining the intermediate Compound 185 (11 mg, 30%) as white solid.

$^1$H NMR (400 MHz, CDCl$_3$); atropisomer mixture; δ 7.84 (s, 1H), 7.82-7.77 (m, 1H), 7.74, 7.71 (2s, 2H), 7.61 (dd, J=13.5, 2.1, 1H), 6.87 (dd, J=8.6, 11.3, 1H), 5.62, 5.49 (2d, J=8.1, 1H), 4.42-4.32 (m, 2H), 4.04-3.83 (m, 4H), 3.81, 3.79 (2s, 3H), 3.53, 3.35 (d, J=14.8, 1H), 2.41-2.04 (m, 2H), 1.91 (bs, 2H), 1.52-1.42 (m, 2H), 1.03-1.00 (m, 6H), 0.35 (dd, J=8.9, 6.5, 3H). MS (ESI) m/z 611 (M$^+$+H).

Compound 187

(4S,5R)-5-(3,5-bis(trifluoromethyl)phenyl)-3-((2-(5-(3-hydroxyazetidine-1-carbonyl)-2-methoxyphenyl)-5,5-dimethylcyclohex-1-enyl)methyl)-4-methyloxazolidin-2-one Compound 187 (16 mg, 52%) as white solid was obtained according to the same method as the synthesis of compound 67.

$^1$H NMR (400 MHz, CDCl$_3$); atropisomer mixture; δ 7.85 (s, 1H), 7.74 (d, J=4.0, 2H), 7.54 (dd, J=8.5, 2.2, 0.5H), 7.47 (dd, J=8.5, 2.1, 0.5H), 7.41 (d, J=2.1, 0.5H), 7.30 (d, J=2.2, 0.5H), 6.86 (dd, J=8.6, 4.0, 1H), 5.61, 5.56 (2d, J=8.0, 1H), 4.69 (bm, 1H), 4.44 (bs, 2H), 4.15-3.93 (m, 3H), 3.82, 3.79 (2s, 3H), 3.52, 3.37 (2d, J=14.6, 1H), 3.13, 3.03 (2d, J=5.4, 1H), 2.47-2.08 (m, 2H), 1.92 (bs, 2H), 1.53-1.44 (m, 2H), 1.04-1.01 (m, 6H), 0.44, 0.37 (2d, J=6.5, 3H). MS (ESI) m/z 642, 663 ((M+H)$^+$, (M+H)$^+$+21).

Compound 188

(4S,5R)-5-(3,5-bis(trifluoromethyl)phenyl)-3-((2-(5-((R)-4-isopropyl-4,5-dihydrooxazol-2-yl)-2-methoxyphenyl)-5,5-dimethylcyclohex-1-enyl)methyl)-4-methyloxazolidin-2-one Compound 188 (14 mg, 40%) as white solid was obtained according to the same method as the synthesis of compound 185.

$^1$H NMR (400 MHz, CDCl$_3$); atropisomer mixture; δ 7.84-7.77 (m, 2H), 7.74, 7.71 (2s, 2H), 7.59 (dd, J=12.1, 2.1, 1H), 6.85 (dd, J=8.6, 12.4, 1H), 5.63, 5.50 (2d, J=8.0, 1H), 4.38-4.30 (m, 1H), 4.12-3.93 (m, 4H), 3.80, 3.78 (2s, 3H), 3.52, 3.36 (2d, J=14.8, 1H), 2.47-2.12 (m, 2H), 1.92 (bs, 2H), 1.87-1.71 (m, 1H), 1.50-1.45 (m, 2H), 1.06-1.01 (m, 7.5H), 0.91-0.89 (m, 3H), 0.80 (d, J=6.7, 1.5H), 0.36 (2d, J=6.5, 3H). MS (ESI) m/z 653 (M$^+$+H).

Compound 189

1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)cyclopropanecarbonitrile According to the same method as the synthesis of Compound 12 in reaction scheme 4, a pinacolato compound was synthesized. And then the synthesis procedure was operated according to the same method as shown in reaction scheme 2, to obtain Compound 189 (0.25 g, 81%) as green foam.

$^1$H NMR (400 MHz, CDCl$_3$); atropisomer mixture; δ 7.85 (s, 1H), 7.74 (d, J=5.7, 2H), 7.16 (dd, J=8.5, 2.5, 0.5H), 7.07 (d, J=2.4, 0.5H), 7.02 (dd, J=8.5, 2.5, 0.5H), 6.90 (d, J=2.5, 0.5H), 6.81 (dd, J=8.5, 11.4, 1H), 5.59 (dd, J=8.3, 10.4, 1H), 4.00-3.94 (m, 2H), 3.76, 3.73 (2s, 3H), 3.50, 3.35 (2d, J=14.7, 1H), 2.50-2.04 (m, 2H), 1.92 (bs, 2H), 1.68-1.56 (m, 2H), 1.50-1.47 (m, 2H), 1.34-1.23 (m, 2H), 1.04-1.00 (m, 6H), 0.43, 0.36 (2d, J=6.5, 3H). MS (ESI) m/z 607 (M$^+$+H).

Compound 190

1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)cyclopropanecarboxamide Compound 189 (0.1 g, 0.165 mmol), 30% hydrogen peroxide (0.6 mL) and 7M potassium hydroxide (60 μl) were dissolved in ethanol (1 mL). The obtained solution was stirred at 85° C. for 4 hours. After the completion of the reaction, the reaction mixture was diluted with ethyl acetate, washed with brine, dried with anhydrous magnesium sulfate, filtered, and concentrated under reduced pressure. The residue was separated by column chromatography, thus obtaining intermediate compound (27 mg, 28%). The obtained intermediate compound (26 mg, 0.04 mmol) was dissolved in anhydrous methylene chloride (1 mL). Diisopropylamine (45 μl, 0.26 mmol) and triphosgene (6 mg, 0.02 mmol) were added dropwise to the obtained solution at 0° C., and stirred at room temperature for 2 hours. After the completion of the reaction, the reaction mixture was diluted with ethyl acetate, washed with brine, dried with anhydrous magnesium sulfate, filtered, and concentrated under reduced pressure. The residue was separated by column chromatography, thus obtaining Compound 190 (19 mg, 70%) as white solid.

$^1$H NMR (400 MHz, CDCl$_3$); atropisomer mixture; δ 7.85 (s, 1H), 7.72 (d, J=7.6, 2H), 7.30-7.27 (m, 1H), 7.07, 7.03 (2d, J=2.3, 1H), 6.86, 6.81 (2d, J=8.4, 1H), 5.88 (bs, 0.5H), 5.61, 5.54 (2d, J=8.3, 1H), 5.52-5.42 (bm, 1.5H), 4.20-3.93 (m, 2H), 3.81 (s, 1.7H), 3.74 (s, 1.3H), 3.44, 3.20 (2d, J=14.5, 1H), 2.50-2.03 (m, 2H), 1.93 (bs, 2H), 1.59-1.46 (m, 4H), 1.04-1.02 (m, 6H), 1.00-0.94 (m, 2H), 0.53, 0.38 (2d, J=6.5, 3H). MS (ESI) m/z 625 (M$^+$+H).

Compound 191

(4S,5R)-5-(3,5-bis(trifluoromethyl)phenyl)-3-((2-(4-fluoro-2-methoxy-5-(2,2,2-trifluoroacetyl)phenyl)-5,5-dimethylcyclohex-1-enyl)methyl)-4-methyloxazolidin-2-one Compound 191 (33 mg, 55%) as yellow oil was obtained according to the same method as the synthesis of compound 170.

MS (ESI) m/z 656 (M$^+$+H).

Compound 192

(4S,5R)-5-(3,5-bis(trifluoromethyl)phenyl)-3-((2-(5-(cyclopropanecarbonyl)-4-fluoro-2-methoxyphenyl)-5,5-dimethylcyclohex-1-enyl)methyl)-4-methyloxazolidin-2-one According to the same method as the synthesis of Compound 133, 2-bromo-4-fluorophenol, a starting material, was subjected to several synthesis processes to obtain a pinacolato compound. The obtained pinacolato compound was reacted with Compound 4, to synthesize an amino alcohol compound, which is an intermediate compound. The obtained amino alcohol compound was reacted with triphosgene to obtain Compound 192 (4 mg, 48%) as brown oil.

$^1$H NMR (400 MHz, CDCl$_3$); atropisomer mixture; δ 7.86 (s, 1H), 7.73 (s, 2H), 6.76-6.79 (m, 1H), 6.50-6.57 (m, 1H), 5.59-5.62 (m, 1H), 3.90-3.98 (m, 2H), 3.73 (s, 3H), 3.53-3.73 (m, 1H), 3.10-3.16 (m, 1H), 2.02-2.45 (m, 2H), 1.91-1.93 (m, 2H), 1.50-1.54 (m, 2H), 1.01-1.05 (m, 6H), 0.32-0.42 (m, 3H). MS (ESI) m/z 628 (M$^+$+H).

Compound 193

(4S,5R)-5-(3,5-bis(trifluoromethyl)phenyl)-3-((2-(2-methoxy-5-(trifluoromethyl)phenyl)-5-(trifluoromethyl)cyclohex-1-enyl)methyl)-4-methyloxazolidin-2-one Compound 193 (1 g, 99%) as yellow solid was obtained according to the same method as the synthesis of compound 18.

MS (ESI) m/z 560 (M$^+$+H).

Compound 194

(4S,5R)-5-(3,5-bis(trifluoromethyl)phenyl)-3-((2-(2-methoxy-5-nitrophenyl)-5-(trifluoromethyl)cyclohex-1-enyl)methyl)-4-methyloxazolidin-2-one Compound 194 (0.1 g, 80%) as white solid was obtained according to the same method as the synthesis of compound 52.

MS (ESI) m/z 627 (M$^+$+H).

Compound 195

(4S,5R)-3-((2-(5-amino-2-methoxyphenyl)-5-(trifluoromethyl)cyclohex-1-enyl)methyl)-5-(3,5-bis(trifluoromethyl)phenyl)-4-methyloxazolidin-2-one Compound 194 (0.1 g, 0.16 mmol) was dissolved in methanol (3 mL). Raney-nickel (3 mL) was added dropwise to the obtained solution at room temperature, and stirred at room temperature under hydrogen balloon. After the completion of the reaction, the reaction mixture was filtered with celite, and concentrated under reduced pressure. The reaction mixture was diluted with ethyl acetate, washed with brine, dried with anhydrous magnesium sulfate, filtered, and concentrated under reduced pressure. The residue was separated by MPLC (12 g silica, 1:1=hexane/EtOAc), thus obtaining Compound 195 (35 g, 35%) as yellow solid.

MS (ESI) m/z 597 (M$^+$+H).

Compound 196

N-(3-(2-(((4S,5R)-5-(3,5-bis(trifluoromethyl)phenyl)-4-methyl-2-oxooxazolidin-3-yl)methyl)-4-(trifluoromethyl)cyclohex-1-enyl)-4-methoxyphenyl)acetamide Compound 196 (40 mg, 70%) as yellow oil was obtained according to the same method as the synthesis of compound 110.

MS (ESI) m/z 640 (M$^+$+H).

Compound 197 methyl 5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxybenzoate According to the same method as the synthesis of Compound 133, 2-fluoro-4-methoxybenzoic acid, a starting material, was subjected to several synthesis processes to obtain a pinacolato compound. The obtained pinacolato compound was reacted with Compound 4 to synthesize an amino alcohol compound, which is an intermediate compound. The obtained amino alcohol compound was reacted with triphosgene, thus obtaining Compound 197 (0.21 g, 88%) as yellow oil.

$^1$H NMR (400 MHz, CDCl$_3$); atropisomer mixture; δ 7.86 (s, 1H), 7.74 (s, 1H), 7.71 (s, 1H), 7.57 (dd, J=8.3, 10.2, 1H), 6.61 (dd, J=8.8, 12.6, 1H), 5.64, 5.55 (2d, J=8.1, 1H), 3.98-3.89 (m, 2H), 3.84, 3.82 (2s, 3H), 3.80, 3.79 (2s, 3H), 3.53, 3.33 (2d, J=14.6, 1H), 2.41-2.01 (m, 2H), 1.92-1.87 (bm, 2H), 1.51-1.42 (m, 2H), 1.02 (dd, 13.0, 2.0, 6H), 0.43, 0.39 (2d, J=6.5, 3H). MS (ESI) m/z 618 (M$^+$+H).

Compound 204

5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxybenzoic acid Compound 204 (83 mg, 45%) as white solid was obtained according to the same method as the synthesis of compound 34.

$^1$H NMR (400 MHz, CDCl$_3$); atropisomer mixture; δ 7.85 (s, 1H), 7.73 (d, J=8.2, 2H), 7.63 (dd, J=8.4, 3.9, 1H), 6.65 (dd, J=9.0, 12.6, 1H), 5.65, 5.56 (2d, J=8.0, 1H), 4.00-3.92 (m, 2H), 3.83 (d, J=11.2, 3H), 3.53, 3.31 (2d, J=14.8, 1H), 2.41-2.04 (m, 2H), 1.97-1.84 (m, 2H), 1.50-1.44 (m, 2H), 1.04-1.00 (m, 6H), 0.43 (t, J=6.8, 3H). MS (ESI) m/z 604 (M$^+$+H).

Compound 206

(4S,5R)-5-(3,5-bis(trifluoromethyl)phenyl)-3-((2-(2-methoxy-5-nitro-4-(trifluoromethyl)phenyl)-5,5-dimethylcyclohex-1-enyl)methyl)-4-methyloxazolidin-2-one As shown in reaction scheme 1,4-methoxy-1-nitro-2-(trifluoromethyl)benzene, a starting material, was subjected to iodination using iodine. The obtained compound was subjected to Ullmann reaction using Compound 2 (Martin G. Banwell et al. Org. Lett. 2004, 6, 2741), to synthesize a compound, and then according to the same method as the synthesis of compound 52, Compound 206 (0.65 g, 83%) as yellow foam was obtained.

$^1$H NMR (400 MHz, CDCl$_3$); atropisomer mixture; δ 7.87 (s, 1H), 7.74 (d, J=4.9, 2H), 7.69 (d, J=2.4, 1H), 7.22 (d, J=11.4, 1H), 5.66, 5.77 (2d, J=8.2, 1H), 4.03-3.93 (m, 2H), 3.94, 3.93 (2s, 3H), 3.50, 3.31 (2d, J=14.9, 1H), 2.40-2.03 (m, 2H), 1.95 (bs, 2H), 1.53-1.47 (m, 2H), 1.05-1.01 (m, 6H), 0.50 (t, J=6.8, 3H).

Compound 207

(4S,5R)-3-((2-(5-amino-2-methoxy-4-(trifluoromethyl)phenyl)-5,5-dimethylcyclohex-1-enyl)methyl)-5-(3,5-bis(trifluoromethyl)phenyl)-4-methyloxazolidin-2-one Compound 207 (0.33 mg, 56%) as white foam was obtained according to the same method as the synthesis of compound 195.

MS (ESI) m/z 625 (M$^+$+H).

Compound 209

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)trifluoro-N-methylmethanesulfonamide Compound 209 (27 mg, 56%) as yellow solid was obtained according to the same method as the synthesis of compound 112.

$^1$H NMR (400 MHz, CDCl$_3$); atropisomer mixture; δ 7.86 (d, J=9.6, 1H), 7.74-7.70 (m, 2H), 7.17-7.13 (m, 1H), 7.06 (d, J=4.8, 1H), 5.65-5.46 (m, 1H), 4.03-3.53 (m, 6H), 3.41-3.29 (m, 3H), 2.22-2.06 (m, 2H), 2.02-1.87 (m, 2H), 1.52-1.46 (m, 2H), 1.04-0.99 (m, 2H), 1.50-0.47 (m, 1H), 0.38 (d, J=6.5, 1H), 0.32 (d, J=6.5, 1H). MS (ESI) m/z 771 (M$^+$+H).

Compound 210

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)-N-methylacetamide According to the same method as the synthesis of Compound 112, Compound 210 (31 mg, 84%) as white solid was obtained.

$^1$H NMR (400 MHz, CDCl$_3$); atropisomer mixture; δ 7.86 (s, 1H), 7.72 (s, 2H), 7.16-7.13 (m, 1H), 6.95 (d, J=6.2, 1H), 5.63 (dd, J=4.4, 8.0, 1H), 4.03-3.91 (m, 2H), 3.86, 3.83 (2s, 3H), 3.45-3.26 (m, 1H), 3.17-3.05 (m, 3H), 2.46-2.03 (m, 2H), 1.97-1.90 (bm, 2H), 1.76-1.71 (m, 3H), 1.53-1.45 (m, 2H), 1.04-0.96 (m, 6H), 0.50-0.36 (m, 3H). MS (ESI) m/z 681 (M$^+$+H).

Compound 212

(4S,5R)-5-(3,5-bis(trifluoromethyl)phenyl)-3-((2-(2-methoxy-5-(methyl(4-(trifluoromethyl)thiazol-2-yl)amino)phenyl)-5,5-dimethylcyclohex-1-enyl)methyl)-4-methyloxazolidin-2-one Compound 212 (58.2 mg, 40.3%) as white solid was obtained according to the same method as the synthesis of compound 112.

¹H NMR (400 MHz, CDCl₃); atropisomer mixture; δ 7.86 (s, 1H), 7.73, 7.72 (2s, 2H), 7.22, 7.19 (2dd, J=2.8, 0.9, 1H), 7.02, 7.00 (2d, J=2.7, 1H), 6.92, 6.89 (2d, J=8.8, 1H), 6.84, 6.79 (2t, J=1.0, 1H), 5.61 (d, J=8.1, 1H), 4.01 (m, 2H), 3.81, 3.78 (2s, 3H), 3.59, 3.47 (2d, J=14.6, 15.0, 1H), 3.50, 3.44 (2s, 3H), 2.55-1.86 (brm, 4H), 1.51 (m, 2H), 1.27 (m, 2H), 1.05, 1.03, 1.00 (3s, 6H). MS (ESI) m/z 766 (M+K)⁺.

Compound 213

(4S,5R)-5-(3,5-bis(trifluoromethyl)phenyl)-3-((2-(2-methoxy-5-(4-(trifluoromethyl)thiazol-2-ylamino) phenyl)-5,5-dimethylcyclohex-1-enyl)methyl)-4-methyloxazolidin-2-one As shown in reaction scheme 5, intermediate 17 was synthesized. Intermediate 17 (0.3 g, 0.486 mmol) was dissolved in chloroform/saturated sodium carbonate solution (10 mL, V/V 3:1). Thiophosgene (62.5 μl) was added dropwise to the obtained solution at room temperature, and stirred at room temperature for 2 hours. After the completion of the reaction, the reaction mixture was diluted with ethyl acetate. The obtained organic layer was washed with water and brine. The organic layer was dried with anhydrous magnesium sulfate, filtered, and concentrated under reduced pressure to remove the solvent. The residue was dissolved in methanol (3 mL). Ammonia water (0.5 mL) was added dropwise to the obtained solution at room temperature, and stirred at room temperature for 5 hours. After the completion of the reaction, the reaction mixture was concentrated under reduced pressure to remove the solvent. The residue was crystallized, thus obtaining the intermediate Compound (0.3 g, 87.2%) as white solid. The obtained intermediate compound (0.16 g, 0.27 mmol) was dissolved in ethanol (3 mL). 3-bromo-1,1,1-trifluoropropane-2-one (44.6 μl) was added dropwise to the obtained solution at room temperature, and then refluxed with stirring at 90° C. for 2 hours. After the completion of the reaction, the reaction mixture was cooled to room temperature. The reaction mixture was diluted with ethyl acetate. And then, the obtained organic layer was washed with saturated sodium hydrogen carbonate solution, water and brine. The organic layer was dried with anhydrous magnesium sulfate, filtered, and concentrated under reduced pressure, thus obtaining Compound 213 (0.18 g, 93.1%) as colorless oil.

¹H NMR (400 MHz, CDCl₃); atropisomer mixture; δ 8.23, 8.06 (2brs, 1H), 7.85, 7.84 (2s, 1H), 7.72 (s, 2H), 7.27-7.15 (m, 1.5H), 6.99-6.84 (m, 2.5H), 5.60 (d, J=8.1, 1H), 4.01 (m, 2H), 3.80, 3.78 (2s, 3H), 3.68, 3.42 (2d, J=14.2, 1H), 2.51-1.88 (brm, 6H), 1.50 (m, 2H), 1.04 (m, 6H), 0.42, 0.35 (2d, J=5.4, 6.5, 3H).

Compound 215

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxyphenyl)-N-methylacetamide Compound 215 (21 mg, 31%) as white foam was obtained according to the same method as the synthesis of compound 112.

¹H NMR (400 MHz, CDCl₃); atropisomer mixture; δ 7.87 (s, 1H), 7.73 (s, 2H), 6.86 (m, 1H), 6.68 (m, 1H), 5.64, 5.62 (2s, 1H), 3.97 (m, 2H), 3.79, 3.76 (2s, 3H), 3.51-3.33 (brm, 2H), 3.19, 3.18, 3.08 (3s, 3H), 2.46-1.62 (brm, 9H), 1.46 (m, 2), 1.00 (m, 6H), 0.49-0.36 (m, 3H). MS (ESI) m/z 631 (M⁺+H).

Compound 216

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxyphenyl)acetamide Compound 216 (82 mg, 79%) as white solid foam was obtained according to the same method as the synthesis of compound 110.

¹H NMR (400 MHz, CDCl₃); atropisomer mixture; δ 7.79-7.76 (m, 4H), 7.21, 7.18 (2s, 1H), 6.64, 6.61 (2d, J=7.4, 1H), 5.63, 5.46 (2d, J=7.9, 1H), 4.12 (m, 1H), 3.94 (m, 1H), 3.56, 3.30 (2d, J=15.0, 1H), 2.19, 2.14 (2s, 3H), 1.93, 1.90 (2s, 2H), 1.45 (m, 2H), 1.01, 1.00, 0.99, 0.98 (4s, 6H), 0.46, 0.32 (2d, J=6.5, 3H). MS (ESI) m/z 617 (M⁺+H).

Compound 217

(4S,5R)-3-((2-(5-amino-4-fluoro-2-methoxyphenyl)-5,5-dimethylcyclohex-1-enyl)methyl)-5-(3,5-bis(trifluoromethyl)phenyl)-4-methyloxazolidin-2-one Compound 217 (0.12 g, 99%) as yellow oil was obtained according to the same method as the synthesis of compound 195.

¹H NMR (400 MHz, CDCl₃); atropisomer mixture; δ 7.85 (s, 1H), 7.73 (s, 2H), 6.58, 6.54 (2d, J=12.6, 1H), 6.44, 6.41 (2d, J=6.1, 1H), 5.60, 5.58 (2d, J=2.9, 1H), 4.0-3.89 (m, 2H), 3.67, 3.64 (2s, 3H), 3.58, 3.47 (2d, J=14.6, 1H), 3.37 (brs, 2H), 2.42-1.89 (brm, 6H), 1.45 (m, 2H), 0.99 (m, 6H), 0.48, 0.34 (2d, J=6.6, 6.5, 3H). MS (ESI) m/z 575 (M⁺+H).

Compound 218

(4S,5R)-5-(3,5-bis(trifluoromethyl)phenyl)-3-((2-(4-fluoro-2-methoxy-5-nitrophenyl)-5,5-dimethylcyclohex-1-enyl)methyl)-4-methyloxazolidin-2-one Compound 218 (0.3 g, 80%) as white solid was obtained according to the same method as the synthesis of compound 206.

¹H NMR (400 MHz, CDCl₃); atropisomer mixture; δ 7.86 (s, 1H), 7.78, 7.77 (2d, J=4.4, 1H), 7.72, 7.71 (2s, 2H), 6.74, 6.71 (2d, J=7.6, 1H), 5.56, 5.59 (2d, J=5.4, 1H), 3.96 (m, 2H), 3.89, 3.86 (2s, 3H), 3.52, 3.30 (2d, J=15.0, 1H), 2.38-1.87 (brm, 6H), 1.48 (m, 2H), 1.09, 1.08, 1.00, 0.99 (4s, 6H), 0.47 (t, J=6.7, 3H). MS (ESI) m/z 649 (M⁺+K).

Compound 219 tert-butyl 3-(((4S,5R)-5-(3,5-bis(trifluoromethyl) phenyl)-4-methyl-2-oxooxazolidin-3-yl)methyl)-4-(4-fluoro-5-isopropyl-2-methoxyphenyl)-5,6-dihydropyridine-1(2H)-carboxylate 1-tert-Butyl 3-ethyl 4-(trifluoromethylsulfonyloxy)-5,6-dihydropyridine-1,3(2H)-dicarboxylate, a starting material, was synthesized, and then was subjected to a Suzuki reaction with boronic acid. The obtained compound was subjected to a reduction using lithium aluminium hydride, and then to the oxidation using Dess-Martin periodinane. The obtained compound was reacted with Compound 4 to synthesize an amino alcohol compound, which is an intermediate compound. The obtained amino alcohol compound was reacted with triphosgene to obtain Compound 219 (39 mg, 45%) as white foam.

¹H NMR (400 MHz, CDCl₃); atropisomer mixture; δ 7.85 (s, 1H), 7.72 (s, 2H), 6.82 (m, 1H), 6.57, 6.53 (2d, J=12.1, 1H), 3.99 (m, 4H), 3.74, 3.70 (2s, 3H), 3.12 (m, 1H), 2.6-2.01 (m, 2H), 1.51 (s, 9H), 1.19 (m, 6H), 0.40, 0.30 (2d, J=6.5, 3H).

Compound 222

(4S,5R)-5-(3,5-bis(trifluoromethyl)phenyl)-3-((2-(4-fluoro-2-methoxy-5-(2,2,2-trifluoroethoxy)phenyl)-5,5-dimethylcyclohex-1-enyl)methyl)-4-methyloxazolidin-2-one According to the same method as the synthesis of Compound 133, 2-fluoro-4-methoxyphenol, a starting material, was subjected to several synthesis processes to obtain an iodobenzene compound. The obtained compound was subjected to Ullmann reaction using Compound 2, thus synthesizing an aldehyde compound. The obtained aldehyde compound was reacted with Compound 4 to synthesize an amino alcohol compound, which is an intermediate compound. The obtained amino alcohol compound was reacted with triphosgene, thus obtaining Compound 222 (7 mg, 47%) as yellow solid.

$^1$H NMR (400 MHz, CDCl$_3$); atropisomer mixture; δ 7.86 (s, 1H), 7.72 (s, 2H), 6.75 (dd, J=15.5, 9.2, 1H), 6.65 (dd, J=12.7, 11.4, 1H), 5.60 (dd, J=8.1, 3.0, 1H), 4.38-4.28 (m, 2H), 3.99-3.88 (m, 2H), 3.74, 3.70 (2s, 3H), 3.52, 3.39 (2d, J=14.6, 1H), 2.45-1.99 (m, 2H), 1.95-1.89 (m, 2H), 1.52-1.41 (m, 2H), 1.03-0.98 (m, 6H), 0.41 (2d, J=6.5, 3H). MS (ESI) m/z 658 (M$^+$+H).

Compound 223

(4S,5R)-5-(3,5-bis(trifluoromethyl)phenyl)-3-((2-(6-methoxybenzo[d][1,3]dioxol-5-yl)-5,5-dimethylcyclohex-1-enyl)methyl)-4-methyloxazolidin-2-one According to the same method as the synthesis of Compound 133, benzo[d][1,3]dioxol-5-ol, a starting material, was subjected to several synthesis processes to obtain a pinacolato compound. The obtained pinacolato compound was subjected to a Suzuki reaction using Compound 2, thus synthesizing an aldehyde compound. The obtained aldehyde compound was reacted with Compound 4 to synthesize an amino alcohol compound, which is an intermediate compound. The obtained amino alcohol compound was reacted with triphosgene, thus obtaining Compound 223 (4 mg, 49%) as colorless oil.

$^1$H NMR (400 MHz, CDCl$_3$); 1:1.5 atropisomer mixture; δ 7.86 (s, 1H), 7.74 (s, 2H), 6.45-6.52 (m, 2H), 5.87-5.92 (m, 2H), 5.62 (t, J=7.7, 1H), 3.90-4.03 (m, 2H), 3.70 (d, J=7.6, 3H), 3.65 (d, J=3.8, 0.6H), 3.50 (d, J=14.9, 0.4H), 2.01-2.45 (m, 2H), 1.89-1.91 (m, 2H), 1.44-1.49 (m, 2H), 1.00-1.04 (m, 6H), 0.49 (d, J=6.6, 1.2H), 0.38 (d, J=6.5, 1.8H). MS (ESI) m/z 586 (M$^+$+H).

Compound 224

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)-N-methylisobutyramide Compound 224 (49 mg, 74%) as colorless oil was obtained according to the same method as the synthesis of compound 112.

$^1$H NMR (400 MHz, CDCl$_3$); atropisomer mixture; δ 7.86 (s, 1H), 7.73 (d, J=4.5, 2H), 7.17-7.13 (m, 1H), 6.95 (d, J=10.4, 1H), 5.64-5.62 (m, 1H), 4.04-3.91 (m, 2H), 3.86-3.81 (m, 3H), 3.46-3.30 (m, 1H), 3.15-3.03 (m, 3H), 2.45-2.03 (m, 3H), 1.97-1.90 (m, 2H), 1.51-1.45 (m, 2H), 1.04-0.87 (m, 12H), 0.56-0.37 (m, 3H). MS (ESI) m/z 709, 710 (M$^+$+H, M$^+$+2).

Compound 225

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)-N-methylpropionamide Compound 225 (33 mg, 70%) as colorless oil was obtained according to the same method as the synthesis of compound 112.

$^1$H NMR (400 MHz, CDCl$_3$); atropisomer mixture; δ 7.86 (s, 1H), 7.73 (d, J=4.5, 2H), 7.15 (d, J=13.2, 1H), 6.92 (d, J=7.2, 1H), 5.64 (dd, J=8.0, 3.3, 1H), 4.03-3.91 (m, 2H), 3.85 (2d, J=12.6, 1.3, 3H), 3.45-3.32 (m, 1H), 3.16 (s, 1H), 3.04 (s, 1H), 2.45-2.02 (m, 2H), 1.97-1.86 (m, 4H), 1.53-1.45 (m, 2H), 1.04-0.96 (m, 9H), 0.50-0.37 (m, 3H). MS (ESI) m/z 695 (M$^+$+H).

Compound 226

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)-N-methylmethanesulfonamide According to the same method as the synthesis of Compound 112, Compound 226 (20 mg, 39%) as white solid was obtained.

$^1$H NMR (400 MHz, CDCl$_3$); atropisomer mixture; δ 7.84 (m, 1H), 7.75 (d, J=12.1, 2H), 7.45-7.06 (m, 2H), 5.63-5.41 (m, 1H), 4.00-3.70 (m, 2H), 3.88-3.80 (m, 3H), 2.50-3.24 (m, 1H), 3.18-3.02 (m, 3H), 2.98, 2.87 (2s, 3H), 2.40-2.03 (m, 2H), 1.97-1.94 (m, 2H), 1.51-1.42 (m, 2H), 1.03-0.97 (m, 6H), 0.54-0.33 (m, 3H). MS (ESI) m/z 717 (M$^+$+H).

Compound 227

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)-2,2,2-trifluoro-N-methylacetamide Compound 227 (8 mg, 73%) as yellow solid was obtained according to the same method as the synthesis of compound 112.

$^1$H NMR (400 MHz, CDCl$_3$); atropisomer mixture; δ 7.87 (s, 1H), 7.76-7.72 (m, 2H), 7.17-7.13 (m, 1H), 7.02-6.95 (m, 1H), 5.66-5.60 (m, 1H), 4.03-3.81 (m, 2H), 3.88-3.84 (m, 3H), 3.52-3.33 (m, 1H), 3.31-3.19 (m, 3H), 2.45-1.99 (m, 2H), 1.97-1.90 (m, 2H), 1.53-1.42 (m, 2H), 1.05-0.89 (m, 6H), 0.53-0.32 (m, 3H). MS (ESI) m/z 735 (M$^+$).

Compound 228

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)trifluoromethanesulfonamide Compound 228 (61 mg, 73%) as yellow oil was obtained according to the same method as the synthesis of compound 110.

$^1$H NMR (400 MHz, CDCl$_3$); atropisomer mixture; δ 7.84 (s, 1H), 7.73 (d, J=7.2, 2H), 7.32-7.27 (m, 1H), 7.10 (d, J=9.8, 1H), 5.62, 5.51 (2d, J=8.0, 1H), 4.00-3.88 (m, 2H), 3.84 (d, J=5.6, 3H), 3.57, 3.26 (2d, J=14.9, 1H), 2.40-2.07 (m, 2H), 1.93 (bs, 2H), 1.51-1.44 (m, 2H), 1.03-0.98 (m, 6H), 0.44, 0.33 (2d, J=6.5, 3H). MS (ESI) m/z 757, 758 (M$^+$, M$^+$+H).

Compound 229

(4S,5R)-5-(3,5-bis(trifluoromethyl)phenyl)-3-((2-(2,4-dimethoxy-5-nitrophenyl)-5,5-dimethylcyclohex-1-enyl)methyl)-4-methyloxazolidin-2-one

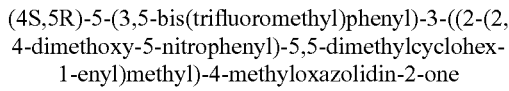

Compound 229 (89 mg, 74%) as colorless oil was obtained according to the same method as the synthesis of compound 110.

¹H NMR (400 MHz, CDCl₃); 1:1.7 atropisomer mixture; δ 7.87 (s, 1H), 7.69-7.78 (m, 2H), 6.49 (d, J=9.1, 1H), 5.67 (d, J=7.4, 0.7H), 5.55 (d, J=8.2, 0.4H), 3.95-4.07 (m, 2H), 4.00-3.97 (m, 3H) 3.86-3.90 (m, 3H), 3.58 (d, J=14.8, 0.5H), 3.34 (d, J=14.9, 0.5H), 2.18-2.38 (m, 2H), 1.87. MS (ESI) m/z 617 (M⁺+H).

Compound 230

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2,4-dimethoxyphenyl)-N-methylacetamide Compound 230 (4 mg, 85%) as colorless oil was obtained according to the same method as the synthesis of compound 112.

¹H NMR (400 MHz, CDCl₃); atropisomer mixture; δ 7.87 (s, 1H), 7.74 (s, 2H), 6.76-6.81 (m, 1H), 6.44-6.48 (m, 1H), 5.61-5.64 (m, 1H), 3.91-4.04 (m, 2H), 3.74-3.85 (m, 6H), 3.40-3.59 (m, 1H), 3.13 (s, 2H), 3.01 (s, 1H), 2.07-2.49 (m, 2H), 1.95-2.10 (m, 3H), 1.78-1.81 (m, 3H), 1.50-1.59 (m, 2H), 1.01-1.08 (m, 6H), 0.07-0.47 (m, 3H). MS (ESI) m/z 643 (M⁺+H).

Compound 231

(4S,5R)-5-(3,5-bis(trifluoromethyl)phenyl)-3-((4-(4-fluoro-5-isopropyl-2-methoxyphenyl)-1-methyl-1,2,5,6-tetrahydropyridin-3-yl)methyl)-4-methyloxazolidin-2-one

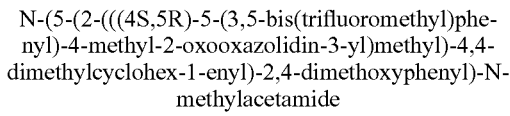

Compound 219 (0.45 g, 0.67 mmol) was dissolved in methylene chloride (3 mL). Trifluoroacetic acid (1 mL) was added dropwise to the obtained solution at 0° C., and then stirred at room temperature for 3 hours. After the completion of the reaction, the reaction mixture was concentrated under reduced pressure to remove the solvent. The residue was diluted with methylene chloride, washed with saturated sodium hydrogen carbonate solution and brine, dried with anhydrous magnesium sulfate, filtered, and concentrated under reduced pressure. The residue was crystallized, thus obtaining an intermediate compound (0.32 mg, 88%) as white solid. The obtained compound was subjected to reaction process according to the same method as the synthesis of compound 47, to obtain Compound 231 (1.0 mg, 10%) as colorless oil.

MS (ESI) m/z 589 (M⁺+K).

Compound 232

(4S,5R)-5-(3,5-bis(trifluoromethyl)phenyl)-3-((2-(4-hydroxy-2-methoxy-5-nitrophenyl)-5,5-dimethylcyclohex-1-enyl)methyl)-4-methyloxazolidin-2-one

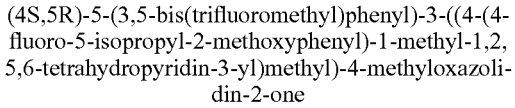

Compound 218 (0.12 g, 0.2 mmol) and 2-(methylsulfonylethanol) (32 mg) were dissolved in dimethylformamide (3 mL). Sodium hydride (15.3 mg) was added dropwise carefully to the obtained solution at room temperature, and stirred at room temperature overnight. After the completion of the reaction, the reaction mixture was diluted with ethyl acetate, washed with saturated ammonium chloride solution and brine, dried with anhydrous magnesium sulfate, filtered, and concentrated under reduced pressure. The residue was crystallized, thus obtaining Compound 232 (91 mg, 77%) as yellow solid.

¹H NMR (400 MHz, CDCl₃); atropisomer mixture; δ 10.98, 10.96 (2s, 1H), 7.86 (s, 1H), 7.79-7.71 (m, 3H), 6.53, 6.51 (2s, 1H), 5.63 (2d, J=8.1, 1H), 4.02-3.93 (m, 2H), 3.87, 3.86 (2s, 3H), 3.45 (2d, J=14.9, 1H), 2.39-1.86 (m, 4H), 1.52-1.43 (m, 2H), 1.01 (2d, J=3.8, 6H), 0.46 (2d, J=6.6, 3H). MS (ESI) m/z 603 (M⁺+H).

Compound 233

(4S,5R)-5-(3,5-bis(trifluoromethyl)phenyl)-3-((2-(2-methoxy-5-(methylamino)-4-(trifluoromethyl)phenyl)-5,5-dimethylcyclohex-1-enyl)methyl)-4-methyloxazolidin-2-one

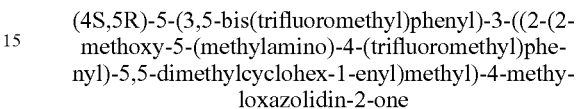

Compound 233 (46 mg, 85%) as yellow oil was obtained according to the same method as the synthesis of compound 120.

¹H NMR (400 MHz, CDCl₃); atropisomer mixture; δ 7.85 (s, 1H), 7.72 (s, 2H), 6.96, 6.89 (2s, 1H), 6.37 (d, J=8.0, 1H), 5.61 (d, J=7.2, 1H), 4.03-3.92 (m, 2H), 3.70 (d, J=7.6, 3H), 3.60-3.49 (m, 1H), 2.84, 2.80 (2s, 3H), 2.49-2.02 (m, 2H), 1.92 (bs, 2H), 1.52-1.46 (m, 2H), 1.04-0.98 (m, 6H), 0.52, 0.36 (2d, J=0.3, 3H). MS (ESI) m/z 639 (M⁺+H).

Compound 234

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-ethyl-4-methoxyphenyl)-N-methylacetamide Compound 234 (1.4 mg, 74%) as yellow oil was obtained according to the same method as the synthesis of compound 112.

¹H NMR (400 MHz, CDCl₃); 1:1 atropisomer mixture; δ 7.86 (s, 1H), 7.63 (s, 2H), 6.77 (m, 2H), 5.62 (m, 1H), 4.04-3.90 (m, 2H), 3.80, 3.77, 3.76 (3s, 3H), 3.56-3.89 (m, 2H), 3.16, 3.15, 3.03 (3s, 3H), 2.51 (m, 2H), 2.50-1.25 (m, 4H), 1.22 (m, 4H), 1.03 (m, 6H), 0.45-0.33 (m, 3H). MS (ESI) m/z 641 (M⁺+H).

Compound 235

(4S,5R)-5-(3,5-bis(trifluoromethyl)phenyl)-3-((2-(5-((2-hydroxy-2-methylpropyl)(methyl)amino)-2-methoxy-4-(trifluoromethyl)phenyl)-5,5-dimethylcyclohex-1-enyl)methyl)-4-methyloxazolidin-2-one

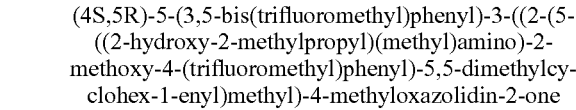

Compound 235 (7 mg, 39%) as yellow solid was obtained according to the same method as the synthesis of compound 120.

MS (ESI) m/z 639 (M⁺+H).

Compound 237

(4S,5R)-5-(3,5-bis(trifluoromethyl)phenyl)-3-((2-(5-cyclopropyl-4-fluoro-2-methoxyphenyl)-5,5-dimethylcyclohex-1-enyl)methyl)-4-methyloxazolidin-2-one

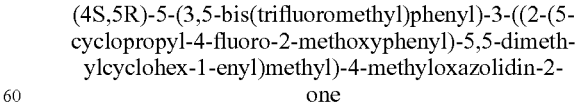

According to the same method as the synthesis of Compound 133, 3-fluoro-4-bromoanisole, a starting material, was subjected to several synthesis processes to obtain a boronic acid compound. The obtained compound was subjected to a Suzuki reaction with Compound 2. The obtained compound was reacted with Compound 4, to obtain an amino alcohol

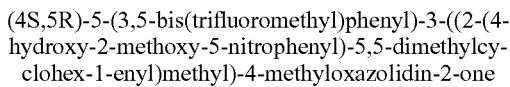
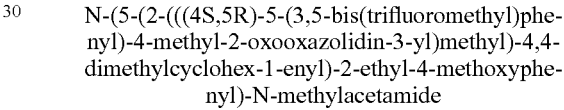

compound, which is an intermediate compound. The obtained amino alcohol compound was reacted with triphosgene, thus obtaining Compound 237 (2 mg, 22%) as white solid.

$^1$H NMR (400 MHz, CDCl$_3$); 1:1.3 atropisomer mixture; δ 7.85 (s, 1H), 7.73-7.72 (m, 2H), 6.57-6.44 (m, 2H), 5.60 (t, J=8.0, 1H), 3.98-3.88 (m, 2H), 3.71, 3.68 (2s, 3H), 3.50, 3.38 (2d, J=14.5, 1H), 2.45-1.87 (m, 4H), 1.49-1.40 (m, 2H), 1.02-0.92 (m, 6H), 0.91-0.82 (m, 4H), 0.63-0.59 (m, 1H), 0.40 (d, J=6.5, 1.3H), 0.32 (d, J=6.5, 1.7H). MS (ESI) m/z 600 (M$^+$+H).

Compound 240

1-((5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)(methyl)amino)-2-methyl-1-oxopropan-2-yl acetate Compound 240 (28 mg, 53%) as white solid was obtained according to the same method as the synthesis of compound 110.

$^1$H NMR (400 MHz, CDCl$_3$); atropisomer mixture; δ 7.85-7.74 (m, 3H), 7.11-7.07 (m, 1H), 6.86-6.78 (m, 1H), 5.65, 5.44 (2d, J=7.6, 1H), 4.12-3.32 (m, 6H), 3.26 (d, J=9.4, 3H), 2.45-1.88 (m, 7H), 1.49-1.47 (m, 6H), 1.45-1.39 (m, 2H), 1.02-0.97 (m, 6H), 0.65-0.36 (m, 3H). MS (ESI) m/z 767 (M$^+$+H).

Compound 241

(4S,5R)-5-(3,5-bis(trifluoromethyl)phenyl)-3-((2-(4-fluoro-5-isopropoxy-2-methoxyphenyl)-5,5-dimethylcyclohex-1-enyl)methyl)-4-methyloxazolidin-2-one According to the same method as the synthesis of Compound 133, 2-fluoro-4-methoxyphenol, a starting material, was subjected to several synthesis processes to obtain boronic acid compound. The obtained compound was subjected to a Suzuki reaction with Compound 2. And then the obtained compound was reacted with Compound 4, to obtain an amino alcohol compound, which is an intermediate compound. The obtained amino alcohol compound was reacted with triphosgene, thus obtaining Compound 241 (3 mg, 60%) as white solid.

$^1$H NMR (400 MHz, CDCl$_3$); 1:1.5 atropisomer mixture; δ 7.85 (s, 1H), 7.72 (s, 2H), 6.66-6.58 (m, 2H), 5.61 (dd, J=8.0, 4.6, 1H), 4.39-4.21 (m, 1H), 4.02-3.88 (m, 2H), 3.70, 3.67 (2s, 3H), 3.56, 3.46 (2d, J=14.5, 1H), 2.47-1.99 (m, 2H), 1.94-1.88 (m, 2H), 1.51-1.40 (m, 2H), 1.31 (d, J=6.0, 3H), 1.21-1.17 (m, 3H), 1.03-0.98 (m, 6H), 0.44 (d, J=6.5, 1.2H), 0.33 (d, J=6.5, 1.8H). MS (ESI) m/z 618 (M$^+$+H).

Compound 243

1-((3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)(methyl)amino)-2-methyl-1-oxopropan-2-yl acetate Compound 243 (32 mg, 50%) as yellow solid was obtained according to the same method as the synthesis of compound 110.

$^1$H NMR (400 MHz, CDCl$_3$); atropisomer mixture; δ 7.83 (s, 1H), 7.75 (s, 2H), 7.05 (d, J=8.6, 1H), 6.85-6.78 (m, 2H), 5.62-5.57 (m, 1H), 4.02-3.90 (m, 2H), 3.77, 3.74 (2s, 3H), 3.52 (d, J=14.7, 0.6H), 3.40 (d, J=14.7, 0.4H), 3.38-3.00 (bm, 3H), 2.42-2.07 (m, 2H), 2.02-1.87 (m, 2H), 1.70-1.40 (bm, 9H), 1.02-0.98 (m, 6H), 0.44-0.38 (m, 3H). MS (ESI) m/z 699 (M$^+$+H).

Compound 244

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-hydroxy-N,2-dimethylpropanamide Compound 243 (19 mg, 0.027 mmol) was added to methanol (0.8 mL). The solution of potassium carbonate (4 mg, 0.029 mmol) in water (0.2 mL) was added dropwise to the obtained mixture, and stirred at room temperature overnight. After the completion of the reaction, the reaction mixture was concentrated under reduced pressure, diluted with methylene chloride, washed with brine, dried with anhydrous magnesium sulfate, filtered, and concentrated under reduced pressure. The residue was separated by PTLC (silica, 70% Hexane/EtOAc), thus obtaining Compound 244 (11 mg, 65%) as white solid.

$^1$H NMR (400 MHz, CDCl$_3$); atropisomer mixture; δ 7.87 (s, 1H), 7.74 (d, J=5.7, 2H), 7.12-7.09 (m, 1H), 6.91-6.84 (m, 2H), 5.61 (dd, J=8.0, 2.1, 1H), 4.36 (bs, 1H), 4.06-3.93 (m, 2H), 3.82, 3.79 (2s, 3H), 3.53, 3.42 (2d, J=14.6, 1H), 3.29, 3.22 (2s, 3H), 2.47-1.99 (m, 2H), 1.94-1.92 (m, 2H), 1.56-1.46 (m, 2H), 1.20-1.10 (bm, 6H), 1.06-1.02 (m, 6H), 0.50, 0.41 (2d, J=6.5, 3H). MS (ESI) m/z 657 (M$^+$+H).

Compound 245

(4S,5R)-5-(3,5-bis(trifluoromethyl)phenyl)-3-((4-(4-fluoro-5-isopropyl-2-methoxyphenyl)-1-(trifluoromethyl)-1,2,5,6-tetrahydropyridin-3-yl)methyl)-4-methyloxazolidin-2-one Compound 219 (0.45 g, 0.67 mmol) was dissolved in methylene chloride (3 mL). Trifluoroacetic acid (1 mL) was added dropwise to the obtained solution at 0° C., and stirred at room temperature for 1 hour. After the completion of the reaction, the reaction mixture was concentrated under reduced pressure to remove the solvent. The residue was diluted with methylene chloride, washed with saturated sodium hydrogen carbonate solution and brine, dried with anhydrous magnesium sulfate, filtered, and concentrated under reduced pressure. The residue was crystallized, thus obtaining an intermediate compound (0.32 g, 88%) as white solid. The obtained compound was dissolved in tetrahydropuran (5 mL). Lithium diisopropyl silane (0.35 mL) was added to the obtained solution at −78° C., and stirred for 10 minutes. Carbon disulfide (24.6 µl) and iodomethane (34.3 µl) was added dropwise to the reaction mixture, and then stirred at room temperature for 30 minutes. After the completion of the reaction, the reaction mixture was concentrated under reduced pressure to remove the solvent. The residue was separated by MPLC (silica, 12 g, 20%~60%, Hexane/EtOAc), thus obtaining an intermediate compound (0.21 g, 85%) as colorless oil. The obtained intermediate compound (83.5 mg, 0.13 mmol) was dissolved in methylene chloride (5 mL). The solution of TBAH$_2$F$_3$ (0.19 g) and DBH (0.14 g) in methylene chloride (2 mL) was added dropwise slowly to the obtained solution at 0° C., and then stirred at 0° C. for 30 minutes. After the completion of the reaction, the reaction mixture was diluted with ethyl acetate, washed with water and brine, dried with anhydrous magnesium sulfate, filtered, and concentrated under reduced pressure, to remove the solvent. The residue was separated by MPLC (4 g silica, 3:1, Hexane/EtOAc), thus obtaining Compound 245 (12.5 mg, 15%) as white foam.

$^1$H NMR (400 MHz, CDCl$_3$); atropisomer mixture; δ 7.86 (s, 1H), 7.72 (s, 2H), 6.84-6.80 (m, 1H), 6.61-6.52 (m, 1H), 5.67-5.62 (m, 1H), 4.17-3.15 (m, 11H), 3.11 (m, 1H), 2.42-2.39 (m, 2H), 1.27-1.11 (m, 6H), 0.40-0.29 (m, 3H).

Compound 246

(4S,5R)-5-(3,5-bis(trifluoromethyl)phenyl)-3-((2-(2-methoxy-4-methyl-5-nitrophenyl)-5,5-dimethylcyclohex-1-enyl)methyl)-4-methyloxazolidin-2-one Compound 246 (0.13 g, 69.1%) as colorless oil was obtained according to the same method as the synthesis of compound 206.

$^1$H NMR (400 MHz, CDCl$_3$); atropisomer mixture; δ 7.86 (s, 1H), 7.76 (d, J=8.0, 1H), 7.73 (d, J=7.3, 2H), 6.72 (d, J=10.5, 1H), 5.60 (dd, J=38.2, 8.1, 1H), 3.97 (m, 2H), 3.87, 3.83 (2s, 3H), 3.55, 3.34 (2d, J=14.9, 1H), 2.64, 2.63 (2s, 3H), 2.40-1.92 (m, 4H), 1.50 (m, 2H), 1.05, 1.04, 1.01 (3s, 6H), 0.47, 0.45, 0.44, 0.43 (4s, 3H). MS (ESI) m/z 601 (M$^+$+H).

Compound 247

(4S,5R)-3-((2-(5-amino-2-methoxy-4-methylphenyl)-5,5-dimethylcyclohex-1-enyl)methyl)-5-(3,5-bis(trifluoromethyl)phenyl)-4-methyloxazolidin-2-one Compound 247 (76.6 mg, 73%) as colorless oil was obtained according to the same method as the synthesis of compound 195.

$^1$H NMR (400 MHz, CDCl$_3$); atropisomer mixture; δ 7.84 (s, 1H), 7.73 (s, 2H), 6.60, 6.54 (2s, 1H), 6.33, 6.31 (2s, 1H), 5.59, 5.57 (2d, J=8.0, 1H), 4.05-3.84 (m, 2H), 3.67-3.50 (m, 4H), 3.33 (brs, 2H), 2.49-1.90 (m, 7H), 1.50-1.41 (m, 2H), 1.03, 1.01, 0.99 (3s, 6H), 0.47, 0.31 (2d, J=6.6, 6.5, 3H). MS (ESI) m/z 571 (M$^+$+H).

Compound 248

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-methylphenyl)acetamide Compound 248 (28.8 mg, 67.1%) as colorless oil was obtained according to the same method as the synthesis of compound 110.

$^1$H NMR (400 MHz, CDCl$_3$); atropisomer mixture; δ 7.83-7.79 (m, 3H), 7.40, 7.21 (2s, 1H), 6.82, 6.76 (2s, 1H), 6.68, 6.65 (2s, 1H), 5.59, 5.46 (2d, J=8.0, 1H), 4.07 (m, 1H), 3.94 (m, 1H), 3.74, 3.73 (2s, 3H), 3.61, 3.39 (2d, J=14.7, 1H), 2.23-1.91 (m, 10H), 1.45 (m, 2H), 1.01, 1.00, 0.98 (3s, 6H), 0.44, 0.31 (2d, J=6.5, 3H). MS (ESI) m/z 613 (M$^+$+H).

Compound 249

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-methylphenyl)-N-methylacetamide Compound 249 (9.2 mg, 45.8%) as colorless oil was obtained according to the same method as the synthesis of compound 112.

$^1$H NMR (400 MHz, CDCl$_3$); atropisomer mixture; δ 7.86 (s, 1H), 7.73 (s, 2H), 6.77-6.70 (m, 2H), 5.61 (m, 1H), 4.03-3.91 (m, 2H), 3.78, 3.75, 3.74 (3s, 3H), 3.55-3.27 (m, 1H), 3.15, 3.14, 3.03 (3s, 3H), 2.50-1.45 (m, 12H), 1.13-0.96 (m, 6H). 0.48-0.31 (m, 3H). MS (ESI) m/z 627 (M$^+$+H).

Compound 250

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-methylphenyl)trifluoromethanesulfonamide Compound 250 (24.2 mg, 57.3%) as colorless oil was obtained according to the same method as the synthesis of compound 110.

$^1$H NMR (400 MHz, CDCl$_3$); atropisomer mixture; δ 7.84 (d, J=4.0, 1H), 7.72 (d, J=6.9, 2H), 7.01, 6.94 (2s, 1H), 6.72, 6.70 (2s, 1H), 5.60, 5.53 (2d, J=8.0, 1H), 3.93 (m, 2H), 3.77, 3.76 (2s, 3H), 3.57, 3.34 (2d, J=14.7, 1H), 2.43-1.91 (m, 7H), 1.47 (m, 2H), 1.02, 0.99, 0.98 (3s, 6H), 0.36, 0.29 (2d, J=6.5, 3H). MS (ESI) m/z 703 (M$^+$+H).

Compound 251

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-methylphenyl)trifluoro-N-methylmethanesulfonamide Compound 251 (9.5 mg, 42.8%) as colorless oil was obtained according to the same method as the synthesis of compound 112.

$^1$H NMR (400 MHz, CDCl$_3$); atropisomer mixture; δ 7.7.86, 7.84 (2s, 1H), 7.74, 7.71 (2s, 2H), 6.90-6.73 (m, 2H), 5.58-5.46 (m, 1H), 4.02-3.25 (m, 9H), 2.41-1.95 (m, 7H), 1.49 (m, 2H), 1.03, 1.01, 1.00 (3s, 6H), 0.44-0.32 (m, 3H). MS (ESI) m/z 717 (M$^+$+H).

Compound 259

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-methylethanethioamide Compound 112 (35 mg, 0.057 mmol) was dissolved in toluene (1.3 mL). Lawesson's reagent (23 mg, 0.06 mmol) was added dropwise to the solution, and then stirred at 80° C. overnight. After the completion of the reaction, the reaction mixture was concentrated under reduced pressure to remove the solvent. The residue was separated by MPLC (10-20% hexane/EtOAc), thus obtaining Compound 259 (28 mg, 78%) as solid.

$^1$H NMR (400 MHz, CDCl$_3$): atropisomer mixture; δ 7.86 (s, 1H), 7.73 (d, 2H, J=4.6 Hz), 7.06-7.03 (m, 1H), 6.91-6.86 (m, 1H), 6.83 (q, 1H, J=2.7 Hz), 5.62 (dd, 1H, J=4.1, 8.4 Hz), 4.05-3.91 (m, 2H), 3.81, 3.78 (2s, 3H), 3.70, 3.64 (2s, 3H), 3.49, 3.39 (2d, 1H, J=14.5 Hz), 2.49-2.43 (m, 1H), 2.38, 2.34 (2s, 3H), 2.29-2.00 (m, 2H), 1.93-1.85 (m, 2H), 1.53-1.43 (m, 2H), 1.05-1.01 (m, 6H), 0.47, 0.36 (2d, 3H, J=6.6 Hz); MS (ESI) m/z 629.0 (M$^+$+H).

Compound 261

(4S,5R)-5-(3,5-bis(trifluoromethyl)phenyl)-3-((4-(4-fluoro-5-isopropyl-2-methoxyphenyl)-1-(2,2,2-trifluoroacetyl)-1,2,5,6-tetrahydropyridin-3-yl)methyl)-4-methyloxazolidin-2-one Compound 267 (0.05 g, 0.087 mmol) was dissolved in anhydrous methylene chloride (20 mL). Triethylamine (0.02 mL) and trifluoroacetic anhydride (0.02 g) were added dropwise to the obtained solution at room temperature, and stirred at room temperature overnight. After the completion of the reaction, the reaction mixture was washed with saturated ammonium chloride solution and water, dried with anhydrous magnesium sulfate, filtered, and concentrated under reduced pressure. The residue was separated by MPLC (silica, 4:1=hexane: EtOAc), thus obtaining Compound 261 (0.04 g, 72%) as white solid foam.

$^1$H NMR (400 MHz, MeOD); atropisomer mixture; δ 7.99 (s, 1H), 7.93 (m, 2H), 7.06 (m, 1H), 6.79 (m, 1H), 5.87 (m, 1H), 4.20-3.62 (m, 10H), 3.16 (m, 1H), 2.75-2.30 (m, 2H), 1.21 (m, 6H), 0.43 (m, 3H).

Compound 262

(4S,5R)-5-(3,5-bis(trifluoromethyl)phenyl)-3-((4-(4-fluoro-5-isopropyl-2-methoxyphenyl)-1-(trifluoromethylsulfonyl)-1,2,5,6-tetrahydropyridin-3-yl)methyl)-4-methyloxazolidin-2-one Compound 262 (37 mg, 60%) as white solid foam was obtained according to the same method as the synthesis of compound 261.

$^1$H NMR (400 MHz, MeOD); atropisomer mixture; δ 7.99 (s, 1H), 7.90 (m, 2H), 7.06 (m, 1H), 7.79 (m, 1H), 5.87 (m, 1H), 4.86 (s, 2H), 4.29-3.57 (m, 10H), 3.16 (m, 1H), 2.7-2.25 (m, 2H), 1.2 (m, 6H), 0.43 (m, 3H).

Compound 263

(4S,5R)-3-((1-acetyl-4-(4-fluoro-5-isopropyl-2-methoxyphenyl)-1,2,5,6-tetrahydropyridin-3-yl)methyl)-5-(3,5-bis(trifluoromethyl)phenyl)-4-methyloxazolidin-2-one Compound 263 (42 mg, 78%) as white solid foam was obtained according to the same method as the synthesis of compound 261.

$^1$H NMR (400 MHz, MeOD); atropisomer mixture; δ 7.98 (s, 1H), 7.93 (m, 2H), 7.03 (m, 1H), 6.78 (m, 1H), 5.86 (m, 1H), 4.20-3.52 (m, 10H), 3.15 (m, 1H), 2.70-2.30 (m, 2H), 2.20 (m, 3H), 1.21 (m, 6H), 0.43 (m, 3H); MS (ESI): 616.0 (M)$^+$.

Compound 264

(4S,5R)-5-(3,5-bis(trifluoromethyl)phenyl)-3-((4-(4-fluoro-5-isopropyl-2-methoxyphenyl)-1-(methylsulfonyl)-1,2,5,6-tetrahydropyridin-3-yl)methyl)-4-methyloxazolidin-2-one Compound 264 (45 mg, 79%) as white solid foam was obtained according to the same method as the synthesis of compound 261.

$^1$H NMR (400 MHz, MeOD); atropisomer mixture; δ 7.98 (s, 1H), 7.92 (s, 2H), 7.05, 6.98 (2d, 1H, J=8.64, 8.64 Hz), 6.78, 6.75 (2d, 1H, J=8.44, 8.40 Hz), 4.2-3.0 (m, 12H), 2.70-2.20 (m, 2H), 1.26 (m, 6H), 0.42 (m, 3H); MS (ESI): 652.0 (M)$^+$.

Compound 265

(4S,5R)-5-(3,5-bis(trifluoromethyl)phenyl)-3-((4-(4-fluoro-5-isopropyl-2-methoxyphenyl)-1-isopropyl-1,2,5,6-tetrahydropyridin-3-yl)methyl)-4-methyloxazolidin-2-one Compound 267 (0.05 g, 0.087 mmol) was dissolved in methanol (20 mL). 2-Iodopropane (0.02 mL) was added dropwise to the obtained solution, and stirred at room temperature overnight. After the completion of the reaction, the reaction mixture was concentrated under reduced pressure to remove the solvent. The residue was separated by PTLC (SiO$_2$, EA:DCM:MeOH=5:4:1, thus obtaining Compound 265 (3 mg, 6%) as white solid foam.

$^1$H NMR (400 MHz, MeOD); atropisomer mixture; δ 8.00 (s, 1H), 7.92 (s, 2H), 7.05 (m, 1H), 6.78 (m, 1H), 5.90 (m, 1H), 4.30-2.20 (m, 11H), 1.26 (m, 6H), 0.42 (m, 3H); MS (ESI): 616.7 (M)$^+$.

Compound 267

(4S,5R)-5-(3,5-bis(trifluoromethyl)phenyl)-3-((4-(4-fluoro-5-isopropyl-2-methoxyphenyl)-1,2,5,6-tetrahydropyridin-3-yl)methyl)-4-methyloxazolidin-2-one Compound 219 (1.65 g, 2.46 mmol) was dissolved in methylene chloride (10 mL). Trifluoroacetic acid (3 mL) was added dropwise to the obtained solution at room temperature, and stirred at room temperature for 1 hour. After the completion of the reaction, ethyl acetate was added dropwise to the reaction mixture. And then, the obtained reaction mixture washed with saturated sodium hydrogen carbonate solution, water and brine, and concentrated under reduced pressure. The obtained residue was separated by MPLC (SiO$_2$, 5%-20% DCM/MeOH), thus obtaining Compound 267 (1.0 g, 71%) as white foam.

$^1$H NMR (400 MHz, CDCl$_3$); atropisomer mixture; δ 7.84 (s, 1H), 7.72 (s, 2H), 6.89, 6.84 (2d, J=8.6, 8.5 Hz, 1H), 6.57, 6.53 (2d, J=12.1 Hz, 1H), 5.70, 5.67 (2d, J=8.0 Hz, 1H), 4.03-3.99 (m, 2H), 3.76, 3.71 (2s, 3H), 3.60-3.41 (m, 4H), 3.28-3.06 (m, 3H), 2.66-2.12 (m, 4H), 1.26-1.10 (m, 6H), 0.33, 0.29 (2d, J=6.5 Hz, 3H); MS (ESI): 575 (M$^+$+H).

Compound 268

(4S,5R)-5-(3,5-bis(trifluoromethyl)phenyl)-3-((4-(4-fluoro-5-isopropyl-2-methoxyphenyl)-1-(2,2,2-trifluoroethyl)-1,2,5,6-tetrahydropyridin-3-yl)methyl)-4-methyloxazolidin-2-one Compound 268 (14 mg, 25%) as white solid foam was obtained according to the same method as the synthesis of compound 265.

$^1$H NMR (400 MHz, MeOD); atropisomer mixture; δ 7.87 (s, 1H), 7.72 (s, 2H), 6.91, 6.86 (2d, 1H, J=8.56, 8.60 Hz), 6.60, 6.56 (2d, 1H, J=12.12, 12.08 Hz), 5.60 (m, 1H), 4.0 (m, 2H), 3.80-2.80 (m, 11H), 2.70-2.30 (m, 2H), 1.21 (m, 6H), 0.40, 0.33 (2d, 3H, J=6.52, 6.56 Hz); MS (ESI): 656.7 (M)$^+$.

Compound 271

N-(3-(2-(((4S,5R)-5-(3,5-bis(trifluoromethyl)phenyl)-4-methyl-2-thiooxooxazolidin-3-yl)methyl)-4,4-dimethylcyclohex-1-enyl)-4-methoxyphenyl)-N-methylacetamide Compound 112 (60 mg, 0.098 mmol) was dissolved in 2-propanol (0.6 mL). The solution of potassium hydroxide (28 mg) in water (0.1 mL) was added dropwise to the obtained solution at room temperature, and stirred at 80° C. overnight. After the completion of the reaction, the reaction mixture was cooled down to room temperature, and concentrated under reduced pressure to remove the solvent. Ethyl acetate was added dropwise to the residue. The obtained mixture was washed with water and brine, and concentrated under reduced pressure. The obtained residue was separated by MPLC (SiO$_2$, 10%-70% Hexane/EtOAc), thus obtaining an amino alcohol compound (26 mg, 45%) as colorless oil. The obtained amino alcohol compound was dissolved in methylene chloride (1.5 mL). Thiophosgene (2 μL, 0.02 mmol) and diisopropylamine (0.05 mL, 0.27 mmol) were added dropwise to the obtained solution, and then stirred at room temperature for 2 hours. After the completion of the reaction, the reaction mixture was diluted with methylene, and washed with water and brine. The organic layer was dried with anhydrous magnesium sulfate, filtered, and concentrated under reduced pressure. The residue was separated by MPLC (SiO$_2$, 30%-90% hexane/EtOAc), thus obtaining Compound 271 (12 mg, 43%) as yellow solid.

$^1$H NMR (400 MHz, CDCl$_3$); atropisomer mixture; δ 7.88 (s, 1H), 7.75 (s, 2H), 7.06 (dt, 1H, J=2.4, 8.6 Hz), 6.90-6.81 (m, 2H), 5.77-5.74 (m, 1H), 4.66-4.63 (m, 1H), 4.25-4.09 (m, 1H), 3.83, 3.79 (2s, 3H), 3.72, 3.66 (2d, 1H, J=14.8 Hz), 3.22, 3.14 (2s, 3H), 2.53-1.89 (m, 4H), 1.84, 1.79 (2s, 3H), 1.53-1.44 (m, 2H), 1.05-1.02 (m, 6H), 0.51, 0.37 (2d, 1H, J=6.7 Hz); MS (ESI) m/z 628.8 (M$^+$).

Compound 272 methyl 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)propanoate Compound 272 (0.12 g, 95.9%) as white solid foam was obtained according to the same method as the synthesis of compound 133.

$^1$H NMR (400 MHz, CDCl$_3$); atropisomer mixture; δ 7.85 (s, 1H), 7.75 (m, 2H), 7.27 (2d, 1H, J=2.12, 2.08 Hz), 6.83 (m, 2H), 5.60 (m, 1H), 4.05-3.41 (m, 9H), 2.89 (m, 2H), 2.6 (m, 2H), 2.50-2.00 (m, 2H), 1.89 (m, 2H), 1.50 (m, 2H), 1.05 (m, 6H), 0.40 (m, 3H).

Compound 273

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)propanoic acid Compound 273 (2 mg, 1.9%) as colorless oil was obtained according to the same method as the synthesis of compound 134.

$^1$H NMR (400 MHz, CDCl$_3$); atropisomer mixture; δ 7.86 (s, 1H), 7.73 (s, 2H), 7.05-7.07 (m, 1H), 6.74-6.85 (m, 2H), 5.56-5.61 (m, 1H), 3.72-3.89 (m, 3H), 3.42-3.58 (m, 1H), 2.83-2.90 (m, 2H), 2.61-2.66 (m, 2H), 2.26-2.59 (m, 2H), 1.87-1.93 (m, 2H), 1.44-1.53 (m, 2H), 1.01-1.05 (m, 6H), 0.30, 0.45 (2d, 3H, J=4.86, 4.92 Hz); MS (ESI) m/z 614.2 (M$^+$+H).

Compound 274

(4S,5R)-5-(3,5-bis(trifluoromethyl)phenyl)-3-((6-(4-fluoro-5-isopropyl-2-methoxyphenyl)spiro[2.5]oct-5-en-5-yl)methyl)-4-methyloxazolidin-2-one Compound 274 (0.12 g, 76.5%) as white solid was obtained according to the same method as the synthesis of compound 18.

$^1$H NMR (400 MHz, CDCl$_3$); atropisomer mixture; δ 7.86 (s, 1H), 7.72 (d, J=0.4 Hz, 2H), 6.84, 6.80 (2d, J=8.7 Hz, 1H), 6.56, 6.52 (2d, J=12.2 Hz, 1H), 5.59 (t, J=8.4 Hz, 1H), 4.01-3.88 (m, 2H), 3.73, 3.71 (2s, 3H), 3.59, 3.46 (2d, J=14.6 Hz, 1H), 3.13 (m, 1H), 2.44-1.13 (m, 16H), 0.44-0.34 (m, 7H); MS (ESI): 600 (M$^+$+H).

Compound 275 tert-butyl 6-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxyindoline-1-carboxylate tert-Butyl 5-methoxy-6-(4,4,5,5-tetramethyl-1,3,2-dioxaborolane-2-yl)indoline-1-carboxylate was synthesized using 4-methoxyindoline as a starting material, and then Compound 275 (0.24 g, 72.1%) as white solid foam was obtained according to the similar method to the synthesis of compound 133.

$^1$H NMR (400 MHz, CDCl$_3$); atropisomer mixture; δ 7.84, 7.77, 7.73 (3s, 3H), 7.53-7.05 (brs, 1H), 6.70, 6.66 (2s, 1H), 5.65-5.58 (m, 1H), 4.10-3.88 (m, 4H), 3.71-3.39 (m, 4H), 3.07-3.02 (m, 2H), 2.45-1.85 (m, 4H), 1.51-1.18 (m, 16H), 1.02-0.94 (m, 6H), 0.85 (m, 3H), 0.43, 0.37 (2d, 3H, J=6.5, 6.3 Hz); MS (ESI): 683 (M$^+$+H).

Compound 276

(4S,5R)-5-(3,5-bis(trifluoromethyl)phenyl)-3-((2-(5-methoxyindolin-6-yl)-5,5-dimethylcyclohex-1-enyl)methyl)-4-methyloxazolidin-2-one Compound 276 (0.13 g, 63.5%) as colorless oil was obtained according to the same method as the synthesis of compound 267.

$^1$H NMR (400 MHz, CDCl$_3$); atropisomer mixture; δ 7.84 (s, 1H), 7.73 (s, 2H), 6.74, 6.67 (2s, 1H), 6.31, 6.29 (2s, 1H), 5.59, 5.58 (2s, 1H), 4.05-3.87 (m, 2H), 3.67-3.63 (m, 4H), 3.55-2.48 (m, 3H), 3.01-2.97 (m, 2H), 2.45-1.86 (m, 4H), 1.45 (m, 2H), 1.03, 1.01, 0.99 (3s, 6H), 0.48, 0.33 (2d, 3H, J=6.5 Hz); MS (ESI): 583 (M$^+$+H).

Compound 277

(4S,5R)-3-((2-(1-acetyl-5-methoxyindolin-6-yl)-5,5-dimethylcyclohex-1-enyl)methyl)-5-(3,5-bis(trifluoromethyl)phenyl)-4-methyloxazolidin-2-one Compound 277 (18 mg, 64.6%) as colorless oil was obtained according to the same method as the synthesis of compound 261.

$^1$H NMR (400 MHz, CDCl$_3$); atropisomer mixture; δ 7.91-7.74 (m, 4H), 6.71 (d, 1H, J=12.7 Hz), 6.54, 5.50 (2d, 1H, J=8.08, 8.04 Hz), 4.12-3.91 (m, 4H), 3.73, 3.72 (2s, 3H), 3.59, 3.37 (2d, 1H, J=14.7 Hz), 3.17 (m, 2H), 2.37-1.91 (m, 6H), 1.46 (m, 2H), 1.02, 1.00, 0.99 (3s, 6H), 0.41, 0.38 (2d, 3H, J=6.5 Hz); MS (ESI): 625 (M$^+$+H).

Compound 278

(4S,5R)-5-(3,5-bis(trifluoromethyl)phenyl)-3-((2-(5-methoxy-1-(2,2,2-trifluoroethyl)indolin-6-yl)-5,5-dimethylcyclohex-1-enyl)methyl)-4-methyloxazolidin-2-one Compound 278 (4 mg, 11.3%) as colorless oil was obtained according to the same method as the synthesis of compound 261.

$^1$H NMR (400 MHz, CDCl$_3$); atropisomer mixture; δ 7.85 (s, 1H), 7.73 (s, 2H), 6.74, 6.68 (2s, 1H), 6.12 (s, 1H), 5.58, 5.56 (2d, 1H, J=4.2 Hz), 4.03-3.85 (m, 2H), 3.69, 3.67 (2s, 3H), 3.63-3.38 (m, 5H), 3.02-2.98 (m, 2H), 2.47-1.87 (m, 6H), 1.47 (m, 2H), 1.25 (m, 6H), 0.37, 0.35 (2d, 3H, J=6.5 Hz); MS (ESI): 665 (M$^+$+H).

Compound 280

(4S,5R)-5-(3,5-bis(trifluoromethyl)phenyl)-3-((2-(5-methoxy-1-(methylsulfonyl)indolin-6-yl)-5,5-dimethylcyclohex-1-enyl)methyl)-4-methyloxazolidin-2-one Compound 280 (19 mg, 64.4%) as colorless oil was obtained according to the same method as the synthesis of compound 261.

$^1$H NMR (400 MHz, CDCl$_3$); atropisomer mixture; δ 7.85 (s, 1H), 7.74 (s, 2H), 7.06 (d, 1H, J=16.2 Hz), 6.75 (d, 1H, J=13.6 Hz), 5.59 (2d, 1H, J=8.2 Hz), 3.99-3.87 (m, 4H), 3.75-3.72 (2s, 3H), 3.52, 3.33 (2d, 1H, J=14.9, 14.6 Hz), 3.14-3.09 (m, 2H), 2.84, 2.79 (2s, 3H), 2.38-1.91 (m, 4H), 1.45 (m, 2H), 1.03, 1.01, 1.00 (3s, 6H), 0.47, 0.41 (2d, 3H, J=6.5 Hz); MS (ESI): 661, 683 (M$^+$+H).

Compound 281 tert-butyl 4-(((4S,5R)-5-(3,5-bis(trifluoromethyl)phenyl)-4-methyl-2-oxooxazolidin-3-yl)methyl)-3-(4-fluoro-5-isopropyl-2-methoxyphenyl)-5,6-dihydropyridine-1(2H)-carboxylate Compound 281 (0.38 g, 88%) as white solid foam was obtained according to the same method as the synthesis of compound 219.

$^1$H NMR (400 MHz, CDCl$_3$); atropisomer mixture; δ 7.86 (s, 1H), 7.71 (s, 2H), 6.87 (dd, 1H, J=13.4, 8.7 Hz), 6.57 (dd, 1H, J=14.8, 12.0 Hz), 5.61 (d, 1H, J=7.9 Hz), 4.25-3.83 (m, 4H), 3.71, 3.68 (2s, 3H), 3.47-3.44 (m, 1H), 3.15-3.10 (m, 1H), 2.30-2.25 (m, 2H), 1.48 (s, 9H), 1.24-1.12 (m, 6H), 0.42, 0.37 (2d, 3H, J=6.5 Hz).

Compound 282

(4S,5R)-5-(3,5-bis(trifluoromethyl)phenyl)-3-((3-(4-fluoro-5-isopropyl-2-methoxyphenyl)-1,2,5,6-tetrahydropyridin-4-yl)methyl)-4-methyloxazolidin-2-one Compound 282 (0.19 g, 61%) as white solid foam was obtained according to the same method as the synthesis of compound 267.

$^1$H NMR (400 MHz, CDCl$_3$); atropisomer mixture; δ 7.82 (s, 1H), 7.74 (d, 2H, J=5.5 Hz), 6.92, 6.83 (2d, 1H, J=8.4 Hz), 6.55 (dd, 1H, J=18.5, 12.0 Hz), 5.69 (dd, 1H, J=13.5, 8.0 Hz), 5.44 (brs, 1H), 4.18-4.01 (m, 2H), 3.84 (d, 0.6H, J=16.7 Hz), 3.73, 3.72 (2s, 3H), 3.69-3.35 (m, 3.4H), 3.20-3.07 (m, 2H), 2.62-2.52 (m, 1H), 2.33-2.27 (m, 1H), 1.24-1.09 (m, 6H), 0.38, 0.31 (2d, 1H, J=6.6 Hz).

Compound 283

(4S,5R)-5-(3,5-bis(trifluoromethyl)phenyl)-3-((3-(4-fluoro-5-isopropyl-2-methoxyphenyl)-1-(2,2,2-trifluoroethyl)-1,2,5,6-tetrahydropyridin-4-yl)methyl)-4-methyloxazolidin-2-one Compound 283 (40 mg, 88%) as brown oil was obtained according to the same method as the synthesis of compound 265.

$^1$H NMR (400 MHz, CDCl$_3$); atropisomer mixture; δ 7.85 (s, 1H), 7.72 (s, 2H), 6.85 (t, 1H, J=9.0 Hz), 6.55 (dd, 1H, J=16.5, 12.0 Hz), 5.62 (dd, 1H, J=7.9, 6.0 Hz), 4.05-3.95 (m, 2H), 3.74, 3.71 (2s, 3H), 3.56-3.22 (m, 2.5H), 3.19-3.06 (m, 3.5H), 3.03-2.98 (m, 1H), 2.94-2.87 (m, 1H), 2.39-2.25 (m, 2H), 1.25-1.12 (m, 6H), 0.43, 0.35 (2d, 1H, J=6.6 Hz).

Compound 284

(4S,5R)-5-(3,5-bis(trifluoromethyl)phenyl)-3-((3-(4-fluoro-5-isopropyl-2-methoxyphenyl)-1-(trifluoromethylsulfonyl)-1,2,5,6-tetrahydropyridin-4-yl)methyl)-4-methyloxazolidin-2-one Compound 284 (27 mg, 54%) as brown oil was obtained according to the same method as the synthesis of compound 261.

$^1$H NMR (400 MHz, CDCl$_3$); atropisomer mixture; δ 7.87 (s, 1H), 7.72 (s, 2H), 6.84 (t, 1H, J=8.4 Hz), 5.63 (t, 1H, J=9.1 Hz), 4.41 (brd, 0.5H, J=16.6 Hz), 4.12-3.80 (m, 5 H), 3.74, 3.73 (2s, 3H), 3.58 (brd, 1.5H, J=14.8 Hz), 3.17-3.08 (m, 1H), 2.53-2.34 (m, 2H), 1.25-1.09 (m, 6H), 0.49, 0.37 (2d, 1H, J=6.6 Hz); MS (ESI) m/z 706.8 (M$^+$).

Compound 285 methyl 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2-dimethylpropanoate As shown in reaction scheme 6, Compound 22, an intermediate compound, was synthesized, and then subjected to reductive amination using Compound 4, which is an amino alcohol compound, to synthesize Compound 23. The obtained Compound 23 (0.21 g, 0.34 mmol) was dissolved in methylene chloride (3 mL). Diisopropylamine (0.36 mL) and triphosgene (0.15 g) were added dropwise in sequence to the obtained solution at room temperature, and stirred at room temperature for 2 hours. After the completion of the reaction, the reaction mixture was diluted with ethyl acetate, washed with water and brine, dried with anhydrous magnesium sulfate, filtered, and concentrated under reduced pressure to remove the solvent. The residue was separated by MPLC (12 g silica, 3:1=n-hexane: EtOAc), thus obtaining Compound 285 (0.1 g, 45%) as white solid foam.

$^1$H NMR (400 MHz, DMSO-d$_6$); atropisomer mixture; δ 7.85 (s, 1H), 7.73 (d, 1H, J=9.4 Hz), 6.92-6.95 (m, 1H), 6.67-6.77 (m, 2H), 5.58-5.61 (m, 1H), 3.87-4.01 (m, 2H), 3.71, 3.73 (2s, 3H), 3.63, 3.64 (2s, 3H), 3.50, 3.59 (2d, 1H, J=11.25, 10.86 Hz), 2.73-2.77 (m, 2H), 2.15-2.50 (m, 2H), 1.90-2.05 (m, 2H), 1.45-1.50 (m, 2H), 1.12-1.15 (m, 6H), 0.90-1.04 (m, 6H), 0.28, 0.41 (2d, 3H, J=4.86, 4.92 Hz); MS (ESI) m/z 656 (M$^+$+H).

Compound 286

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2-dimethylpropanoic acid Compound 286 (27 mg, 42.4%) as white solid foam was obtained according to the same method as the synthesis of compound 134.

$^1$H NMR (400 MHz, DMSO-d$_6$); atropisomer mixture; δ 7.85 (s, 1H), 7.73-7.75 (m, 2H), 6.99-7.02 (m, 1H), 6.72-6.81 (m, 2H), 5.61 (d, 1H, J=8.1 Hz), 3.88-4.02 (m, 2H), 3.71-3.74 (m, 3H), 3.52, 3.58 (2d, 1H, J=14.96, 14.52 Hz), 2.72-2.87 (m, 2H), 2.00-2.50 (m, 2H), 1.93 (m, 2H), 1.14-1.17 (m, 6H), 0.99-1.04 (m, 6H), 0.28, 0.44 (d, 3H, J=6.52, 6.56 Hz); MS (ESI) m/z 656, 547 (M$^+$+H).

Compound 291

(R)—N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3,3,3-trifluoro-2-methoxy-2-phenylpropanamide Compound 291 (53 mg, 76%) as white solid foam was obtained according to the same method as the synthesis of compound 110.

$^1$H NMR (400 MHz, CDCl$_3$); atropisomer mixture; δ 8.55, 8.53 (2s, 1H), 7.87-6.81 (m, 11H, ArH), 5.60 (d, 0.5H, J=8.2), 5.53 (d, 0.5H, J=8.1), 4.08-3.93 (m, 2H), 3.77, 3.76 (2s, 3H), 3.52-3.56 (m, 4H), 2.48-2.08 (m, 3H), 1.92 (broad signal, 2H), 1.55-1.39 (m, 2H), 1.04, 1.01 (2s, 6H), 0.40 (d, 1.5H, J=6.5), 0.36 (d, 1.5H, J=6.5); MS (ESI) m/z 773.2 (M$^+$+H).

Compound 292

(S)—N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3,3,3-trifluoro-2-methoxy-2-phenylpropanamide Compound 292 (54 mg, 78%) as white solid foam was obtained according to the same method as the synthesis of compound 110.

$^1$H NMR (400 MHz, CDCl$_3$); atropisomer mixture; δ 8.54, 8.50 (2s, 1H), 7.87-6.80 (m, 11H, ArH), 5.59 (d, 0.5H, J=8.1), 5.55 (d, 0.5H, J=8.1), 4.06-3.94 (m, 2H), 3.77, 3.76 (2s, 3H), 3.55-3.37 (m, 4H), 2.48-2.06 (m, 3H), 1.91 (broad signal, 2H), 1.54-1.40 (m, 2H), 1.04, 1.03, 1.01 (3s, 6H), 0.39 (d, 1.5H, J=6.5), 0.33 (d, 1.5H, J=6.5); MS (ESI) m/z 773.2 (M$^+$+H).

Compound 293

(4S,5R)-5-(3,5-bis(trifluoromethyl)phenyl)-3-((6-(2-methoxyphenyl)spiro[2.5]oct-5-en-5-yl)methyl)-4-methyloxazolidin-2-one Compound 293 (0.73 g, 71%) as white solid foam was obtained according to the same method as the synthesis of compound 18.

$^1$H NMR (400 MHz, CDCl$_3$); atropisomer mixture; δ 7.85 (s, 1H), 7.72 (s, 2H), 7.25-7.20 (m, 1H), 7.04-6.83 (m, 3H), 5.58 (t, 1H, J=8.5 Hz), 4.03-3.90 (m, 2H), 3.75, 3.74 (2s, 3H), 3.59, 3.48 (2d, 1H, J=15.0, 14.6 Hz), 2.47-1.21 (m, 10H), 0.44-0.31 (m, 7H); MS (ESI): 542 (M$^+$+H).

Compound 294

(4S,5R)-5-(3,5-bis(trifluoromethyl)phenyl)-3-((6-(2-methoxy-5-nitrophenyl)spiro[2.5]oct-5-en-5-yl)methyl)-4-methyloxazolidin-2-one Compound 294 (0.73 g, 71%) as white solid foam was obtained according to the same method as the synthesis of compound 52.

$^1$H NMR (400 MHz, CDCl$_3$); atropisomer mixture; δ 8.18-8.14 (m, 1H), 7.94 (dd, 1H, J=9.8, 2.8 Hz), 7.85 (s, 1H), 7.71 (d, 2H, J=4.7 Hz), 6.95 (t, 1H, J=9.4 Hz), 5.63, 5.58 (2d, 1H, J=8.1 Hz), 4.01-3.94 (m, 2H), 3.91, 3.88 (2s, 3H), 3.53, 3.36 (2d, 1H, J=15.0 Hz), 2.39-1.31 (m, 7H), 0.46-0.35 (m, 7H); MS (ESI) m/z 585 (M$^+$+H).

Compound 295

(4S,5R)-3-((6-(5-amino-2-methoxyphenyl)spiro[2.5]oct-5-en-5-yl)methyl)-5-(3,5-bis(trifluoromethyl)phenyl)-4-methyloxazolidin-2-one Compound 294 (0.21 g, 0.36 mmol) was dissolved in methanol (3 mL). Raney-nickel (3 mL) was added dropwise to the obtained solution at room temperature, and stirred under hydrogen gas overnight. After the completion of the reaction, the reaction mixture was filtered with celite, and concentrated under reduced pressure to remove the solvent. The residue was separated by MPLC (25%-60% n-hexane/EtOAc), thus obtaining Compound 295 (0.12 g, 60%) as colorless oil.

$^1$H NMR (400 MHz, CDCl$_3$); atropisomer mixture; δ 7.84 (s, 1H), 7.71 (d, 2H, J=4.1 Hz), 6.73-6.46 (m, 2H), 5.59, 5.53 (2d, 1H, J=8.0 Hz), 4.09-3.89 (m, 2H), 3.74, 3.70 (2s, 3H), 3.70-3.49 (m, 1H), 2.47-1.23 (m, 7H), 0.50-0.35 (m, 7H); MS (ESI) m/z 555 (M$^+$+H).

Compound 296

(R)—N-(3-(5-(((4S,5R)-5-(3,5-bis(trifluoromethyl)phenyl)-4-methyl-2-oxooxazolidin-3-yl)methyl)spiro[2.5]oct-5-en-6-yl)-4-methoxyphenyl)-3,3,3-trifluoro-2-methoxy-2-phenylpropanamide Compound 296 (15 mg, 15%) as white solid was obtained according to the same method as the synthesis of compound 110.

$^1$H NMR (400 MHz, CDCl$_3$); atropisomer mixture; δ 8.56 (s, 1H), 7.97-7.94 (m, 1H), 7.85-7.69 (m, 3H), 7.51 (m, 2H), 7.44-7.34 (m, 4H), 6.84 (t, 1H, J=8.6 Hz), 5.56, 5.52 (2d, 1H, J=8.2 Hz), 4.11-3.89 (m, 3H), 3.77, 3.76 (2s, 3H), 3.56-3.34 (m, 4H), 2.44-1.24 (m, 11H), 0.46-0.29 (m, 9H); MS (ESI) m/z 771 (M$^+$+H).

Compound 297

(S)—N-(3-(5-(((4S,5R)-5-(3,5-bis(trifluoromethyl)phenyl)-4-methyl-2-oxooxazolidin-3-yl)methyl)spiro[2.5]oct-5-en-6-yl)-4-methoxyphenyl)-3,3,3-trifluoro-2-methoxy-2-phenylpropanamide Compound 297 (17 mg, 21%) as white solid was obtained according to the same method as the synthesis of compound 110.

$^1$H NMR (400 MHz, CDCl$_3$); atropisomer mixture; δ 8.55, 8.53 (2s, 1H), 7.84 (s, 1H), 7.72-7.65 (m, 3H), 7.56 (m, 1H), 7.43-7.40 (m, 3H), 7.33-7.17 (m, 3H), 6.84, 6.81 (2d, 1H, J=8.9 Hz), 5.54 (d, 1H, J=8.1 Hz), 4.04-3.89 (m, 3H), 3.77, 3.76 (2s, 3H), 3.57-3.39 (m, 4H), 2.45-1.23 (m, 9H), 0.46-0.34 (m, 8H); MS (ESI) m/z 771 (M$^+$+H).

Compound 298

(R)—N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3,3,3-trifluoro-2-methoxy-N-methyl-2-phenylpropanamide Compound 298 (30 mg, 82%) as white solid was obtained according to the same method as the synthesis of compound 112.

$^1$H NMR (400 MHz, CDCl$_3$); atropisomer mixture; δ 7.85 (m, 1H), 7.72-7.78 (m, 2H), 7.59-7.60 (m, 1H), 7.41-7.45 (m, 2H), 7.30-7.36 (m, 2H), 7.01-7.04 (m, 1H), 6.84-6.90 (m, 2 h), 5.57-5.59 (m, 1H), 3.90-4.10 (m, 2H), 3.82-3.85 (m, 3H), 3.47-3.65 (m, 3H), 3.47-3.65 (m, 3H), 2.91-3.29 (m, 3H), 2.10-2.50 (m, 2H), 1.80-2.00 (m, 2H), 1.46-1.50 (m, 2H), 0.94-1.04 (m, 6H), 0.29-0.50 (m, 3H); MS (ESI) m/z 787 (M$^+$+H).

Compound 299

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)propanamide Compound 273 (0.48 g, 0.78 mmol) was dissolved in methylene chloride (5 mL). Thionyl chloride (0.1 mL) and dimethylformamide (1 drop) were added dropwise to the obtained solution, and stirred for 5 hours. After the completion of the reaction, the reaction mixture was cooled down to room temperature, and concentrated under reduced pressure to remove the solvent. The residue was dissolved in tetrahydropuran (10 mL). Ammonia water (2 mL) was added dropwise to the obtained solution, and stirred for 1 hour at room temperature. Ethyl acetate was added dropwise to the reaction mixture. And then, the obtained reaction mixture was washed with water and brine, dried with anhydrous magnesium sulfate, filtered, and concentrated under reduced pressure. The residue was separated by MPLC ($SiO_2$, 4:1 hexane/EtOAc), thus obtaining Compound 299 (0.39 g, 84%) as colorless oil.

$^1$H NMR (400 MHz, DMSO-$d_6$); atropisomer mixture; δ 7.86 (s, 1H), 7.73 (d, 1H, J=4.6 Hz), 7.04-7.08 (m, 1H), 6.73-6.87 (m, 2H), 5.47-5.62 (m, 3H), 3.93-3.97 (m, 2H), 3.71, 3.77 (2s, 3H), 3.38, 3.55 (2d, 1H, J=11.25, 10.89 Hz), 2.85-2.91 (m, 2H), 2.44-2.51 (m, 2H), 1.90-2.30 (m, 4H), 1.45-1.48 (m, 2H), 1.01-1.05 (m, 6H), 0.33, 0.47 (2d, 3H, J=4.89, 4.92 Hz); MS (ESI) m/z 613.2 ($M^+$+H).

Compound 300

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)propanenitrile Compound 299 (0.19 g, 0.32 mmol) was dissolved in pyridine (5 mL). Phosphoryl chloride (0.12 mL) and imidazole (40 mg) were added dropwise to the obtained solution, and stirred at −20° C. for 1 hour. The reaction was quenched with 1M HCl (hydrochloride) solution. The reaction mixture was extracted with ethyl acetate, washed with water and brine, dried with anhydrous magnesium sulfate, filtered, and concentrated under reduced pressure. The residue was separated by MPLC ($SiO_2$, 4:1 hexane/EtOAc), thus obtaining Compound 300 (0.14 g, 74%) as white oil.

$^1$H NMR (400 MHz, DMSO-$d_6$); atropisomer mixture; δ 7.85 (s, 1H), 7.74 (s, 2H), 7.06-7.12 (m, 1H), 6.79-6.93 (m, 2H), 5.58, 5.61 (2d, 1H, J=6.18, 6.09 Hz), 3.89-4.00 (m, 2H), 3.74, 3.77 (2s, 3H), 3.46, 3.60 (2d, 1H, J=11.28, 10.98 Hz), 2.82-2.90 (m, 2H), 2.60-2.62 (m, 2H), 2.20-2.59 (m, 2H), 1.94 (m, 2H), 1.47-1.51 (m, 2H), 1.01-1.05 (m, 6H), 0.35, 0.42 (2d, 3H, J=4.86, 4.92 Hz); MS (ESI) m/z 595.2 ($M^+$+H).

Compound 301

(4S,5R)-3-((2-(5-(2-(2H-tetrazol-5-yl)ethyl)-2-methoxyphenyl)-5,5-dimethylcyclohex-1-enyl)methyl)-5-(3,5-bis(trifluoromethyl)phenyl)-4-methyloxazolidin-2-one Compound 300 (0.1 g, 0.16 mmol) was dissolved in dimethylformamide (5 mL). Sodium azide (0.04 g) and ammonium chloride (0.04 g, 0.82 mmol) were added dropwise to the obtained solution, and stirred at 120° C. overnight. After the reaction was quenched with 1M HCl (hydrochloride) solution, the reaction mixture was extracted with ethyl acetate, washed with water and brine, dried with anhydrous magnesium sulfate, filtered, and concentrated under reduced pressure. The residue was separated by MPLC ($SiO_2$, 20:1 DCM/MeOH), thus obtaining Compound 301 (11 mg, 11%) as white oil.

$^1$H NMR (400 MHz, DMSO-$d_6$); atropisomer mixture; δ 7.88 (s, 1H), 7.69-7.77 (m, 2H), 6.73-6.83 (m, 2H), 6.60-6.67 (m, 1H), 5.41, 5.74 (2d, 1H, J=6.42, 5.97 Hz), 4.49-4.95 (m, 1H), 4.15-4.33 (m, 1H), 3.70, 3.84 (2s, 3H), 2.90-3.36 (m, 4H), 1.98-2.50 (m, 2H), 1.90-1.98 (m, 2H), 1.46-1.50 (m, 2H), 1.00-1.05 (m, 6H), 0.60-0.70 (2d, 3H, J=4.92, 4.98 Hz); MS (ESI) m/z 638.2 ($M^+$+H).

Compound 302

(4S,5R)-5-(3,5-bis(trifluoromethyl)phenyl)-3-((2-(4-fluoro-2-methoxy-5-(1-methylcyclopropyl)phenyl)-5,5-dimethylcyclohex-1-enyl)methyl)-4-methyloxazolidin-2-one Compound 302 (0.12 g, 88.4%) as white solid foam was obtained according to the same method as the synthesis of compound 18.

$^1$H NMR (400 MHz, $CDCl_3$); atropisomer mixture; δ 7.86 (s, 1H), 7.73 (d, 1H, J=3.6 Hz), 6.86, 6.83 (2d, 1H, J=8.7 Hz), 6.53, 6.49 (2d, 1H, J=12.2 Hz), 5.60 (t, 1H, J=7.5 Hz), 3.99-3.89 (m, 2H), 3.72, 3.68 (2s, 3H), 3.51, 3.39 (2d, 1H, J=14.6 Hz), 2.42-1.89 (m, 4H), 1.45 (m, 2H), 1.29-1.23 (m, 6H), 1.03-0.85 (m, 8H), 0.73-0.60 (m, 4H), 0.38, 0.31 (2d, 3H, J=6.5 Hz); MS (ESI): 614 ($M^+$+H).

Compound 303

(4S,5R)-5-(3,5-bis(trifluoromethyl)phenyl)-3-((6-(4-fluoro-2-methoxy-5-(1-methylcyclopropyl)phenyl) spiro[2.5]oct-5-en-5-yl)methyl)-4-methyloxazolidin-2-one Compound 303 (80 mg, 54.7%) as white solid foam was obtained according to the same method as the synthesis of compound 18.

$^1$H NMR (400 MHz, $CDCl_3$); atropisomer mixture; δ 7.85 (s, 1H), 7.72 (s, 2H), 6.92, 6.88 (2d, 1H, J=8.8, 8.7 Hz), 6.55, 6.51 (2d, 1H, J=12.2, 12.1 Hz), 5.59 (t, 1H, J=7.8 Hz), 4.00-3.95 (m, 2H), 3.73, 3.70 (2s, 3H), 3.54, 3.44 (2d, 1H, J=14.9, 14.6 Hz), 2.42-1.24 (m, 10H), 0.74-0.61 (m, 4H), 0.44-0.37 (m, 7H); MS (ESI): 612 ($M^+$+H).

Compound 304

(4S,5R)-5-(3,5-bis(trifluoromethyl)phenyl)-3-((2-(3',5'-difluoro-4-methoxy-4'-(methoxymethoxy)biphenyl-3-yl)-5,5-dimethylcyclohex-1-enyl)methyl)-4-methyloxazolidin-2-one 3'-(2-(Bromomethyl)-4,4-dicyclohex-1-enyl)-3,5-difluoro-4'-methoxy-4-(methoxy methoxy)biphenyl, which is an intermediate compound, was dissolved in dimethylformamide (DMF). (4S,5R)-5-(3,5-bis(trifluoromethyl)phenyl)-4-oxazolidin-2-one and sodium hydride were added dropwise to the obtained solution at room temperature. After the completion of the reaction, the reaction mixture was extracted with ethyl acetate, washed with water and brine, dried with anhydrous magnesium sulfate, filtered, and concentrated under reduced pressure. The residue was separated by MPLC ($SiO_2$, 5:1 n-hexane: EtOAc), thus obtaining Compound 304 (60 mg, 46%) as white oil.

$^1$H NMR (400 MHz, DMSO-$d_6$); atropisomer mixture; δ 7.86 (s, 1H), 7.79 (s, 2H), 7.36-7.39 (m, 1H), 6.88-6.95 (m, 3H), 5.57-5.62 (m, 1H), 5.17 (d, 1H, J=9.9 Hz), 3.96-4.04 (m, 2H), 3.79-3.82 (2s, 3H), 3.58-3.62 (m, 3H), 3.44-3.58 (m, 1H), 2.00-2.50 (m, 2H), 1.93-1.95 (m, 2H), 1.50-1.55 (m, 2H), 1.02-1.07 (m, 6H), 0.37, 0.43 (2d, 3H, J=6.6, 6.5 Hz); MS (ESI) m/z 714 (M$^+$+H).

Compound 305

(4S,5R)-5-(3,5-bis(trifluoromethyl)phenyl)-3-((2-(3', 5'-difluoro-4'-hydroxy-4-methoxybiphenyl-3-yl)-5,5-dimethylcyclohex-1-enyl)methyl)-4-methyloxazolidin-2-one Compound 304 (0.03 g, 0.04 mmol), a starting material, was dissolved in methanol (2 mL). The solution (0.5 mL) of hydrogen chloride in methanol was added dropwise to the obtained solution, and stirred at room temperature for 3 hours. After the completion of the reaction, the reaction mixture was extracted with ethyl acetate, washed with water and brine, dried with anhydrous magnesium sulfate, filtered, and concentrated under reduced pressure. The residue was separated by MPLC (SiO$_2$, 5:1 n-hexane: EtOAc), thus obtaining Compound 305 (20 mg, 71%) as white solid.

$^1$H NMR (400 MHz, DMSO-d$_6$); atropisomer mixture; δ 7.86 (s, 1H), 7.72 (s, 2H), 7.34-7.37 (m, 1H), 6.99-7.12 (m, 3H), 6.89, 6.94 (2d, 1H, J=8.60, 8.60 Hz), 5.95 (br s, 1H), 5.61 (t, 1H, J=7.8 Hz), 3.93-4.05 (m, 2H), 3.78, 3.81 (2s, 3H), 3.49, 3.63 (2d, 1H, J=15.04, 14.64 Hz), 2.10-2.54 (m, 2H), 1.95 (m, 2H), 1.47-1.55 (m, 2H), 1.02-1.06 (m, 6H), 0.37, 0.43 (2d, 3H, J=6.48, 6.56 Hz); MS (ESI) m/z 670 (M$^+$+H).

Compound 306

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2-dimethylpropanamide Compound 306 (42 mg, 56%) as white solid foam was obtained according to the same method as the synthesis of compound 299.

$^1$H NMR (400 MHz, DMSO-d$_6$); atropisomer mixture; δ 7.85 (s, 1H), 7.73-7.74 (m, 2H), 7.00-7.03 (m, 1H), 6.70-6.81 (m, 1H), 5.52-5.60 (m, 3H), 3.88-4.03 (m, 2H), 3.71, 3.75 (2s, 3H), 3.39, 3.58 (2d, 1H, J=14.84, 14.48 Hz), 2.65-2.82 (m, 2H), 2.00-2.50 (m, 2H), 1.92 (m, 2H), 1.45-1.50 (m, 2H), 1.14-1.18 (m, 6H), 1.01-1.64 (m, 6H), 0.29, 0.46 (2d, 3H, J=6.48, 6.56 Hz); MS (ESI) m/z 641 (M$^+$+H).

Compound 307

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2-dimethylpropanenitrile Compound 307 (12 mg, 48%) as white solid foam was obtained according to the same method as the synthesis of compound 300.

$^1$H NMR (400 MHz, DMSO-d$_6$); atropisomer mixture; δ 7.73-7.93 (m, 3H), 6.82-7.16 (m, 3H), 5.58-5.60 (m, 1H), 3.89-4.02 (m, 2H), 3.75-3.77 (m, 3H), 3.43-3.67 (m, 1H), 2.57-2.86 (m, 2H), 1.85-2.47 (m, 4H), 1.94 (m, 2H), 1.21-1.78 (m, 6H), 0.85-0.89 (m, 6H), 0.30-0.40 (m, 3H); MS (ESI) m/z 623.3 (M$^+$+H).

Compound 308 methyl 3-(3-(2-(((4S,5R)-5-(3,5-bis(trifluoromethyl) phenyl)-4-methyl-2-oxooxazolidin-3-yl)methyl)-4,4-dimethylcyclohex-1-enyl)-4-methoxyphenyl)-3-methylbutanoate Methyl 3-(4-methoxyphenyl)-3-methylbutanoate, an intermediate compound, was synthesized, and then Compound 308 (0.9 g, 66.5%) as white solid foam was obtained according to the same method as the synthesis of compound 285.

$^1$H NMR (400 MHz, DMSO-d$_6$); atropisomer mixture; δ 7.85 (s, 1H), 7.73 (s, 2H), 7.18-7.21 (m, 1H), 6.92-6.96 (m, 1H), 6.74-6.81 (m, 1H), 5.58-5.61 (m, 1H), 3.87-4.00 (m, 2H), 3.73, 3.74 (2s, 3H), 3.47, 3.60 (2d, 1H, J=11.22 10.89 Hz), 3.49, 3.50 (2s, 3H), 2.54-2.59 (m, 2H), 2.00-2.30 (m, 2H), 1.93-1.94 (m, 2H), 1.46-1.48 (m, 2H), 1.38-1.41 (m, 6H), 1.01-1.05 (m, 6H), 0.28, 0.41 (2d, 3H, J=4.89, 4.92 Hz); MS (ESI) m/z 656.3 (M$^+$+H).

Compound 309

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3-methylbutanoic acid Compound 309 (0.24 g, 32.7%) as white solid foam was obtained according to the same method as the synthesis of compound 134.

$^1$H NMR (400 MHz, DMSO-d$_6$); atropisomer mixture; δ 7.85 (s, 1H), 7.73 (s, 2H), 7.20-7.23 (m, 1H), 6.94-6.98 (m, 1H), 6.75-6.82 (m, 1H), 5.57-5.60 (m, 1H), 3.85-4.01 (m, 2H), 3.73, 3.75 (2s, 3H), 3.49, 3.58 (2d, 1H, J=10.98, 10.83 Hz), 2.55-2.64 (m, 2H), 2.05-2.08 (m, 2H), 1.92-1.94 (m, 2H), 1.47-1.51 (m, 2H), 1.43-1.44 (m, 6H), 1.00-1.05 (m, 6H), 0.26, 0.43 (2d, 3H, J=4.95, 4.86 Hz); MS (ESI) m/z 642.2 (M$^+$+H).

Compound 310 methyl 4-(3-(2-(((4S,5R)-5-(3,5-bis(trifluoromethyl) phenyl)-4-methyl-2-oxooxazolidin-3-yl)methyl)-4,4-dimethylcyclohex-1-enyl)-4-methoxyphenyl)-2,2-dimethylbutanoate Compound 310 (0.7 g, 96.1%) as white solid foam was obtained according to the same method as the synthesis of compound 285.

$^1$H NMR (400 MHz, DMSO-d$_6$); atropisomer mixture; δ 7.86 (s, 1H), 7.73-7.75 (m, 2H), 6.99-7.02 (m, 1H), 6.71-6.79 (m, 2H), 5.59-5.62 (m, 1H), 3.91-4.02 (m, 2H), 3.71, 3.74 (2s, 3H), 3.63, 3.68 (2s, 3H), 3.47, 3.59 (2d, 1H, J=11.10, 10.95 Hz), 2.40-2.47 (m, 2H), 2.00-2.38 (m, 2H), 1.91-1.93 (m, 2H), 1.76-1.80 (m, 2H), 1.46-1.49 (m, 2H), 1.24-1.28 (m, 6H), 1.19 (d, 1H, J=3.4 Hz), 1.01-1.05 (m, 6H), 0.31, 0.43 (2d, 3H, J=4.86, 4.95 Hz); MS (ESI) m/z 670.2 (M$^+$+H).

Compound 311

4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2-dimethylbutanoic acid Compound 311 (0.11 g, 20%) as white solid foam was obtained according to the same method as the synthesis of compound 134.

$^1$H NMR (400 MHz, DMSO-d$_6$); atropisomer mixture; δ 7.86 (s, 1H), 7.73-7.75 (m, 2H), 7.70-7.04 (m, 1H), 6.72-6.76 (m, 2H), 5.59-5.61 (m, 1H), 3.95-4.00 (m, 2H), 3.71-3.80 (m, 3H), 3.40-3.59 (m, 1H), 2.46-2.54 (m, 2H), 2.00-2.15 (m, 4H), 1.84-1.93 (m, 2H), 1.70-1.84 (m, 2H), 1.46-1.49 (m, 2H), 1.22-1.24 (m, 6H), 0.31, 0.44 (2d, 3H, J=5.01, 4.83 Hz); MS (ESI) m/z 656.3 (M$^+$+H).

Compound 312 ethyl 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclobutanecarboxylate Compound 312 (0.38 g, 85%) as white solid foam was obtained according to the same method as the synthesis of compound 285.

$^1$H NMR (400 MHz, CDCl$_3$); atropisomer mixture; δ 7.84, 7.77, 7.73 (3 brs, 3H), 7.70-6.95 (m, 1H), 6.76-6.69 (m, 2H), 5.58 (t, 1H, J=8.0 Hz), 4.13-4.05 (m, 2H), 3.99-3.85 (m, 2H), 3.72, 3.70 (2s, 3H), 3.56, 3.45 (2d, 1H, J=14.9, 14.5 Hz), 2.99-2.94 (m, 2H), 2.37-1.97 (m, 11H), 1.46 (m, 2H), 1.27-1.18 (m, 5H), 1.03-0.86 (m, 6H), 0.34, 0.25 (2d, 3H, J=6.5 Hz); MS (ESI): 726 (M$^+$+H).

Compound 313

1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclobutanecarboxylic acid Compound 313 (0.15 g, 47.4%) as white solid foam was obtained according to the same method as the synthesis of compound 134.

$^1$H NMR (400 MHz, CDCl$_3$); atropisomer mixture; δ 7.84, 7.75, 7.72 (3s, 3H), 7.04-7.01 (m, 1H), 6.82-6.70 (m, 2H), 5.58 (d, 1H, J=8.1 Hz), 3.99-3.86 (m, 2H), 3.72, 3.70 (2s, 3H), 3.56, 3.46 (2d, 1H, J=14.9, 14.6 Hz), 3.04-2.96 (m, 2H), 2.47-1.81 (m, 12H), 1.46 (m, 2H), 1.03-0.98 (m, 6H), 0.38, 0.25 (2d, 3H, J=6.5 Hz); MS (ESI): 654 (M$^+$+H).

Compound 314

1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclobutanecarboxamide Compound 314 (0.04 g, 59.5%) as colorless oil was obtained according to the same method as the synthesis of compound 299.

$^1$H NMR (400 MHz, CDCl$_3$); atropisomer mixture; δ 7.85 (s, 1H), 7.73 (s, 2H), 7.06, 7.03 (2d, 1H, J=7.06, 7.04 Hz), 6.84, 6.79 (2d, 1H, J=6.84, 6.79 Hz), 6.77, 6.72 (2d, 1H, J=8.4 Hz), 5.58, 5.50 (2d, 1H, J=8.1, 8.0 Hz), 5.34-5.26 (brs, 2H), 4.12-3.85 (m, 2H), 3.77, 3.70 (2s, 3H), 3.54, 3.30 (2d, 1H, J=14.8, 14.5 Hz), 2.96 (d, 2H, J=10.6 Hz), 2.75-1.79 (m, 11H), 1.46 (m, 2H), 1.02-1.00 (m, 3H); MS (ESI): 697 (M$^+$+H).

Compound 315 methyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-methylpropanoate Methyl 2-(4-methoxyphenyl)-2-methylpropanoate, an intermediate compound, was synthesized, and then Compound 315 (0.16 g, 76.8%) as colorless oil was obtained according to the same method as the synthesis of compound 285.

$^1$H NMR (400 MHz, CDCl$_3$); atropisomer mixture; δ 7.85 (s, 1H), 7.73 (d, 2H, J=4.4 Hz), 7.19, 7.17 (2t, 1H, J=2.7 Hz), 6.94, 6.90 (2d, 1H, J=2.5 Hz), 6.81, 6.76 (2d, 1H, J=8.7 Hz), 5.59, 5.55 (2d, 1H, J=8.2 Hz), 3.96-3.88 (m, 2H), 3.75, 3.73 (2s, 3H), 3.63, 3.55 (2s, 3H), 3.54, 3.40 (2d, 1H, J=14.8, 13.3 Hz), 2.52-1.93 (m, 5H), 1.55-1.44 (m, 10H), 1.04, 1.02, 1.00 (3s, 6H), 0.35, 0.27 (2d, 3H, J=6.7, 6.5 Hz); MS (ESI): 642 (M$^+$+H).

Compound 316

(4S,5R)-5-(3,5-bis(trifluoromethyl)phenyl)-3-((2-(2-methoxy-5-(trifluoromethyl)pyridin-3-yl)-5,5-dimethylcyclohex-1-enyl)methyl)-4-methyloxazolidin-2-one Compound 316 (0.08 g, 30.6%) as white solid foam was obtained according to the same method as the synthesis of compound 18.

$^1$H NMR (400 MHz, CDCl$_3$); atropisomer mixture; δ 8.37 (m, 1H), 7.88 (s, 1H), 7.74 (s, 2H), 7.49 (m, 1H), 5.64 (m, 1H), 4.02-3.94 (m, 5H), 3.47-3.36 (m, 1H), 2.60-2.00 (m, 2H), 1.94 (s, 2H), 1.55 (m, 2H), 1.10 (m, 6H), 0.40 (m, 3H); MS (ESI): 611.2 (M+H)$^+$.

Compound 317 methyl 2-(7-(2-(((4S,5R)-5-(3,5-bis(trifluoromethyl)phenyl)-4-methyl-2-oxooxazolidin-3-yl)methyl)-4,4-dimethylcyclohex-1-enyl)benzo[d][1,3]dioxol-5-yl)acetate Compound 317 (0.2 g, 77%) as white solid foam was obtained according to the same method as the synthesis of compound 18.

$^1$H NMR (400 MHz, CDCl$_3$); atropisomer mixture; δ 7.86 (s, 1H), 7.76 (s, 2H), 6.67 (m, 1H), 6.50 (m, 1H), 5.95 (2d, 2H, J=1.04, 1.32 Hz), 5.57 (m, 1H), 4.09 (m, 1H), 3.95 (m, 1H), 3.64 (m, 4H), 3.50 (s, 2H), 2.40-2.20 (m, 2H), 1.95 (s, 2H), 1.51 (m, 2H), 1.03 (m, 6H), 0.41 (m, 3H); MS (ESI): 628.1 (M+H)$^+$.

Compound 318

2-(7-(2-(((4S,5R)-5-(3,5-bis(trifluoromethyl)phenyl)-4-methyl-2-oxooxazolidin-3-yl)methyl)-4,4-dimethylcyclohex-1-enyl)benzo[d][1,3]dioxol-5-yl)acetic acid Compound 318 (0.09 g, 76.7%) as colorless oil was obtained according to the same method as the synthesis of compound 134.

$^1$H NMR (400 MHz, CDCl$_3$); atropisomer mixture; δ 7.85 (s, 1H), 7.73 (s, 2H), 6.65 (m, 1H), 6.46 (m, 1H), 5.93 (m, 2H), 5.59 (m, 1H), 4.09-3.91 (m, 2H), 3.66 (m, 1H), 3.49 (s, 2H), 2.40-2.18 (m, 2H), 1.93 (s, 2H), 1.50 (m, 2H), 1.03 (m, 6H), 0.42 (m, 3H); MS (ESI): 614.1 (M+H)$^+$.

Compound 319

2-(7-(2-(((4S,5R)-5-(3,5-bis(trifluoromethyl)phenyl)-4-methyl-2-oxooxazolidin-3-yl)methyl)-4,4-dimethylcyclohex-1-enyl)benzo[d][1,3]dioxol-5-yl)-N-methylacetamide Compound 318 (0.06 g, 0.1 mmol) was dissolved in methylene chloride (10 mL). Methylamine (0.02 g), 1-(3-dimethylaminopropyl)-3-ethylcarbodiimide (0.04 g) and hydroxybenzotriazole (0.03 g) were added to the obtained solution at room temperature, and stirred at room temperature overnight. After the completion of the reaction, ethyl acetate was added dropwise to the reaction mixture. The obtained reaction mixture was washed with saturated sodium hydrogen carbonate solution and brine, dried with anhydrous magnesium sulfate, filtered, and concentrated under reduced pressure. The residue was separated by MPLC (SiO₂, 4:1 hexane/EtOAc), thus obtaining Compound 319 (0.03 g, 49%) as white solid.

$^1$H NMR (400 MHz, CDCl₃); atropisomer mixture; δ 7.86 (s, 1H), 7.75 (s, 2H), 6.64 (m, 1H), 6.49 (m, 1H), 5.96 (2d, 2H, J=1.16, 1.28 Hz), 5.69 (br s, 1H), 5.56 (m, 1H), 4.17 (m, 1H), 4.03 (m, 1H), 3.53 (m, 1H), 3.34 (s, 2H), 2.74 (m, 3H), 2.40-2.20 (m, 2H), 1.94 (s, 2H), 1.51 (m, 2H), 1.02 (m, 6H), 0.49 (m, 3H).

Compound 320

2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-methylpropanoic acid Compound 320 (0.05 g, 31.4%) as white solid foam was obtained according to the same method as the synthesis of compound 134.

$^1$H NMR (400 MHz, CDCl₃); atropisomer mixture; δ 7.84 (s, 1H), 7.71 (d, 2H, J=4.6 Hz), 7.24-7.21 (m, 1H), 6.97, 6.96 (2d, 1H, J=2.6 Hz), 6.82, 6.77 (2d, 1H, J=8.7 Hz), 5.55 (t, 2H, J=7.9 Hz), 3.98-3.85 (m, 2H), 3.75, 3.73 (2s, 3H), 3.54, 3.39 (2d, 1H, J=15.0, 14.6 Hz), 2.56-1.92 (m, 5H), 1.54-1.44 (m, 8H), 1.04, 1.01, 1.00 (3s, 6H), 0.38, 0.28 (2d, 3H, J=6.6, 6.5 Hz); MS (ESI): 628 (M⁺+H).

Compound 321

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N,2,2-trimethylpropanamide Compound 321 (78 mg, 76.4%) as white solid foam was obtained according to the same method as the synthesis of compound 319.

$^1$H NMR (400 MHz, DMSO-d₆); atropisomer mixture; δ 7.86 (s, 1H), 7.73-7.75 (m, 2H), 6.94-6.98 (m, 1H), 6.71-6.76 (m, 2H), 5.31-5.60 (m, 2H), 3.88-4.06 (m, 2H), 3.71, 3.76 (2s, 3H), 3.37, 3.56 (2d, 1H, J=14.92, 14.40 Hz), 2.47-2.84 (m, 2H), 2.67-2.76 (m, 3H), 2.00-2.50 (m, 2H), 1.93 (m, 2H), 1.44-1.57 (m, 6H), 1.11-1.14 (m, 6H), 1.01-1.05 (m, 6H), 0.29, 0.46 (2d, 3H, J=6.48, 6.56 Hz); MS (ESI) m/z 655 (M⁺+H).

Compound 323 methyl 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclopentanecarboxylate Compound 323 (81 mg, 51%) as white solid foam was obtained according to the same method as the synthesis of compound 285.

$^1$H NMR (400 MHz, CDCl₃); atropisomer mixture; δ 7.84 (s, 1H), 7.77, 7.72 (2s, 2H), 6.94-6.90 (m, 1H), 6.74-6.66 (m, 2H), 5.59 (t, 1H, J=8.0 Hz), 3.99-3.84 (m, 2H), 3.75, 3.70 (2s, 3H), 3.63, 3.59 (2s, 3H), 3.57, 3.46 (2d, 1H, J=14.5 Hz), 2.85, 2.81 (2d, 1H, J=3.7 Hz), 2.53-2.42 (m, 1H), 2.24-2.16 (m, 1H), 2.02-1.93 (m, 5H), 1.64-1.44 (m, 7H), 1.03-0.99 (m, 6H), 0.38, 0.26 (2d, 3H, J=6.6 Hz); MS (ESI) m/z 682.2, 704.1 (M⁺+H, M⁺+Na).

Compound 324

1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclopentanecarboxylic acid Compound 324 (6 mg, 9.4%) as white solid foam was obtained according to the same method as the synthesis of compound 134.

$^1$H NMR (400 MHz, CDCl₃); atropisomer mixture; δ 7.84 (s, 1H), 7.73 (s, 2H), 7.03-6.99 (m, 1H), 6.84 (dd, 1H, J=9.9, 2.2 Hz), 6.73 (dd, 1H, J=16.4, 8.4 Hz), 5.62-5.58 (m, 1H), 3.99-3.89 (m, 2H), 3.73, 3.70 (2s, 3H), 3.54-3.50 (m, 1H), 2.99-2.77 (m, 2H), 2.17-1.88 (m, 7H), 1.66-1.32 (m, 7H), 1.03-0.98 (m, 6H), 0.47, 0.32 (2d, 3H, J=6.6 Hz); MS (ESI) m/z 668.1, 690.1 (M⁺+H, M⁺+Na).

Compound 325

3-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxyphenyl)-2,2-dimethylpropanoic acid Compound 325 (1.07 g, 90%) as white solid foam was obtained according to the same method as the synthesis of compound 134.

$^1$H NMR (400 MHz, CDCl₃); atropisomer mixture; δ 7.85 (s, 1H), 7.74 (d, 2H, J=7.0 Hz), 6.92 (t, 0H, J=58.5 Hz), 6.57-6.51 (m, 1H), 5.62 (dd, 1H, J=8.2, 2.3 Hz), 4.00-3.81 (m, 2H), 3.73, 3.70 (2s, 3H), 3.51-3.47 (m, 1H), 2.88-2.79 (m, 2H), 2.49-2.41 (m, 1H), 2.14-2.11 (m, 1H), 1.90-1.88 (m, 2H), 1.49-1.40 (m, 2H), 1.29-1.10 (m, 6H), 1.02-0.95 (m, 6H), 0.46 (2d, 3H, J=6.6 Hz); MS (ESI) m/z 660.2 (M⁺+H).

Compound 326 methyl 7-(2-(((4S,5R)-5-(3,5-bis(trifluoromethyl)phenyl)-4-methyl-2-oxooxazolidin-3-yl)methyl)-4,4-dimethylcyclohex-1-enyl)-6-methoxy-1,2,3,4-tetrahydronaphthalene-2-carboxylate Methyl 6-methoxy-1,2,3,4-tetrahydronaphthalene-2-carboxylate, which is an intermediate compound, was synthesized, and then Compound 326 (0.21 g, 65%) as white solid foam was obtained according to the same method as the synthesis of compound 285.

$^1$H NMR (400 MHz, CDCl₃); atropisomer mixture; δ 7.85 (d, 1H, J=5.0 Hz), 7.73 (d, 2H, J=4.5 Hz), 6.67-6.50 (m, 2H), 5.62-5.58 (m, 1H), 4.02-3.90 (m, 2H), 3.72-3.41 (m, 7H), 2.90-1.78 (m, 10H), 1.46 (m, 2H), 1.28 (m, 5H), 1.03-0.96 (m, 6H), 0.45 (t, 1.3H, J=5.9 Hz), 0.33 (d, 1.7H, J=6.5 Hz); MS(ESI): 654 (M⁺+H).

Compound 327

7-(2-(((4S,5R)-5-(3,5-bis(trifluoromethyl)phenyl)-4-methyl-2-oxooxazolidin-3-yl)methyl)-4,4-dimethylcyclohex-1-enyl)-6-methoxy-1,2,3,4-tetrahydronaphthalene-2-carboxylic acid Compound 327 (0.07 g, 38.7%) as white solid foam was obtained according to the same method as the synthesis of compound 134.

$^1$H NMR (400 MHz, CDCl₃); atropisomer mixture; δ 7.85 (s, 1H), 7.73 (d, 2H, J=4.3 Hz), 6.67, 6.66 (2d, 1H, J=2.2, 1.6 Hz), 6.56, 6.51, 6.50 (3s, 1H), 5.60 (t, 1H, J=6.6 Hz), 4.02-3.90 (m, 2H), 3.71, 3.69, 3.68 (3s, 3H), 3.62-3.43 (m, 3H), 2.52-1.81 (m, 4H), 1.46 (m, 2H), 1.04, 1.03, 0.99 (3s, 6H), 0.48-0.33 (m, 3H); MS(ESI): 640 (M$^+$+H).
Compound 328 methyl 3-(5-(2-(((4S,5R)-5-(3,5-bis(trifluoromethyl) phenyl)-4-methyl-2-oxooxazolidin-3-yl)methyl)-4,4-dimethylcyclohex-1-enyl)-2-fluoro-4-methoxyphenyl)-2,2-dimethylpropanoate Compound 328 (1.52 g, 98%) as white solid foam was obtained according to the same method as the synthesis of compound 285.
$^1$H NMR (400 MHz, CDCl$_3$); atropisomer mixture; δ 7.85 (s, 1H), 7.76, 7.72 (2s, 2H), 6.67 (dd, 1H, J=16.1, 8.6 Hz), 6.53 (dd, 1H, J=14.7, 11.7 Hz), 5.60 (t, 1H, J=7.4 Hz), 3.98-3.84 (m, 2H), 3.72, 3.70 (2s, 3H), 3.64 (s, 3H), 3.54, 3.44 (2d, 1H, J=14.4 Hz), 2.85-2.72 (m, 2H), 2.47-2.41 (m, 1H), 2.23-2.14 (m, 1H), 2.00-1.91 (m, 2H), 1.52-1.41 (m, 2H), 1.18-1.12 (m, 6H), 1.05-0.98 (m, 6H), 0.41, 0.31 (2d, 3H, J=6.6 Hz); MS (ESI) m/z 674 (M$^+$+H).
Compound 329

3-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxyphenyl)-2,2-dimethylpropanamide Compound 329 (23 mg, 23%) as white solid was obtained according to the same method as the synthesis of compound 299.
$^1$H NMR (400 MHz, CDCl$_3$); atropisomer mixture; δ 7.84 (s, 1H), 7.73 (d, 1H, J=7.2 Hz), 6.82 (dd, 1H, J=17.7, 8.6 Hz), 6.54 (dd, 1H, J=15.4, 11.6 Hz), 5.68 (brs, 0.47H), 5.59 (dd, 1H, J=8.1, 3.0 Hz), 5.55 (brs, 0.13H), 5.41 (brs, 0.4H), 4.00-3.86 (m, 2H), 3.73, 3.69 (2s, 3H), 3.53, 3.32 (2d, 1H, J=14.6 Hz), 2.88-2.72 (m, 2H), 2.45-1.97 (m, 2H), 1.89 (brs, 2H), 1.50-1.39 (m, 2H), 1.17 (t, 6H, J=9.9 Hz), 1.00 (dd, 6H, J=5.3, 12.1 Hz), 0.44, 0.31 (2d, 3H, J=6.6 Hz); MS (ESI) m/z 659.1 (M$^+$+H).
Compound 330 ethyl 1-(3-(2-(((4S,5R)-5-(3,5-bis(trifluoromethyl) phenyl)-4-methyl-2-oxooxazolidin-3-yl)methyl)-4,4-dimethylcyclohex-1-enyl)-4-methoxyphenethyl)cyclobutanecarboxylate Compound 330 (0.03 g, 72.2%) as white solid was obtained according to the same method as the synthesis of compound 285.
$^1$H NMR (400 MHz, CDCl$_3$); atropisomer mixture; δ 7.86 (s, 1H), 7.74 (s, 2H), 7.03 (m, 1H), 6.79 (m, 2H), 5.62 (m, 1H), 4.20-3.90 (m, 4H), 3.75 (m, 3H), 3.60 (m, 1H), 2.50-1.83 (m, 13H), 1.50 (m, 2H), 1.30 (m, 5H), 1.05 (m, 6H), 0.44 (2d, 3H, J=6.56, 6.52 Hz).
Compound 331

1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenethyl)cyclobutanecarboxylic acid Compound 331 (3 mg, 10.4%) as white solid was obtained according to the same method as the synthesis of compound 286.
$^1$H NMR (400 MHz, CDCl$_3$); atropisomer mixture; δ 7.85 (s, 1H), 7.74 (s, 2H), 7.05 (m, 1H), 6.80 (m, 1H), 4.04-3.90 (m, 2H), 3.76 (m, 3H), 3.60 (m, 1H), 2.50-1.83 (m, 13H), 1.50 (m, 2H), 1.30 (m, 5H), 1.05 (m, 6H), 0.46 (m, 3H).
Compound 332

3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzonitrile Compound 332 (0.2 g, 56.1%) as white solid foam was obtained according to the same method as the synthesis of compound 18.
$^1$H NMR (400 MHz, CDCl$_3$); atropisomer mixture; δ 7.88 (s, 1H), 7.75 (m, 2H), 7.59 (m, 1H), 7.29 (m, 1H), 6.95 (m, 1H), 5.66, 5.60 (2d, 1H, J=8.20, 8.08 Hz), 4.01-4.90 (m, 2H), 3.85 (m, 3H), 3.52-3.30 (m, 1H), 2.20-2.04 (m, 2H), 1.52-1.47 (m, 2H), 1.05-0.98 (m, 6H), 1.47 (m, 3H); MS (ESI): 610.1 (M+H)$^+$.
Compound 333

(4S,5R)-5-(3,5-bis(trifluoromethyl)phenyl)-3-((2-(2-methoxy-5-(2H-tetrazol-5-yl)phenyl)-5,5-dimethylcyclohex-1-enyl)methyl)-4-methyloxazolidin-2-one Compound 333 (0.01 g, 18.6%) as white solid foam was obtained according to the same method as the synthesis of compound 301.
$^1$H NMR (400 MHz, CDCl$_3$); atropisomer mixture; δ 8.13 (m, 1H), 7.92-7.72 (m, 4H), 7.03-6.99 (m, 1H), 5.77, 5.62 (2d, 1H, J=8.00, 8.24 Hz), 4.20-4.03 (m, 2H), 3.86 (m, 3H), 3.12 (m, 1H), 2.60-2.04 (m, 2H), 1.54-1.41 (m, 2H), 1.05-0.98 (m, 6H), 1.52, 0.46 (2d, 3H, J=6.56, 6.52 Hz); MS (ESI): 610.1 (M+H)$^+$.
Compound 334

(4R,5R)-5-(3,5-bis(trifluoromethyl)phenyl)-3-((2-(4-fluoro-5-isopropyl-2-methoxyphenyl)-5,5-dimethylcyclohex-1-enyl)methyl)-4-methyloxazolidin-2-one Referring to the published article "Cameron J. Smith et al., J. Med. Chem. 2011 54 4880", (1R,2R)-2-amino-1-(3,5-bis (trifluoromethyl)phenyl)propane-ol was synthesized, and then Compound 334 (0.11 g, 61.1%) as white solid foam was obtained according to the same method as the synthesis of compound 18.
$^1$H NMR (400 MHz, DMSO-d$_6$); atropisomer mixture; δ 7.91 (s, 1H), 7.79 (s, 2H), 6.74-6.78 (m, 2H), 6.54-6.58 (m, 2H), 5.00 (t, 1H, J=5.7 Hz), 3.85-3.94 (m, 1H), 3.66-3.73 (2s, 3H), 3.44-3.60 (m, 1H), 3.34-3.50 (m, 1H), 3.12-3.19 (m, 1H), 2.12-2.40 (m, 2H), 1.85-2.07 (m, 2H), 1.15-1.45 (m, 2H), 1.20-1.38 (m, 6H), 0.95-1.19 (m, 3H), 0.60-1.00 (m, 6H); MS (ESI) m/z 602 (M$^+$+H).
Compound 335

(4S,5S)-5-(3,5-bis(trifluoromethyl)phenyl)-3-((2-(4-fluoro-5-isopropyl-2-methoxyphenyl)-5,5-dimethylcyclohex-1-enyl)methyl)-4-methyloxazolidin-2-one Referring to the published article "Cameron J. Smith et al., J. Med. Chem. 2011 54 4880", (1S,2S)(3,5-bis(trifluoromethyl)phenyl)propane-ol was synthesized, and then Compound 335 (0.16 g, 86%) as white solid foam was obtained according to the same method as the synthesis of compound 18.
$^1$H NMR (400 MHz, CDCl$_3$); atropisomer mixture; δ 7.89 (s, 1H), 7.78 (s, 2H), 6.75 (dd, 1H, J=5.6, 8.6 Hz), 6.55 (dd, 1H, J=12.2, 3.2 Hz), 4.99 (t, 0H, J=5.6 Hz), 3.93-3.84 (m, 1H), 3.73, 3.65 (2s, 3H), 3.59-3.32 (m, 2H), 3.16-3.11 (m, 1H), 2.34-2.11 (m, 2H), 1.94-1.84 (m, 2H), 1.44-1.25 (m, 2H), 1.22-1.16 (m, 6H), 1.09, 0.98 (2d, 3H, J=6.2 Hz), 0.94 (s, 1.3H), 0.90 (s, 1.7H), 0.77 (s, 1.3H), 0.59 (s, 1.7H); MS (ESI) m/z 602.1 (M$^+$+H). (ratio=1:1.25).

Compound 336

(4R,5S)-5-(3,5-bis(trifluoromethyl)phenyl)-3-((2-(4-fluoro-5-isopropyl-2-methoxyphenyl)-5,5-dimethyl-cyclohex-1-enyl)methyl)-4-methyloxazolidin-2-one Referring to the published article "Cameron J. Smith et al., J. Med. Chem. 2011 54 4880", (1S,2R)(3,5-bis(trifluoromethyl)phenyl)propane-ol was synthesized, and then Compound 336 (0.09 g, 57%) as white solid foam was obtained according to the same method as the synthesis of compound 18.

$^1$H NMR (400 MHz, CDCl$_3$); atropisomer mixture; δ 7.85 (s, 1H), 7.73 (s, 2H), 6.81 (2d, 1H, J=12.64, 12.68 Hz), 6.56 (2d, 1H, J=12.24, 12.12 Hz), 5.63 (m, 1H), 4.01-3.90 (m, 2H), 3.72 (m, 3H), 3.56 (m, 1H), 3.14 (m, 1H), 2.50-2.00 (m, 2H), 1.92 (m, 2H), 1.51-1.47 (m, 2H), 1.20 (m, 6H), 1.04 (m, 6H), 0.40 (m, 3H).

Compound 337

7-(2-(((4S,5R)-5-(3,5-bis(trifluoromethyl)phenyl)-4-methyl-2-oxooxazolidin-3-yl)methyl)-4,4-dimethyl-cyclohex-1-enyl)-6-methoxy-1,2,3,4-tetrahydronaphthalene-2-carboxamide Compound 337 (0.03 g, 79.5%) as white solid foam was obtained according to the same method as the synthesis of compound 299.

$^1$H NMR (400 MHz, CDCl$_3$); atropisomer mixture; δ 7.85 (s, 1H), 7.73 (d, 2H, J=4.3 Hz), 6.67, 6.66 (2d, 1H, J=2.2, 1.6 Hz), 6.56, 6.51, 6.50 (3s, 1H), 5.60 (t, 1H, J=6.6 Hz), 4.02-3.90 (m, 2H), 3.71, 3.69, 3.68 (3s, 3H), 3.62-3.43 (m, 3H), 2.52-1.81 (m, 4H), 1.46 (m, 2H), 1.04, 1.03 (m, 6H).

Compound 338

(4S,5R)-5-(3,5-bis(trifluoromethyl)phenyl)-3-((2-(2-methoxy-5-(2-methyl-2H-tetrazol-5-yl)phenyl)-5,5-dimethylcyclohex-1-enyl)methyl)-4-methyloxazolidin-2-one Compound 333 (0.03 g, 0.048 mmol) was dissolved in acetonitrile (10 mL). Potassium carbonate (7 mg) and iodomethane (7 mg) were added to the obtained solution, and then stirred at 100° C. overnight. After the completion of the reaction, the reaction mixture was concentrated under reduced pressure to remove the solvent. The residue was PTLC (SiO$_2$, Hx:EA=1:1, thus obtaining Compound 338 (0.01 g, 39.1%) as colorless oil.

$^1$H NMR (400 MHz, CDCl$_3$); atropisomer mixture; δ 8.04 (m, 1H), 7.85-7.71 (m, 4H), 6.99-6.94 (m, 1H), 5.66, 5.54 (2d, 1H, J=8.04, 8.04 Hz), 4.40 (m, 3H), 4.03 (m, 2H), 3.83 (m, 3H), 3.62-3.40 (m, 1H), 2.53-2.05 (m, 2H), 1.95 (m, 2H), 1.50 (m, 2H), 1.06 (m, 6H), 0.38 (m, 3H); MS (ESI) 624.1 (M+H)$^+$.

Compound 339

(4S,5R)-5-(3,5-bis(trifluoromethyl)phenyl)-3-((2-(2-methoxy-5-(1-methyl-1H-tetrazol-5-yl)phenyl)-5,5-dimethylcyclohex-1-enyl)methyl)-4-methyloxazolidin-2-one Compound 339 (0.01 g, 39.1%) as colorless oil was obtained according to the same method as the synthesis of compound 338.

$^1$H NMR (400 MHz, CDCl$_3$); atropisomer mixture; δ 7.85 (s, 1H), 7.75 (m, 2H), 7.65-7.48 (m, 2H), 7.06-7.02 (m, 1H), 5.63, 5.57 (2d, 1H, J=8.24, 8.04 Hz), 4.21 (m, 3H), 4.10-3.95 (m, 2H), 3.90-3.82 (m, 3H), 3.58-3.35 (m, 1H), 2.53-2.05 (m, 2H), 1.95 (m, 2H), 1.50 (m, 2H), 1.06 (m, 6H), 0.48, 0.44 (2d, 1H, J=6.60, 6.62 Hz); MS (ESI): 624.1 (M+H)$^+$.

Compound 340

(4S,5R)-5-(3,5-bis(trifluoromethyl)phenyl)-3-((2-(2-methoxy-5-(2-methyl-2-(2H-tetrazol-5-yl)propyl)phenyl)-5,5-dimethylcyclohex-1-enyl)methyl)-4-methyloxazolidin-2-one Compound 340 (0.04 g, 26.7%) as white solid foam was obtained according to the same method as the synthesis of compound 301.

$^1$H NMR (400 MHz, CDCl$_3$); atropisomer mixture; δ 8.00 (s, 1H), 7.86, 7.84 (2s, 1H), 7.73, 7.71 (2s, 1H), 6.72-6.33 (m, 2H), 5.62, 5.50 (2d, 1H, J=8.0 Hz), 4.37-4.04 (m, 2H), 3.80, 3.66 (2s, 3H), 3.10, 2.83 (2d, 1H, J=15, 8.4 Hz), 2.38-1.89 (m, 4H), 1.60-1.31 (m, 8H), 1.03-0.97 (m, 6H), 0.64, 0.38 (2d, 3H, J=6.6 Hz); MS (ESI): 666 (M$^+$+H).

Compound 341

(4S,5R)-5-(3,5-bis(trifluoromethyl)phenyl)-3-((2-(2-methoxy-5-(2-methyl-2-(2-methyl-2H-tetrazol-5-yl)propyl)phenyl)-5,5-dimethylcyclohex-1-enyl)methyl)-4-methyloxazolidin-2-one Compound 341 (6 mg, 32.6%) as white solid foam was obtained according to the same method as the synthesis of compound 338.

$^1$H NMR (400 MHz, CDCl$_3$); atropisomer mixture; δ 7.85 (s, 1H), 7.76, 7.72 (2s, 2H), 6.82-6.79 (m, 1H), 6.68, 6.64 (2d, 1H, J=8.4 Hz), 6.43, 6.41 (2d, 1H, J=2.2 Hz), 5.60, 5.56 (2d, 1H, J=8.2 Hz), 4.27, 4.26 (2s, 3H), 3.93-3.73 (m, 2H), 3.70, 3.68 (2s, 3H), 3.42, 3.35 (2d, 1H, J=14.9 Hz), 3.03-2.85 (m, 2H), 2.48-1.64 (m, 6H), 1.46-1.20 (m, 8H), 1.06-0.98 (m, 6H), 0.38, 0.21 (2d, 3H, J=6.5 Hz); MS (ESI): 680 (M+H).

Compound 342 tert-butyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzamido)acetate Compound 37 (0.1 g, 0.17 mmol) was dissolved in methylene chloride (3 mL). tert-Butyl 2-aminoacetate HCl (37 mg, 0.22 mmol), diisopropylethylamine (0.09 mL, 0.51 mmol) and hydroxybenzotriazole (46 mg, 0.34 mmol) were added dropwise to the obtained solution, and stirred at room temperature 10 minutes. 1-(3-Dimethylaminopropyl)-3-ethyl-carbodiimide (66 mg, 0.34 mmol) was added dropwise to the reaction mixture, and then stirred at room temperature for 1 hour. After the completion of the reaction, the reaction mixture was diluted with methylene chloride, and washed with water and brine. The organic layers were collected, dried with anhydrous magnesium sulfate, filtered, and concentrated under reduced pressure. The residue was separated by MPLC (SiO$_2$, 20%-30% Hexane/EtOAc), thus obtaining Compound 342 (0.1 g, 87%) as white solid.

$^1$H NMR (400 MHz, CDCl$_3$); atropisomer mixture; δ 7.82 (d, 1H, J=4.7 Hz), 7.73-7.70 (m, 2.5H), 7.65 (dd, 0.5H, J=8.6, 2.3 Hz), 7.53, 7.47 (2d, 1H, J=2.4 Hz), 6.86 (t, 1H, J=8.6 Hz), 6.67-6.60 (m, 1H), 5.56 (dd, 1H, J=16.3, 8.1 Hz), 4.12-4.03 (m, 2H), 3.99-3.92 (m, 2H), 3.80, 3.77 (2s, 3H), 3.47, 3.32 (2d, 1H, J=14.8 Hz), 2.45-2.00 (m, 2H), 1.90 (brs, 2H), 1.48-

1.44 (m, 11H), 1.00 (dd, 6H, J=11.0, 2.3 Hz), 0.41, 0.34 (2d, 3H, J=6.5 Hz); MS (ESI) m/z 699.1 (M⁺+H).

Compound 343 tert-butyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-N-methylbenzamido)acetate Compound 343 (21 mg, 21%) as white solid was obtained according to the same method as the synthesis of compound 112.

¹H NMR (400 MHz, CDCl₃); atropisomer mixture; δ 7.84 (s, 1H), 7.74 (s, 2H), 7.41-7.34 (m, 1H), 7.20-7.12 (m, 1H), 6.86-6.83 (m, 1H), 5.62, 6.83 (2d, 1H, J=8.1 Hz), 4.13-3.82 (m, 4H), 3.79, 3.77 (2s, 3H), 3.52-3.34 (m, 1H), 3.05-3.02 (m, 3H), 2.39-2.04 (m, 2H), 1.92 (brs, 2H), 1.51-1.45 (m, 11H), 1.03-1.00 (m, 6H), 0.43, 0.37 (d, 3H, J=6.6 Hz); MS (ESI) m/z 713.1 (M⁺+H).

Compound 344

(R)-methyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzamido)-3-methylbutanoate Compound 344 (96 mg, 81%) as white solid was obtained according to the same method as the synthesis of compound 342.

¹H NMR (400 MHz, CDCl₃); atropisomer mixture; δ 7.84 (s, 1H), 7.73 (s, 2H), 7.71 (dd, 0.5H, J=8.6, 2.4 Hz), 7.65 (dd, 0.5H, J=8.6, 2.4 Hz), 7.53, 7.48 (2d, 1H, J=2.3 Hz), 6.89 (t, 1H, J=8.8 Hz), 6.58-6.54 (m, 1H), 5.55 (dd, 1H, J=19.5, 8.0 Hz), 4.76-4.69 (m, 1H), 4.01-3.93 (m, 2H), 3.83, 3.80 (2s, 3H), 3.77, 3.74 (2s, 3H), 3.50, 3.33 (2d, 1H, J=15.0 Hz), 2.45-2.21 (m, 2H), 1.93 (brs, 2H), 1.52-1.46 (m, 2H), 1.04-0.89 (m, 12H), 0.41 (t, 3H, J=6.7 Hz); MS (ESI) m/z 699.1 (M⁺+H).

Compound 345

(R)-methyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-N-methylbenzamido)-3-methylbutanoate Compound 345 (50 mg, 55%) as white solid was obtained according to the same method as the synthesis of compound 112.

¹H NMR (400 MHz, CDCl₃); atropisomer mixture; δ 7.84 (s, 1H), 7.74 (d, 2H, J=8.5 Hz), 7.32 (dd, 1H, J=8.5, 2.2 Hz), 7.12 (dd, 1H, J=10.5, 2.2 Hz), 6.88-6.53 (m, 1H), 5.61 (d, 0.5H, J=8.4 Hz), 5.46 (d, 0.5H, J=7.2 Hz), 4.08-3.90 (m, 3H), 3.82-3.73 (m, 6H), 3.68-3.36 (m, 2H), 3.01-2.96 (m, 3H), 2.44-2.19 (m, 2H), 1.96-1.87 (m, 2H), 1.53-1.41 (m, 2H), 1.03-0.75 (m, 12H), 0.41, 0.36 (2d, 3H, J=6.5 Hz); MS (ESI) m/z 713.2 (M⁺+H).

Compound 346

(R)-2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzamido)-3-methylbutanoic acid Compound 346 (21 mg, 48%) as white solid was obtained according to the same method as the synthesis of compound 134.

¹H NMR (400 MHz, CDCl₃); atropisomer mixture; δ 7.85 (s, 1H), 7.73 (s, 2H), 7.43-7.37 (m, 1H), 7.22-7.09 (m, 1H), 6.90-6.86 (m, 1H), 5.63-5.48 (m, 1H), 4.23-3.95 (m, 4H), 3.82, 3.80 (2s, 3H), 3.51-3.32 (m, 1H), 3.06 (brs, 3H), 2.56-2.17 (m, 2H), 1.92-1.87 (m, 2H), 1.49-1.41 (m, 2H), 1.10-0.84 (m, 12H), 0.43, 0.38 (2d, 3H, J=6.0 Hz); MS (ESI) m/z 699.1 (M⁺+H).

Compound 347 methyl 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclobutanecarboxylate Compound 313 (0.03 g, 0.046 mmol) was dissolved in dimethylformamide (3 mL). Potassium carbonate (8.2 mg) and iodomethane (4.0 μL) were added dropwise to the obtained solution at room temperature, and stirred at room temperature for 2 hours. After the completion of the reaction, the reaction mixture was diluted with ethyl acetate, washed with water and brine, dried with anhydrous magnesium sulfate, filtered, and concentrated under reduced pressure to remove the solvent. The residue was separated by MPLC (SiO₂, 5%-20% n-hexane/EtOAc), thus obtaining Compound 347 (0.02 g, 75.1%) as white solid foam.

¹H NMR (400 MHz, CDCl₃); atropisomer mixture; δ 7.84 (s, 1H), 7.77, 7.73 (2s, 2H), 6.96-6.93 (m, 1H), 6.76-6.69 (m, 2H), 5.58 (t, 1H, J=8.2 Hz), 3.98-3.84 (m, 2H), 3.72, 3.70 (2s, 3H), 3.63, 3.61 (2s, 3H), 3.55, 3.46 (2d, 1H, J=14.5 Hz), 3.00-2.94 (m, 2H), 2.39-1.81 (m, 11H), 1.46 (m, 2H), 1.03-0.99 (m, 6H), 0.35, 0.25 (2d, 3H, J=6.5 Hz); 668 (M⁺+H).

Compound 348

2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-N-methylbenzamido)acetic acid Compound 348 (1.4 mg, 8%) as white solid was obtained according to the same method as the synthesis of compound 134.

MS (ESI) m/z 657.1 (M⁺+H).

Compound 349

Methyl 3-(5-(2-(((4S,5R)-5-(3,5-bis(trifluoromethyl)phenyl)-4-methyl-2-oxooxazolidin-3-yl)methyl)-4,4-dimethylcyclohex-1-enyl)-6-methoxypyridin-3-yl)-2,2-dimethylpropanoate As shown in reaction scheme 7, Compound 31, an intermediate compound, was synthesized, and then Compound 349 (0.28 g, 69.5%) as white solid foam was obtained according to the similar method to the synthesis of compound 285.

¹H NMR (400 MHz, DMSO-d₆); atropisomer mixture; δ 7.86 (m, 1H), 7.81, 7.83 (2d, 1H, J=1.77, 1.83 Hz), 7.74-7.75 (m, 2H), 7.02, 7.05 (2d, 1H, J=1.77, 1.77 Hz), 5.60, 5.63 (2d, 1H, J=5.94, 6.00 Hz), 3.91-4.03 (m, 2H), 3.85, 3.88 (2d, 3H), 3.64, 3.65 (2s, 3H), 3.46-3.52 (m, 1H), 2.73-2.80 (m, 2H), 1.90-1.95 (m, 2H), 1.43-1.48 (m, 2H), 1.16-1.20 (m, 6H), 1.01-1.09 (m, 6H), 0.28, 0.49 (2d, 3H, J=4.89, 4.89 Hz); MS (ESI) m/z 657.2 (M⁺+H).

Compound 350

3-(5-(2-(((4S,5R)-5-(3,5-bis(trifluoromethyl)phenyl)-4-methyl-2-oxooxazolidin-3-yl)methyl)-4,4-dimethylcyclohex-1-enyl)-6-methoxypyridin-3-yl)-2,2-dimethylpropanoic acid Compound 350 (75 mg, 54%) as white solid was obtained according to the same method as the synthesis of compound 134.
$^1$H NMR (400 MHz, DMSO-d$^6$); atropisomer mixture; δ 7.90, 7.90 (2d, 1H, J=2.36, 2.36 Hz), 7.85-7.86 (m, 1H), 7.73-7.74 (2s, 2H), 7.13, 7.15 (2d, 1H, J=2.40, 2.36 Hz), 5.60, 5.64 (2d, 1H, J=8.16, 8.00 Hz), 3.91-4.02 (m, 2H), 3.85-3.88 (2s, 3H), 3.50, 3.55 (2d, 1H, J=14.64, 15.16 Hz), 2.71-2.86 (m, 2H), 2.00-2.53 (m, 2H), 1.86-1.95 (m, 2H), 1.46-1.49 (m, 2H), 1.12-1.18 (m, 6H), 1.00-1.04 (m, 6H), 0.30, 0.52 (2d, 3H, J=6.52, 6.60 Hz); MS (ESI) m/z 643.2 (M$^+$+H).

Compound 353

(4S,5R)-5-(3,5-bis(trifluoromethyl)phenyl)-3-((2-(5-chloro-2-methoxyphenyl)-5,5-dimethylcyclohex-1-enyl)methyl)-4-methyloxazolidin-2-one Compound 353 (1.2 g, 62.6%) as white solid foam was obtained according to the same method as the synthesis of compound 18.
$^1$H NMR (400 MHz, CDCl$_3$); atropisomer mixture; δ 7.87 (s, 1H), 7.75 (m, 2H), 7.20-7.17 (m, 1H), 6.96 (m, 1H), 6.81, 6.77 (2d, 1H, J=8.80, 8.80 Hz), 5.65, 5.59 (2d, 1H, J=8.16, 8.24 Hz), 4.01-3.90 (m, 2H), 3.76 (m, 3H), 3.58-3.38 (m, 1H), 2.50-2.00 (m, 2H), 1.92 (m, 2H), 1.50-1.40 (m, 2H), 1.04 (m, 6H), 0.40 (m, 3H); MS (ESI): 576.0 (M+H)$^+$.

Compound 354 tert-butyl 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-5,6-dihydropyridine-1(2H)-carboxylate Compound 353 (0.1 g, 0.174 mmol), tert-butyl 4-(4,4,5,5-tetramethyl-1,3,2-dioxaborolane-2-yl)-5,6-dihydropyridine-1(2H)-carboxylate (0.05 g, 0.17 mmol), sodium carbonate (0.06 g) and palladium (0.01 g) were dissolved in dimethoxyethane/water (0.8 mL, v/v 3:1). The obtained solution in microwave-reactor was stirred at 120° C. for 30 minutes. After the completion of the reaction, the reaction mixture was cooled down to room temperature, diluted with EtOAc, washed with water and brine, dried with anhydrous magnesium sulfate, filtered, and concentrated under reduced pressure to remove the solvent. The residue was separated by MPLC (SiO$_2$, 10:1 hexane/EtOAc), thus obtaining Compound 354 (10 mg, 8%) as colorless oil.
$^1$H NMR (400 MHz, DMSO-d$_6$); atropisomer mixture; δ 7.85 (s, 1H), 7.73 (s, 2H), 7.24 (m, 1H), 7.00 (m, 1H), 6.85, 6.80 (2d, 1H, J=8.68, 8.68 Hz), 5.90 (m, 1H), 5.59 (m, 1H), 4.10-3.85 (m, 4H), 3.74 (m, 3H), 3.60-3.40 (m, 3H), 2.60-2.03 (m, 5H), 1.92 (m, 2H), 1.44 (m, 9H), 1.03-1.00 (m, 6H), 0.40 (m, 3H).

Compound 355

(4S,5R)-5-(3,5-bis(trifluoromethyl)phenyl)-3-((2-(5-(3,6-dihydro-2H-pyran-4-yl)-2-methoxyphenyl)-5,5-dimethylcyclohex-1-enyl)methyl)-4-methyloxazolidin-2-one Compound 355 (30 mg, 27.7%) as white solid foam was obtained according to the same method as the synthesis of compound 354.
$^1$H NMR (400 MHz, CDCl$_3$); atropisomer mixture; δ 7.86 (s, 1H), 7.73 (s, 2H), 7.25 (m, 1H), 7.02 (m, 1H), 6.85, 6.81 (2d, 1H, J=8.60, 8.64 Hz), 6.04-5.96 (m, 1H), 5.61 (m, 1H), 4.32-4.26 (m, 1H), 4.00-3.48 (m, 8H), 2.48 (m, 2H), 2.40-2.03 (m, 2H), 1.94 (m, 2H), 1.50 (m, 2H), 1.03-1.00 (m, 6H), 0.40, 0.33 (2d, 3H, J=6.56, 6.52 Hz).

Compound 356

(4S,5R)-5-(3,5-bis(trifluoromethyl)phenyl)-3-((2-(5-(hydroxymethyl)-2-methoxyphenyl)-5,5-dimethylcyclohex-1-enyl)methyl)-4-methyloxazolidin-2-one According to the same method as the synthesis of Compound 79, the aldehyde compound was synthesized. The obtained aldehyde compound (0.03 g, 0.05 mmol) and (s)-3-fluoropyrrolidine (5 mg) were dissolved in methylene chloride (10 mL). Acetic acid (30 μL) was added dropwise to the obtained solution, and stirred for 1 hour at room temperature. Sodium cyanoborohydride (4 mg) was added dropwise to the reaction mixture. The reaction mixture was stirred overnight, diluted with methylene chloride, washed with saturated sodium hydrogen carbonate solution, water and brine, dried with anhydrous magnesium sulfate, filtered, and concentrated under reduced pressure to remove the solvent. The residue was separated by PTLC (SiO$_2$, Hx:EA=1:1, thus obtaining "by-product" Compound 356 (0.01 g, 33.2%) as white solid foam.
$^1$H NMR (400 MHz, CDCl$_3$); atropisomer mixture; δ 7.85 (s, 1H), 7.73 (m, 2H), 7.24 (m, 1H), 7.06-6.98 (m, 1H), 6.87, 6.82 (2d, 1H, J=8.44, 8.40 Hz), 5.59, 5.51 (2d, 1H, J=7.96, 8.16 Hz), 4.62-4.53 (m, 2H), 4.07-3.92 (m, 2H), 3.79-3.74 (m, 3H), 3.56-3.37 (m, 1H), 2.51-2.05 (m, 2H), 1.93 (m, 2H), 1.53 (m, 2H), 1.05-1.02 (m, 6H), 0.45, 0.34 (2d, 3H, J=6.60, 6.52 Hz).

Compound 357 methyl 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-1,2,4-oxadiazole-5-carboxylate Compound 332 (0.03 g, 0.053 mmol) was dissolved in ethanol (20 mL). Sodium carbonate (22 mg) and hydroxylamine (11 mg) were added dropwise to the obtained solution at room temperature, and stirred at 90° C. overnight. After the completion of the reaction, the reaction mixture was cooled down to room temperature, and concentrated under reduced pressure to remove the solvent. The residue was dissolved in pyridine (5 mL). Methyl 2-chloro-2-oxoacetate (20 mg) was added dropwise to the obtained solution at room temperature, and stirred at 40° C. overnight. After the completion of the reaction, the reaction mixture was cooled down to room temperature. The reaction mixture was diluted with EtOAc, washed with saturated ammonium solution and brine, dried with anhydrous magnesium sulfate, filtered, and concentrated under reduced pressure to remove the solvent. The residue was separated by MPLC (SiO$_2$, Hx:EA=4:1, thus obtaining Compound 357 (5 mg, 45%) as white solid foam.
$^1$H NMR (400 MHz, CDCl$_3$); atropisomer mixture; δ 8.07 (m, 1H), 7.87 (m, 2H), 7.74 (m, 2H), 7.00, 6.97 (2d, 1H, J=8.64, 8.68 Hz), 5.66, 5.56 (2d, 1H, J=8.12, 8.24 Hz), 4.12 (m, 3H), 4.03 (m, 3H), 3.86 (m, 3H), 3.58-3.36 (m, 1H), 2.45-2.03 (m, 2H), 1.95 (m, 2H), 1.55-1.46 (m, 2H), 1.06-1.01 (m, 6H), 0.39 (m, 3H).

Compound 358

(4S,5R)-5-(3,5-bis(trifluoromethyl)phenyl)-3-((2-(2-methoxy-5-(1,2,3,6-tetrahydropyridin-4-yl)phenyl)-5,5-dimethylcyclohex-1-enyl)methyl)-4-methyloxazolidin-2-one Compound 354 (0.03 g, 0.042 mmol) was dissolved in methanol/HCl solution. The obtained solution was stirred at room temperature overnight. After the completion of the reaction, the reaction mixture was concentrated under reduced pressure. The residue was separated by column chromatography, thus obtaining Compound 358 (0.02 g, 77%) as yellow solid.

$^1$H NMR (400 MHz, CDCl$_3$); atropisomer mixture; δ 7.99 (m, 1H), 7.92 (m, 2H), 7.40 (m, 1H), 7.20-6.98 (m, 2H), 6.10-6.00 (m, 1H), 5.90-5.80 (m, 1H), 4.20 (m, 1H), 3.82-3.78 (m, 5H), 3.60-3.40 (m, 3H), 2.80 (m, 2H), 2.45-1.85 (m, 4H), 1.55-1.46 (m, 2H), 1.09-1.01 (m, 6H), 0.48, 0.38 (2d, 1H, J=5.64, 6.40 Hz).

Compound 359 methyl 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-5,6-dihydropyridine-1 (2H)-carboxylate Compound 359 (20 mg, 62.5%) as white solid was obtained according to the same method as the synthesis of compound 110.

$^1$H NMR (400 MHz, CDCl$_3$); atropisomer mixture; δ 7.86 (s, 1H), 7.73 (s, 2H), 7.24 (m, 1H), 7.00 (m, 1H), 6.85, 6.80 (2d, 1H, J=8.68, 8.64 Hz), 6.00-6.84 (m, 1H), 5.61 (m, 1H), 4.11-3.90 (m, 4H), 3.80-3.44 (m, 9H), 2.52-1.91 (m, 6H), 1.52-1.45 (m, 2H), 1.06-1.01 (m, 6H), 0.39 (2d, 3H); MS (ESI): 681.1 (M+H)$^+$.

Compound 360

(S)-methyl 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)pyrrolidine-2-carboxylate Compound 360 (65 mg, 54%) as colorless oil was obtained according to the same method as the synthesis of compound 356.

MS (ESI) m/z 683.2 (M$^+$+H).

Compound 361

(R)-methyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzylamino)-3-methylbutanoate Compound 361 (68 mg, 57%) as yellow oil was obtained according to the same method as the synthesis of compound 356.

$^1$H NMR (400 MHz, CDCl$_3$); atropisomer mixture; δ 7.84 (s, 1H), 7.72 (s, 2H), 7.16 (dd, 1H, J=8.4, 2.2 Hz), 6.92 (dd, 1H, J=7.4, 2.2 Hz), 6.81-6.74 (m, 1H), 5.60 (dd, 1H, J=3.6, 8.1 Hz), 4.03-3.86 (m, 2.5H), 3.75-3.68 (m, 7H), 3.65-3.41 (m, 2.5H), 3.00-2.94 (m, 1H), 2.45-2.05 (m, 2H), 1.91-1.81 (m, 2H), 1.51-1.42 (m, 2H), 1.03-1.00 (m, 6H), 0.94-0.83 (m, 6H), 0.42, 0.30 (2d, 3H, J=6.6 Hz); MS (ESI) m/z 685.2 (M$^+$+H).

Compound 362

4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)cyclohex-3-enecarboxylic acid According to the same method as the synthesis of Compound 354, the obtained methyl 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)cyclohex-3-enecarboxylate was dissolved in dioxan/water (5 mL, v/v 2:1). Lithium hydroxide (10 mg) was added dropwise to the obtained solution at room temperature, and stirred at room temperature for 5 hours. After the completion of the reaction, the reaction mixture was acidified with 2 M HCl solution. The reaction mixture was diluted with EtOAc, was washed with water and brine. The organic layers were collected, dried with anhydrous magnesium sulfate, filtered, and concentrated under reduced pressure to remove the solvent. The residue was separated by MPLC (3:1 hexane:EtOAc), thus obtaining Compound 362 (30 mg, 24%) as white solid foam.

$^1$H NMR (400 MHz, DMSO-d$_6$); atropisomer mixture; δ 7.86 (s, 1H), 7.73 (s, 2H), 7.21-7.25 (m, 1H), 6.99-7.00 (m, 1H), 6.78, 6.83 (2d, 1H, J=8.68, 8.68 Hz), 5.94-6.03 (m, 1H), 5.58, 5.61 (2d, 1H, J=8.04, 8.20 Hz), 3.91-4.01 (m, 2H), 3.72-3.78 (m, 3H), 3.49, 3.61 (2d, 1H, J=15.08, 14.68 Hz), 2.10-2.70 (m, 8H), 1.90-1.93 (m, 2H), 1.43-1.53 (m, 2H), 1.01-1.05 (m, 6H), 0.32-0.43 (2d, 3H, J=6.48, 5.76 Hz); MS (ESI) m/z 666 (M$^+$+H).

Compound 363

(R)-methyl 2-((3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)(methyl)amino)-3-methylbutanoate Compound 363 (13 mg, 21%) as colorless oil was obtained according to the same method as the synthesis of compound 112.

$^1$H NMR (400 MHz, CDCl$_3$); atropisomer mixture; δ 7.85 (d, 1H, J=4.9 Hz), 7.72 (s, 2H), 7.16 (d, 1H, J=8.4 Hz), 6.90 (d, 1H, J=2.0 Hz), 6.78 (dd, 1H, J=18.2, 8.4 Hz), 5.61-5.57 (m, 1H), 4.03-3.88 (m, 2H), 3.74-3.69 (m, 6H), 3.65-3.30 (m, 3H), 2.79 (dd, 1H, J=7.0, 10.7 Hz), 2.52-2.18 (m, 3H), 2.10-2.01 (m, 3H), 1.92-1.90 (m, 2H), 1.51-1.44 (m, 2H), 1.04-0.95 (m, 9H), 0.87-0.81 (m, 3H), 0.40, 0.27 (2d, 3H, J=6.6 Hz); MS (ESI) m/z 699.2 (M$^+$+H).

Compound 364

(4S,5R)-5-(3,5-bis(trifluoromethyl)phenyl)-3-((2-(2-methoxy-5-(((R)-2-(trifluoromethyl)pyrrolidin-1-yl)methyl)phenyl)-5,5-dimethylcyclohex-1-enyl)methyl)-4-methyloxazolidin-2-one Compound 364 (22 mg, 36%) as colorless oil was obtained according to the same method as the synthesis of compound 356.

$^1$H NMR (400 MHz, CDCl$_3$); atropisomer mixture; δ 7.84 (s, 1H), 7.73 (d, 1H, J=4.2 Hz), 7.18 (dd, 0.5H, J=8.4, 2.1 Hz), 7.10 (dd, 0.5H, J=8.3, 2.0 Hz), 6.94, 6.88 (2d, 1H, J=2.0 Hz), 6.77 (d, 1H, J=8.4 Hz), 5.60 (dd, 1H, J=14.2, 8.1 Hz), 4.08-3.88 (m, 3H), 3.74, 3.72 (2s, 3H), 3.58, 3.50 (2d, 1H, J=14.8 Hz), 3.42-3.36 (m, 1H), 3.23-3.18 (m, 1H), 2.92-2.70 (m, 1H), 2.47-2.05 (m, 3H), 2.07-1.76 (m, 6H), 1.53-1.43 (m, 2H), 1.03 (d, 6H, J=12.1 Hz), 0.37, 0.29 (2d, 3H, J=6.6 Hz); MS (ESI) m/z 693.1 (M$^+$+H).

Compound 366

(4S,5R)-5-(3,5-bis(trifluoromethyl)phenyl)-3-((2-(6-isopropyl-3-methoxypyridin-2-yl)-5,5-dimethylcyclohex-1-enyl)methyl)-4-methyloxazolidin-2-one As shown in reaction scheme 8,2-bromopyridin-3-ol, as a starting material, was subjected to the several processes, to synthesize 2-(2-(ethoxycarbonyl)-4,4-dimethylcyclohex-1-enyl)-6-diisopropyl-3-methoxypyridin 1-oxide. The synthesized compound was reacted with diisobutylaluminium hydride (DIBAL-H) and Dess-Martin periodinane (DMP) reagent, thus synthesizing an aldehyde compound. The obtained aldehyde compound was subjected to reductive amination using amino alcohol, thereby an amino alcohol compound was synthesized. 2-(2-(ethoxycarbonyl)-4,4-dimethylcyclohex-1-enyl)-6-diisopropyl-3-methoxypyridin-1-oxide (62 mg, 0.11 mmol), a starting compound, was dissolved in methylene chloride (5 mL). Diisopropylamine (0.11 mL) and triphosgene (0.05 g, 0.16 mmol) were added dropwise to the obtained solution at room temperature, and stirred at room temperature for 2 hours. After the completion of the reaction, the reaction mixture was diluted with EtOAc, washed with water and brine, dried with anhydrous magnesium sulfate, filtered, and concentrated under reduced pressure to remove the solvent. The residue was separated by MPLC (12 g silica, 3:1=n-hexane:EtOAc, thus obtaining Compound 43 (32 mg, 48.4%) as colorless oil. Compound 43 (32 mg, 0.05 mmol) was dissolved in ethanol (5 mL). Indium (7 mg) and saturated ammonium solution (4 mL) were added dropwise to the obtained solution, and stirred at 80° C. overnight. After the completion of the reaction, the reaction mixture was cooled down to room temperature. The reaction mixture was diluted with EtOAc, washed with water and brine, dried with sodium sulfate anhydrous, filtered, and concentrated under reduced pressure to remove the solvent. The residue was separated by MPLC (4 g silica, 1:1=n-hexane:EtOAc, thus obtaining Compound 366 (5 mg, 16.1%) as colorless oil.

$^1$H NMR (400 MHz, DMSO-d$_6$); δ 7.85 (s, 1H), 7.73 (s, 2H), 7.10 (d, 1H, J=8.6 Hz), 7.02 (d, 1H, J=8.5 Hz), 5.54 (d, 1H, J=7.6 Hz), 3.97-4.05 (m, 2H), 3.77 (m, 3H), 3.40 (d, 1H, J=15.0 Hz), 2.94-3.01 (m, 1H), 2.18-2.48 (m, 2H), 1.95 (m, 2H), 1.41-1.55 (m, 2H), 1.20-1.25 (m, 6H), 0.33 (d, 3H, J=6.5 Hz); MS (ESI) m/z 585 (M$^+$+H).

Compound 367

(4S,5R)-5-(3,5-bis(trifluoromethyl)phenyl)-3-((2-(5-(((S)-3-fluoropyrrolidin-1-yl)methyl)-2-methoxyphenyl)-5,5-dimethylcyclohex-1-enyl)methyl)-4-methyloxazolidin-2-one Compound 367 (10 mg, 30%) as white solid foam was obtained according to the same method as the synthesis of compound 356.

$^1$H NMR (400 MHz, CDCl$_3$); atropisomer mixture; δ 7.85 (s, 1H), 7.74 (m, 2H), 7.21-6.95 (m, 2H), 6.82 (2d, 1H, J=8.52, 8.36 Hz), 5.62 (m, 1H), 5.30-5.03 (m, 1H), 4.04-3.91 (m, 2H), 3.76 (m, 3H), 3.70-3.42 (m, 3H), 2.82-2.40 (m, 3H), 2.30-1.98 (m, 4H), 1.94 (m, 2H), 1.53-1.44 (m, 2H), 1.05-1.01 (m, 6H), 0.40 (2d, 1H, J=6.56, 6.52 Hz); MS (ESI): 643.1 (M+H)$^+$.

The chemical structures of compounds 15 to 367 as described above are shown in Tables 1 to 45 below.

TABLE 1

| Compound | Structure | Compound | Structure |
|---|---|---|---|
| 15 | 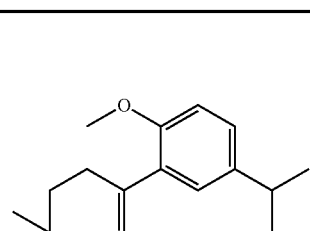 | 16 | 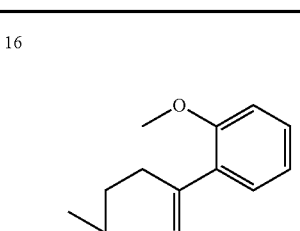 |

TABLE 1-continued

| Compound | Structure | Compound | Structure |
| --- | --- | --- | --- |
| 17 | 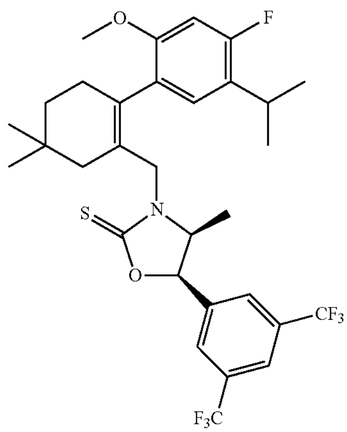 [SMILES: COc1cc(F)c(C(C)C)cc1C1=C(CN2C(=S)O[C@H](c3cc(C(F)(F)F)cc(C(F)(F)F)c3)[C@@H]2C)CC(C)(C)CC1] | 18 | 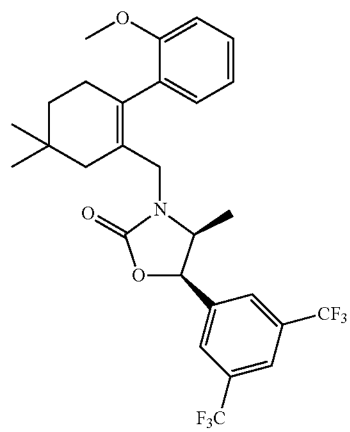 [SMILES: COc1ccccc1C1=C(CN2C(=O)O[C@H](c3cc(C(F)(F)F)cc(C(F)(F)F)c3)[C@@H]2C)CC(C)(C)CC1] |
| 19 | 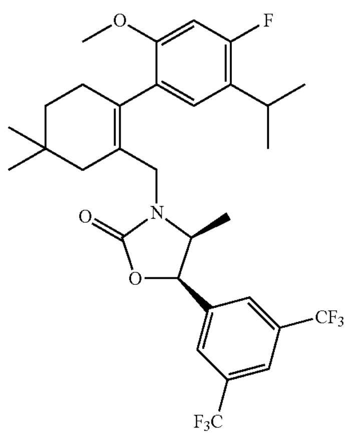 [SMILES: COc1cc(F)c(C(C)C)cc1C1=C(CN2C(=O)O[C@H](c3cc(C(F)(F)F)cc(C(F)(F)F)c3)[C@@H]2C)CC(C)(C)CC1] | 25 | 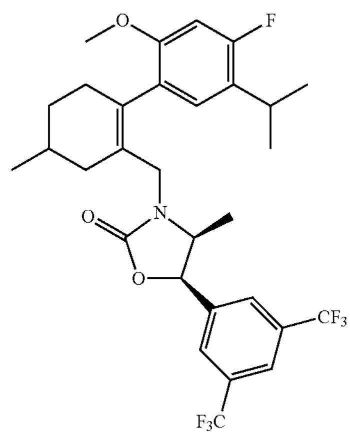 |

TABLE 2

| Compound | Structure | Compound | Structure |
| --- | --- | --- | --- |
| 26 | 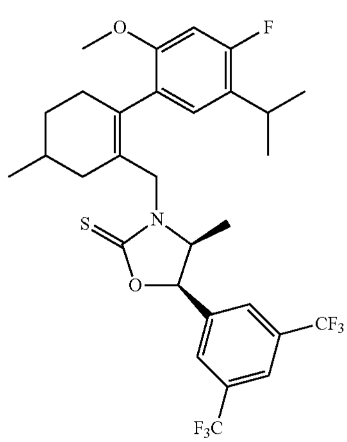 [SMILES: COc1cc(F)c(C(C)C)cc1C1=C(CN2C(=O)O[C@H](c3cc(C(F)(F)F)cc(C(F)(F)F)c3)[C@@H]2C)CC(C)CC1] | 27 | 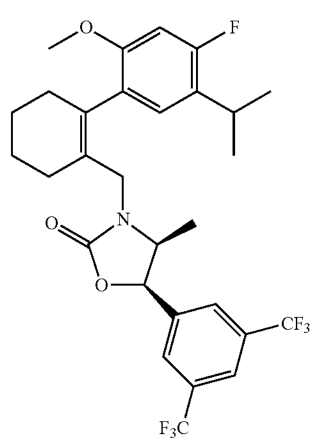 [SMILES: COc1cc(F)c(C(C)C)cc1C1=C(CN2C(=O)O[C@H](c3cc(C(F)(F)F)cc(C(F)(F)F)c3)[C@@H]2C)CCCC1] |

TABLE 2-continued

| Compound | Structure | Compound | Structure |
| --- | --- | --- | --- |
| 28 | 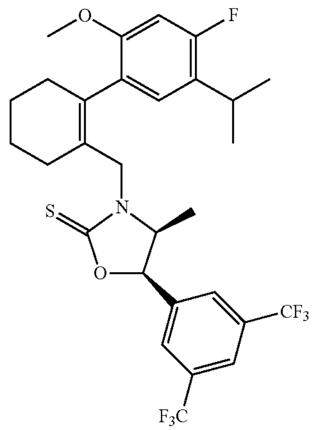 [SMILES: COc1cc(F)c(C(C)C)cc1C1=C(CN2C(=S)O[C@H](c3cc(C(F)(F)F)cc(C(F)(F)F)c3)[C@@H]2C)CCCC1] | 29 | 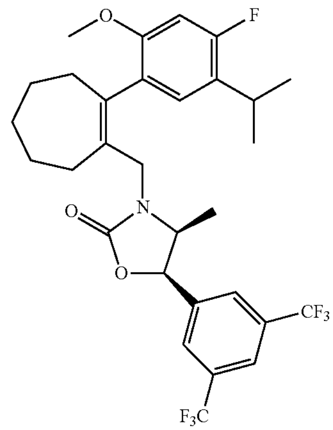 [SMILES: COc1cc(F)c(C(C)C)cc1C1=C(CN2C(=O)O[C@H](c3cc(C(F)(F)F)cc(C(F)(F)F)c3)[C@@H]2C)CCCCC1] |
| 30 | 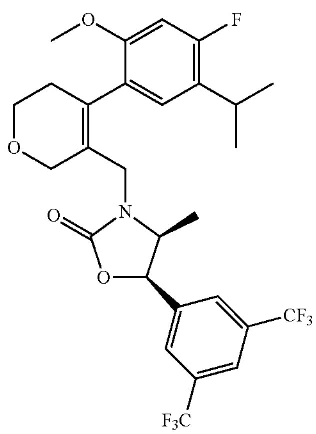 [SMILES: COc1cc(F)c(C(C)C)cc1C1=C(CN2C(=O)O[C@H](c3cc(C(F)(F)F)cc(C(F)(F)F)c3)[C@@H]2C)COCC1] | 31 | 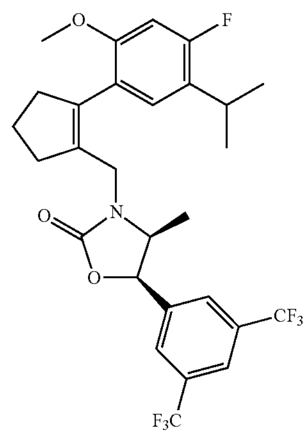 [SMILES: COc1cc(F)c(C(C)C)cc1C1=C(CN2C(=O)O[C@H](c3cc(C(F)(F)F)cc(C(F)(F)F)c3)[C@@H]2C)CCC1] |

TABLE 3

| Compound | Structure | Compound | Structure |
| --- | --- | --- | --- |
| 32 | 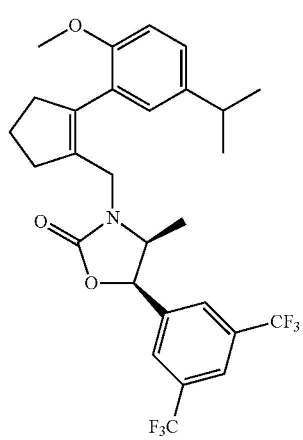 [SMILES: COc1ccc(C(C)C)cc1C1=C(CN2C(=O)O[C@H](c3cc(C(F)(F)F)cc(C(F)(F)F)c3)[C@@H]2C)CCC1] | 34 | 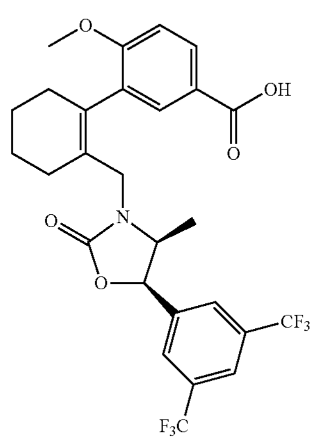 [SMILES: COc1ccc(C(=O)O)cc1C1=C(CN2C(=O)O[C@H](c3cc(C(F)(F)F)cc(C(F)(F)F)c3)[C@@H]2C)CCCC1] |

TABLE 3-continued

| Compound | Structure | Compound | Structure |
|---|---|---|---|
| 36 | 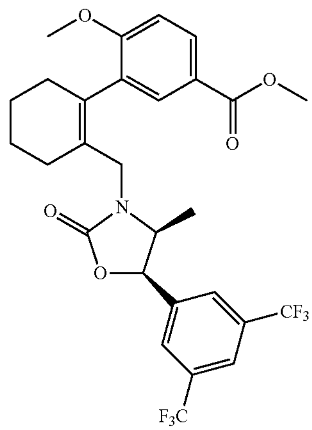 [SMILES: COC(=O)c1ccc(OC)c(C2=C(CN3C(=O)O[C@H](c4cc(C(F)(F)F)cc(C(F)(F)F)c4)[C@@H]3C)CCCC2)c1] | 37 | 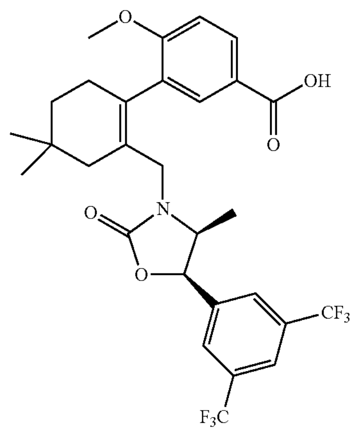 [SMILES: COc1ccc(C(=O)O)cc1C1=C(CN2C(=O)O[C@H](c3cc(C(F)(F)F)cc(C(F)(F)F)c3)[C@@H]2C)CC(C)(C)CC1] |
| 41 | 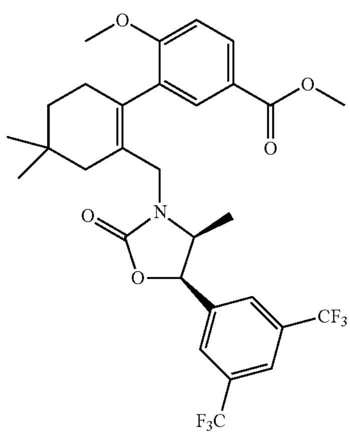 | 42 | 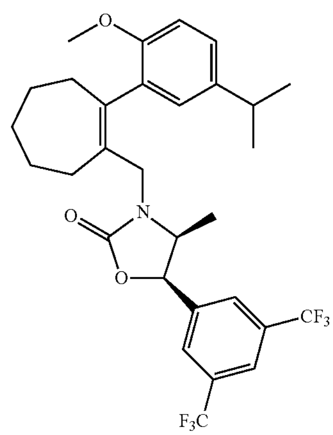 [SMILES: COc1ccc(C(C)C)cc1C1=C(CN2C(=O)O[C@H](c3cc(C(F)(F)F)cc(C(F)(F)F)c3)[C@@H]2C)CCCCC1] |

TABLE 4

| Compound | Structure | Compound | Structure |
|---|---|---|---|
| 43 | 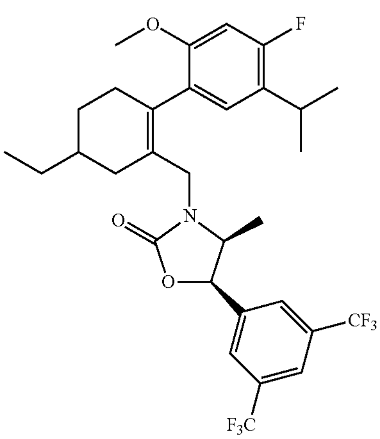 [SMILES: CCC1CCC(c2cc(C(C)C)c(F)cc2OC)=C(CN2C(=O)O[C@H](c3cc(C(F)(F)F)cc(C(F)(F)F)c3)[C@@H]2C)C1] | 44 | 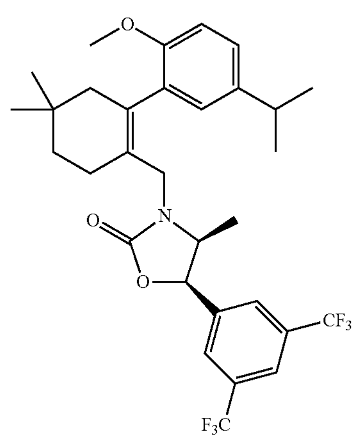 [SMILES: COc1ccc(C(C)C)cc1C1=C(CN2C(=O)O[C@H](c3cc(C(F)(F)F)cc(C(F)(F)F)c3)[C@@H]2C)CCC(C)(C)C1] |

TABLE 4-continued

| Compound | Structure | Compound | Structure |
|---|---|---|---|
| 46 | 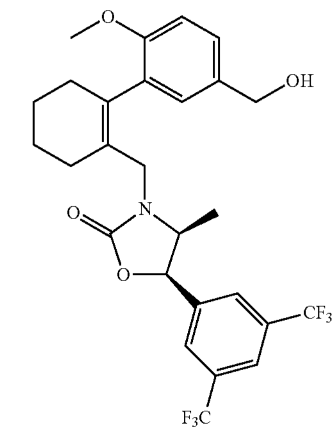 [SMILES: COc1ccc(CO)cc1C1=C(CN2C(=O)O[C@H](c3cc(C(F)(F)F)cc(C(F)(F)F)c3)[C@@H]2C)CCCC1] | 47 | 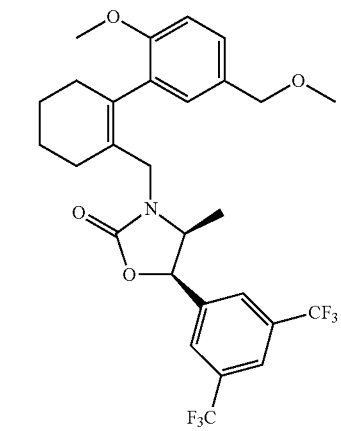 [SMILES: COCc1ccc(OC)c(C2=C(CN3C(=O)O[C@H](c4cc(C(F)(F)F)cc(C(F)(F)F)c4)[C@@H]3C)CCCC2)c1] |
| 48 | 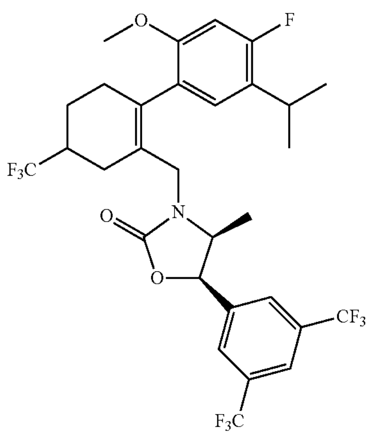 [SMILES: COc1cc(F)c(C(C)C)cc1C1=C(CN2C(=O)O[C@H](c3cc(C(F)(F)F)cc(C(F)(F)F)c3)[C@@H]2C)CC(C(F)(F)F)CC1] | 49 | 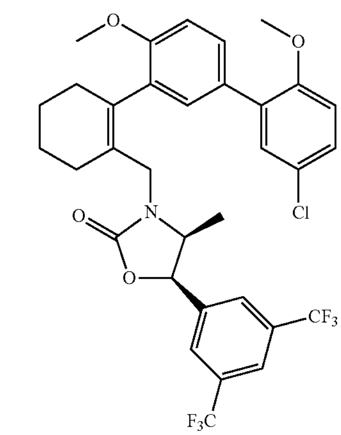 [SMILES: COc1ccc(-c2cc(Cl)ccc2OC)cc1C1=C(CN2C(=O)O[C@H](c3cc(C(F)(F)F)cc(C(F)(F)F)c3)[C@@H]2C)CCCC1] |

TABLE 5

| Compound | Structure | Compound | Structure |
|---|---|---|---|
| 50 | 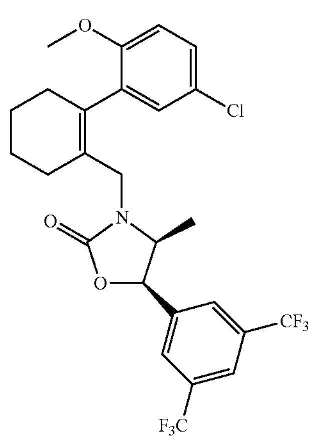 [SMILES: COc1ccc(Cl)cc1C1=C(CN2C(=O)O[C@H](c3cc(C(F)(F)F)cc(C(F)(F)F)c3)[C@@H]2C)CCCC1] | 51 | 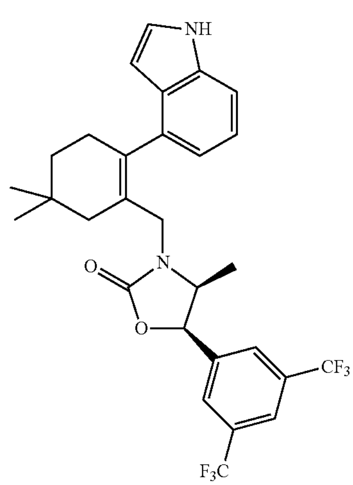 [SMILES: C[C@H]1[C@@H](c2cc(C(F)(F)F)cc(C(F)(F)F)c2)OC(=O)N1CC1=C(c2cccc3[nH]ccc23)CCC(C)(C)C1] |

TABLE 5-continued

| Compound | Structure | Compound | Structure |
| --- | --- | --- | --- |
| 52 | 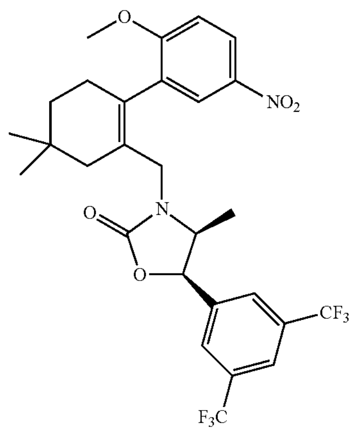 [SMILES: COc1ccc([N+](=O)[O-])cc1C1=C(CN2C(=O)O[C@H](c3cc(C(F)(F)F)cc(C(F)(F)F)c3)[C@@H]2C)CC(C)(C)CC1] | 55 | 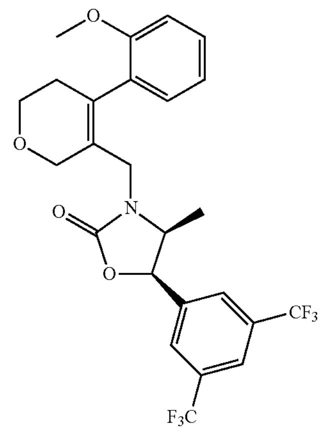 [SMILES: COc1ccccc1C1=C(CN2C(=O)O[C@H](c3cc(C(F)(F)F)cc(C(F)(F)F)c3)[C@@H]2C)COCC1] |
| 56 | 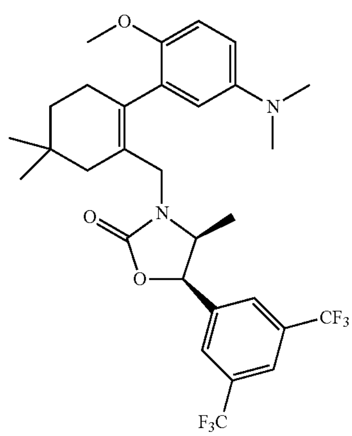 [SMILES: COc1ccc(N(C)C)cc1C1=C(CN2C(=O)O[C@H](c3cc(C(F)(F)F)cc(C(F)(F)F)c3)[C@@H]2C)CC(C)(C)CC1] | 57 | 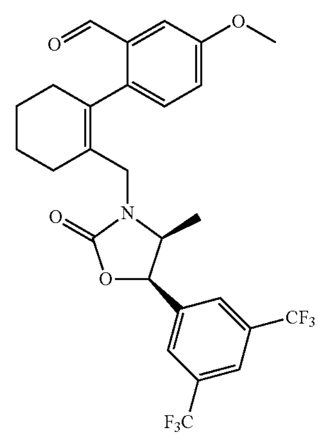 [SMILES: COc1ccc(C2=C(CN3C(=O)O[C@H](c4cc(C(F)(F)F)cc(C(F)(F)F)c4)[C@@H]3C)CCCC2)c(C=O)c1] |

TABLE 6

| Compound | Structure | Compound | Structure |
| --- | --- | --- | --- |
| 58 | 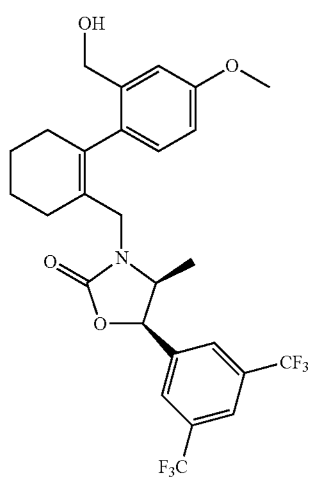 [SMILES: COc1ccc(C2=C(CN3C(=O)O[C@H](c4cc(C(F)(F)F)cc(C(F)(F)F)c4)[C@@H]3C)CCCC2)c(CO)c1] | 59 | 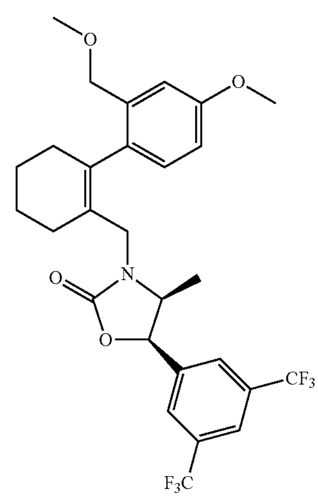 [SMILES: COCc1cc(OC)ccc1C1=C(CN2C(=O)O[C@H](c3cc(C(F)(F)F)cc(C(F)(F)F)c3)[C@@H]2C)CCCC1] |

TABLE 6-continued
| Compound | Structure | Compound | Structure |
|---|---|---|---|
| 60 | 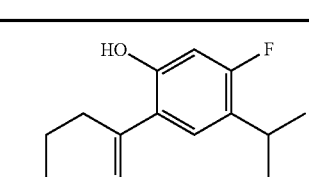 | 61 | 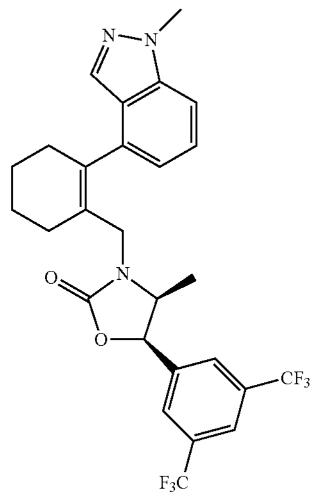 [SMILES: C[C@H]1[C@@H](c2cc(C(F)(F)F)cc(C(F)(F)F)c2)OC(=O)N1CC1=C(c2cccc3c2cnn3C)CCCC1] |
| 62 | 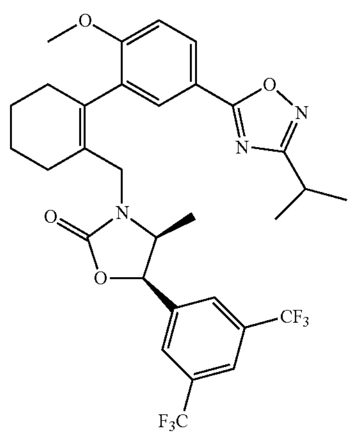 [SMILES: COc1ccc(-c2nc(C(C)C)no2)cc1C1=C(CN2C(=O)O[C@H](c3cc(C(F)(F)F)cc(C(F)(F)F)c3)[C@@H]2C)CCCC1] | 63 | 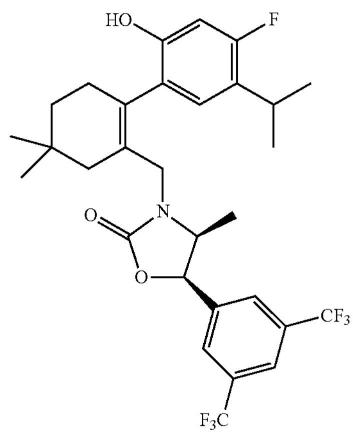 [SMILES: CC(C)c1cc(C2=C(CN3C(=O)O[C@H](c4cc(C(F)(F)F)cc(C(F)(F)F)c4)[C@@H]3C)CC(C)(C)CC2)c(O)cc1F] |
TABLE 7
| Compound | Structure | Compound | Structure |
|---|---|---|---|
| 64 | 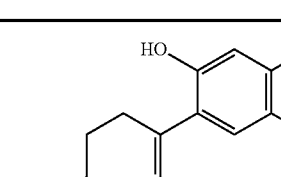 | 65 | 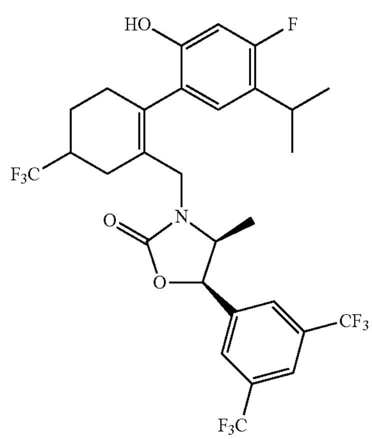 [SMILES: CC(C)c1cc(C2=C(CN3C(=O)O[C@H](c4cc(C(F)(F)F)cc(C(F)(F)F)c4)[C@@H]3C)CC(C(F)(F)F)CC2)c(O)cc1F] |

TABLE 7-continued

| Compound | Structure | Compound | Structure |
| --- | --- | --- | --- |
| 66 | 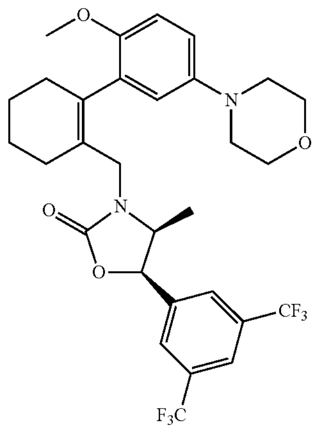 [SMILES: COc1ccc(N2CCOCC2)cc1C1=C(CN2C(=O)O[C@H](c3cc(C(F)(F)F)cc(C(F)(F)F)c3)[C@@H]2C)CCCC1] | 67 | 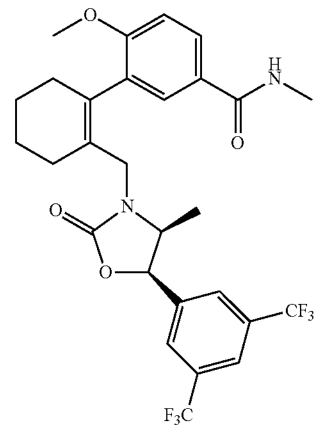 [SMILES: CNC(=O)c1ccc(OC)c(C2=C(CN3C(=O)O[C@H](c4cc(C(F)(F)F)cc(C(F)(F)F)c4)[C@@H]3C)CCCC2)c1] |
| 68 | 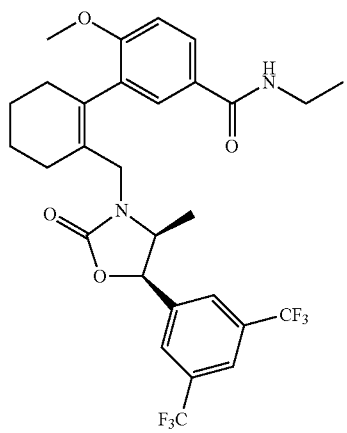 [SMILES: CCNC(=O)c1ccc(OC)c(C2=C(CN3C(=O)O[C@H](c4cc(C(F)(F)F)cc(C(F)(F)F)c4)[C@@H]3C)CCCC2)c1] | 69 | 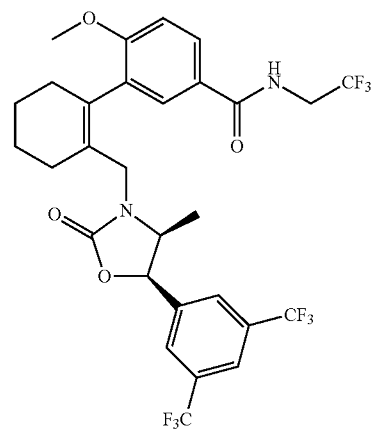 [SMILES: COc1ccc(C(=O)NCC(F)(F)F)cc1C1=C(CN2C(=O)O[C@H](c3cc(C(F)(F)F)cc(C(F)(F)F)c3)[C@@H]2C)CCCC1] |

TABLE 8

| Compound | Structure | Compound | Structure |
| --- | --- | --- | --- |
| 70 | 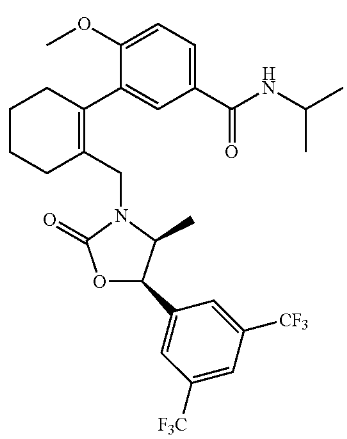 [SMILES: COc1ccc(C(=O)NC(C)C)cc1C1=C(CN2C(=O)O[C@H](c3cc(C(F)(F)F)cc(C(F)(F)F)c3)[C@@H]2C)CCCC1] | 71 | 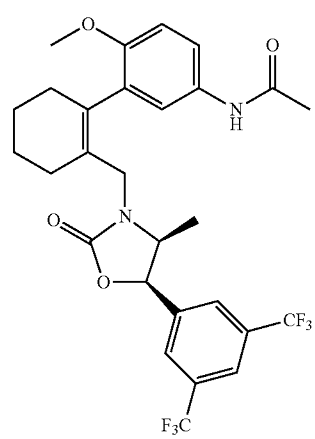 [SMILES: COc1ccc(NC(C)=O)cc1C1=C(CN2C(=O)O[C@H](c3cc(C(F)(F)F)cc(C(F)(F)F)c3)[C@@H]2C)CCCC1] |

TABLE 8-continued

| Compound | Structure | Compound | Structure |
|---|---|---|---|
| 72 | 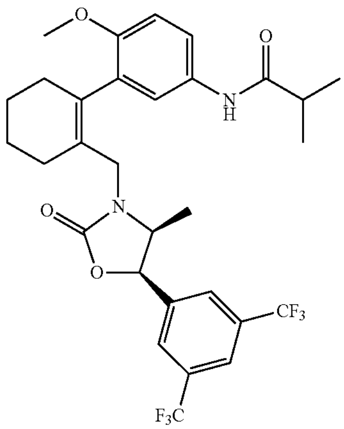 [SMILES: COc1ccc(NC(=O)C(C)C)cc1C1=C(CN2C(=O)O[C@H](c3cc(C(F)(F)F)cc(C(F)(F)F)c3)[C@@H]2C)CCCC1] | 76 | 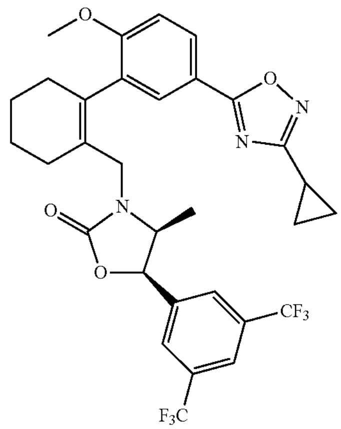 [SMILES: COc1ccc(-c2nc(C3CC3)no2)cc1C1=C(CN2C(=O)O[C@H](c3cc(C(F)(F)F)cc(C(F)(F)F)c3)[C@@H]2C)CCCC1] |
| 79 | 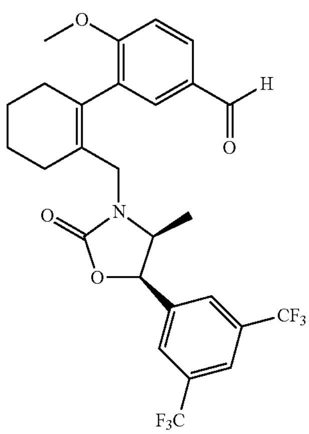 [SMILES: COc1ccc(C=O)cc1C1=C(CN2C(=O)O[C@H](c3cc(C(F)(F)F)cc(C(F)(F)F)c3)[C@@H]2C)CCCC1] | 80 | 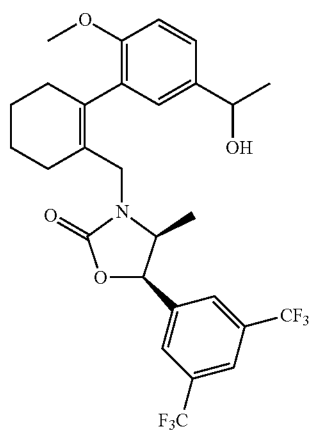 [SMILES: COc1ccc(C(C)O)cc1C1=C(CN2C(=O)O[C@H](c3cc(C(F)(F)F)cc(C(F)(F)F)c3)[C@@H]2C)CCCC1] |

TABLE 9

| Compound | Structure | Compound | Structure |
|---|---|---|---|
| 81 | 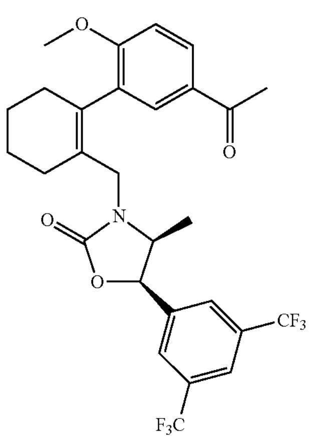 [SMILES: COc1ccc(C(C)=O)cc1C1=C(CN2C(=O)O[C@H](c3cc(C(F)(F)F)cc(C(F)(F)F)c3)[C@@H]2C)CCCC1] | 82 | 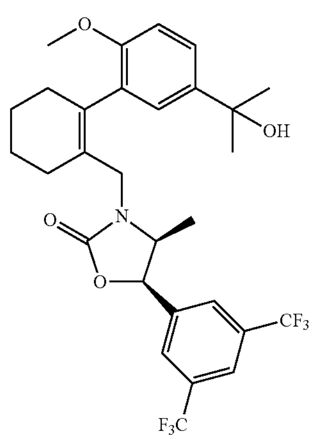 [SMILES: COc1ccc(C(C)(C)O)cc1C1=C(CN2C(=O)O[C@H](c3cc(C(F)(F)F)cc(C(F)(F)F)c3)[C@@H]2C)CCCC1] |

TABLE 9-continued

| Compound | Structure | Compound | Structure |
| --- | --- | --- | --- |
| 83 | 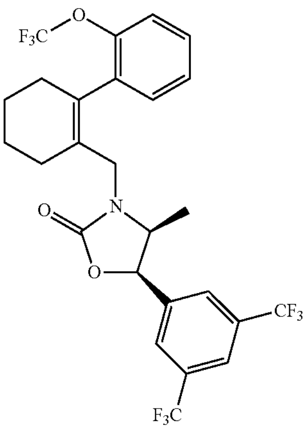 [SMILES: C[C@H]1[C@@H](c2cc(C(F)(F)F)cc(C(F)(F)F)c2)OC(=O)N1CC1=C(c2ccccc2OC(F)(F)F)CCCC1] | 84 | 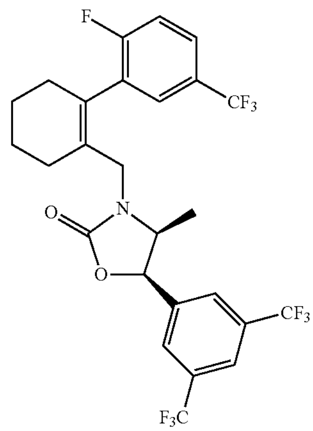 [SMILES: C[C@H]1[C@@H](c2cc(C(F)(F)F)cc(C(F)(F)F)c2)OC(=O)N1CC1=C(c2cc(C(F)(F)F)ccc2F)CCCC1] |
| 85 | 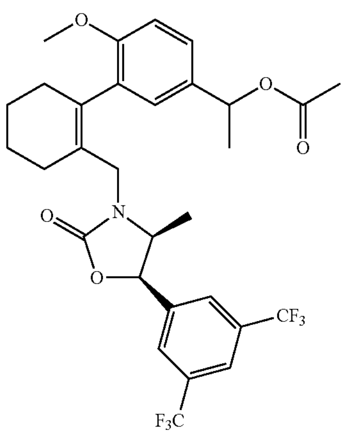 [SMILES: COc1ccc(C(C)OC(C)=O)cc1C1=C(CN2C(=O)O[C@H](c3cc(C(F)(F)F)cc(C(F)(F)F)c3)[C@@H]2C)CCCC1] | 86 | 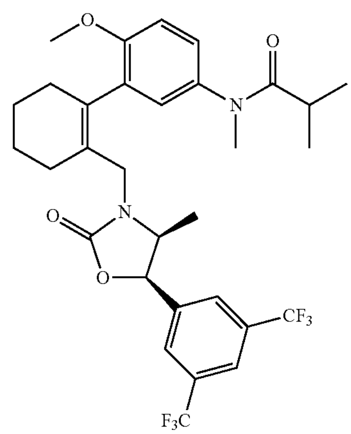 [SMILES: COc1ccc(N(C)C(=O)C(C)C)cc1C1=C(CN2C(=O)O[C@H](c3cc(C(F)(F)F)cc(C(F)(F)F)c3)[C@@H]2C)CCCC1] |

TABLE 10

| Compound | Structure | Compound | Structure |
| --- | --- | --- | --- |
| 87 | 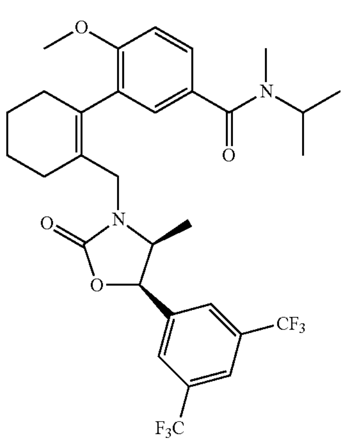 [SMILES: COc1ccc(C(=O)N(C)C(C)C)cc1C1=C(CN2C(=O)O[C@H](c3cc(C(F)(F)F)cc(C(F)(F)F)c3)[C@@H]2C)CCCC1] | 96 | 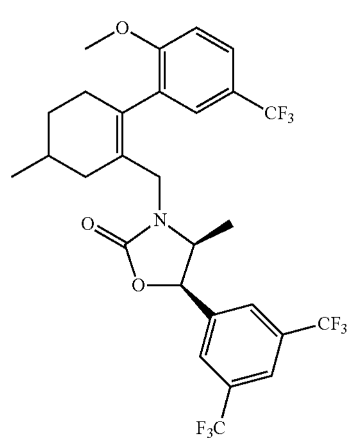 [SMILES: COc1ccc(C(F)(F)F)cc1C1=C(CN2C(=O)O[C@H](c3cc(C(F)(F)F)cc(C(F)(F)F)c3)[C@@H]2C)CC(C)CC1] |

TABLE 10-continued

| Compound | Structure | Compound | Structure |
| --- | --- | --- | --- |
| 97 | 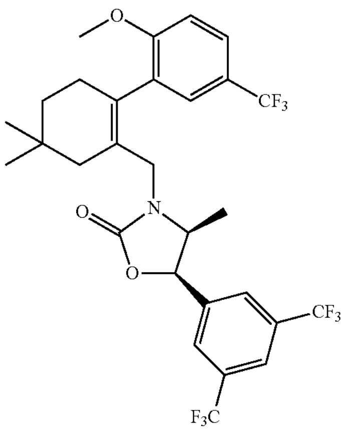 [SMILES: COc1ccc(C(F)(F)F)cc1C1=C(CN2C(=O)O[C@H](c3cc(C(F)(F)F)cc(C(F)(F)F)c3)[C@@H]2C)CC(C)(C)CC1] | 101 | 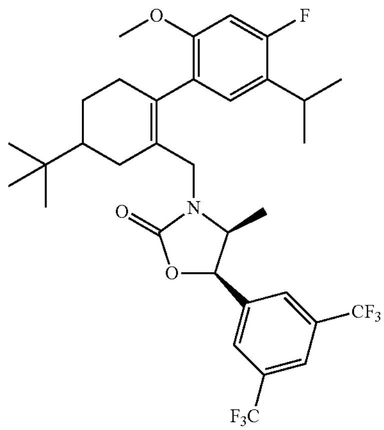 [SMILES: COc1cc(F)c(C(C)C)cc1C1=C(CN2C(=O)O[C@H](c3cc(C(F)(F)F)cc(C(F)(F)F)c3)[C@@H]2C)CC(C(C)(C)C)CC1] |
| 103 | 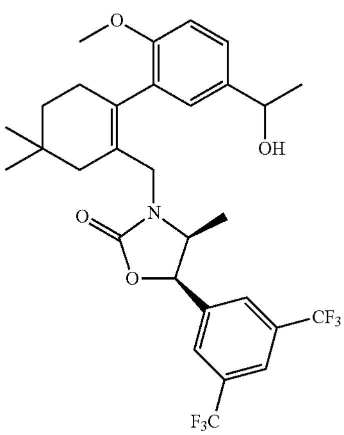 [SMILES: COc1ccc(C(C)O)cc1C1=C(CN2C(=O)O[C@H](c3cc(C(F)(F)F)cc(C(F)(F)F)c3)[C@@H]2C)CC(C)(C)CC1] | 104 | 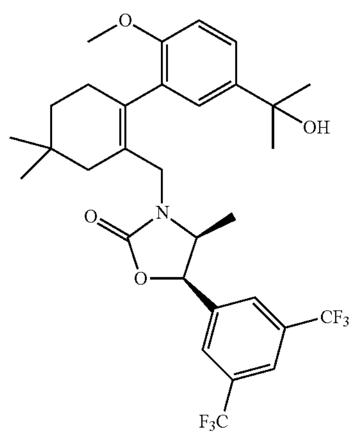 [SMILES: COc1ccc(C(C)(C)O)cc1C1=C(CN2C(=O)O[C@H](c3cc(C(F)(F)F)cc(C(F)(F)F)c3)[C@@H]2C)CC(C)(C)CC1] |

TABLE 11

| Compound | Structure | Compound | Structure |
| --- | --- | --- | --- |
| 107 | 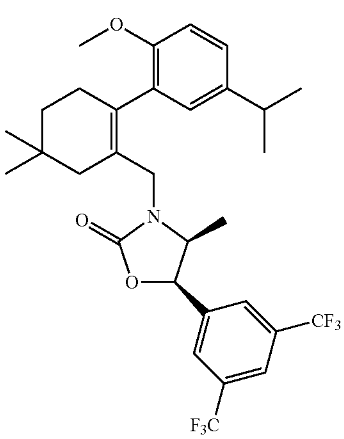 [SMILES: COc1ccc(C(C)C)cc1C1=C(CN2C(=O)O[C@H](c3cc(C(F)(F)F)cc(C(F)(F)F)c3)[C@@H]2C)CC(C)(C)CC1] | 108 | 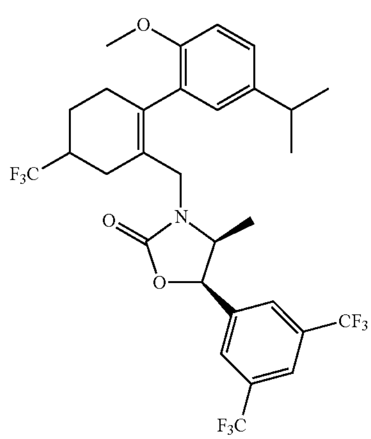 [SMILES: COc1ccc(C(C)C)cc1C1=C(CN2C(=O)O[C@H](c3cc(C(F)(F)F)cc(C(F)(F)F)c3)[C@@H]2C)CC(C(F)(F)F)CC1] |

TABLE 11-continued
| Compound | Structure | Compound | Structure |
| --- | --- | --- | --- |
| 109 | 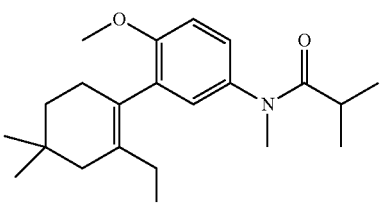 | 110 | 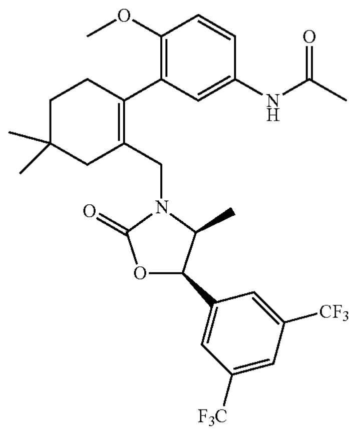 [SMILES: COc1ccc(NC(C)=O)cc1C1=C(CN2C(=O)O[C@H](c3cc(C(F)(F)F)cc(C(F)(F)F)c3)[C@@H]2C)CC(C)(C)CC1] |
| 111 | 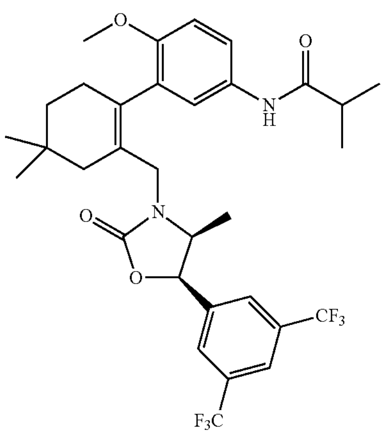 | 112 | 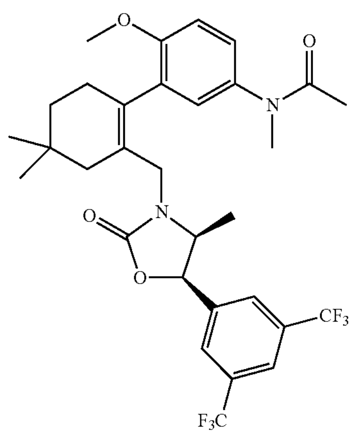 [SMILES: COc1ccc(N(C)C(C)=O)cc1C1=C(CN2C(=O)O[C@H](c3cc(C(F)(F)F)cc(C(F)(F)F)c3)[C@@H]2C)CC(C)(C)CC1] |
TABLE 12
| Compound | Structure | Compound | Structure |
| --- | --- | --- | --- |
| 113 | 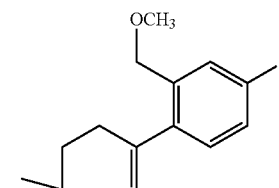 | 114 | 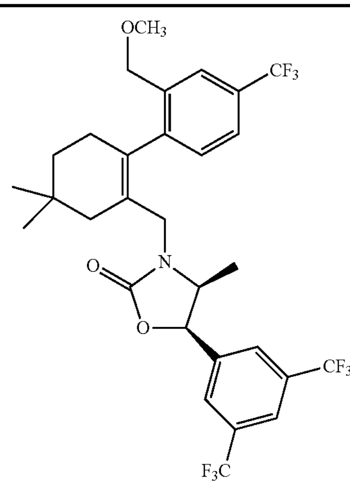 |

TABLE 12-continued

| Compound | Structure | Compound | Structure |
| --- | --- | --- | --- |
| 115 | 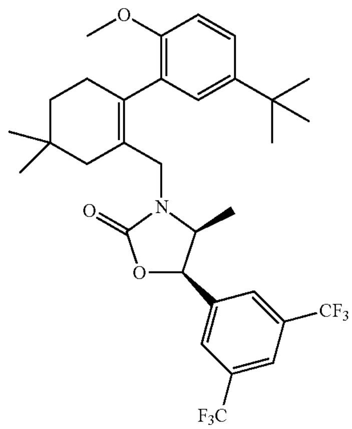 [SMILES: COc1ccc(C(C)(C)C)cc1C1=C(CN2C(=O)O[C@H](c3cc(C(F)(F)F)cc(C(F)(F)F)c3)[C@@H]2C)CC(C)(C)CC1] | 116 | 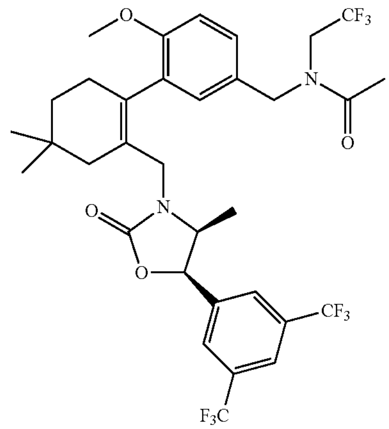 [SMILES: COc1ccc(CN(CC(F)(F)F)C(C)=O)cc1C1=C(CN2C(=O)O[C@H](c3cc(C(F)(F)F)cc(C(F)(F)F)c3)[C@@H]2C)CC(C)(C)CC1] |
| 117 | 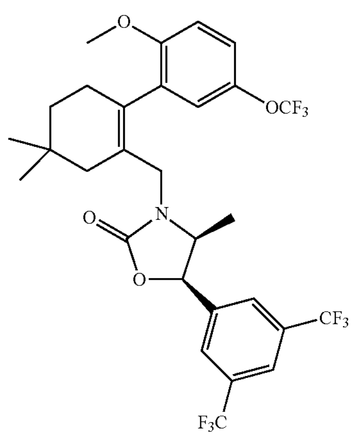 | 118 | 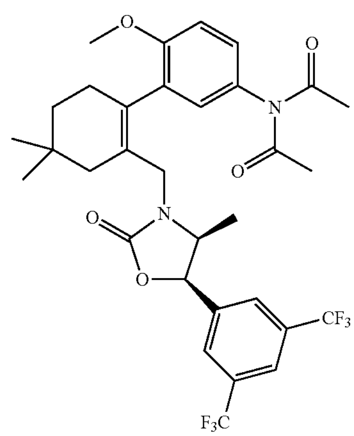 [SMILES: COc1ccc(N(C(C)=O)C(C)=O)cc1C1=C(CN2C(=O)O[C@H](c3cc(C(F)(F)F)cc(C(F)(F)F)c3)[C@@H]2C)CC(C)(C)CC1] |

TABLE 13

| Compound | Structure | Compound | Structure |
| --- | --- | --- | --- |
| 120 | 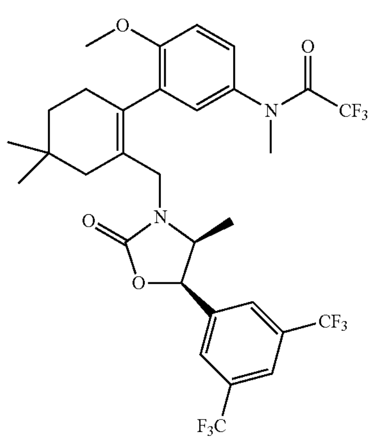 [SMILES: COc1ccc(N(C)C(=O)C(F)(F)F)cc1C1=C(CN2C(=O)O[C@H](c3cc(C(F)(F)F)cc(C(F)(F)F)c3)[C@@H]2C)CC(C)(C)CC1] | 121 | 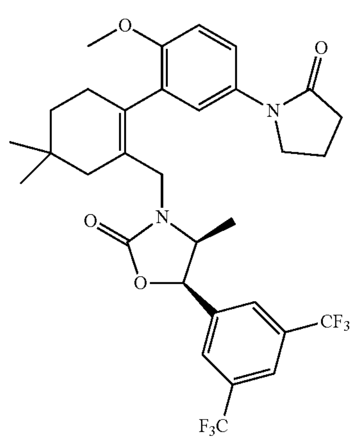 [SMILES: COc1ccc(N2CCCC2=O)cc1C1=C(CN2C(=O)O[C@H](c3cc(C(F)(F)F)cc(C(F)(F)F)c3)[C@@H]2C)CC(C)(C)CC1] |

TABLE 13-continued

| Compound | Structure | Compound | Structure |
| --- | --- | --- | --- |
| 122 | 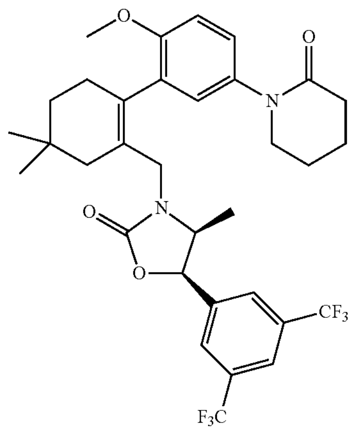 [SMILES: COc1ccc(N2CCCCC2=O)cc1C1=C(CN2C(=O)O[C@H](c3cc(C(F)(F)F)cc(C(F)(F)F)c3)[C@@H]2C)CC(C)(C)CC1] | 123 | 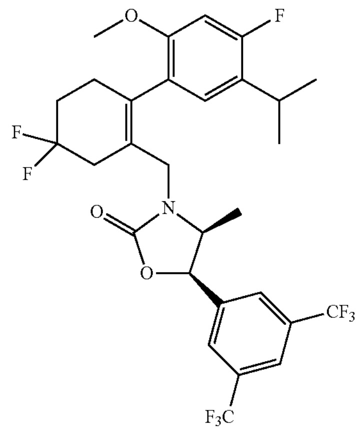 [SMILES: COc1cc(F)c(C(C)C)cc1C1=C(CN2C(=O)O[C@H](c3cc(C(F)(F)F)cc(C(F)(F)F)c3)[C@@H]2C)CC(F)(F)CC1] |
| 124 | 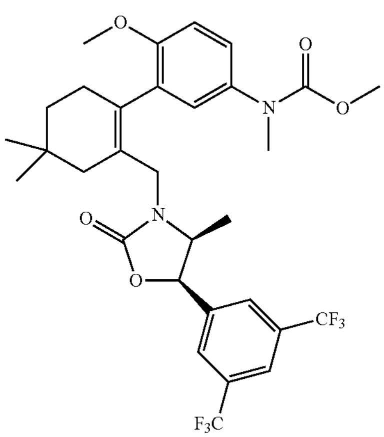 | 128 | 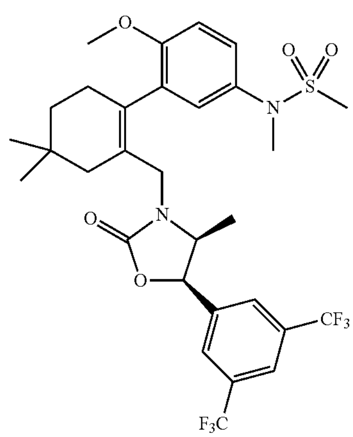 |

TABLE 14

| Compound | Structure | Compound | Structure |
| --- | --- | --- | --- |
| 130 | 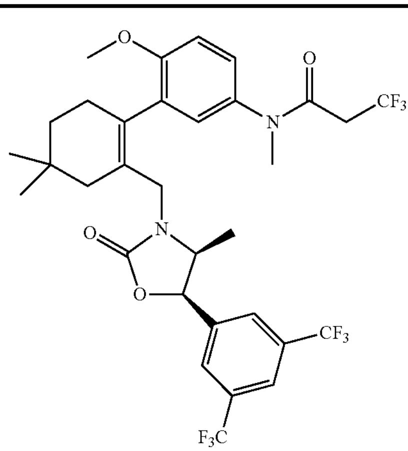 | 132 | 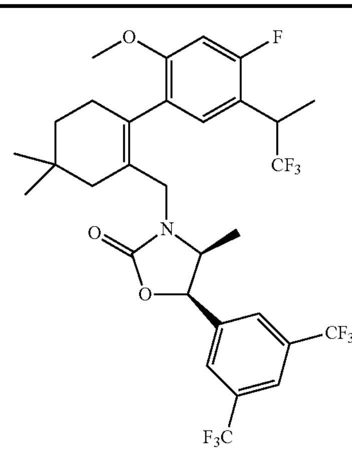 |

TABLE 14-continued

| Compound | Structure | Compound | Structure |
|---|---|---|---|
| 133 | 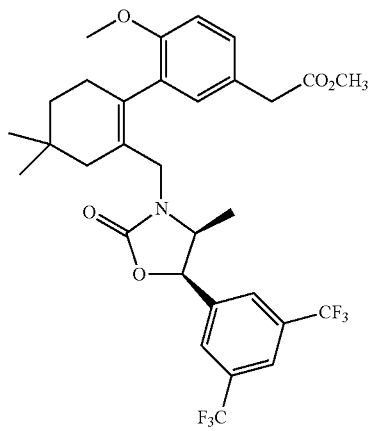 [SMILES: COC(=O)Cc1ccc(OC)c(C2=C(CN3C(=O)O[C@H](c4cc(C(F)(F)F)cc(C(F)(F)F)c4)[C@@H]3C)CC(C)(C)CC2)c1] | 134 | 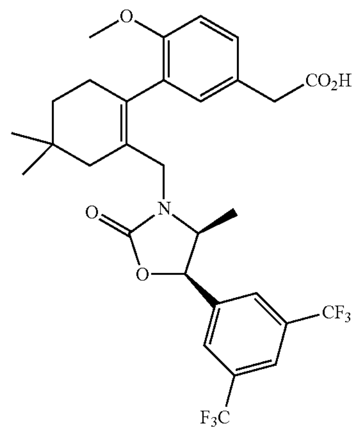 [SMILES: COc1ccc(CC(=O)O)cc1C1=C(CN2C(=O)O[C@H](c3cc(C(F)(F)F)cc(C(F)(F)F)c3)[C@@H]2C)CC(C)(C)CC1] |
| 136 | 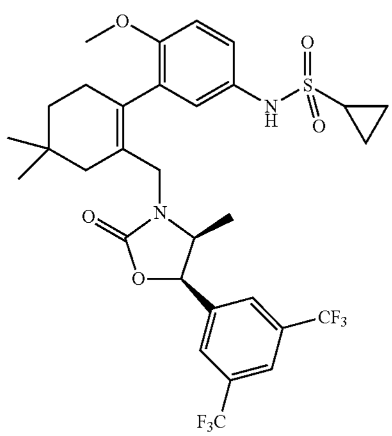 [SMILES: COc1ccc(NS(=O)(=O)C2CC2)cc1C1=C(CN2C(=O)O[C@H](c3cc(C(F)(F)F)cc(C(F)(F)F)c3)[C@@H]2C)CC(C)(C)CC1] | 137 | 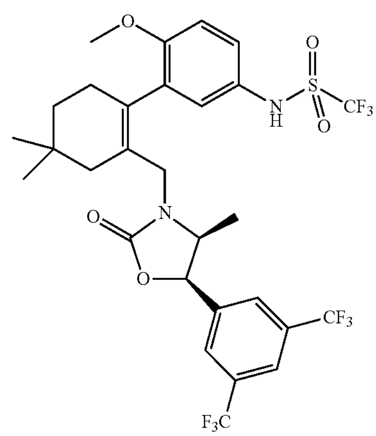 [SMILES: COc1ccc(NS(=O)(=O)C(F)(F)F)cc1C1=C(CN2C(=O)O[C@H](c3cc(C(F)(F)F)cc(C(F)(F)F)c3)[C@@H]2C)CC(C)(C)CC1] |

TABLE 15

| Compound | Structure | Compound | Structure |
|---|---|---|---|
| 138 | 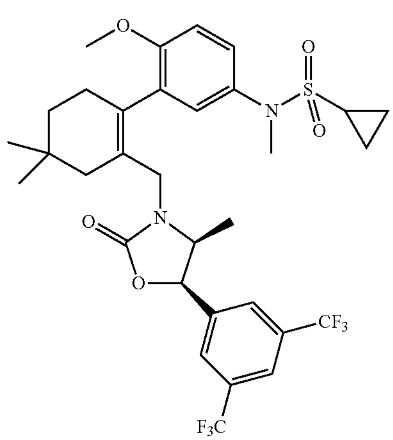 [SMILES: COc1ccc(N(C)S(=O)(=O)C2CC2)cc1C1=C(CN2C(=O)O[C@H](c3cc(C(F)(F)F)cc(C(F)(F)F)c3)[C@@H]2C)CC(C)(C)CC1] | 140 | 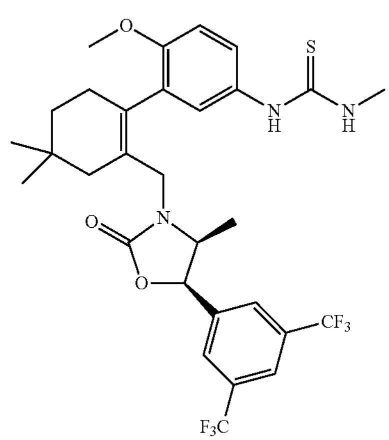 |

TABLE 15-continued
| Compound | Structure | Compound | Structure |
|---|---|---|---|
| 141 | 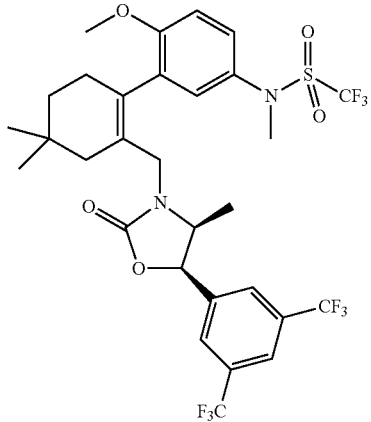 [SMILES: COc1ccc(N(C)S(=O)(=O)C(F)(F)F)cc1C1=C(CN2C(=O)O[C@H](c3cc(C(F)(F)F)cc(C(F)(F)F)c3)[C@@H]2C)CC(C)(C)CC1] | 142 | 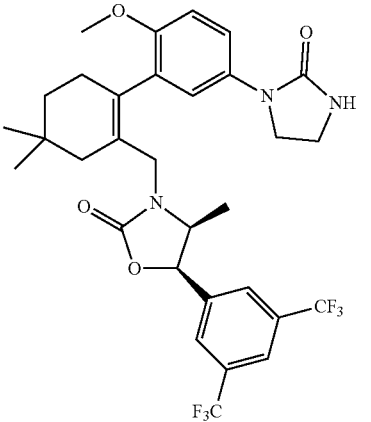 [SMILES: COc1ccc(N2CCNC2=O)cc1C1=C(CN2C(=O)O[C@H](c3cc(C(F)(F)F)cc(C(F)(F)F)c3)[C@@H]2C)CC(C)(C)CC1] |
| 143 | 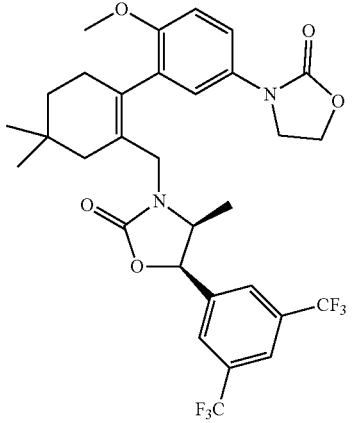 [SMILES: COc1ccc(N2CCOC2=O)cc1C1=C(CN2C(=O)O[C@H](c3cc(C(F)(F)F)cc(C(F)(F)F)c3)[C@@H]2C)CC(C)(C)CC1] | 144 | 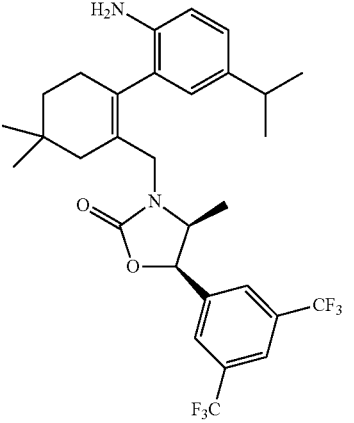 [SMILES: CC(C)c1ccc(N)c(C2=C(CN3C(=O)O[C@H](c4cc(C(F)(F)F)cc(C(F)(F)F)c4)[C@@H]3C)CC(C)(C)CC2)c1] |
TABLE 16
| Compound | Structure | Compound | Structure |
|---|---|---|---|
| 145 | 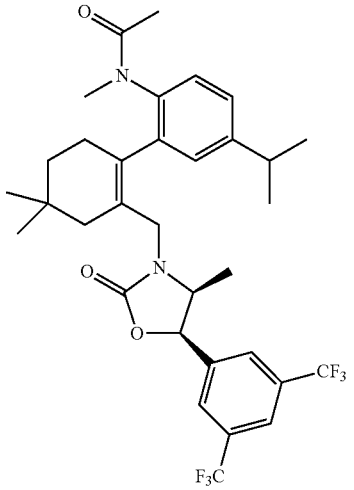 [SMILES: CC(=O)N(C)c1ccc(C(C)C)cc1C1=C(CN2C(=O)O[C@H](c3cc(C(F)(F)F)cc(C(F)(F)F)c3)[C@@H]2C)CC(C)(C)CC1] | 146 | 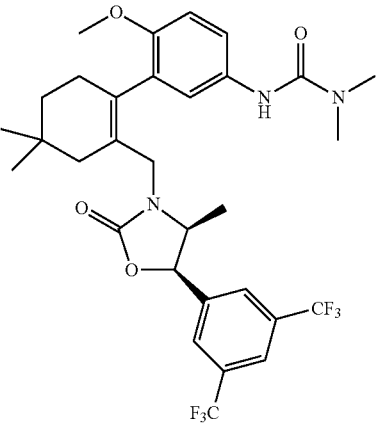 |

TABLE 16-continued

| Compound | Structure | Compound | Structure |
|---|---|---|---|
| 147 | 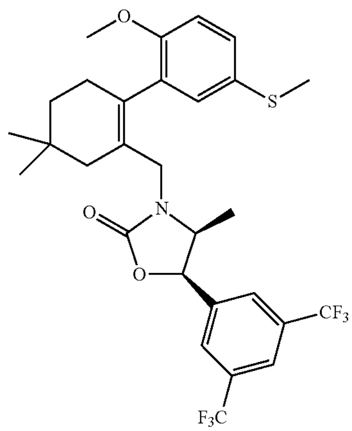 [SMILES: COc1ccc(SC)cc1C1=C(CN2C(=O)O[C@H](c3cc(C(F)(F)F)cc(C(F)(F)F)c3)[C@@H]2C)CC(C)(C)CC1] | 148 | 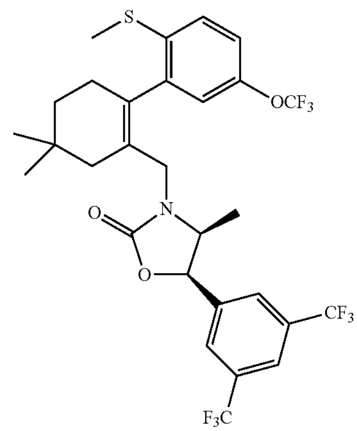 [SMILES: CSc1ccc(OC(F)(F)F)cc1C1=C(CN2C(=O)O[C@H](c3cc(C(F)(F)F)cc(C(F)(F)F)c3)[C@@H]2C)CC(C)(C)CC1] |
| 149 | 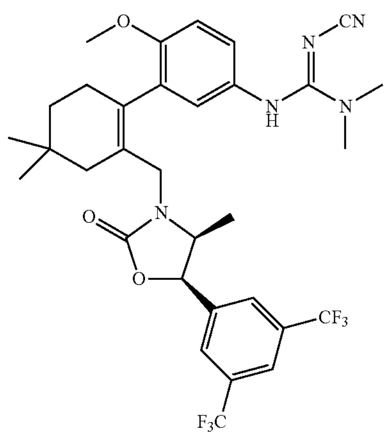 | 151 | 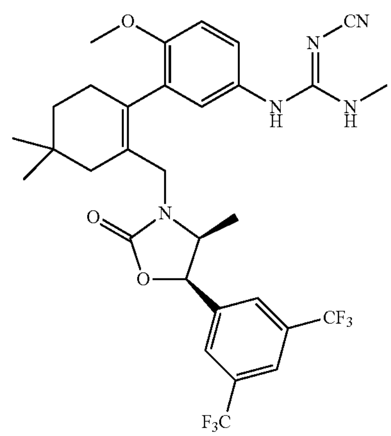 |

TABLE 17

| Compound | Structure | Compound | Structure |
|---|---|---|---|
| 153 | 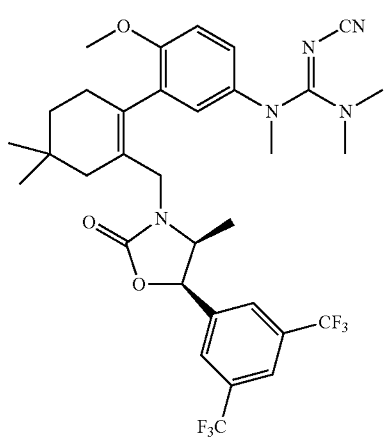 | 156 | 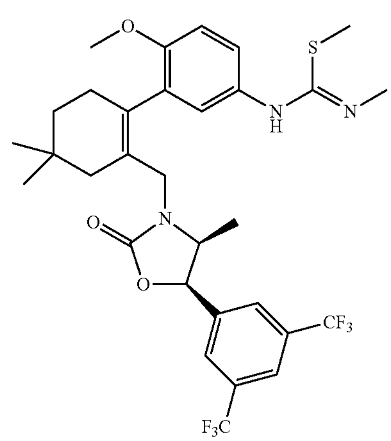 |

TABLE 17-continued

| Compound | Structure | Compound | Structure |
| --- | --- | --- | --- |
| 157 | 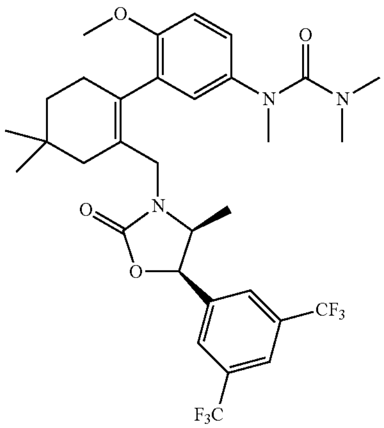 | 159 | 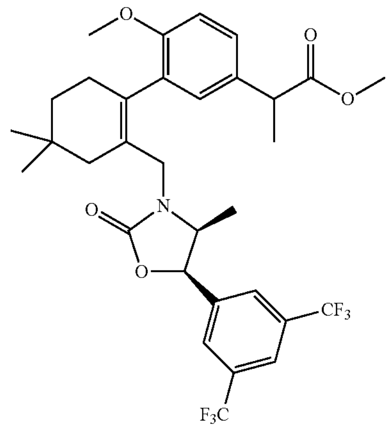 |
| 160 | 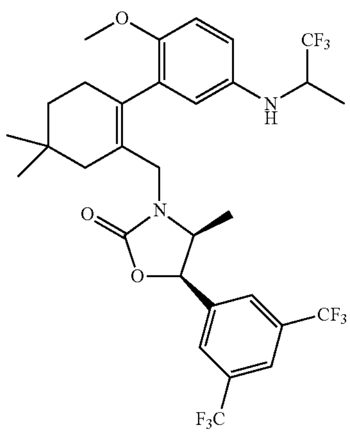 [SMILES: COc1ccc(NC(C)C(F)(F)F)cc1C1=C(CN2C(=O)O[C@H](c3cc(C(F)(F)F)cc(C(F)(F)F)c3)[C@@H]2C)CC(C)(C)CC1] | 161 | 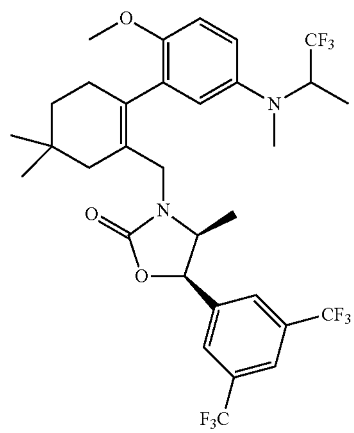 [SMILES: COc1ccc(N(C)C(C)C(F)(F)F)cc1C1=C(CN2C(=O)O[C@H](c3cc(C(F)(F)F)cc(C(F)(F)F)c3)[C@@H]2C)CC(C)(C)CC1] |

TABLE 18

| Compound | Structure | Compound | Structure |
| --- | --- | --- | --- |
| 162 | 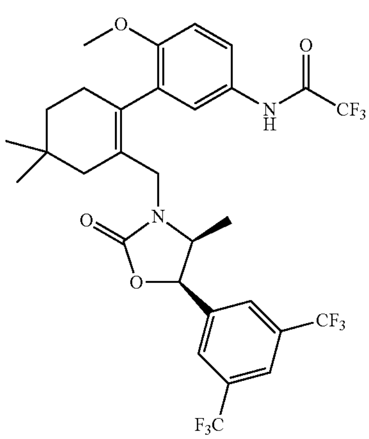 [SMILES: COc1ccc(NC(=O)C(F)(F)F)cc1C1=C(CN2C(=O)O[C@H](c3cc(C(F)(F)F)cc(C(F)(F)F)c3)[C@@H]2C)CC(C)(C)CC1] | 163 | 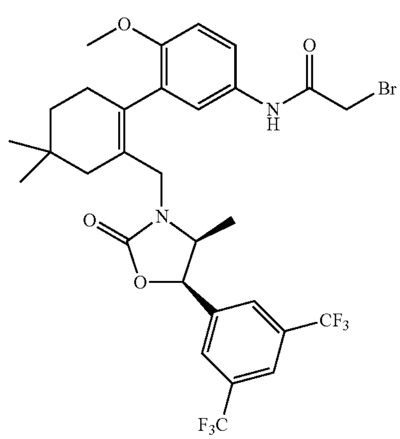 [SMILES: COc1ccc(NC(=O)CBr)cc1C1=C(CN2C(=O)O[C@H](c3cc(C(F)(F)F)cc(C(F)(F)F)c3)[C@@H]2C)CC(C)(C)CC1] |

TABLE 18-continued

| Compound | Structure | Compound | Structure |
| --- | --- | --- | --- |
| 166 | 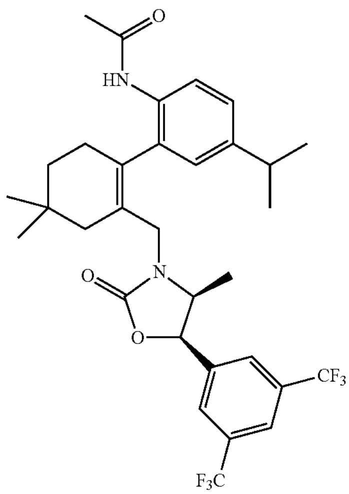 [SMILES: CC(=O)Nc1ccc(C(C)C)cc1C1=C(CN2C(=O)O[C@H](c3cc(C(F)(F)F)cc(C(F)(F)F)c3)[C@@H]2C)CC(C)(C)CC1] | 167 | 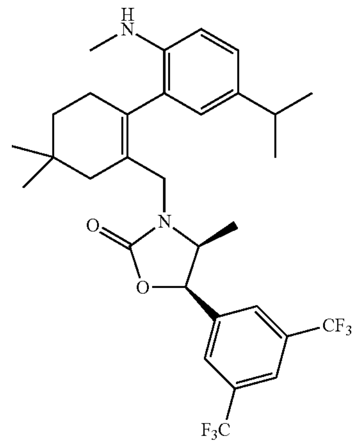 [SMILES: CNc1ccc(C(C)C)cc1C1=C(CN2C(=O)O[C@H](c3cc(C(F)(F)F)cc(C(F)(F)F)c3)[C@@H]2C)CC(C)(C)CC1] |
| 168 | 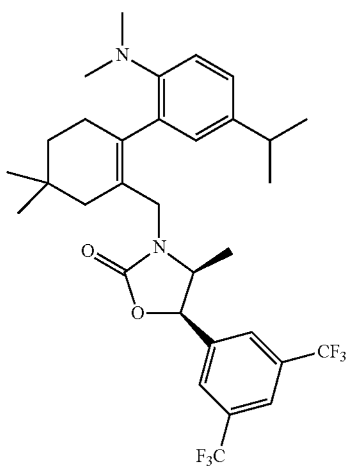 [SMILES: CC(C)c1ccc(N(C)C)c(C2=C(CN3C(=O)O[C@H](c4cc(C(F)(F)F)cc(C(F)(F)F)c4)[C@@H]3C)CC(C)(C)CC2)c1] | 170 | 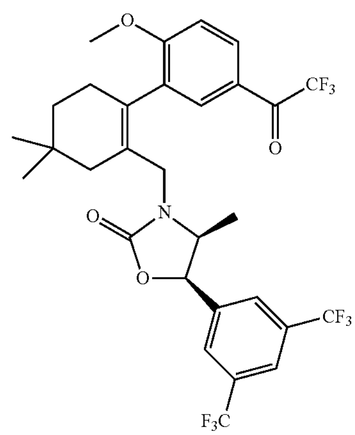 [SMILES: COc1ccc(C(=O)C(F)(F)F)cc1C1=C(CN2C(=O)O[C@H](c3cc(C(F)(F)F)cc(C(F)(F)F)c3)[C@@H]2C)CC(C)(C)CC1] |

TABLE 19

| Compound | Structure | Compound | Structure |
| --- | --- | --- | --- |
| 171 | 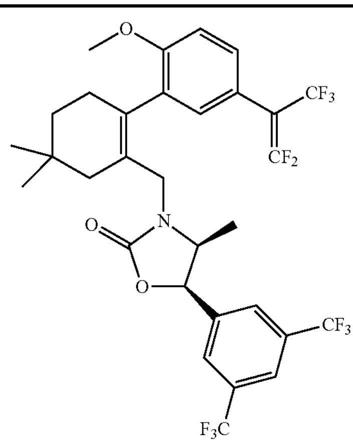 | 172 | 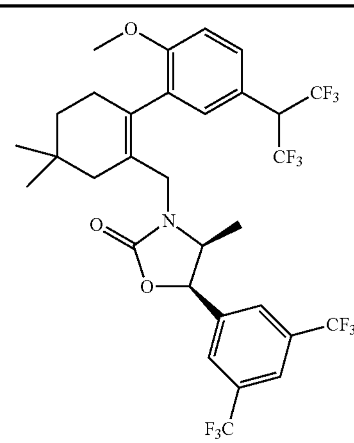 |

TABLE 19-continued

| Compound | Structure | Compound | Structure |
| --- | --- | --- | --- |
| 173 | 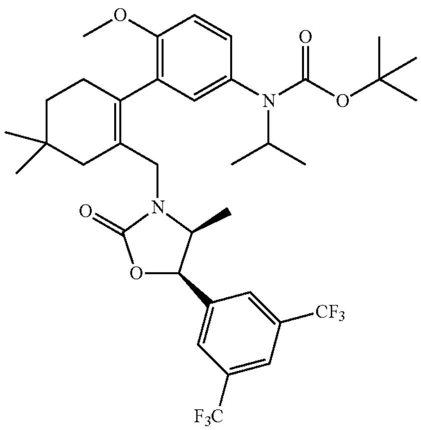 [SMILES: COc1ccc(N(C(=O)OC(C)(C)C)C(C)C)cc1C1=C(CN2C(=O)O[C@H](c3cc(C(F)(F)F)cc(C(F)(F)F)c3)[C@@H]2C)CC(C)(C)CC1] | 174 | 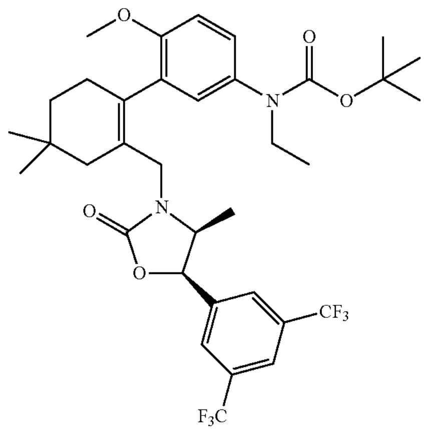 [SMILES: CCN(C(=O)OC(C)(C)C)c1ccc(OC)c(C2=C(CN3C(=O)O[C@H](c4cc(C(F)(F)F)cc(C(F)(F)F)c4)[C@@H]3C)CC(C)(C)CC2)c1] |
| 177 | 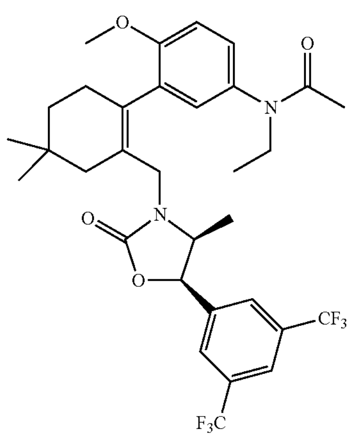 [SMILES: CCN(C(C)=O)c1ccc(OC)c(C2=C(CN3C(=O)O[C@H](c4cc(C(F)(F)F)cc(C(F)(F)F)c4)[C@@H]3C)CC(C)(C)CC2)c1] | 178 | 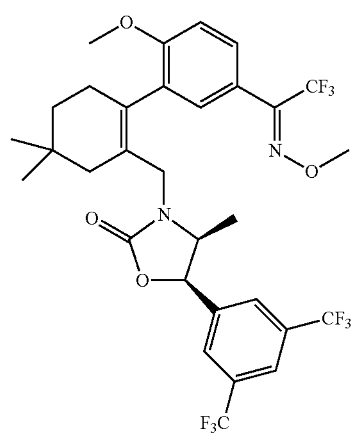 |

TABLE 20

| Compound | Structure | Compound | Structure |
| --- | --- | --- | --- |
| 179 | 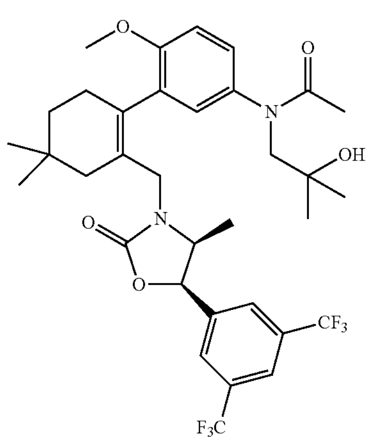 [SMILES: COc1ccc(N(CC(C)(C)O)C(C)=O)cc1C1=C(CN2C(=O)O[C@H](c3cc(C(F)(F)F)cc(C(F)(F)F)c3)[C@@H]2C)CC(C)(C)CC1] | 180 | 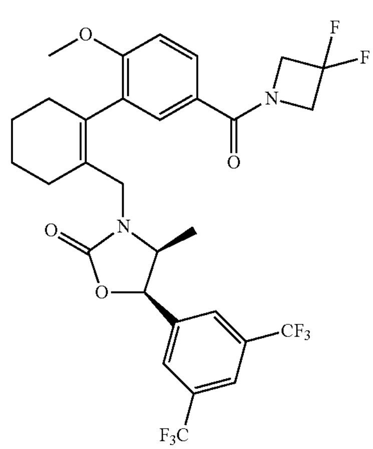 [SMILES: COc1ccc(C(=O)N2CC(F)(F)C2)cc1C1=C(CN2C(=O)O[C@H](c3cc(C(F)(F)F)cc(C(F)(F)F)c3)[C@@H]2C)CCCC1] |

TABLE 20-continued

| Compound | Structure | Compound | Structure |
| --- | --- | --- | --- |
| 181 | 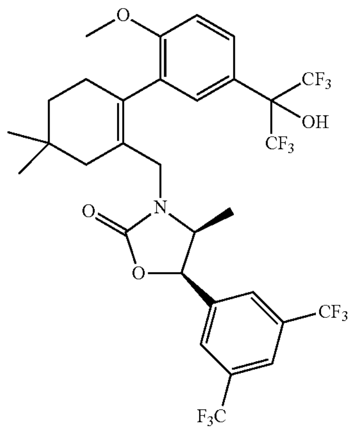 [SMILES: COc1ccc(C(O)(C(F)(F)F)C(F)(F)F)cc1C1=C(CN2C(=O)O[C@H](c3cc(C(F)(F)F)cc(C(F)(F)F)c3)[C@@H]2C)CC(C)(C)CC1] | 182 | 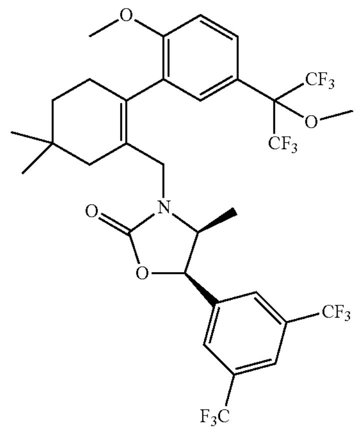 |
| 183 | 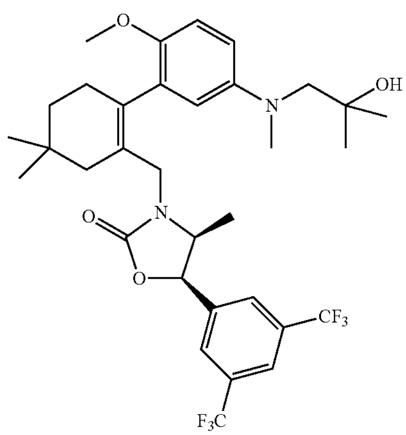 [SMILES: COc1ccc(N(C)CC(C)(C)O)cc1C1=C(CN2C(=O)O[C@H](c3cc(C(F)(F)F)cc(C(F)(F)F)c3)[C@@H]2C)CC(C)(C)CC1] | 184 | 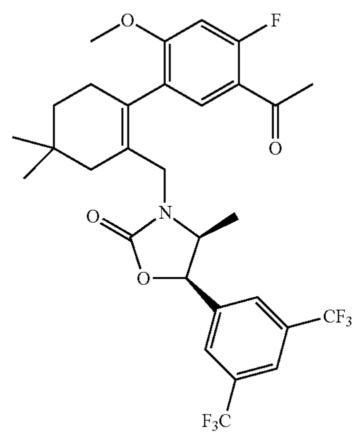 [SMILES: COc1cc(F)c(C(C)=O)cc1C1=C(CN2C(=O)O[C@H](c3cc(C(F)(F)F)cc(C(F)(F)F)c3)[C@@H]2C)CC(C)(C)CC1] |

TABLE 21

| Compound | Structure | Compound | Structure |
| --- | --- | --- | --- |
| 185 | 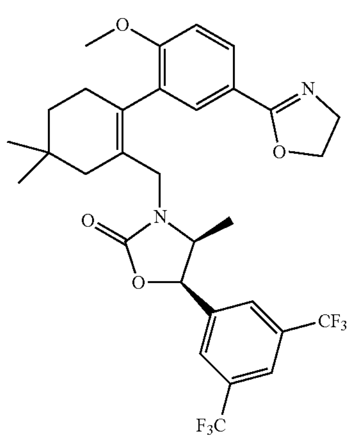 [SMILES: COc1ccc(C2=NCCO2)cc1C1=C(CN2C(=O)O[C@H](c3cc(C(F)(F)F)cc(C(F)(F)F)c3)[C@@H]2C)CC(C)(C)CC1] | 187 | 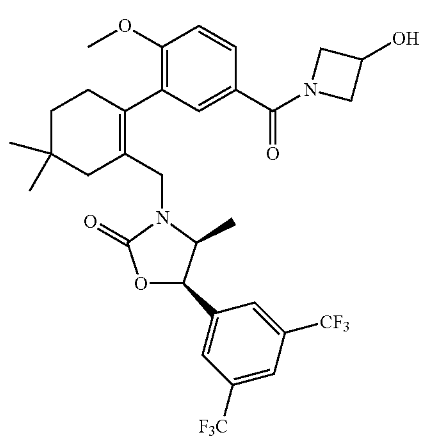 [SMILES: COc1ccc(C(=O)N2CC(O)C2)cc1C1=C(CN2C(=O)O[C@H](c3cc(C(F)(F)F)cc(C(F)(F)F)c3)[C@@H]2C)CC(C)(C)CC1] |

TABLE 21-continued

| Compound | Structure | Compound | Structure |
| --- | --- | --- | --- |
| 188 | 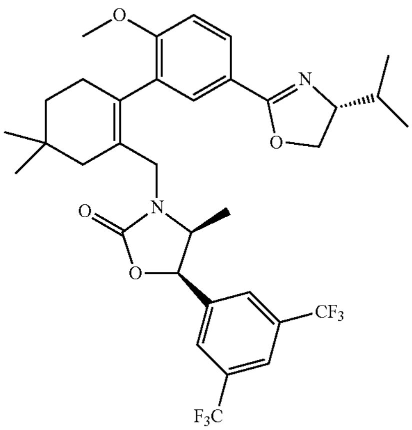 [SMILES: COc1ccc(C2=N[C@H](C(C)C)CO2)cc1C1=C(CN2C(=O)O[C@H](c3cc(C(F)(F)F)cc(C(F)(F)F)c3)[C@@H]2C)CC(C)(C)CC1] | 189 | 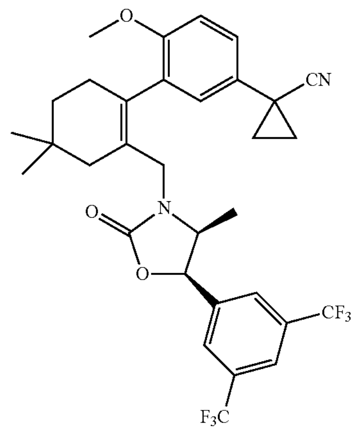 [SMILES: COc1ccc(C2(C#N)CC2)cc1C1=C(CN2C(=O)O[C@H](c3cc(C(F)(F)F)cc(C(F)(F)F)c3)[C@@H]2C)CC(C)(C)CC1] |
| 190 | 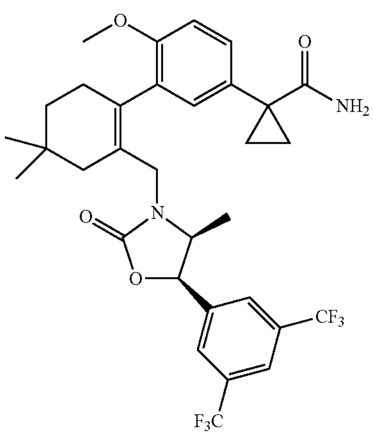 [SMILES: COc1ccc(C2(C(N)=O)CC2)cc1C1=C(CN2C(=O)O[C@H](c3cc(C(F)(F)F)cc(C(F)(F)F)c3)[C@@H]2C)CC(C)(C)CC1] | 191 | 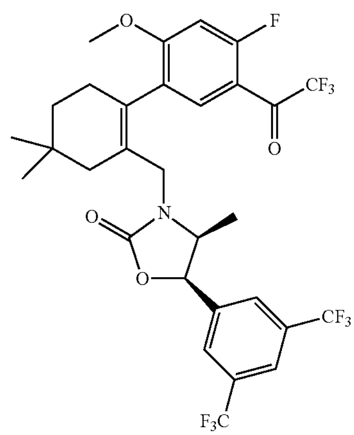 [SMILES: COc1cc(F)c(C(=O)C(F)(F)F)cc1C1=C(CN2C(=O)O[C@H](c3cc(C(F)(F)F)cc(C(F)(F)F)c3)[C@@H]2C)CC(C)(C)CC1] |

TABLE 22

| Compound | Structure | Compound | Structure |
| --- | --- | --- | --- |
| 192 | 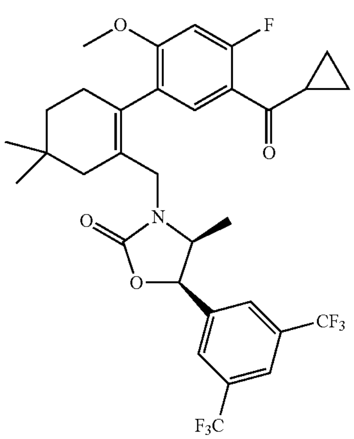 [SMILES: COc1cc(F)c(C(=O)C2CC2)cc1C1=C(CN2C(=O)O[C@H](c3cc(C(F)(F)F)cc(C(F)(F)F)c3)[C@@H]2C)CC(C)(C)CC1] | 193 | 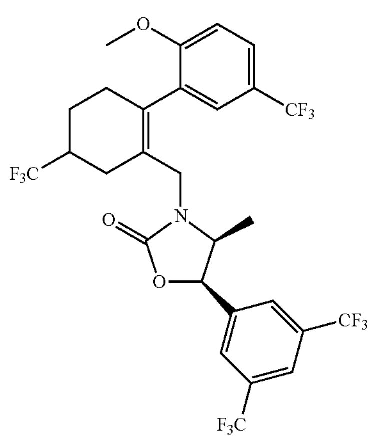 [SMILES: COc1ccc(C(F)(F)F)cc1C1=C(CN2C(=O)O[C@H](c3cc(C(F)(F)F)cc(C(F)(F)F)c3)[C@@H]2C)CC(C(F)(F)F)CC1] |

TABLE 22-continued

| Compound | Structure | Compound | Structure |
| --- | --- | --- | --- |
| 194 | 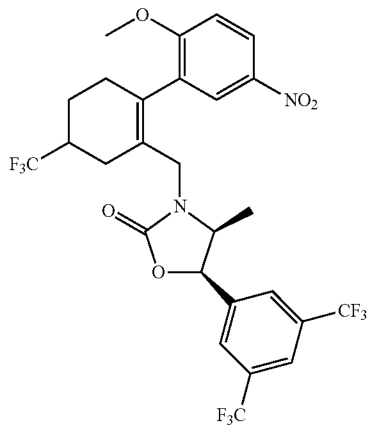 [SMILES: COc1ccc([N+](=O)[O-])cc1C1=C(CN2C(=O)O[C@H](c3cc(C(F)(F)F)cc(C(F)(F)F)c3)[C@@H]2C)CC(C(F)(F)F)CC1] | 195 | 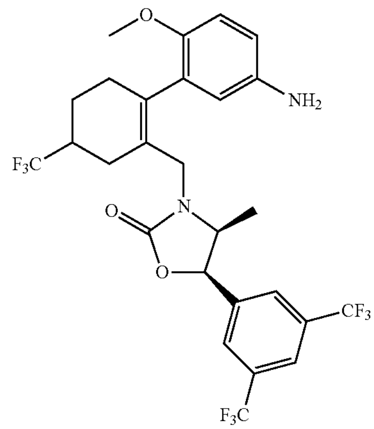 |
| 196 | 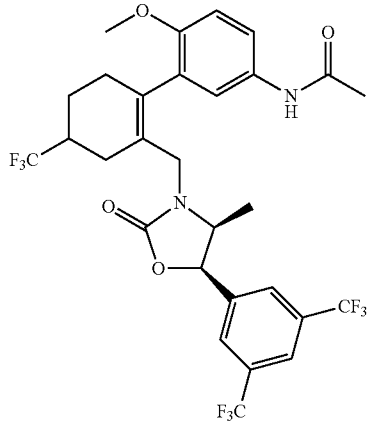 [SMILES: COc1ccc(NC(C)=O)cc1C1=C(CN2C(=O)O[C@H](c3cc(C(F)(F)F)cc(C(F)(F)F)c3)[C@@H]2C)CC(C(F)(F)F)CC1] | 197 | 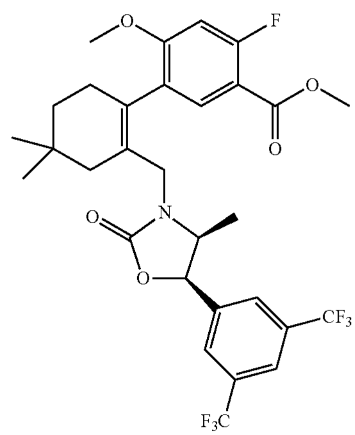 |

TABLE 23

| Compound | Structure | Compound | Structure |
| --- | --- | --- | --- |
| 204 | 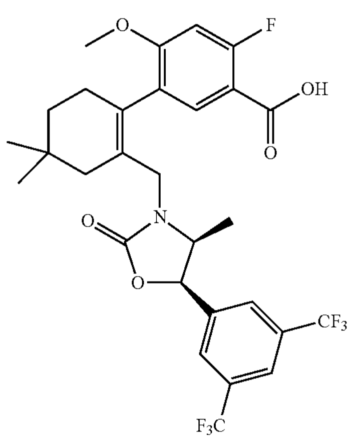 [SMILES: COc1cc(F)c(C(=O)O)cc1C1=C(CN2C(=O)O[C@H](c3cc(C(F)(F)F)cc(C(F)(F)F)c3)[C@@H]2C)CC(C)(C)CC1] | 206 | 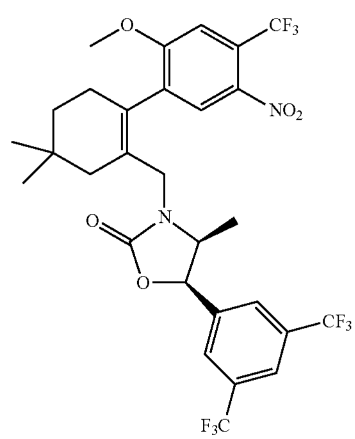 [SMILES: COc1cc(C(F)(F)F)c([N+](=O)[O-])cc1C1=C(CN2C(=O)O[C@H](c3cc(C(F)(F)F)cc(C(F)(F)F)c3)[C@@H]2C)CC(C)(C)CC1] |

TABLE 23-continued

| Compound | Structure | Compound | Structure |
| --- | --- | --- | --- |
| 207 | 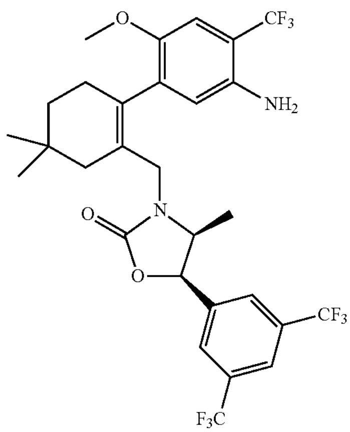 | 209 | 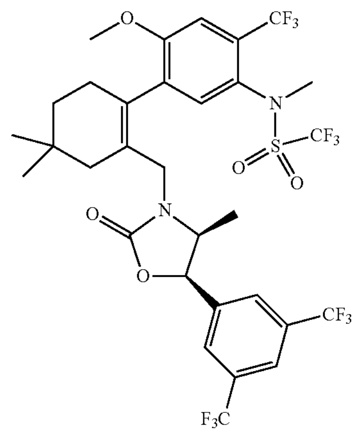 [SMILES: COc1cc(C(F)(F)F)c(N(C)S(=O)(=O)C(F)(F)F)cc1C1=C(CN2C(=O)O[C@H](c3cc(C(F)(F)F)cc(C(F)(F)F)c3)[C@@H]2C)CC(C)(C)CC1] |
| 210 | 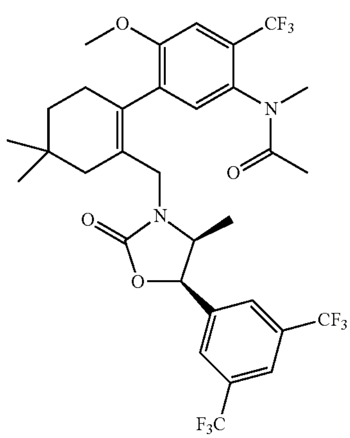 | 212 | 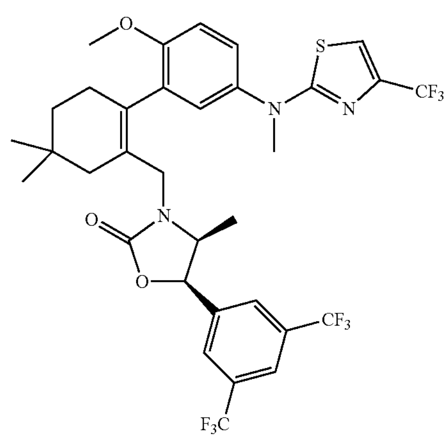 [SMILES: COc1ccc(N(C)c2nc(C(F)(F)F)cs2)cc1C1=C(CN2C(=O)O[C@H](c3cc(C(F)(F)F)cc(C(F)(F)F)c3)[C@@H]2C)CC(C)(C)CC1] |

TABLE 24

| Compound | Structure | Compound | Structure |
| --- | --- | --- | --- |
| 213 | 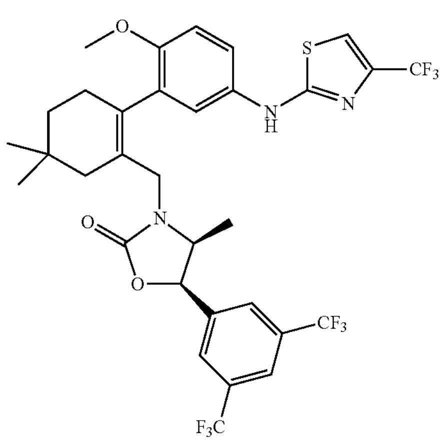 [SMILES: COc1ccc(Nc2nc(C(F)(F)F)cs2)cc1C1=C(CN2C(=O)O[C@H](c3cc(C(F)(F)F)cc(C(F)(F)F)c3)[C@@H]2C)CC(C)(C)CC1] | 215 | 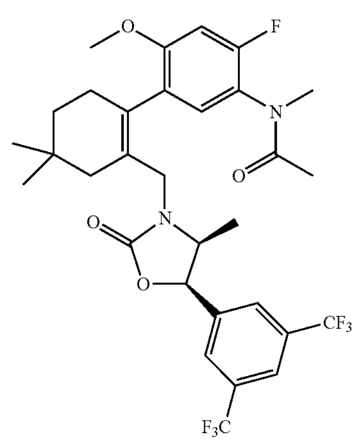 [SMILES: COc1cc(F)c(N(C)C(C)=O)cc1C1=C(CN2C(=O)O[C@H](c3cc(C(F)(F)F)cc(C(F)(F)F)c3)[C@@H]2C)CC(C)(C)CC1] |

TABLE 24-continued

| Compound | Structure | Compound | Structure |
| --- | --- | --- | --- |
| 216 | 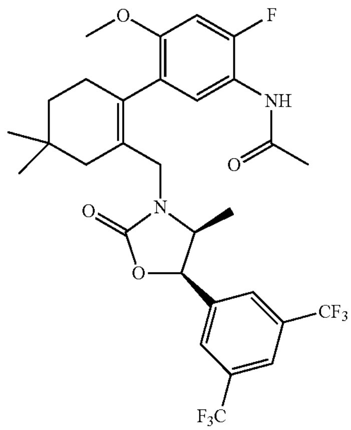 [SMILES: COc1cc(F)c(NC(C)=O)cc1C1=C(CN2C(=O)O[C@H](c3cc(C(F)(F)F)cc(C(F)(F)F)c3)[C@@H]2C)CC(C)(C)CC1] | 217 | 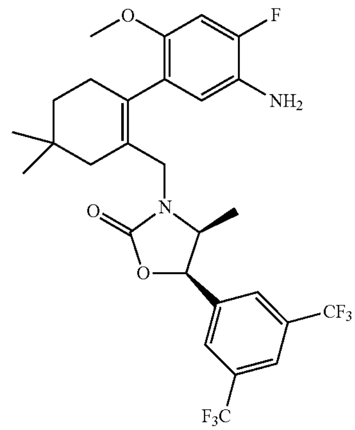 [SMILES: COc1cc(F)c(N)cc1C1=C(CN2C(=O)O[C@H](c3cc(C(F)(F)F)cc(C(F)(F)F)c3)[C@@H]2C)CC(C)(C)CC1] |
| 218 | 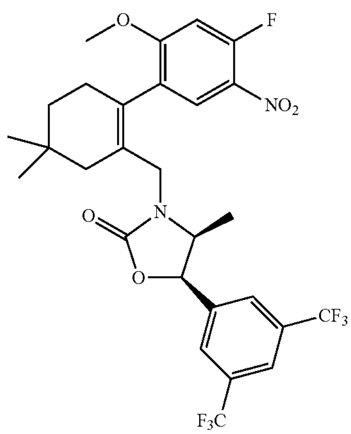 [SMILES: COc1cc(F)c([N+](=O)[O-])cc1C1=C(CN2C(=O)O[C@H](c3cc(C(F)(F)F)cc(C(F)(F)F)c3)[C@@H]2C)CC(C)(C)CC1] | 219 | 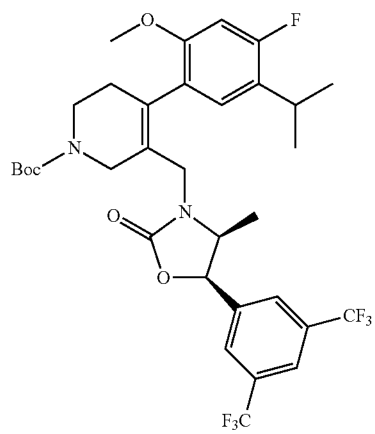 |

TABLE 25

| Compound | Structure | Compound | Structure |
| --- | --- | --- | --- |
| 222 | 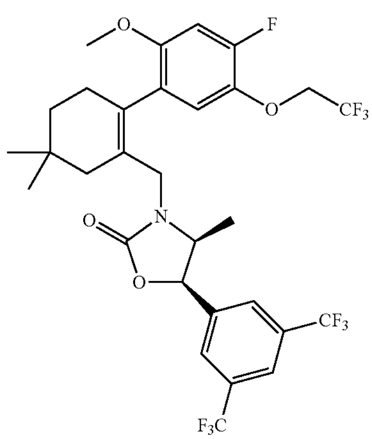 [SMILES: COc1cc(F)c(OCC(F)(F)F)cc1C1=C(CN2C(=O)O[C@H](c3cc(C(F)(F)F)cc(C(F)(F)F)c3)[C@@H]2C)CC(C)(C)CC1] | 223 | 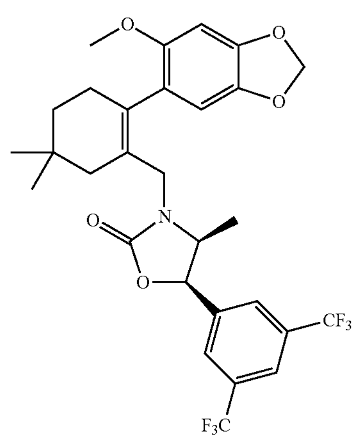 [SMILES: COc1cc2c(cc1C1=C(CN3C(=O)O[C@H](c4cc(C(F)(F)F)cc(C(F)(F)F)c4)[C@@H]3C)CC(C)(C)CC1)OCO2] |

TABLE 25-continued

| Compound | Structure | Compound | Structure |
| --- | --- | --- | --- |
| 224 | 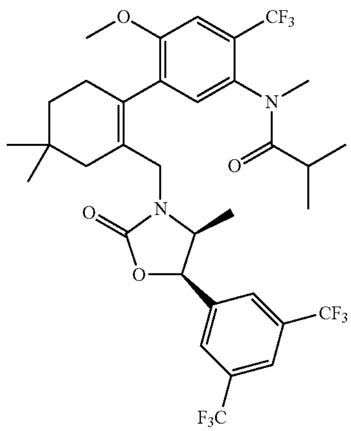 [SMILES: COc1cc(C(F)(F)F)c(N(C)C(=O)C(C)C)cc1C1=C(CN2C(=O)O[C@H](c3cc(C(F)(F)F)cc(C(F)(F)F)c3)[C@@H]2C)CC(C)(C)CC1] | 225 | 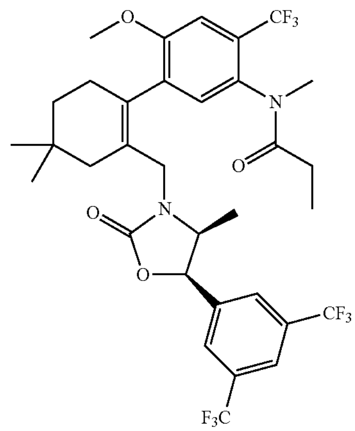 [SMILES: CCC(=O)N(C)c1cc(C2=C(CN3C(=O)O[C@H](c4cc(C(F)(F)F)cc(C(F)(F)F)c4)[C@@H]3C)CC(C)(C)CC2)c(OC)cc1C(F)(F)F] |
| 226 | 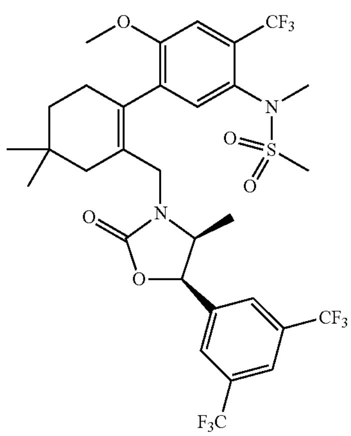 [SMILES: COc1cc(C(F)(F)F)c(N(C)S(C)(=O)=O)cc1C1=C(CN2C(=O)O[C@H](c3cc(C(F)(F)F)cc(C(F)(F)F)c3)[C@@H]2C)CC(C)(C)CC1] | 227 | 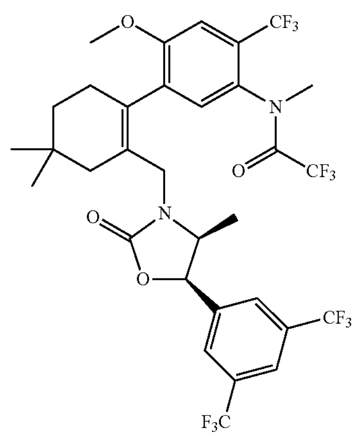 [SMILES: COc1cc(C(F)(F)F)c(N(C)C(=O)C(F)(F)F)cc1C1=C(CN2C(=O)O[C@H](c3cc(C(F)(F)F)cc(C(F)(F)F)c3)[C@@H]2C)CC(C)(C)CC1] |

TABLE 26

| Compound | Structure | Compound | Structure |
| --- | --- | --- | --- |
| 228 | 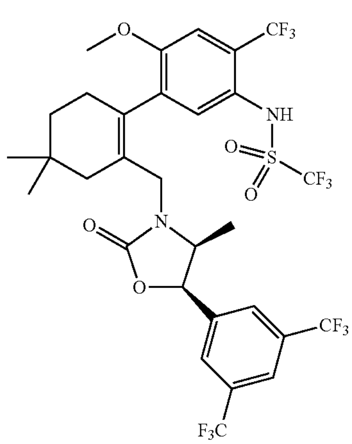 [SMILES: COc1cc(C(F)(F)F)c(NS(=O)(=O)C(F)(F)F)cc1C1=C(CN2C(=O)O[C@H](c3cc(C(F)(F)F)cc(C(F)(F)F)c3)[C@@H]2C)CC(C)(C)CC1] | 229 | 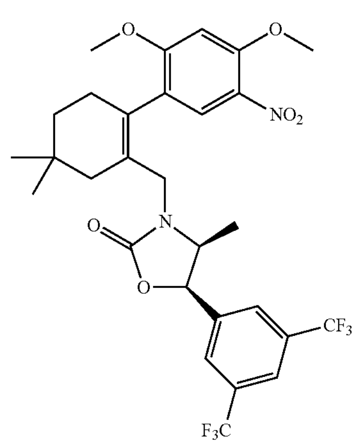 [SMILES: COc1cc(OC)c([N+](=O)[O-])cc1C1=C(CN2C(=O)O[C@H](c3cc(C(F)(F)F)cc(C(F)(F)F)c3)[C@@H]2C)CC(C)(C)CC1] |

TABLE 26-continued

| Compound | Structure | Compound | Structure |
| --- | --- | --- | --- |
| 230 | 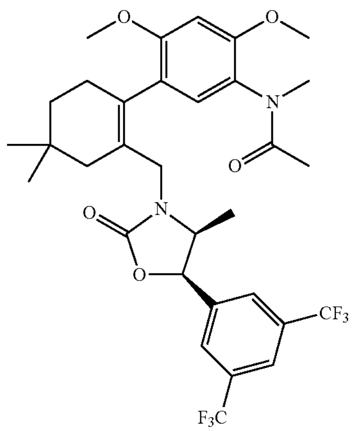 [SMILES: COc1cc(OC)c(N(C)C(C)=O)cc1C1=C(CN2C(=O)O[C@H](c3cc(C(F)(F)F)cc(C(F)(F)F)c3)[C@@H]2C)CC(C)(C)CC1] | 231 | 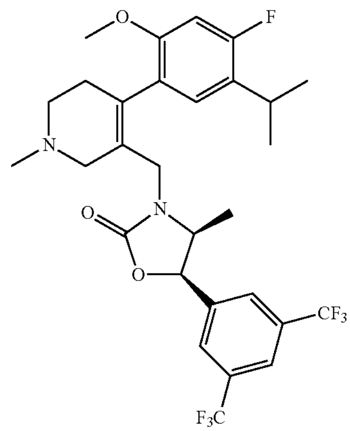 [SMILES: COc1cc(F)c(C(C)C)cc1C1=C(CN2C(=O)O[C@H](c3cc(C(F)(F)F)cc(C(F)(F)F)c3)[C@@H]2C)CN(C)CC1] |
| 232 | 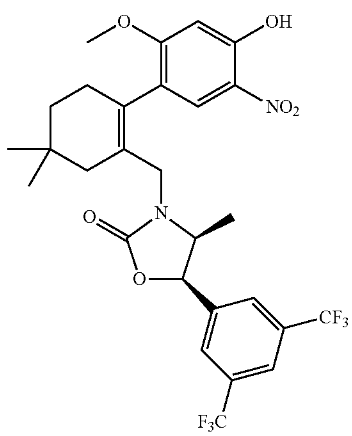 [SMILES: COc1cc(O)c([N+](=O)[O-])cc1C1=C(CN2C(=O)O[C@H](c3cc(C(F)(F)F)cc(C(F)(F)F)c3)[C@@H]2C)CC(C)(C)CC1] | 233 | 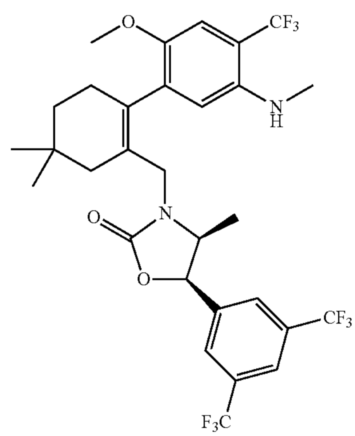 [SMILES: CNc1cc(C2=C(CN3C(=O)O[C@H](c4cc(C(F)(F)F)cc(C(F)(F)F)c4)[C@@H]3C)CC(C)(C)CC2)c(OC)cc1C(F)(F)F] |

TABLE 27

| Compound | Structure | Compound | Structure |
| --- | --- | --- | --- |
| 234 | 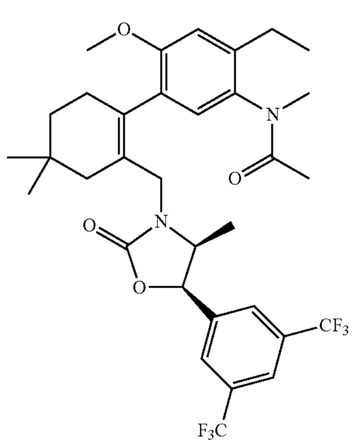 [SMILES: CCc1cc(OC)c(C2=C(CN3C(=O)O[C@H](c4cc(C(F)(F)F)cc(C(F)(F)F)c4)[C@@H]3C)CC(C)(C)CC2)cc1N(C)C(C)=O] | 235 | 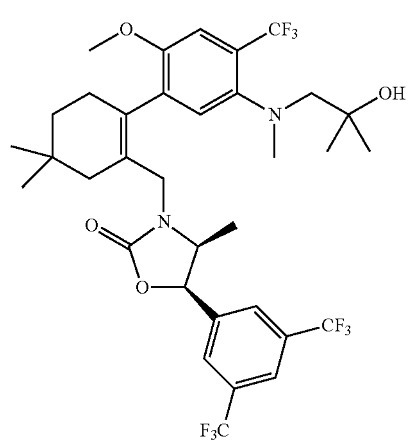 [SMILES: COc1cc(C(F)(F)F)c(N(C)CC(C)(C)O)cc1C1=C(CN2C(=O)O[C@H](c3cc(C(F)(F)F)cc(C(F)(F)F)c3)[C@@H]2C)CC(C)(C)CC1] |

TABLE 27-continued

| Compound | Structure | Compound | Structure |
| --- | --- | --- | --- |
| 237 | 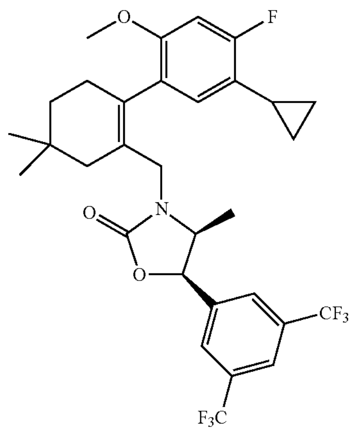 [SMILES: COc1cc(F)c(C2CC2)cc1C1=C(CN2C(=O)O[C@H](c3cc(C(F)(F)F)cc(C(F)(F)F)c3)[C@@H]2C)CC(C)(C)CC1] | 240 | 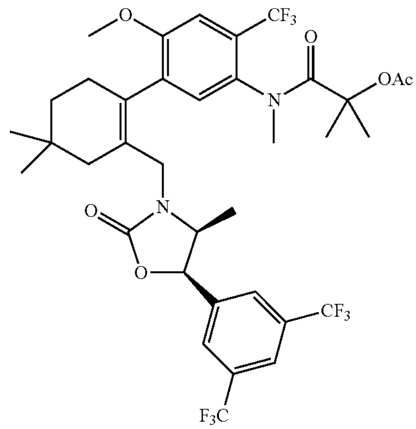 [SMILES: COc1cc(C(F)(F)F)c(N(C)C(=O)C(C)(C)OC(C)=O)cc1C1=C(CN2C(=O)O[C@H](c3cc(C(F)(F)F)cc(C(F)(F)F)c3)[C@@H]2C)CC(C)(C)CC1] |
| 241 | 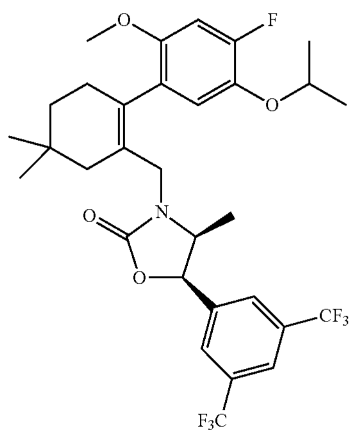 [SMILES: COc1cc(F)c(OC(C)C)cc1C1=C(CN2C(=O)O[C@H](c3cc(C(F)(F)F)cc(C(F)(F)F)c3)[C@@H]2C)CC(C)(C)CC1] | 243 | 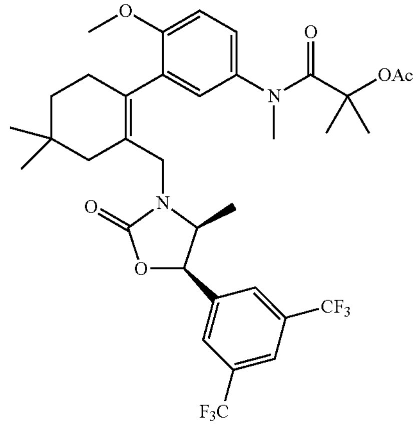 [SMILES: COc1ccc(N(C)C(=O)C(C)(C)OC(C)=O)cc1C1=C(CN2C(=O)O[C@H](c3cc(C(F)(F)F)cc(C(F)(F)F)c3)[C@@H]2C)CC(C)(C)CC1] |

TABLE 28

| Compound | Structure | Compound | Structure |
| --- | --- | --- | --- |
| 244 | 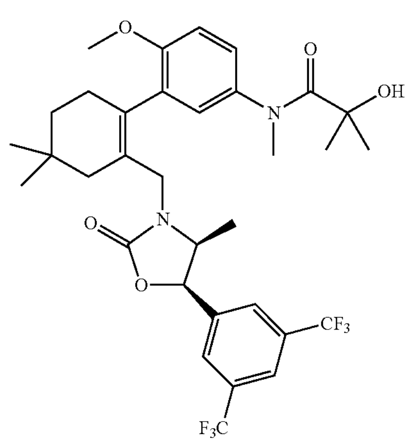 [SMILES: COc1ccc(N(C)C(=O)C(C)(C)O)cc1C1=C(CN2C(=O)O[C@H](c3cc(C(F)(F)F)cc(C(F)(F)F)c3)[C@@H]2C)CC(C)(C)CC1] | 245 | 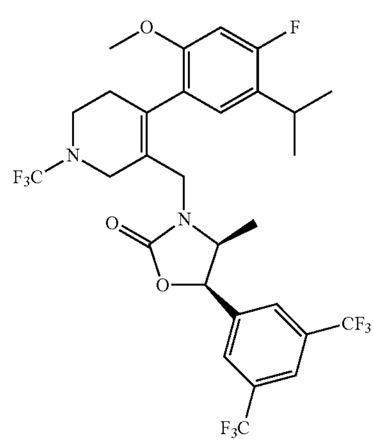 [SMILES: COc1cc(F)c(C(C)C)cc1C1=C(CN2C(=O)O[C@H](c3cc(C(F)(F)F)cc(C(F)(F)F)c3)[C@@H]2C)CN(C(F)(F)F)CC1] |

TABLE 28-continued

| Compound | Structure | Compound | Structure |
| --- | --- | --- | --- |
| 246 | 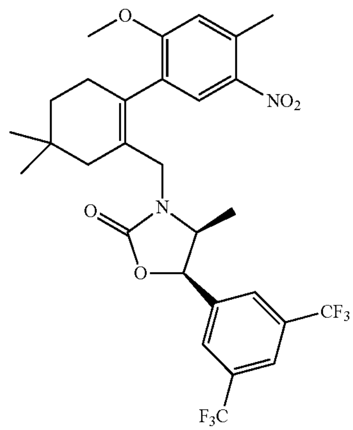 | 247 | 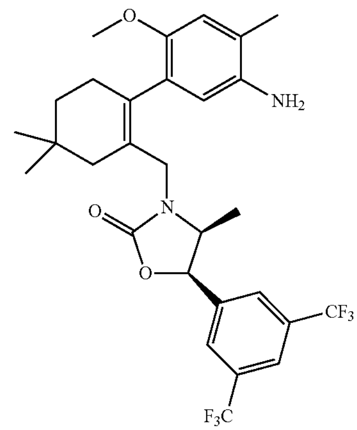 [SMILES: COc1cc(C)c([N+](=O)[O-])cc1C1=C(CN2C(=O)O[C@H](c3cc(C(F)(F)F)cc(C(F)(F)F)c3)[C@@H]2C)CC(C)(C)CC1] |
| 248 | 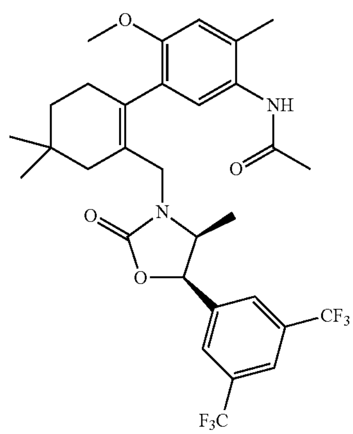 | 249 | 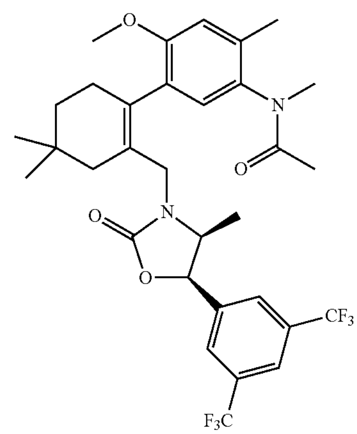 |

TABLE 29

| Compound | Structure | Compound | Structure |
| --- | --- | --- | --- |
| 250 | 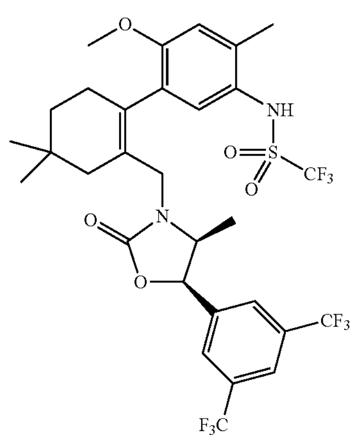 [SMILES: COc1cc(C)c(NS(=O)(=O)C(F)(F)F)cc1C1=C(CN2C(=O)O[C@H](c3cc(C(F)(F)F)cc(C(F)(F)F)c3)[C@@H]2C)CC(C)(C)CC1] | 251 | 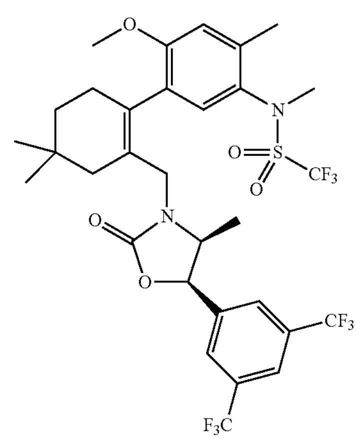 [SMILES: COc1cc(C)c(N(C)S(=O)(=O)C(F)(F)F)cc1C1=C(CN2C(=O)O[C@H](c3cc(C(F)(F)F)cc(C(F)(F)F)c3)[C@@H]2C)CC(C)(C)CC1] |

TABLE 29-continued

| Compound | Structure | Compound | Structure |
|---|---|---|---|
| 259 | 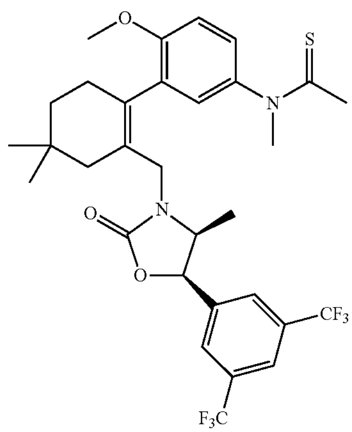 [SMILES: COc1ccc(N(C)C(C)=S)cc1C1=C(CN2C(=O)O[C@H](c3cc(C(F)(F)F)cc(C(F)(F)F)c3)[C@@H]2C)CC(C)(C)CC1] | 261 | 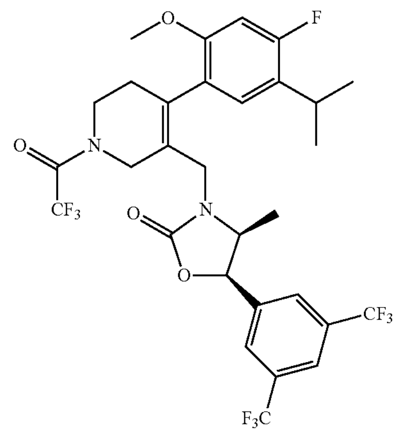 [SMILES: COc1cc(F)c(C(C)C)cc1C1=C(CN2C(=O)O[C@H](c3cc(C(F)(F)F)cc(C(F)(F)F)c3)[C@@H]2C)CN(C(=O)C(F)(F)F)CC1] |
| 262 | 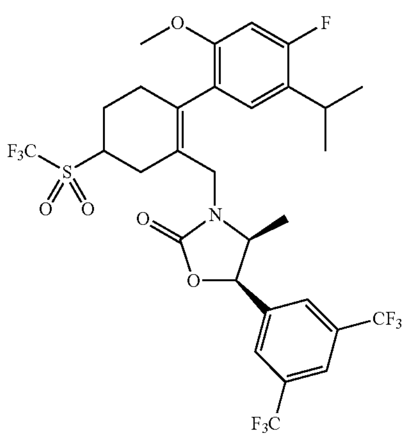 [SMILES: COc1cc(F)c(C(C)C)cc1C1=C(CN2C(=O)O[C@H](c3cc(C(F)(F)F)cc(C(F)(F)F)c3)[C@@H]2C)CC(S(=O)(=O)C(F)(F)F)CC1] | 263 | 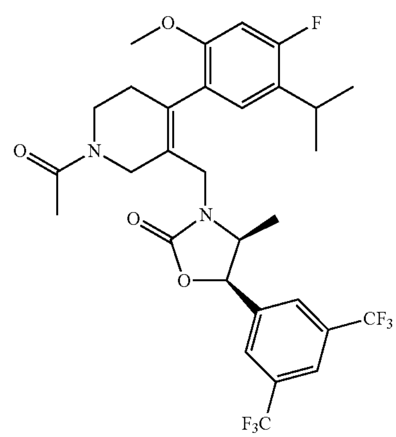 [SMILES: COc1cc(F)c(C(C)C)cc1C1=C(CN2C(=O)O[C@H](c3cc(C(F)(F)F)cc(C(F)(F)F)c3)[C@@H]2C)CN(C(C)=O)CC1] |

TABLE 30

| Compound | Structure | Compound | Structure |
|---|---|---|---|
| 264 | 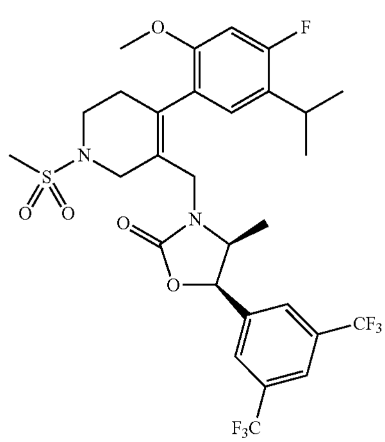 [SMILES: COc1cc(F)c(C(C)C)cc1C1=C(CN2C(=O)O[C@H](c3cc(C(F)(F)F)cc(C(F)(F)F)c3)[C@@H]2C)CN(S(C)(=O)=O)CC1] | 265 | 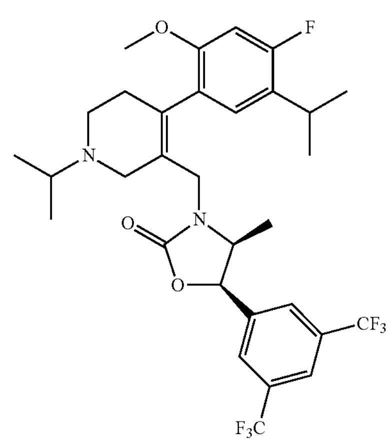 [SMILES: COc1cc(F)c(C(C)C)cc1C1=C(CN2C(=O)O[C@H](c3cc(C(F)(F)F)cc(C(F)(F)F)c3)[C@@H]2C)CN(C(C)C)CC1] |

TABLE 30-continued

| Compound | Structure | Compound | Structure |
| --- | --- | --- | --- |
| 267 | 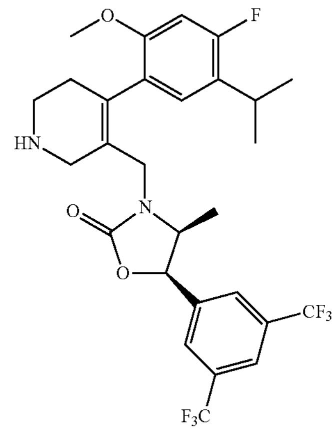 [SMILES: COc1cc(F)c(C(C)C)cc1C1=C(CN2C(=O)O[C@H](c3cc(C(F)(F)F)cc(C(F)(F)F)c3)[C@@H]2C)CNCC1] | 268 | 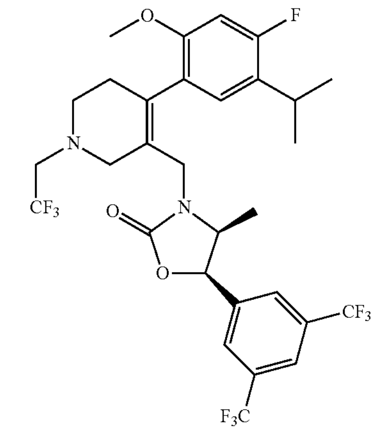 [SMILES: COc1cc(F)c(C(C)C)cc1C1=C(CN2C(=O)O[C@H](c3cc(C(F)(F)F)cc(C(F)(F)F)c3)[C@@H]2C)CN(CC(F)(F)F)CC1] |
| 271 | 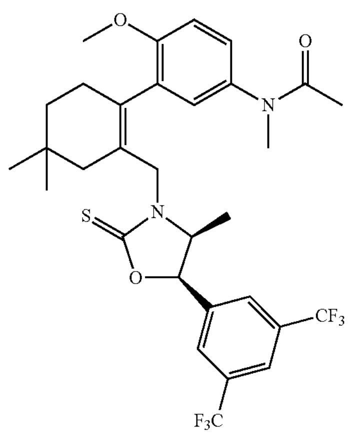 [SMILES: COc1ccc(N(C)C(C)=O)cc1C1=C(CN2C(=S)O[C@H](c3cc(C(F)(F)F)cc(C(F)(F)F)c3)[C@@H]2C)CC(C)(C)CC1] | 272 | 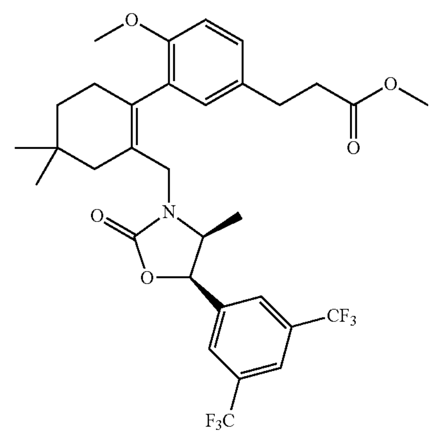 |

TABLE 31

| Compound | Structure | Compound | Structure |
| --- | --- | --- | --- |
| 273 | 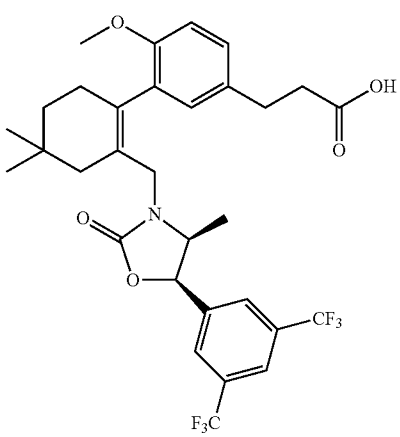 [SMILES: COc1ccc(CCC(=O)O)cc1C1=C(CN2C(=O)O[C@H](c3cc(C(F)(F)F)cc(C(F)(F)F)c3)[C@@H]2C)CC(C)(C)CC1] | 274 | 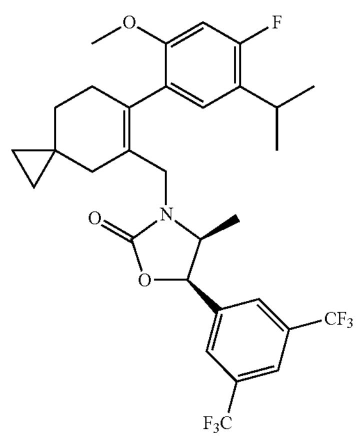 [SMILES: COc1cc(F)c(C(C)C)cc1C1=C(CN2C(=O)O[C@H](c3cc(C(F)(F)F)cc(C(F)(F)F)c3)[C@@H]2C)CC2(CC1)CC2] |

TABLE 31-continued

| Compound | Structure | Compound | Structure |
| --- | --- | --- | --- |
| 275 | 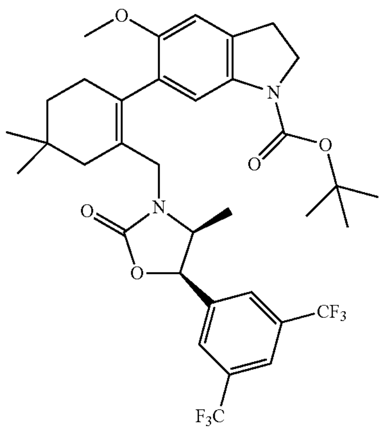 [SMILES: COc1cc2c(cc1C1=C(CN3C(=O)O[C@H](c4cc(C(F)(F)F)cc(C(F)(F)F)c4)[C@@H]3C)CC(C)(C)CC1)N(C(=O)OC(C)(C)C)CC2] | 276 | 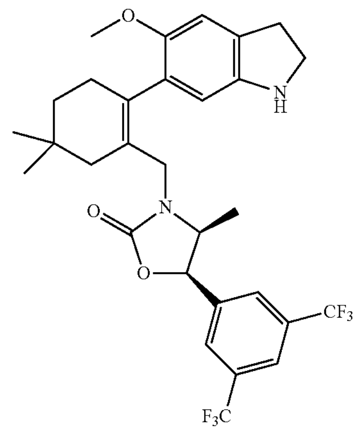 [SMILES: COc1cc2c(cc1C1=C(CN3C(=O)O[C@H](c4cc(C(F)(F)F)cc(C(F)(F)F)c4)[C@@H]3C)CC(C)(C)CC1)NCC2] |
| 277 | 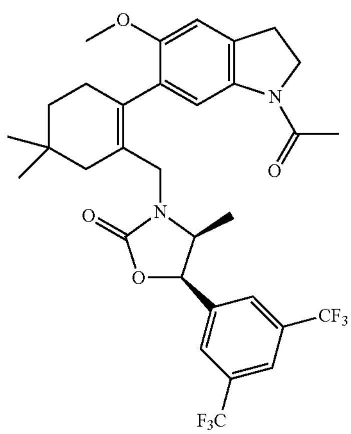 [SMILES: COc1cc2c(cc1C1=C(CN3C(=O)O[C@H](c4cc(C(F)(F)F)cc(C(F)(F)F)c4)[C@@H]3C)CC(C)(C)CC1)N(C(C)=O)CC2] | 278 | 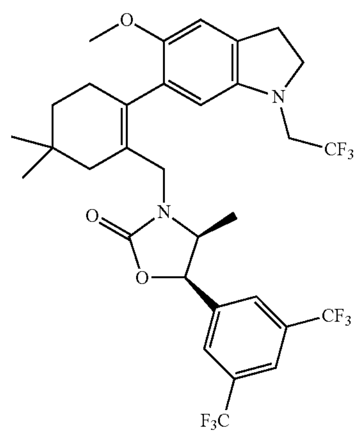 [SMILES: COc1cc2c(cc1C1=C(CN3C(=O)O[C@H](c4cc(C(F)(F)F)cc(C(F)(F)F)c4)[C@@H]3C)CC(C)(C)CC1)N(CC(F)(F)F)CC2] |

TABLE 32

| Compound | Structure | Compound | Structure |
| --- | --- | --- | --- |
| 280 | 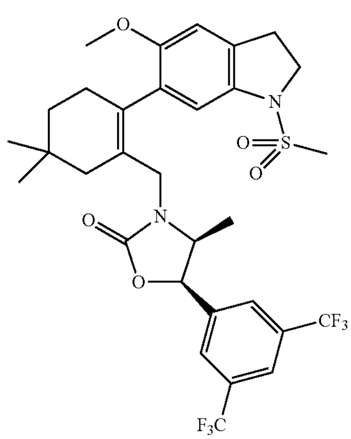 | 281 | 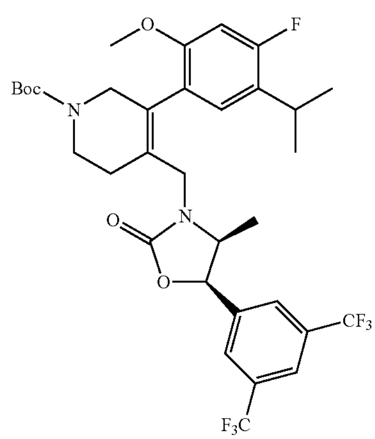 [SMILES: COc1cc(F)c(C(C)C)cc1C1=C(CN2C(=O)O[C@H](c3cc(C(F)(F)F)cc(C(F)(F)F)c3)[C@@H]2C)CCN(C(=O)OC(C)(C)C)C1] |

TABLE 32-continued
| Compound | Structure | Compound | Structure |
|---|---|---|---|
| 282 | 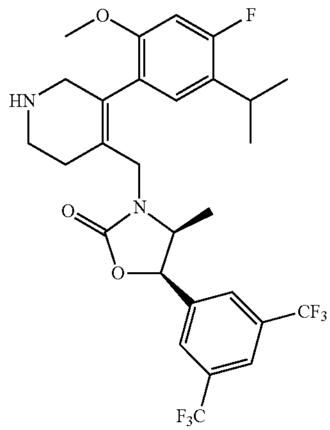 [SMILES: COc1cc(F)c(C(C)C)cc1C1=C(CN2C(=O)O[C@H](c3cc(C(F)(F)F)cc(C(F)(F)F)c3)[C@@H]2C)CCNC1] | 283 | 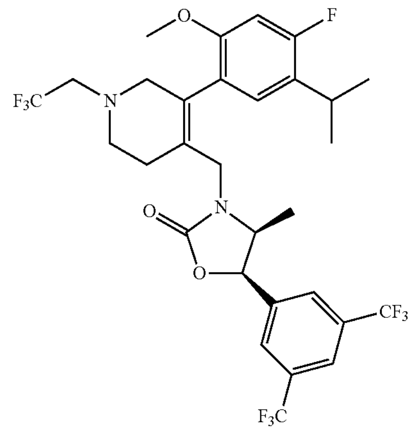 [SMILES: COc1cc(F)c(C(C)C)cc1C1=C(CN2C(=O)O[C@H](c3cc(C(F)(F)F)cc(C(F)(F)F)c3)[C@@H]2C)CCN(CC(F)(F)F)C1] |
| 284 | 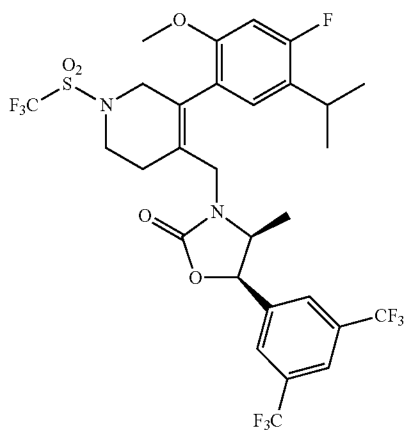 [SMILES: COc1cc(F)c(C(C)C)cc1C1=C(CN2C(=O)O[C@H](c3cc(C(F)(F)F)cc(C(F)(F)F)c3)[C@@H]2C)CCN(S(=O)(=O)C(F)(F)F)C1] | 285 | 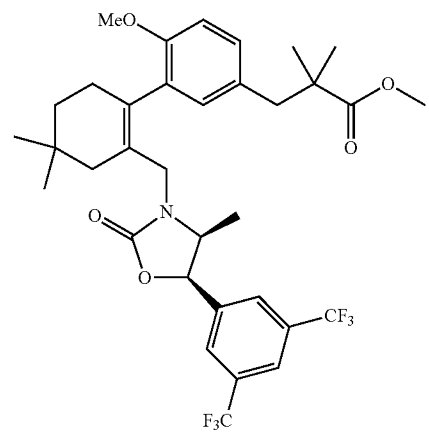 |
TABLE 33
| Compound | Structure | Compound | Structure |
|---|---|---|---|
| 286 | 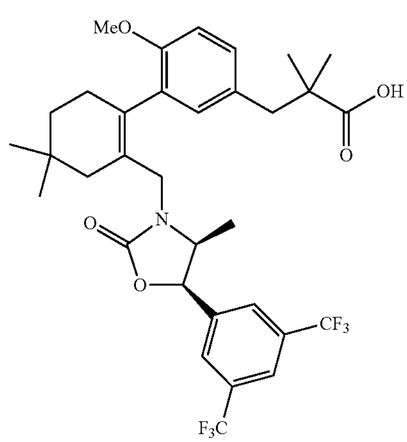 [SMILES: COc1ccc(CC(C)(C)C(=O)O)cc1C1=C(CN2C(=O)O[C@H](c3cc(C(F)(F)F)cc(C(F)(F)F)c3)[C@@H]2C)CC(C)(C)CC1] | 291 | 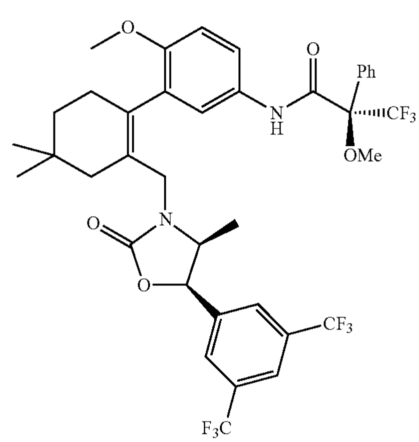 [SMILES: COc1ccc(NC(=O)[C@](OC)(c2ccccc2)C(F)(F)F)cc1C1=C(CN2C(=O)O[C@H](c3cc(C(F)(F)F)cc(C(F)(F)F)c3)[C@@H]2C)CC(C)(C)CC1] |
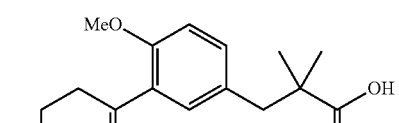
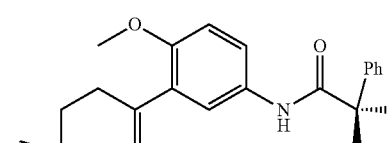

TABLE 33-continued

| Compound | Structure | Compound | Structure |
| --- | --- | --- | --- |
| 292 | 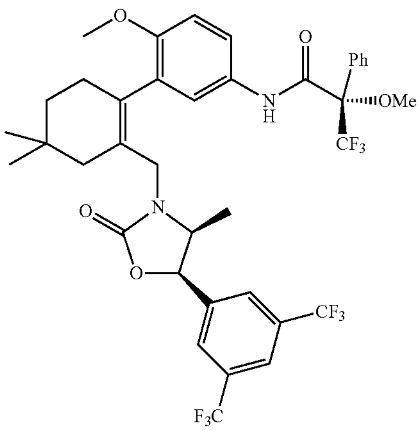 [SMILES: COc1ccc(NC(=O)[C@@](OC)(c2ccccc2)C(F)(F)F)cc1C1=C(CN2C(=O)O[C@H](c3cc(C(F)(F)F)cc(C(F)(F)F)c3)[C@@H]2C)CC(C)(C)CC1] | 293 | 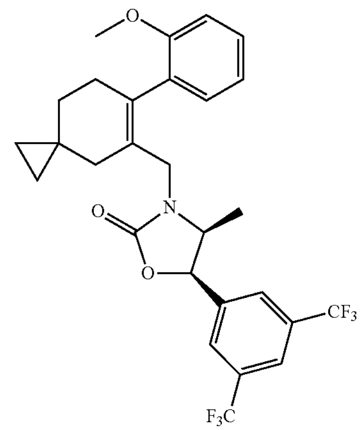 [SMILES: COc1ccccc1C1=C(CN2C(=O)O[C@H](c3cc(C(F)(F)F)cc(C(F)(F)F)c3)[C@@H]2C)CC2(CC1)CC2] |
| 294 | 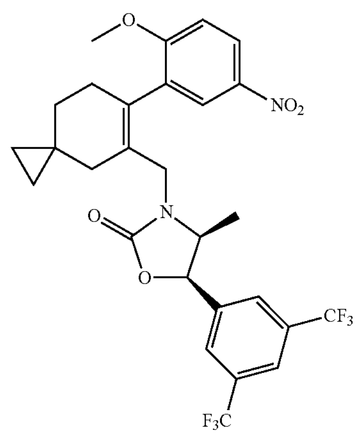 [SMILES: COc1ccc([N+](=O)[O-])cc1C1=C(CN2C(=O)O[C@H](c3cc(C(F)(F)F)cc(C(F)(F)F)c3)[C@@H]2C)CC2(CC1)CC2] | 295 | 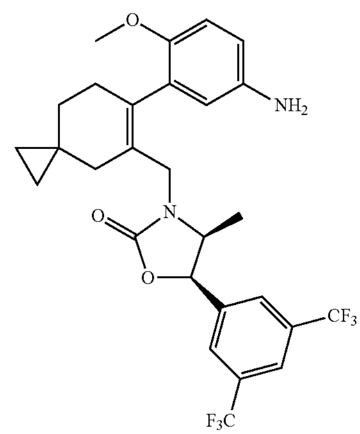 |

TABLE 34

| Compound | Structure | Compound | Structure |
| --- | --- | --- | --- |
| 296 | 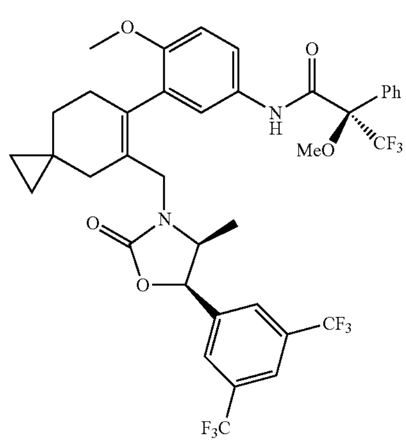 [SMILES: COc1ccc(NC(=O)[C@](OC)(c2ccccc2)C(F)(F)F)cc1C1=C(CN2C(=O)O[C@H](c3cc(C(F)(F)F)cc(C(F)(F)F)c3)[C@@H]2C)CC2(CC1)CC2] | 297 | 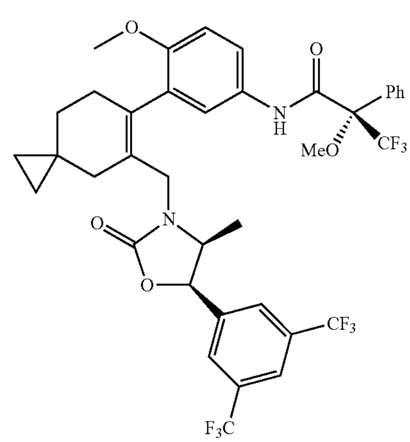 [SMILES: COc1ccc(NC(=O)[C@@](OC)(c2ccccc2)C(F)(F)F)cc1C1=C(CN2C(=O)O[C@H](c3cc(C(F)(F)F)cc(C(F)(F)F)c3)[C@@H]2C)CC2(CC1)CC2] |

TABLE 34-continued

| Compound | Structure | Compound | Structure |
| --- | --- | --- | --- |
| 298 | 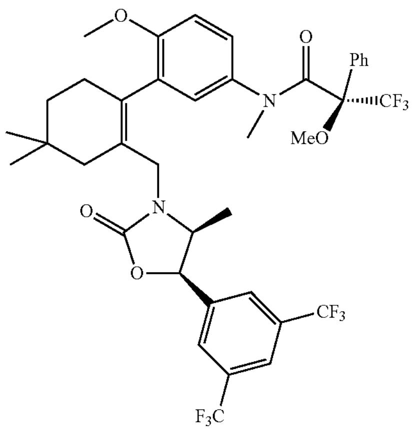 [SMILES: COc1ccc(N(C)C(=O)[C@](OC)(c2ccccc2)C(F)(F)F)cc1C1=C(CN2C(=O)O[C@H](c3cc(C(F)(F)F)cc(C(F)(F)F)c3)[C@@H]2C)CC(C)(C)CC1] | 299 | 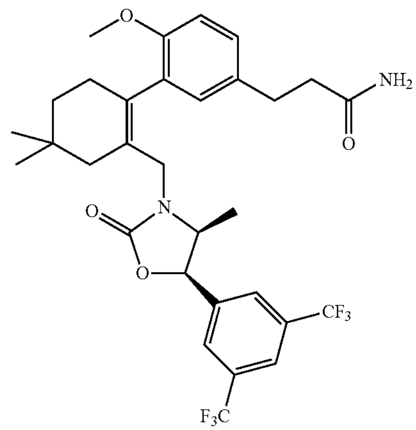 [SMILES: COc1ccc(CCC(N)=O)cc1C1=C(CN2C(=O)O[C@H](c3cc(C(F)(F)F)cc(C(F)(F)F)c3)[C@@H]2C)CC(C)(C)CC1] |
| 300 | 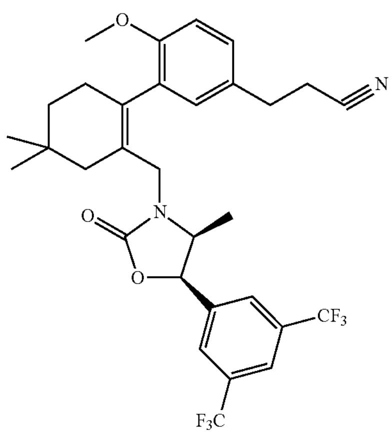 [SMILES: COc1ccc(CCC#N)cc1C1=C(CN2C(=O)O[C@H](c3cc(C(F)(F)F)cc(C(F)(F)F)c3)[C@@H]2C)CC(C)(C)CC1] | 301 | 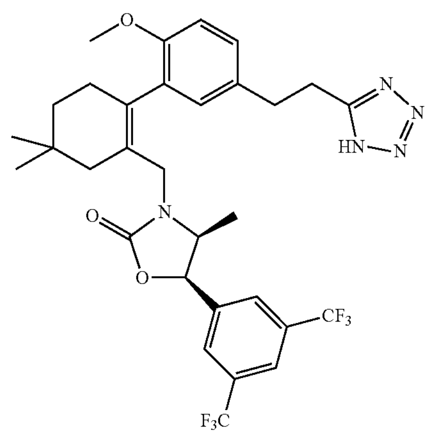 [SMILES: COc1ccc(CCc2nnn[nH]2)cc1C1=C(CN2C(=O)O[C@H](c3cc(C(F)(F)F)cc(C(F)(F)F)c3)[C@@H]2C)CC(C)(C)CC1] |

TABLE 35

| Compound | Structure | Compound | Structure |
| --- | --- | --- | --- |
| 302 | 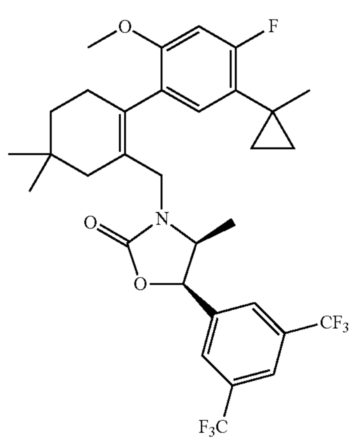 [SMILES: COc1cc(F)c(C2(C)CC2)cc1C1=C(CN2C(=O)O[C@H](c3cc(C(F)(F)F)cc(C(F)(F)F)c3)[C@@H]2C)CC(C)(C)CC1] | 303 | 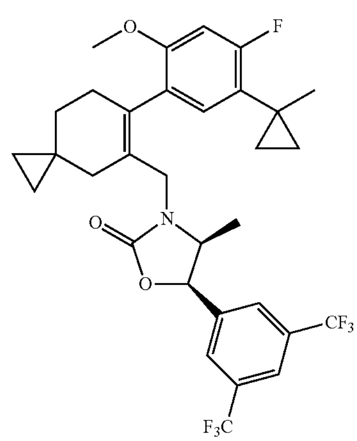 [SMILES: COc1cc(F)c(C2(C)CC2)cc1C1=C(CN2C(=O)O[C@H](c3cc(C(F)(F)F)cc(C(F)(F)F)c3)[C@@H]2C)CC2(CC1)CC2] |

TABLE 35-continued

| Compound | Structure | Compound | Structure |
| --- | --- | --- | --- |
| 304 | 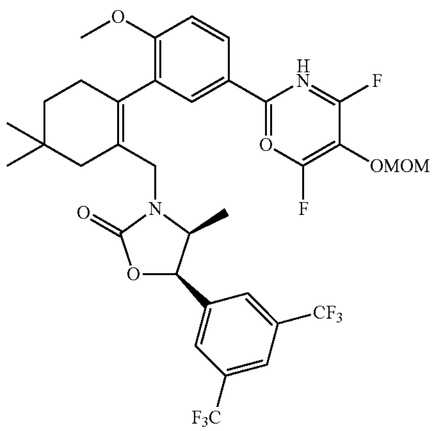 | 305 | 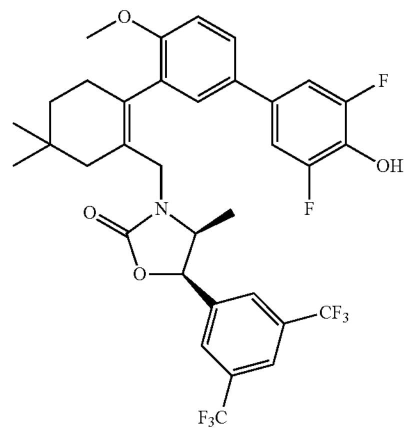 [SMILES: COc1ccc(-c2cc(F)c(O)c(F)c2)cc1C1=C(CN2C(=O)O[C@H](c3cc(C(F)(F)F)cc(C(F)(F)F)c3)[C@@H]2C)CC(C)(C)CC1] |
| 306 | 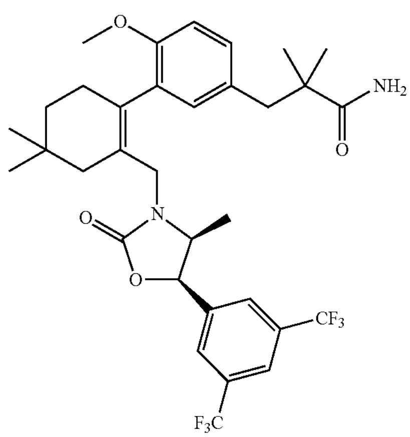 [SMILES: COc1ccc(CC(C)(C)C(N)=O)cc1C1=C(CN2C(=O)O[C@H](c3cc(C(F)(F)F)cc(C(F)(F)F)c3)[C@@H]2C)CC(C)(C)CC1] | 307 | 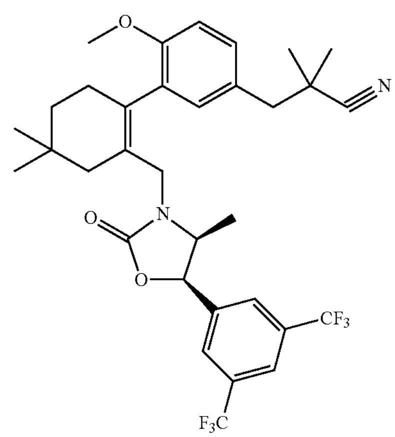 [SMILES: COc1ccc(CC(C)(C)C#N)cc1C1=C(CN2C(=O)O[C@H](c3cc(C(F)(F)F)cc(C(F)(F)F)c3)[C@@H]2C)CC(C)(C)CC1] |

TABLE 36

| Compound | Structure | Compound | Structure |
| --- | --- | --- | --- |
| 308 | 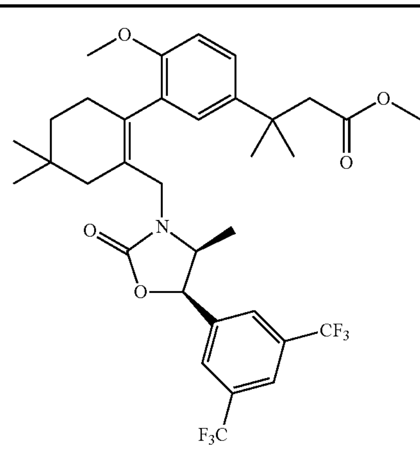 | 309 | 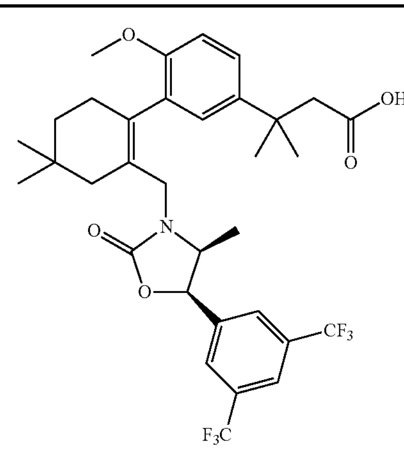 |

TABLE 36-continued
| Compound | Structure | Compound | Structure |
| --- | --- | --- | --- |
| 310 | 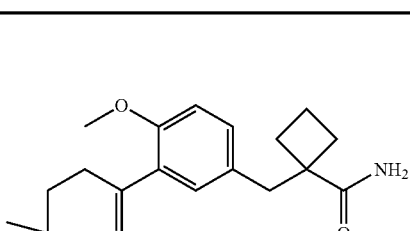 | 311 | 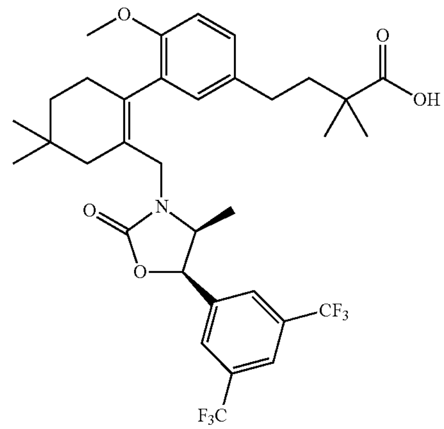 [SMILES: COc1ccc(CCC(C)(C)C(=O)O)cc1C1=C(CN2C(=O)O[C@H](c3cc(C(F)(F)F)cc(C(F)(F)F)c3)[C@@H]2C)CC(C)(C)CC1] |
| 312 | 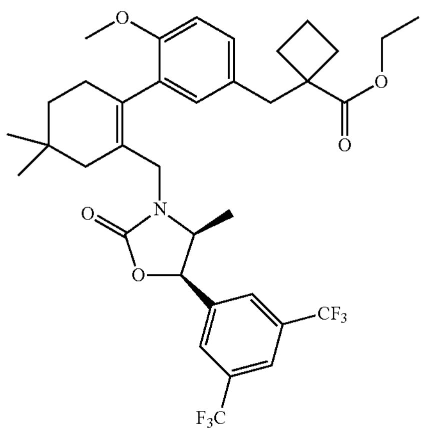 [SMILES: CCOC(=O)C1(Cc2ccc(OC)c(C3=C(CN4C(=O)O[C@H](c5cc(C(F)(F)F)cc(C(F)(F)F)c5)[C@@H]4C)CC(C)(C)CC3)c2)CCC1] | 313 | 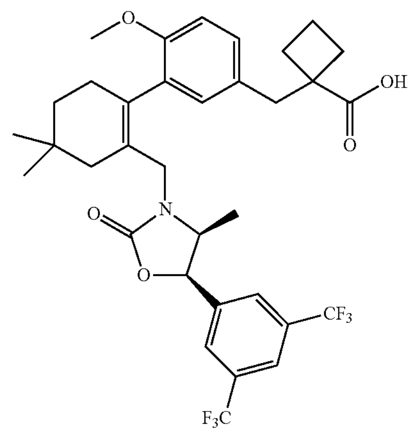 [SMILES: COc1ccc(CC2(C(=O)O)CCC2)cc1C1=C(CN2C(=O)O[C@H](c3cc(C(F)(F)F)cc(C(F)(F)F)c3)[C@@H]2C)CC(C)(C)CC1] |
TABLE 37
| Compound | Structure | Compound | Structure |
| --- | --- | --- | --- |
| 314 | 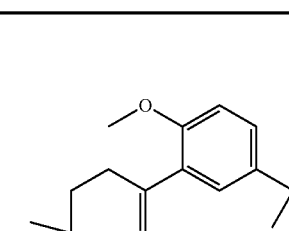 | 315 | 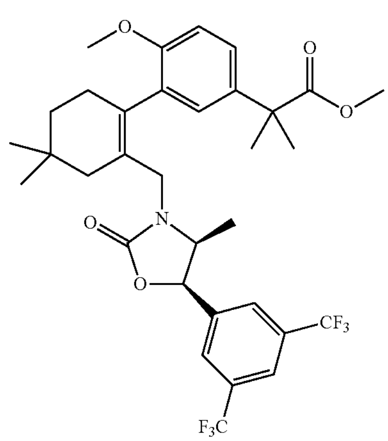 |

TABLE 37-continued

| Compound | Structure | Compound | Structure |
|---|---|---|---|
| 316 | 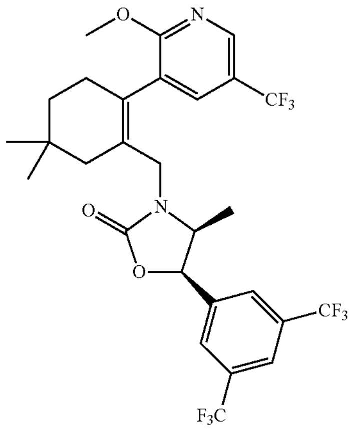 [SMILES: COc1ncc(C(F)(F)F)cc1C1=C(CN2C(=O)O[C@H](c3cc(C(F)(F)F)cc(C(F)(F)F)c3)[C@@H]2C)CC(C)(C)CC1] | 317 | 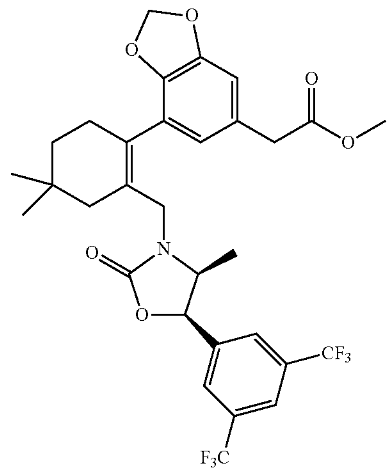 |
| 318 | 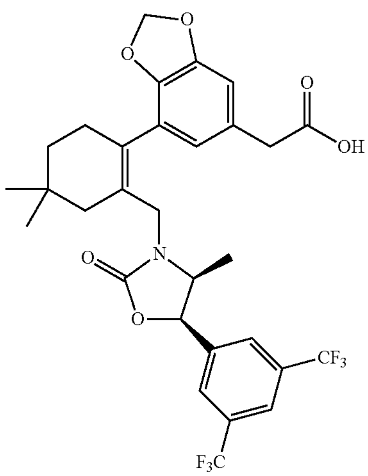 | 319 | 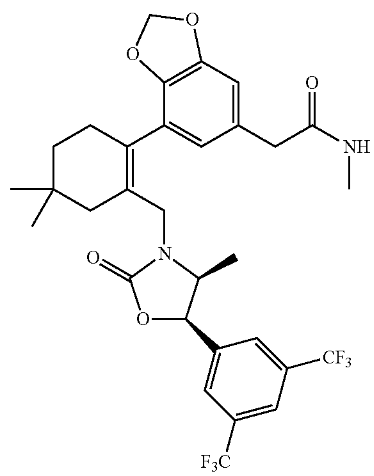 |

TABLE 38

| Compound | Structure | Compound | Structure |
|---|---|---|---|
| 320 | 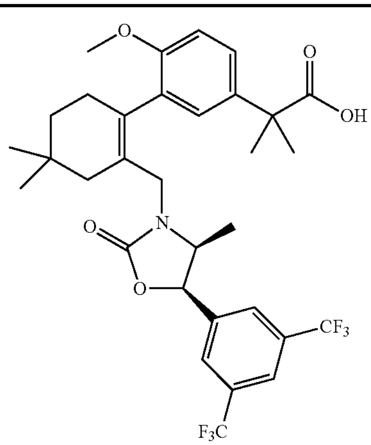 | 321 | 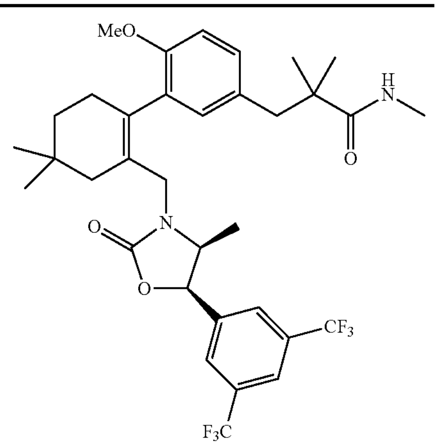 |

TABLE 38-continued

| Compound | Structure | Compound | Structure |
|---|---|---|---|
| 323 | 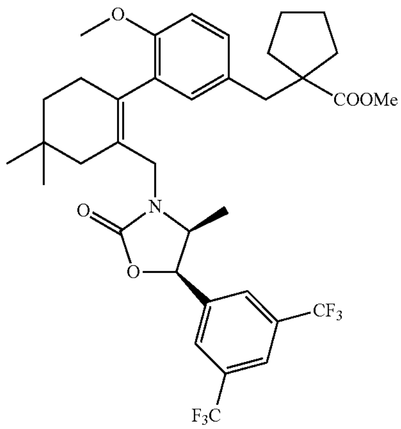 [SMILES: COC(=O)C1(Cc2ccc(OC)c(C3=C(CN4C(=O)O[C@H](c5cc(C(F)(F)F)cc(C(F)(F)F)c5)[C@@H]4C)CC(C)(C)CC3)c2)CCCC1] | 324 | 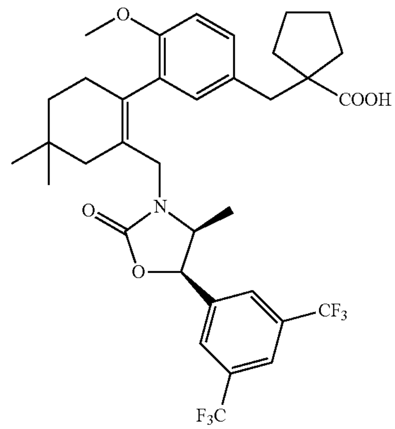 [SMILES: COc1ccc(CC2(C(=O)O)CCCC2)cc1C1=C(CN2C(=O)O[C@H](c3cc(C(F)(F)F)cc(C(F)(F)F)c3)[C@@H]2C)CC(C)(C)CC1] |
| 325 | 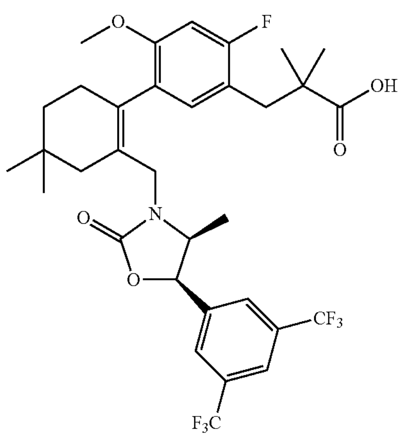 [SMILES: COc1cc(F)c(CC(C)(C)C(=O)O)cc1C1=C(CN2C(=O)O[C@H](c3cc(C(F)(F)F)cc(C(F)(F)F)c3)[C@@H]2C)CC(C)(C)CC1] | 326 | 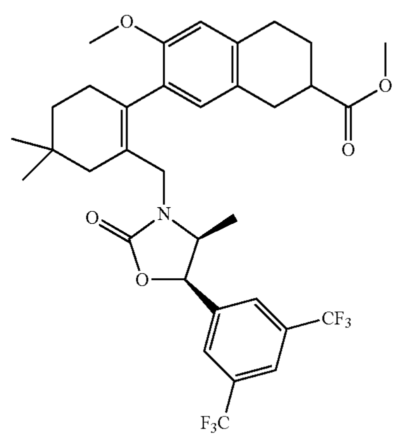 |

TABLE 39

| Compound | Structure | Compound | Structure |
|---|---|---|---|
| 327 | 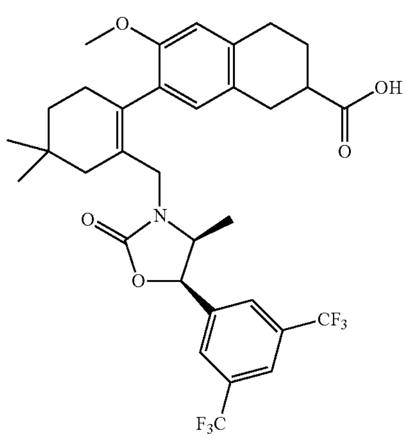 [SMILES: COc1cc2c(cc1C1=C(CN3C(=O)O[C@H](c4cc(C(F)(F)F)cc(C(F)(F)F)c4)[C@@H]3C)CC(C)(C)CC1)CC(C(=O)O)CC2] | 328 | 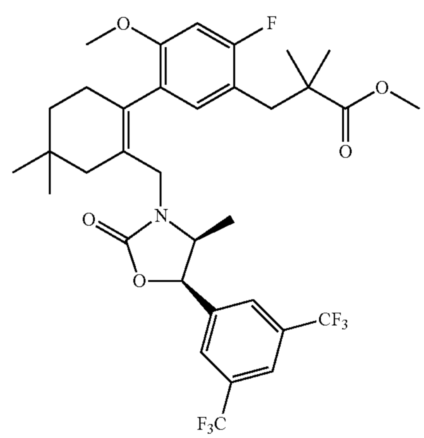 |

TABLE 39-continued

| Compound | Structure | Compound | Structure |
|---|---|---|---|
| 329 | 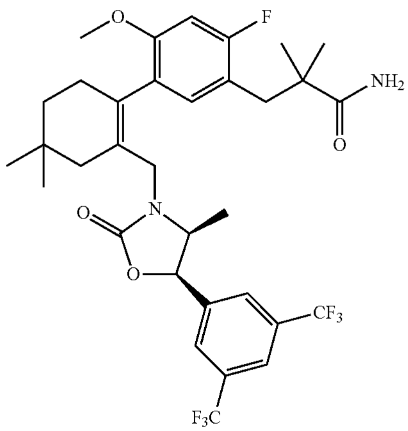 [SMILES: COc1cc(F)c(CC(C)(C)C(N)=O)cc1C1=C(CN2C(=O)O[C@H](c3cc(C(F)(F)F)cc(C(F)(F)F)c3)[C@@H]2C)CC(C)(C)CC1] | 330 | 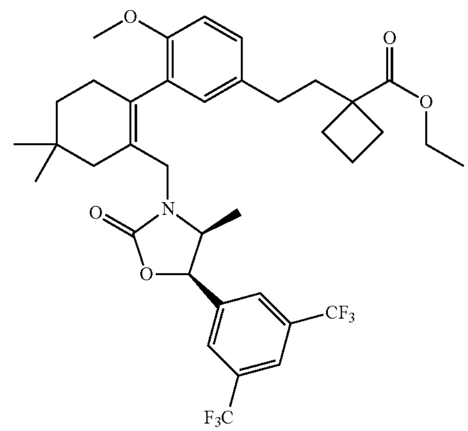 [SMILES: CCOC(=O)C1(CCc2ccc(OC)c(C3=C(CN4C(=O)O[C@H](c5cc(C(F)(F)F)cc(C(F)(F)F)c5)[C@@H]4C)CC(C)(C)CC3)c2)CCC1] |
| 331 | 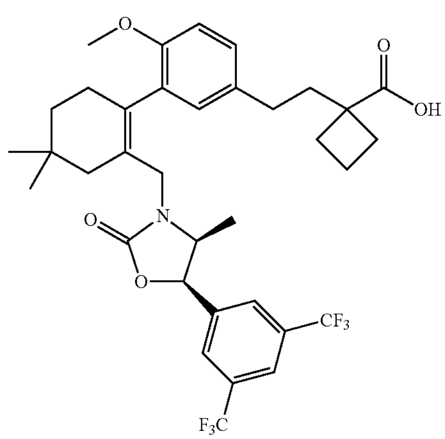 [SMILES: COc1ccc(CCC2(C(=O)O)CCC2)cc1C1=C(CN2C(=O)O[C@H](c3cc(C(F)(F)F)cc(C(F)(F)F)c3)[C@@H]2C)CC(C)(C)CC1] | 332 | 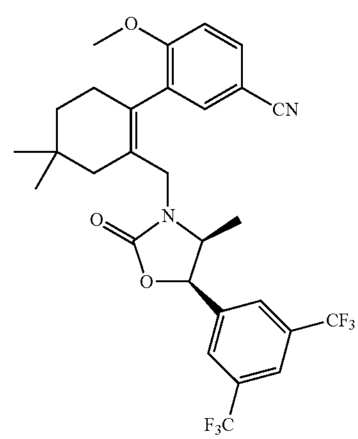 [SMILES: COc1ccc(C#N)cc1C1=C(CN2C(=O)O[C@H](c3cc(C(F)(F)F)cc(C(F)(F)F)c3)[C@@H]2C)CC(C)(C)CC1] |

TABLE 40

| Compound | Structure | Compound | Structure |
|---|---|---|---|
| 333 | 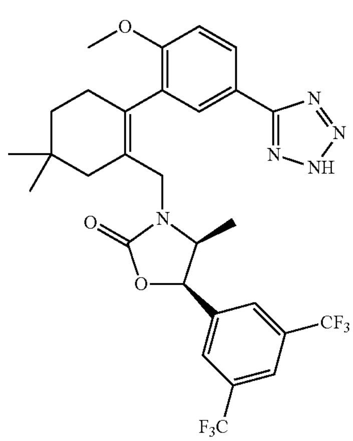 [SMILES: COc1ccc(-c2nn[nH]n2)cc1C1=C(CN2C(=O)O[C@H](c3cc(C(F)(F)F)cc(C(F)(F)F)c3)[C@@H]2C)CC(C)(C)CC1] | 334 | 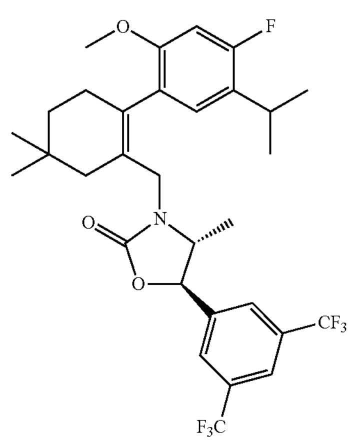 [SMILES: COc1cc(F)c(C(C)C)cc1C1=C(CN2C(=O)O[C@H](c3cc(C(F)(F)F)cc(C(F)(F)F)c3)[C@H]2C)CC(C)(C)CC1] |

TABLE 40-continued

| Compound | Structure | Compound | Structure |
| --- | --- | --- | --- |
| 335 | 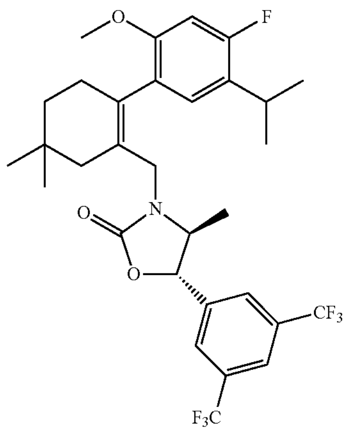 [SMILES: COc1cc(F)c(C(C)C)cc1C1=C(CN2C(=O)O[C@@H](c3cc(C(F)(F)F)cc(C(F)(F)F)c3)[C@@H]2C)CC(C)(C)CC1] | 336 | 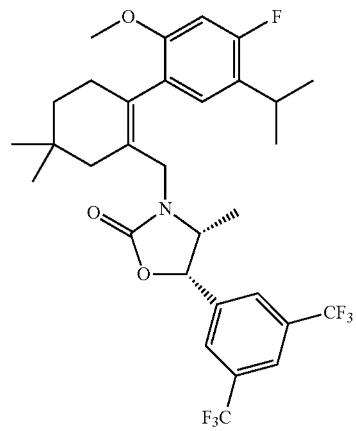 [SMILES: COc1cc(F)c(C(C)C)cc1C1=C(CN2C(=O)O[C@@H](c3cc(C(F)(F)F)cc(C(F)(F)F)c3)[C@H]2C)CC(C)(C)CC1] |
| 337 | 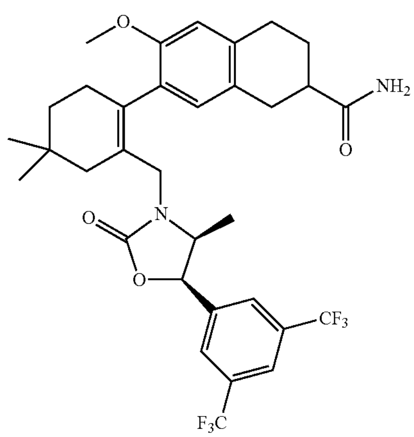 [SMILES: COc1cc2c(cc1C1=C(CN3C(=O)O[C@H](c4cc(C(F)(F)F)cc(C(F)(F)F)c4)[C@@H]3C)CC(C)(C)CC1)CC(C(N)=O)CC2] | 338 | 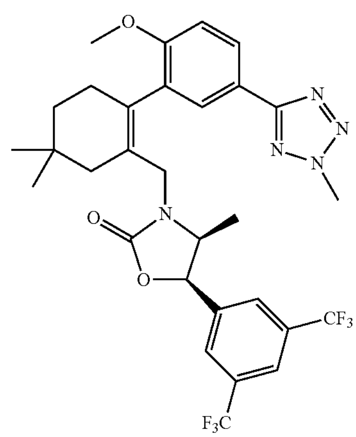 [SMILES: COc1ccc(-c2nnn(C)n2)cc1C1=C(CN2C(=O)O[C@H](c3cc(C(F)(F)F)cc(C(F)(F)F)c3)[C@@H]2C)CC(C)(C)CC1] |

TABLE 41

| Compound | Structure | Compound | Structure |
| --- | --- | --- | --- |
| 339 | 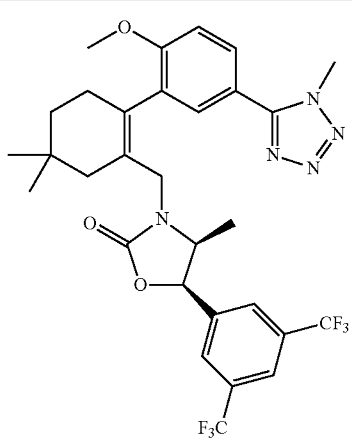 [SMILES: COc1ccc(-c2nnnn2C)cc1C1=C(CN2C(=O)O[C@H](c3cc(C(F)(F)F)cc(C(F)(F)F)c3)[C@@H]2C)CC(C)(C)CC1] | 340 | 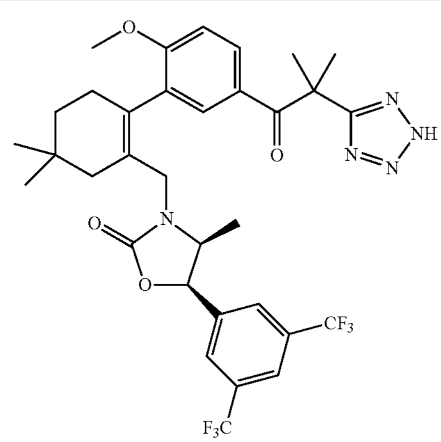 [SMILES: COc1ccc(C(=O)C(C)(C)c2nn[nH]n2)cc1C1=C(CN2C(=O)O[C@H](c3cc(C(F)(F)F)cc(C(F)(F)F)c3)[C@@H]2C)CC(C)(C)CC1] |

TABLE 41-continued
| Compound | Structure | Compound | Structure |
|---|---|---|---|
| 341 | 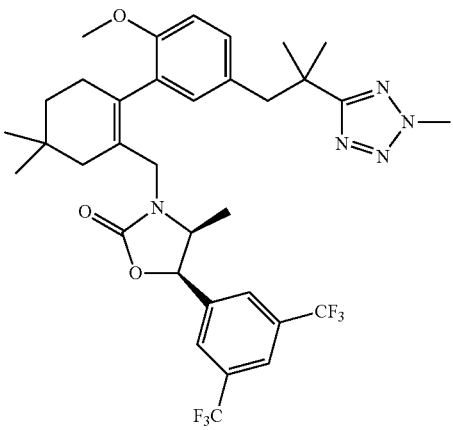 | 342 | 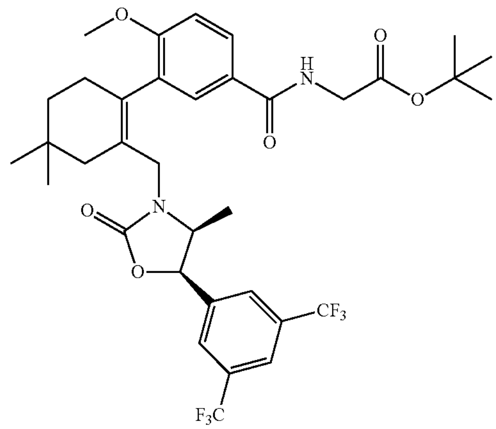 [SMILES: COc1ccc(C(=O)NCC(=O)OC(C)(C)C)cc1C1=C(CN2C(=O)O[C@H](c3cc(C(F)(F)F)cc(C(F)(F)F)c3)[C@@H]2C)CC(C)(C)CC1] |
| 343 | 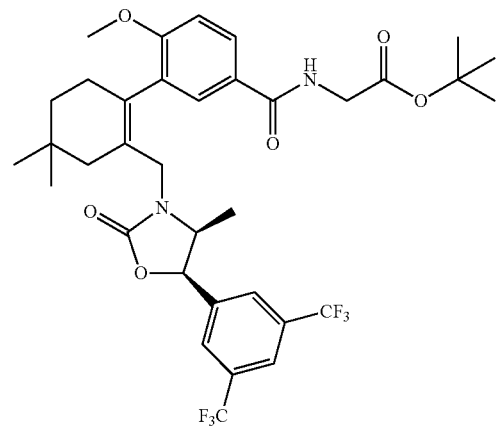 | 344 | 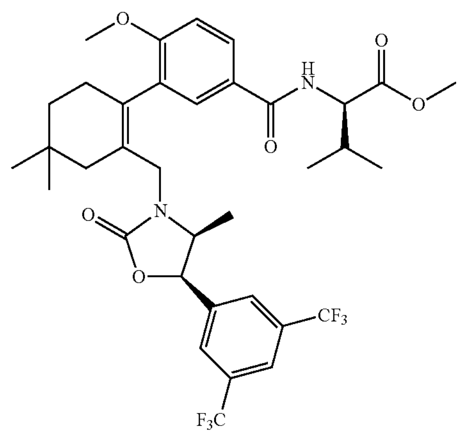 |
TABLE 42
| Compound | Structure | Compound | Structure |
|---|---|---|---|
| 345 | 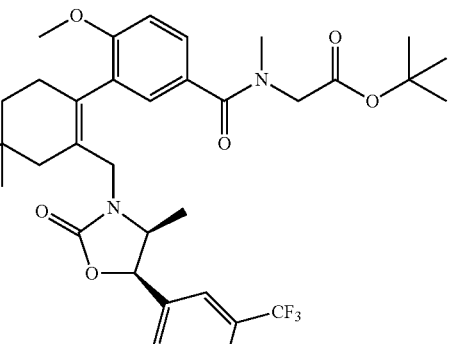 | 346 | 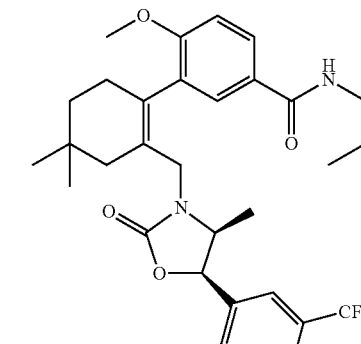 |

TABLE 42-continued
| Compound | Structure | Compound | Structure |
|---|---|---|---|
| 347 | 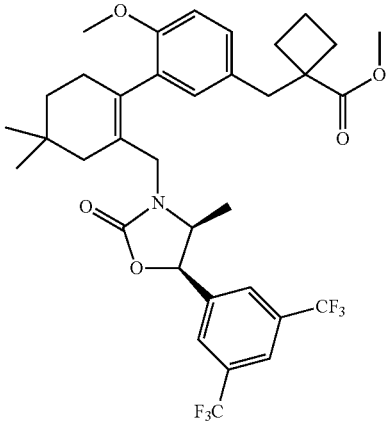 | 348 | 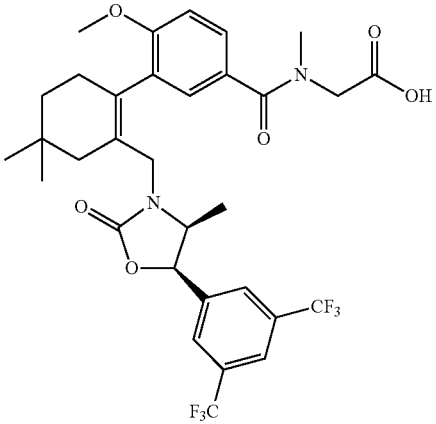 [SMILES: COc1ccc(C(=O)N(C)CC(=O)O)cc1C1=C(CN2C(=O)O[C@H](c3cc(C(F)(F)F)cc(C(F)(F)F)c3)[C@@H]2C)CC(C)(C)CC1] |
| 349 | 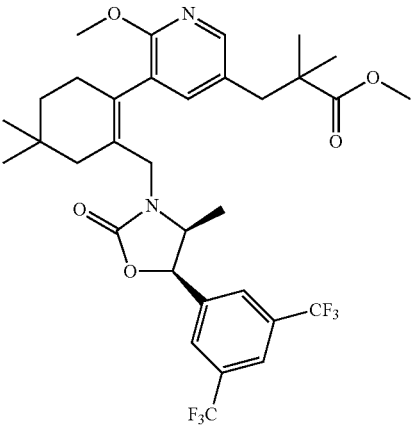 | 350 | 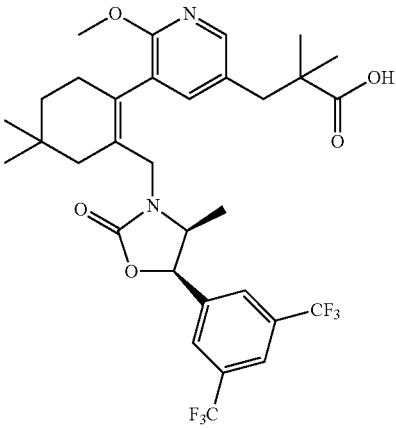 [SMILES: COc1ncc(CC(C)(C)C(=O)O)cc1C1=C(CN2C(=O)O[C@H](c3cc(C(F)(F)F)cc(C(F)(F)F)c3)[C@@H]2C)CC(C)(C)CC1] |
TABLE 43
| Compound | Structure | Compound | Structure |
|---|---|---|---|
| 353 | 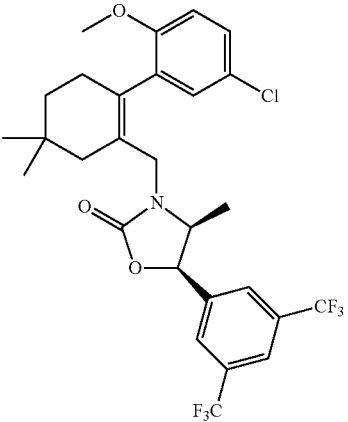 [SMILES: COc1ccc(Cl)cc1C1=C(CN2C(=O)O[C@H](c3cc(C(F)(F)F)cc(C(F)(F)F)c3)[C@@H]2C)CC(C)(C)CC1] | 354 | 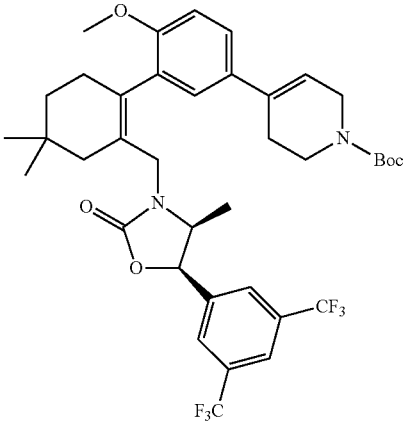 [SMILES: COc1ccc(C2=CCN(C(=O)OC(C)(C)C)CC2)cc1C1=C(CN2C(=O)O[C@H](c3cc(C(F)(F)F)cc(C(F)(F)F)c3)[C@@H]2C)CC(C)(C)CC1] |

TABLE 43-continued

| Compound | Structure | Compound | Structure |
|---|---|---|---|
| 355 | 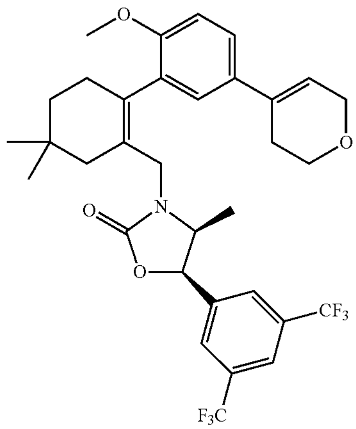 [SMILES: COc1ccc(C2=CCOCC2)cc1C1=C(CN2C(=O)O[C@H](c3cc(C(F)(F)F)cc(C(F)(F)F)c3)[C@@H]2C)CC(C)(C)CC1] | 356 | 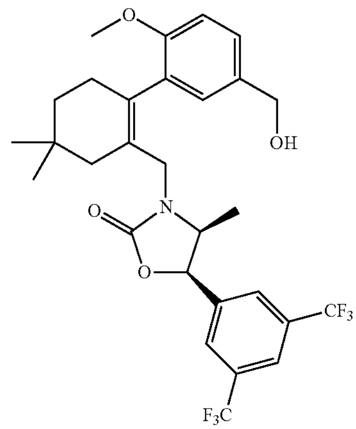 [SMILES: COc1ccc(CO)cc1C1=C(CN2C(=O)O[C@H](c3cc(C(F)(F)F)cc(C(F)(F)F)c3)[C@@H]2C)CC(C)(C)CC1] |
| 357 | 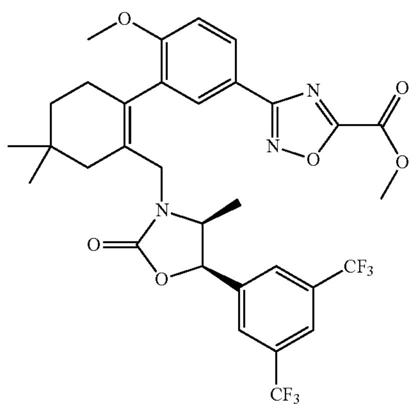 [SMILES: COC(=O)c1nc(-c2ccc(OC)c(C3=C(CN4C(=O)O[C@H](c5cc(C(F)(F)F)cc(C(F)(F)F)c5)[C@@H]4C)CC(C)(C)CC3)c2)no1] | 358 | 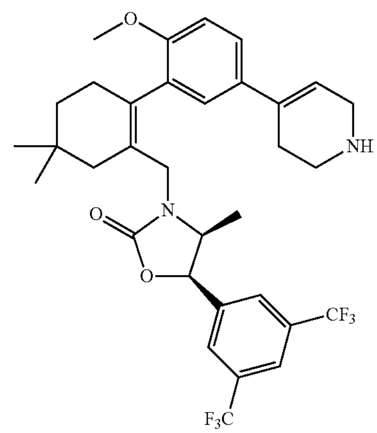 [SMILES: COc1ccc(C2=CCNCC2)cc1C1=C(CN2C(=O)O[C@H](c3cc(C(F)(F)F)cc(C(F)(F)F)c3)[C@@H]2C)CC(C)(C)CC1] |

TABLE 44

| Compound | Structure | Compound | Structure |
|---|---|---|---|
| 359 | 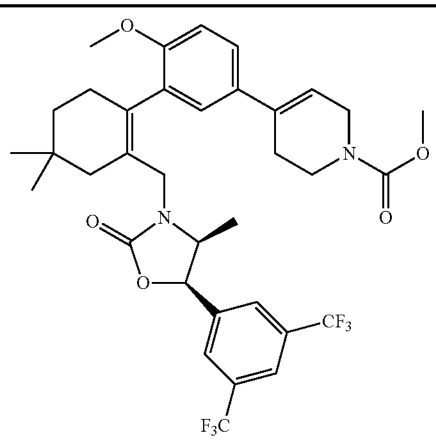 | 360 | 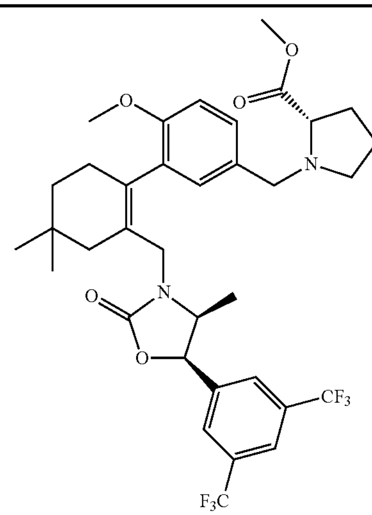 |

TABLE 44-continued

| Compound | Structure | Compound | Structure |
|---|---|---|---|
| 361 | 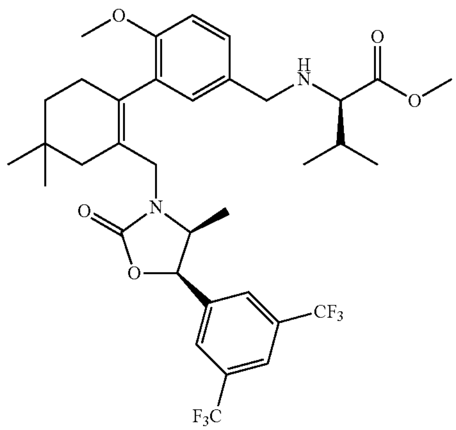 | 362 | 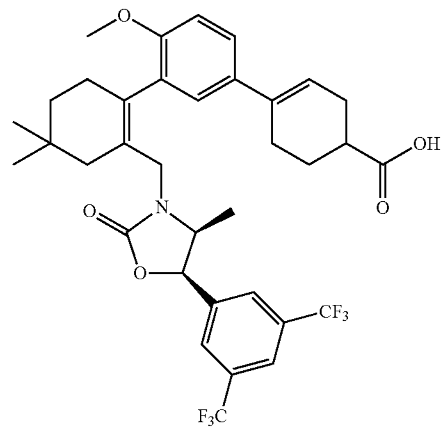 [SMILES: COc1ccc(C2=CCC(C(=O)O)CC2)cc1C1=C(CN2C(=O)O[C@H](c3cc(C(F)(F)F)cc(C(F)(F)F)c3)[C@@H]2C)CC(C)(C)CC1] |
| 363 | 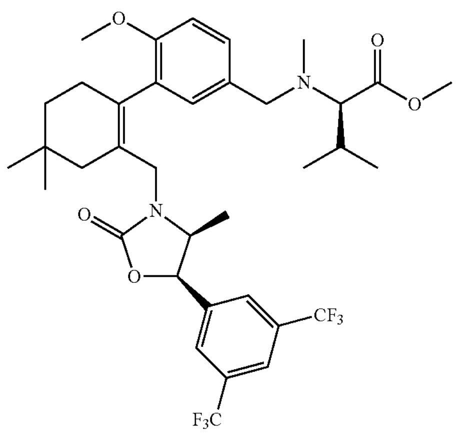 | 364 | 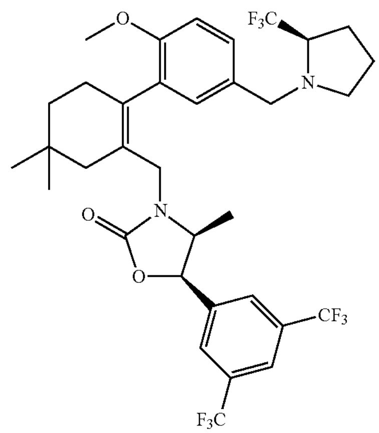 [SMILES: COc1ccc(CN2CCC[C@@H]2C(F)(F)F)cc1C1=C(CN2C(=O)O[C@H](c3cc(C(F)(F)F)cc(C(F)(F)F)c3)[C@@H]2C)CC(C)(C)CC1] |

TABLE 45

| Compound | Structure | Compound | Structure |
|---|---|---|---|
| 366 | 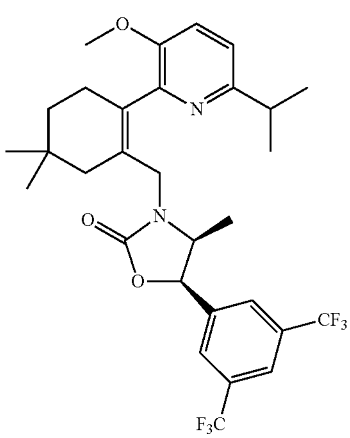 [SMILES: COc1ccc(C(C)C)nc1C1=C(CN2C(=O)O[C@H](c3cc(C(F)(F)F)cc(C(F)(F)F)c3)[C@@H]2C)CC(C)(C)CC1] | 367 | 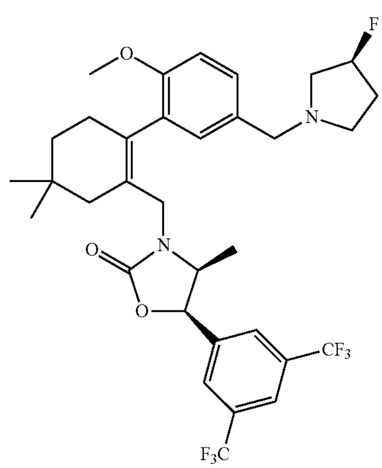 [SMILES: COc1ccc(CN2CC[C@H](F)C2)cc1C1=C(CN2C(=O)O[C@H](c3cc(C(F)(F)F)cc(C(F)(F)F)c3)[C@@H]2C)CC(C)(C)CC1] |

Measurement of activities of the compounds of the present invention—experimental protocols In order to test the effects of the compounds of formula I of the present invention on the prevention and treatment of arteriosclerosis and hyperlipidemia and the safety thereof, comparative tests were carried out using an existing material as a control.

Experimental Example 1

In Vitro Test for the Ability to Inhibit Cholesteryl Ester Transfer

1. Preparation of Cholesteryl Ester Donor

In order to prepare a cholesteryl ester donor to be used in the test, a radiolabeled recombinant HDL containing [$^3$H]-cholesteryl oleate (GE healthcare, TRK886, 3.5 μCi/mg of apoA-1) and apoA-1 was synthesized. Then, rHDL-agarose obtained by immobilizing the recombinant HDL with CNBr-activated Sepharose 4B resin (Amersham Biosciences, Sweden) was used in the test.

2. Cholesteryl Ester Transfer Test

As a source of cholesteryl ester transfer protein, plasma from healthy humans was used, and as cholesteryl ester receptor, LDL from healthy humans was used. Each of test compounds was added to be final concentrations of 16, 80, 400, 2000 and 10000 nM and tested in duplicate. In order to test cholesteryl ester transfer, 20 μl of plasma, 50 μl of LDL (0.25 mg/ml) and 50 μl of rHDL-agarose (0.25 mg/ml) were mixed with each other, and a solution of each test compound was added thereto and reacted thereto at 37° C. Then, the reaction solution was centrifuged at 4° C. for 3 minutes, thereby the reaction was stopped. 150 μl of the supernatant was transferred into a 96-well plate for radioactivity measurement, and the radioactivity thereof was measured with a beta-ray detector.

3. Statistical Processing

The ratio of [$^3$H]-cholesteryl oleate transferred from HDL to LDL was determined, and based on the determined ratio, the IC$_{50}$ value of each compound was determined using GraphPad Prism 5.0. The results are shown in Table 46 below.

TABLE 46

Results of cholesteryl ester transfer test

| Compound | IC$_{50}$ (μM) |
|---|---|
| 15 | 0.60 |
| 17 | 0.51 |
| 18 | 1.36 |
| 19 | 0.002 |
| 25 | 0.20 |
| 26 | 0.92 |
| 27 | 0.24 |
| 28 | 0.39 |
| 36 | 1.09 |
| 44 | 0.43 |
| 48 | 0.005 |
| 79 | 0.89 |
| 80 | 0.10 |
| 82 | 0.08 |
| 86 | 0.11 |
| 97 | 0.02 |
| 101 | 0.07 |
| 103 | 0.03 |
| 104 | 0.18 |
| 107 | 0.004 |
| 108 | 0.02 |
| 109 | 0.02 |
| 110 | 0.23 |
| 112 | 0.008 |
| 115 | 0.01 |
| 117 | 0.08 |
| 123 | 0.02 |
| 124 | 0.02 |
| 128 | 0.06 |
| 130 | 0.02 |
| 132 | 0.05 |
| 137 | 0.08 |
| 181 | 0.05 |
| 182 | 0.05 |
| 184 | 0.02 |
| 185 | 0.18 |
| 188 | 0.12 |
| 189 | 0.02 |
| 190 | 0.01 |
| 191 | 0.09 |
| 192 | 0.06 |
| 193 | 0.04 |
| 194 | 0.1 |
| 195 | 0.84 |
| 196 | 0.49 |
| 209 | 0.01 |
| 210 | 0.008 |
| 212 | 0.08 |
| 215 | 0.02 |
| 222 | 0.04 |
| 223 | 0.1 |
| 227 | 0.14 |
| 231 | 0.70 |
| 234 | 0.02 |
| 237 | 0.009 |
| 241 | 0.39 |
| 243 | 0.009 |
| 244 | 0.02 |
| 245 | 0.81 |
| 249 | 0.001 |
| 251 | 0.69 |
| 262 | 0.196 |
| 265 | 0.164 |
| 268 | 0.046 |
| 272 | 0.222 |
| 273 | 0.217 |
| 274 | 0.014 |
| 285 | 0.033 |
| 286 | 0.012 |
| 300 | 0.001 |
| 302 | 0.006 |
| 303 | 0.005 |
| 308 | 0.007 |
| 313 | 0.020 |
| 316 | 0.030 |
| 317 | 0.054 |
| 321 | 0.104 |
| 323 | 0.058 |
| 324 | 0.097 |
| 329 | 0.009 |
| 338 | 0.035 |
| 340 | 0.008 |
| 341 | 0.013 |
| 350 | 0.051 |
| 353 | 0.030 |
| 366 | 0.006 |
| 367 | 0.083 |

Experimental Example 2

In Vitro Test for Anti-Hyderlipidemia Activity in Hamsters

1. Experimental animals As test animals, 8-week-old male golden syrian hamsters were purchased and used in the experimental. The animal facility was kept at constant temperature and constant humidity with a 12-hr dark/12-hr light cycle, and the animals were allowed to access food and water ad libitum.

2. Experimental for Anti-Hyperlipidemia Activity in Hamsters

The test animals were used in the test after an acclimation of 1 week. The test animals were divided according to body weight into several groups, each consisting of 5-8 animals. 3 mg/kg of each test compound (CETP inhibitor) was administered orally to the animals. Each test compounds was suspended in a solvent vehicle that is a solution of 5% ethanol, 10% solutol and 85% deionized water (DW), to be used. Each of test compounds suspended in a solvent vehicle was administered orally to the mice for 5 days. To the control group, a solvent vehicle itself was administered. And then, after 4 hours from the last administration, blood was collected through the cardiac puncture. The collected blood was centrifuged at 3000 rpm for 15 minutes, and the concentration of HDL-cholesterol (Biosystem) in the separated serum was measured using a biochemical analyzer (ILab 300 plus, Instrumentation Laboratory).

3. Statistical Processing

All the results were expressed as mean±SEM, and each test group and the control group were compared using one-way ANOVA test (Dunnett's test, p<0.001) in order to determine the effect of each test group. The results are shown in Table 47 below.

TABLE 47

Results of measurement of increase in blood HDL-c levels in hamsters

| Compound | HDL-c Increase (%) |
|---|---|
| 019 | 35 |
| 025 | 33 |
| 036 | 11 |
| 048 | 41 |
| 073 | 17 |
| 093 | 17 |
| 097 | 22 |
| 099 | 16 |
| 108 | 23 |
| 102 | 25 |
| 106 | 26 |
| 112 | 43 |
| 113 | 17 |
| 115 | 29 |
| 132 | 33 |
| 205 | 8 |
| 106 | 17 |
| 274 | 21 |
| 286 | 42 |
| 287 | 22 |
| 289 | 53 |
| 302 | 38 |

The invention claimed is:

1. Cycloalkenyl aryl derivatives of the following formula 1, stereoisomers thereof, pharmaceutically acceptable salts thereof, hydrates thereof, or solvates thereof:

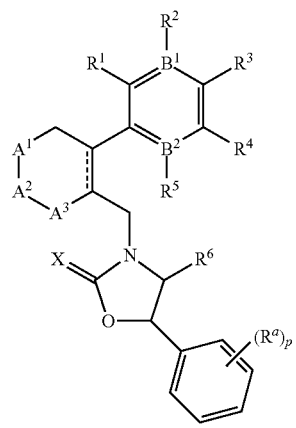

[Formula 1]

wherein
$B^1$ and $B^2$ are each independently N or C, with the proviso that both $B^1$ and $B^2$ cannot be N at the same time, and if one of $B^1$ and $B^2$ is N, $R^2$ or $R^5$ is absent;

$R^1$ and $R^2$ are each independently H, —F, —OH, —$NH_2$, —C(=O)H, —$CH_2OH$, —$OC_1$-$C_6$ alkyl, —$SC_1$-$C_6$ alkyl, —$CH_2OC_1$-$C_6$ alkyl, —NH($C_1$-$C_6$ alkyl), —NH(C=O)($C_1$-$C_6$ alkyl), —N($C_1$-$C_6$ alkyl)$_2$,
or

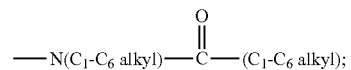

$R^1$ and $R^2$ together with the carbon atoms to which they are bonded may form a 5- or 6-membered heterocyclic aromatic or non-aromatic ring compound having 1 to 3 hetero atoms selected independently from the group consisting of N, O, S, and C(=O), wherein the heterocyclic aromatic or non-aromatic ring compound may optionally be substituted with $R^8$;

$R^3$ is —H, —F, —OH, —$C_1$-$C_6$ alkyl, or —$OC_1$-$C_6$ alkyl;
$R^4$ is —H, halogen, —CN, —$NO_2$, —$C_1$-$C_6$ alkyl, —$C_2$-$C_6$ alkenyl, —$C_3$-$C_6$ cycloalkyl,

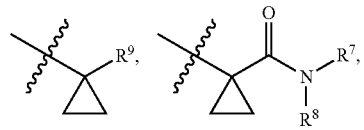

—$OR^7$, —$CH_2OR^7$, —$CH_2NR^7R^8$, —$SR^7$, —C(=O)$R^7$, —$CO_2R^7$, —$CHR^7CO_2R^8$, —C(=O)$NR^7R^8$,

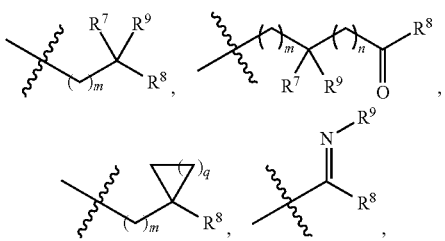

-continued

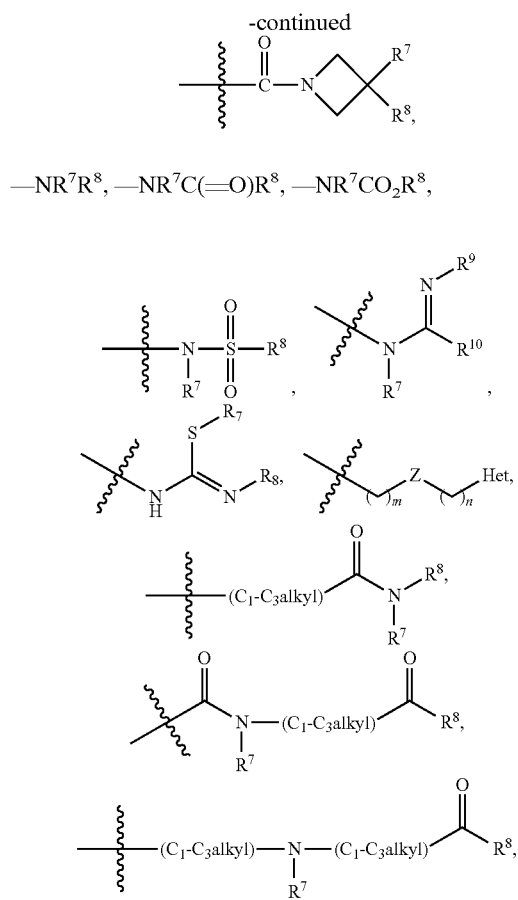

—NR⁷R⁸, —NR⁷C(═O)R⁸, —NR⁷CO₂R⁸,

—NR⁷C(═O)NR⁸R⁹, —NR⁷C(═S)NR⁸R⁹, Ar or Het;

R³ and R⁴ together with the carbon atoms to which they are bonded may form a 5- or 6-membered cycloalkyl or heterocyclic ring compound having 0 to 3 hetero atoms selected independently from the group consisting of N, O, S, and C(═O), wherein the cycloalkyl or heterocyclic ring compound may optionally be substituted with R⁸;

Ar is a C6 monocyclic aromatic compound, which is unsubstituted or optionally substituted with one or more selected from the group consisting of halogen, —OH, —NH₂, —C₁-C₆ alkyl and —OC₁—C₆ alkyl;

Het is a 5- or 6-membered heterocyclic ring compound containing 0 to 2 double bonds and having 1 to 4 hetero atoms selected independently from the group consisting of N, O, S, C(═O) and C(═S), and may be unsubstituted or may optionally be substituted with R⁸;

R⁵ is —H, —F, —OH, —CF₃, —C₁-C₆alkyl, or —OC₁—C₆ alkyl;

R⁶ is —H or —C₁-C₆ alkyl;

R⁷ is —H, halogen, —C(═O)(C₁-C₃ alkyl), —C₁-C₆ alkyl, —OC₁—C₆ alkyl, —C₃-C₆ cycloalkyl, or —OC(═O)(C₁-C₃ alkyl);

R⁸ is —H, halogen, —OH, —CN, —NH₂, —NH(C₁-C₃ alkyl), —C(═O)NH₂, —CO₂H,

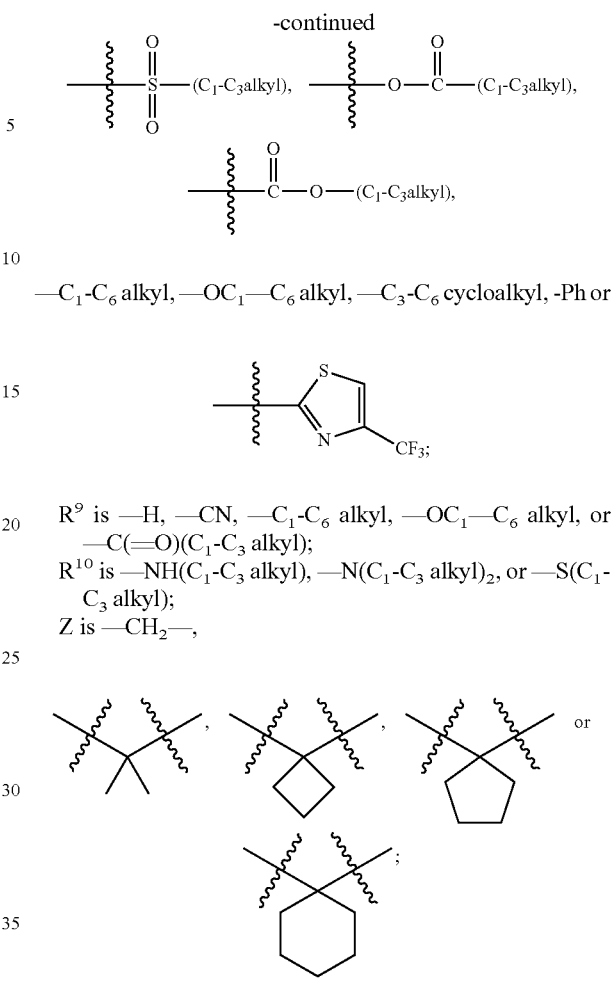

—C₁-C₆ alkyl, —OC₁—C₆ alkyl, —C₃-C₆ cycloalkyl, -Ph or

R⁹ is —H, —CN, —C₁-C₆ alkyl, —OC₁—C₆ alkyl, or —C(═O)(C₁-C₃ alkyl);

R¹⁰ is —NH(C₁-C₃ alkyl), —N(C₁-C₃ alkyl)₂, or —S(C₁-C₃ alkyl);

Z is —CH₂—,

Rᵃ is —H, —C₁ or —CF₃;

p is an integer ranging from 0 to 2;

A¹ and A² are each independently —O—, —(CR¹¹R¹²)—, or —NR¹³, wherein R¹¹ and R¹² are each independently —H, —F, or —C₁-C₆ alkyl, or R¹¹ and R¹² together form a 3- or 4-membered spirocyclic non-aromatic ring compound, and R¹³ is —H, —C₁-C₆ alkyl, —C(═O)(C₁-C₆ alkyl), —CO₂(C₁-C₆ alkyl), —SO₂(C₁-C₆ alkyl), or —C₃-C₆ cycloalkyl;

A³ is —(CH₂)ₙ—;

X is S or O;

m is an integer ranging from 0 to 3;

n is an integer ranging from 0 to 2;

q is an integer ranging from 1 to 3;

wherein said —C₁-C₃ alkyl, —C₃-C₆ cycloalkyl —C₁-C₆ alkyl or —C₂-C₆ alkenyl is unsubstituted or substituted with one or more selected from the group consisting of halogen, —OH, —CF₃, —CN, —CO₂H, —C(═O)CH₃, —OC(═O)CH₃, —C₁-C₃alkyl, —OC₁-C₃alkyl, and -Ph.

2. The cycloalkenyl aryl derivatives of claim 1, stereoisomers thereof, pharmaceutically acceptable salts thereof, hydrates thereof, or solvates thereof, wherein B¹ and B² are each independently N or C, with the proviso that both B¹ and B² cannot be N at the same time, and if any one of B¹ and B² is N, R² or R⁵ is absent;

R¹ is —F, —OH, —NH₂, —C(═O)H, —CH₂OH, —OCH₃, —OCF₃, —SCH₃, —CH₂OCH₃, —NHCH₃,

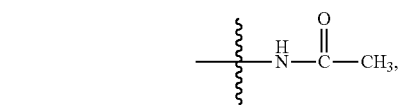

—N(CH$_3$)$_2$, or

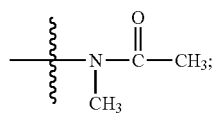

R$^2$ is —H;

R$^1$ and R$^2$ together with the carbon atoms to which they are bonded may form a 5- or 6-membered heterocyclic aromatic or non-aromatic ring compound having 1 to 3 hetero atoms selected independently from the group consisting of N, O, S, and C(=O), wherein the heterocyclic aromatic or non-aromatic ring compound may optionally be substituted with R$^8$;

R$^3$ is —H, —F, —OH, —CH$_3$, —CF$_3$, —CH$_2$CH$_3$, or —OCH$_3$;

R$^4$ is —H, —F, —Cl, —CN, —NO$_2$, —CH$_3$, —CH$_2$CH$_3$, —CH(CH$_3$)$_2$, —C(CH$_3$)$_3$, —CF$_3$, —CH(CF$_3$)$_2$, —CH(CH$_3$)(CF$_3$), —C(OCH$_3$)(CF$_3$)$_2$, —CH(OH)CH$_3$, —C(OH)(CH$_3$)$_2$, —C(OH)(CF$_3$)$_2$, —C(=CF$_2$)CF$_3$, -cyclopropyl,

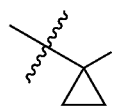 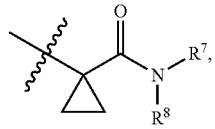

—OCH$_3$, —OCH$_2$CH$_3$, —OCH(CH$_3$)$_2$, —OC(CH$_3$)$_3$, —OCF$_3$, —OCH$_2$CF$_3$, —CH$_2$OH, —CH$_2$OCH$_3$, —CH$_2$NR$^7$R$^8$, —SCH$_3$, —C(=O)R$^7$, —CO$_2$R$^7$, —CHR$^7$CO$_2$R$^8$, —C(=O)NR$^7$R$^8$,

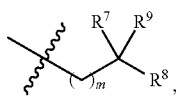 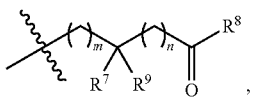

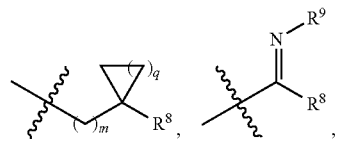

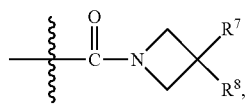

—NR$^7$R$^8$, —NR$^7$C(=O)R$^8$, —NR$^7$CO$_2$R$^8$,

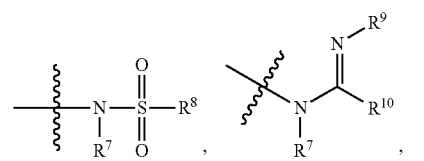

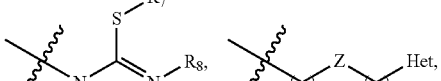

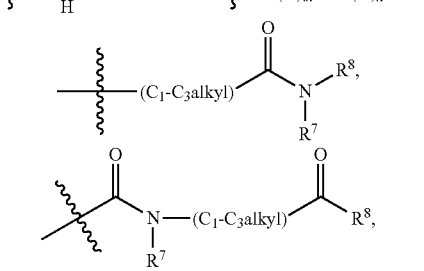

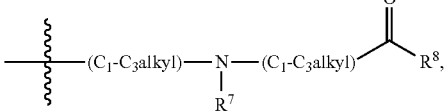

—NR$^7$C(=O)NR$^8$R$^9$, —NR$^7$C(=S)NR$^8$R$^9$, Ar or Het;

R$^3$ and R$^4$ together with the carbon atoms to which they are bonded may form a 5- or 6-membered cycloalkyl or heterocyclic ring compound having 0 to 3 hetero atoms selected independently from the group consisting of N, O, S, and C(=O), wherein the cycloalkyl or heterocyclic ring compound may optionally be substituted with R$^8$;

Ar is a C6 monocyclic aromatic compound, which is unsubstituted or optionally substituted with one or more selected from the group consisting of —F, —Cl, —OH, —NH$_2$, —CH$_3$ and —OCH$_3$;

Het is selected from

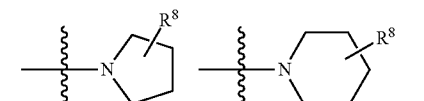

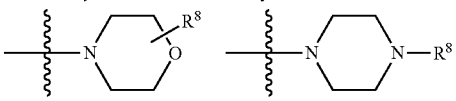

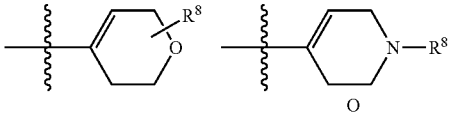

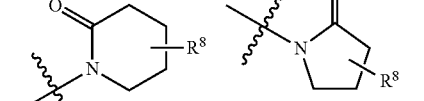

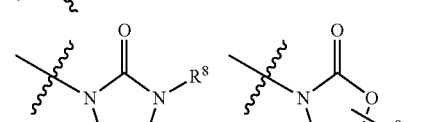

-continued

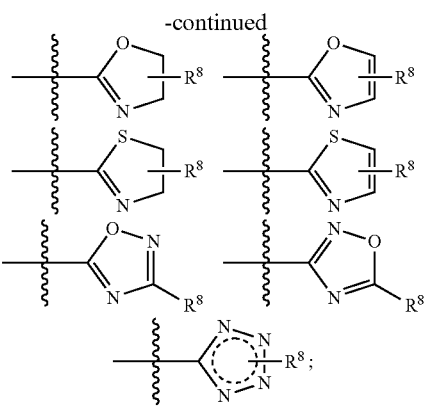

$R^5$ is —H;
$R^6$ is —H or —$CH_3$;
$R^7$ is —H, halogen, —C(=O)($C_1$-$C_3$ alkyl), —$C_1$-$C_6$ alkyl, —$OC_1$—$C_6$ alkyl, —$C_3$-$C_6$ cycloalkyl, or —OC(=O)($C_1$-$C_3$ alkyl);
$R^8$ is —H, halogen, —OH, —CN, —$NH_2$, —NH($C_1$-$C_3$ alkyl), —C(=O)$NH_2$, —$CO_2$H,

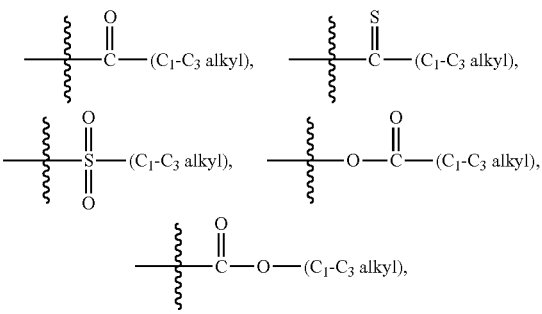

—$C_1$-$C_6$ alkyl, —$OC_1$—$C_6$ alkyl, —$C_3$-$C_6$ cycloalkyl, -Ph or

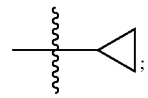

$R^9$ is —H, —CN, —$C_1$-$C_6$ alkyl, —$OC_1$—$C_6$ alkyl, or —C(=O)($C_1$-$C_3$ alkyl);
$R^{10}$ is —NH($C_1$-$C_3$ alkyl), —N($C_1$-$C_3$ alkyl)$_2$, or —S($C_1$-$C_3$ alkyl);
Z is —$CH_2$—,

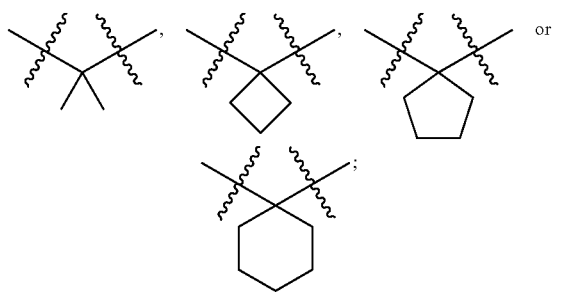

$R^a$ is —H, —$C_1$ or —$CF_3$;
p is 2;
$A^1$ is —$CH_2$—, —C($CH_3$)$_2$—, or —$NR^{13}$;
$A^2$ is —O—, —($CR^{11}R^{12}$)—, or —$NR^{13}$, wherein $R^{11}$ and $R^{12}$ are each independently —H, —F, —$CH_3$, —$CF_3$, —$CH_2CH_3$, —$CH(CH_3)_2$, or —$C(CH_3)_3$, or $R^{11}$ and $R^{12}$ together form a 3- or 4-membered spirocyclic non-aromatic ring compound, and $R^{13}$ is —H, —$CH_3$, —$CF_3$, —$CH_2CH_3$, —$CH(CH_3)_2$, —$CH_2CF_3$, —C(=O)$CH_3$, —C(=O)$CF_3$, —$CO_2C(CH_3)_3$, —$SO_2CH_3$, —$SO_2CF_3$, or $A^3$ is —($CH_2$)$_n$—;
X is S or O;
m is an integer ranging from 0 to 3;
n is an integer ranging from 0 to 2;
q is an integer ranging from 1 to 3;
wherein said —$C_1$-$C_3$ alkyl, —$C_3$-$C_6$ cycloalkyl, —$C_1$-$C_6$ alkyl or —$C_2$-$C_6$ alkenyl is unsubstituted or substituted with one or more selected from the group consisting of —F, —$C_1$, —Br, —OH, —$CF_3$, —CN, —$CO_2$H, —C(=O)$CH_3$, —OC(=O)$CH_3$, —$C_1$-$C_3$ alkyl, —$OC_1$—$C_3$ alkyl, and -Ph.

3. The cycloalkenyl aryl derivatives, stereoisomers thereof, pharmaceutically acceptable salts thereof, hydrates thereof or solvates thereof according to claim 1, wherein the cycloalkenyl aryl derivatives are selected from the group consisting of the following compounds:

(4S,5R)-5-(3,5-bis(trifluoromethyl)phenyl)-3-((2-(5-isopropyl-2-methoxyphenyl)-5,5-dimethylcyclohex-1-enyl)methyl)-4-methyloxazolidine-2-thione;
(4S,5R)-5-(3,5-bis(trifluoromethyl)phenyl)-3-((2-(2-methoxyphenyl)-5,5-dimethylcyclohex-1-enyl)methyl)-4-methyloxazolidine-2-thione;
(4S,5R)-5-(3,5-bis(trifluoromethyl)phenyl)-3-((2-(4-fluoro-5-isopropyl-2-methoxyphenyl)-5,5-dimethylcyclohex-1-enyl)methyl)-4-methyloxazolidine-2-thione;
(4S,5R)-5-(3,5-bis(trifluoromethyl)phenyl)-3-((2-(2-methoxyphenyl)-5,5-dimethylcyclohex-1-enyl)methyl)-4-methyloxazolidin-2-one;
(4S,5R)-5-(3,5-bis(trifluoromethyl)phenyl)-3-((2-(4-fluoro-5-isopropyl-2-methoxyphenyl)-5,5-dimethylcyclohex-1-enyl)methyl)-4-methyloxazolidin-2-one;
(4S,5R)-5-(3,5-bis(trifluoromethyl)phenyl)-3-((2-(4-fluoro-5-isopropyl-2-methoxyphenyl)-5-methylcyclohex-1-enyl)methyl)-4-methyloxazolidin-2-one;
(4S,5R)-5-(3,5-bis(trifluoromethyl)phenyl)-3-((2-(4-fluoro-5-isopropyl-2-methoxyphenyl)-5-methylcyclohex-1-enyl)methyl)-4-methyloxazolidine-2-thione;
(4S,5R)-5-(3,5-bis(trifluoromethyl)phenyl)-3-((2-(4-fluoro-5-isopropyl-2-methoxyphenyl)cyclohex-1-enyl)methyl)-4-methyloxazolidin-2-one;
(4S,5R)-5-(3,5-bis(trifluoromethyl)phenyl)-3-((2-(4-fluoro-5-isopropyl-2-methoxyphenyl)cyclohex-1-enyl)methyl)-4-methyloxazolidine-2-thione;
(4S,5R,Z)-5-(3,5-bis(trifluoromethyl)phenyl)-3-((2-(4-fluoro-5-isopropyl-2-methoxyphenyl)cyclohept-1-enyl)methyl)-4-methyloxazolidin-2-one;
(4S,5R)-5-(3,5-bis(trifluoromethyl)phenyl)-3-((4-(4-fluoro-5-isopropyl-2-methoxyphenyl)-5,6-dihydro-2H-pyran-3-yl)methyl)-4-methyloxazolidin-2-one;

(4S,5R)-5-(3,5-bis(trifluoromethyl)phenyl)-3-((2-(4-fluoro-5-isopropyl-2-methoxyphenyl)cyclopent-1-enyl)methyl)-4-methyloxazolidin-2-one;
(4S,5R)-5-(3,5-bis(trifluoromethyl)phenyl)-3-((2-(5-isopropyl-2-methoxyphenyl)cyclopent-1-enyl)methyl)-4-methyloxazolidin-2-one;
3-(2-(((4S,5R)-5-(3,5-bis(trifluoromethyl)phenyl)-4-methyl-2-oxooxazolidin-3-yl)methyl)cyclohex-1-enyl)-4-methoxybenzoic acid;
methyl 3-(2-(((4S,5R)-5-(3,5-bis(trifluoromethyl)phenyl)-4-methyl-2-oxooxazolidin-3-yl)methyl)cyclohex-1-enyl)-4-methoxybenzoate;
3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzoic acid;
methyl 3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzoate;
(4S,5R,Z)-5-(3,5-bis(trifluoromethyl)phenyl)-3-((2-(5-isopropyl-2-methoxyphenyl)cyclohept-1-enyl)methyl)-4-methyloxazolidin-2-one;
(4S,5R)-5-(3,5-bis(trifluoromethyl)phenyl)-3-((5-ethyl-2-(4-fluoro-5-isopropyl-2-methoxyphenyl)cyclohex-1-enyl)methyl)-4-methyloxazolidin-2-one;
(4S,5R)-5-(3,5-bis(trifluoromethyl)phenyl)-3-((2-(5-isopropyl-2-methoxyphenyl)-4,4-dimethylcyclohex-1-enyl)methyl)-4-methyloxazolidin-2-one;
(4S,5R)-5-(3,5-bis(trifluoromethyl)phenyl)-3-((2-(5-(hydroxymethyl)-2-methoxyphenyl)cyclohex-1-enyl)methyl)-4-methyloxazolidin-2-one;
(4S,5R)-5-(3,5-bis(trifluoromethyl)phenyl)-3-((2-(2-methoxy-5-(methoxymethyl)phenyl)cyclohex-1-enyl)methyl)-4-methyloxazolidin-2-one;
(4S,5R)-5-(3,5-bis(trifluoromethyl)phenyl)-3-((2-(4-fluoro-5-isopropyl-2-methoxyphenyl)-5-(trifluoromethyl)cyclohex-1-enyl)methyl)-4-methyloxazolidin-2-one;
(4S,5R)-5-(3,5-bis(trifluoromethyl)phenyl)-3-((2-(3'-chloro-4,6'-dimethoxybiphenyl-3-yl)cyclohex-1-enyl)methyl)-4-methyloxazolidin-2-one;
(4S,5R)-5-(3,5-bis(trifluoromethyl)phenyl)-3-((2-(5-chloro-2-methoxyphenyl)cyclohex-1-enyl)methyl)-4-methyloxazolidin-2-one;
(4S,5R)-3-((2-(1H-indol-4-yl)-5,5-dimethylcyclohex-1-enyl)methyl)-5-(3,5-bis(trifluoromethyl)phenyl)-4-methyloxazolidin-2-one;
(4S,5R)-5-(3,5-bis(trifluoromethyl)phenyl)-3-((2-(2-methoxy-5-nitrophenyl)-5,5-dimethylcyclohex-1-enyl)methyl)-4-methyloxazolidin-2-one;
(4S,5R)-5-(3,5-bis(trifluoromethyl)phenyl)-3-((4-(2-methoxyphenyl)-5,6-dihydro-2H-pyran-3-yl)methyl)-4-methyloxazolidin-2-one;
(4S,5R)-5-(3,5-bis(trifluoromethyl)phenyl)-3-((2-(5-(dimethylamino)-2-methoxyphenyl)-5,5-dimethylcyclohex-1-enyl)methyl)-4-methyloxazolidin-2-one;
2-(2-(((4S,5R)-5-(3,5-bis(trifluoromethyl)phenyl)-4-methyl-2-oxooxazolidin-3-yl)methyl)cyclohex-1-enyl)-5-methoxybenzaldehyde;
(4S,5R)-5-(3,5-bis(trifluoromethyl)phenyl)-3-((2-(2-(hydroxymethyl)-4-methoxyphenyl)cyclohex-1-enyl)methyl)-4-methyloxazolidin-2-one;
(4S,5R)-5-(3,5-bis(trifluoromethyl)phenyl)-3-((2-(4-methoxy-2-(methoxymethyl)phenyl)cyclohex-1-enyl)methyl)-4-methyloxazolidin-2-one;
(4S,5R)-5-(3,5-bis(trifluoromethyl)phenyl)-4-methyl-3-((2-(quinolin-8-yl)cyclohex-1-enyl)methyl)oxazolidin-2-one;
(4S,5R)-5-(3,5-bis(trifluoromethyl)phenyl)-4-methyl-3-((2-(1-methyl-1H-indazol-4-yl)cyclohex-1-enyl)methyl)oxazolidin-2-one;
(4S,5R)-5-(3,5-bis(trifluoromethyl)phenyl)-3-((2-(5-(3-isopropyl-1,2,4-oxadiazol-5-yl)-2-methoxyphenyl)cyclohex-1-enyl)methyl)-4-methyloxazolidin-2-one;
(4S,5R)-5-(3,5-bis(trifluoromethyl)phenyl)-3-((2-(4-fluoro-2-hydroxy-5-isopropylphenyl)-5,5-dimethylcyclohex-1-enyl)methyl)-4-methyloxazolidin-2-one;
(4S,5R)-5-(3,5-bis(trifluoromethyl)phenyl)-3-((2-(4-fluoro-2-hydroxy-5-isopropylphenyl)-5-methylcyclohex-1-enyl)methyl)-4-methyloxazolidin-2-one;
(4S,5R)-5-(3,5-bis(trifluoromethyl)phenyl)-3-((2-(4-fluoro-2-hydroxy-5-isopropylphenyl)-5-(trifluoromethyl)cyclohex-1-enyl)methyl)-4-methyloxazolidin-2-one;
(4S,5R)-5-(3,5-bis(trifluoromethyl)phenyl)-3-((2-(2-methoxy-5-morpholinophenyl)cyclohex-1-enyl)methyl)-4-methyloxazolidin-2-one;
3-(2-(((4S,5R)-5-(3,5-bis(trifluoromethyl)phenyl)-4-methyl-2-oxooxazolidin-3-yl)methyl)cyclohex-1-enyl)-4-methoxy-N-methylbenzamide;
3-(2-(((4S5R)-5-(3,5-bis(trifluoromethyl)phenyl)-4-methyl-2-oxooxazolidin-3-yl)methyl)cyclohex-1-enyl)-N-ethyl-4-methoxybenzamide;
3-(2-(((4S,5R)-5-(3,5-bis(trifluoromethyl)phenyl)-4-methyl-2-oxooxazolidin-3-yl)methyl)cyclohex-1-enyl)-4-methoxy-N-(2,2,2-trifluoroethyl)benzamide;
3-(2-(((4S,5R)-5-(3,5-bis(trifluoromethyl)phenyl)-4-methyl-2-oxooxazolidin-3-yl)methyl)cyclohex-1-enyl)-N-isopropyl-4-methoxybenzamide;
N-(3-(2-(((4S,5R)-5-(3,5-bis(trifluoromethyl)phenyl)-4-methyl-2-oxooxazolidin-3-yl)methyl)cyclohex-1-enyl)-4-methoxyphenyl)acetamide;
N-(3-(2-(((4S,5R)-5-(3,5-bis(trifluoromethyl)phenyl)-4-methyl-2-oxooxazolidin-3-yl)methyl)cyclohex-1-enyl)-4-methoxyphenyl)isobutyramide;
(4S,5R)-5-(3,5-bis(trifluoromethyl)phenyl)-3-((2-(5-(3-cyclopropyl-1,2,4-oxadiazol-5-yl)-2-methoxyphenyl)cyclohex-1-enyl)methyl)-4-methyloxazolidin-2-one;
3-(2-(((4S,5R)-5-(3,5-bis(trifluoromethyl)phenyl)-4-methyl-2-oxooxazolidin-3-yl)methyl)cyclohex-1-enyl)-4-methoxybenzaldehyde;
(4S,5R)-5-(3,5-bis(trifluoromethyl)phenyl)-3-((2-(5-(1-hydroxyethyl)-2-methoxyphenyl)cyclohex-1-enyl)methyl)-4-methyloxazolidin-2-one;
(4S,5R)-3-((2-(5-acetyl-2-methoxyphenyl)cyclohex-1-enyl)methyl)-5-(3,5-bis(trifluoromethyl)phenyl)-4-methyloxazolidin-2-one;
(4S,5R)-5-(3,5-bis(trifluoromethyl)phenyl)-3-((2-(5-(2-hydroxypropan-2-yl)-2-methoxyphenyl)cyclohex-1-enyl)methyl)-4-methyloxazolidin-2-one;
(4S,5R)-5-(3,5-bis(trifluoromethyl)phenyl)-4-methyl-3-((2-(2-(trifluoromethoxy)phenyl)cyclohex-1-enyl)methyl)oxazolidin-2-one;
(4S,5R)-5-(3,5-bis(trifluoromethyl)phenyl)-3-((2-(2-fluoro-5-(trifluoromethyl)phenyl)cyclohex-1-enyl)methyl)-4-methyloxazolidin-2-one;
1-(3-(2-(((4S,5R)-5-(3,5-bis(trifluoromethyl)phenyl)-4-methyl-2-oxooxazolidin-3-yl)methyl)cyclohex-1-enyl)-4-methoxyphenyl)ethyl acetate;
N-(3-(2-(((4S,5R)-5-(3,5-bis(trifluoromethyl)phenyl)-4-methyl-2-oxooxazolidin-3-yl)methyl)cyclohex-1-enyl)-4-methoxyphenyl)-N-methylisobutyramide;
3-(2-(((4S,5R)-5-(3,5-bis(trifluoromethyl)phenyl)-4-methyl-2-oxooxazolidin-3-yl)methyl)cyclohex-1-enyl)-N-isopropyl-4-methoxy-N-methylbenzamide;

(4S,5R)-5-(3,5-bis(trifluoromethyl)phenyl)-3-((2-(2-methoxy-5-(trifluoromethyl)phenyl)-5-methylcyclohex-1-enyl)methyl)-4-methyloxazolidin-2-one;

(4S,5R)-5-(3,5-bis(trifluoromethyl)phenyl)-3-((2-(2-methoxy-5-(trifluoromethyl)phenyl)-5,5-dimethylcyclohex-1-enyl)methyl)-4-methyloxazolidin-2-one;

(4S,5R)-5-(3,5-bis(trifluoromethyl)phenyl)-3-((5-tert-butyl-2-(4-fluoro-5-isopropyl-2-methoxyphenyl)cyclohex-1-enyl)methyl)-4-methyloxazolidin-2-one;

(4S,5R)-5-(3,5-bis(trifluoromethyl)phenyl)-3-((2-(5-(1-hydroxyethyl)-2-methoxyphenyl)-5,5-dimethylcyclohex-1-enyl)methyl)-4-methyloxazolidin-2-one;

(4S,5R)-5-(3,5-bis(trifluoromethyl)phenyl)-3-((2-(5-(2-hydroxypropan-2-yl)-2-methoxyphenyl)-5,5-dimethylcyclohex-1-enyl)methyl)-4-methyloxazolidin-2-one;

(4S,5R)-5-(3,5-bis(trifluoromethyl)phenyl)-3-((2-(5-isopropyl-2-methoxyphenyl)-5,5-dimethylcyclohex-1-enyl)methyl)-4-methyloxazolidin-2-one;

(4S,5R)-5-(3,5-bis(trifluoromethyl)phenyl)-3-((2-(5-isopropyl-2-methoxyphenyl)-5-(trifluoromethyl)cyclohex-1-enyl)methyl)-4-methyloxazolidin-2-one;

(4S,5R)-5-(3,5-bis(trifluoromethyl)phenyl)-3-((2-(4-fluoro-5-isopropyl-2-methoxyphenyl)-4,4-dimethylcyclohex-1-enyl)methyl)-4-methyloxazolidin-2-one;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)acetamide;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)isobutyramide;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-methylacetamide;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-methylisobutyramide (4S,5R)-5-(3,5-bis(trifluoromethyl)phenyl)-3-((2-(2-(methoxymethyl)-4-(trifluoromethyl)phenyl)-5,5-dimethylcyclohex-1-enyl)methyl)-4-methyloxazolidin-2-one;

(4S,5R)-5-(3,5-bis(trifluoromethyl)phenyl)-3-((2-(5-tert-butyl-2-methoxyphenyl)-5,5-dimethylcyclohex-1-enyl)methyl)-4-methyloxazolidin-2-one;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)-N-(2,2,2)acetamide;

(4S,5R)-5-(3,5-bis(trifluoromethyl)phenyl)-3-((2-(2-methoxy-5-(trifluoromethoxy)phenyl)-5,5-dimethylcyclohex-1-enyl)methyl)-4-methyloxazolidin-2-one;

N-acetyl-N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)acetamide;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2,2-trifluoro-N-methylacetamide;

(4S,5R)-5-(3,5-bis(trifluoromethyl)phenyl)-3-((2-(2-methoxy-5-(2-oxopyrrolidin-1-yl)phenyl)-5,5-dimethylcyclohex-1-enyl)methyl)-4-methyloxazolidin-2-one;

(4S,5R)-5-(3,5-bis(trifluoromethyl)phenyl)-3-((2-(2-methoxy-5-(2-oxopiperidin-1-yl)phenyl)-5,5-dimethylcyclohex-1-enyl)methyl)-4-methyloxazolidin-2-one;

(4S,5R)-5-(3,5-bis(trifluoromethyl)phenyl)-3-((5,5-difluoro-2-(4-fluoro-5-isopropyl-2-methoxyphenyl)cyclohex-1-enyl)methyl)-4-methyloxazolidin-2-one;

methyl 3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl(methyl)carbamate;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-methylmethanesulfonamide;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3,3,3-trifluoro-N-methylpropanamide;

(4S,5R)-5-(3,5-bis(trifluoromethyl)phenyl)-3-((2-(4-fluoro-2-methoxy-5-(1,1,1-trifluoropropan-2-yl)phenyl)-5,5-dimethylcyclohex-1-enyl)methyl)-4-methyloxazolidin-2-one;

methyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)acetate;

2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)acetic acid;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)cyclopropanesulfonamide;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)trifluoromethanesulfonamide;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-methylcyclopropanesulfonamide;

1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3-methylthiourea;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)trifluoro-N-methylmethanesulfonamide;

(4S,5R)-5-(3,5-bis(trifluoromethyl)phenyl)-3-((2-(2-methoxy-5-(2-oxoimidazolidin-1-yl)phenyl)-5,5-dimethylcyclohex-1-enyl)methyl)-4-methyloxazolidin-2-one;

(4S,5R)-5-(3,5-bis(trifluoromethyl)phenyl)-3-((2-(2-methoxy-5-(2-oxooxazolidin-3-yl)phenyl)-5,5-dimethylcyclohex-1-enyl)methyl)-4-methyloxazolidin-2-one;

(4S,5R)-3-((2-(2-amino-5-isopropylphenyl)-5,5-dimethylcyclohex-1-enyl)methyl)-5-(3,5-bis(trifluoromethyl)phenyl)-4-methyloxazolidin-2-one;

N-(2-(2-(((4S,5R)-5-(3,5-bis(trifluoromethyl)phenyl)-4-methyl-2-oxooxazolidin-3-yl)methyl)-4,4-dimethylcyclohex-1-enyl)-4-isopropylphenyl)-N-methylacetamide;

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-1,1-dimethylurea;

(4S,5R)-5-(3,5-bis(trifluoromethyl)phenyl)-3-((2-(2-methoxy-5-(methylthio)phenyl)-5,5-dimethylcyclohex-1-enyl)methyl)-4-methyloxazolidin-2-one;

(4S,5R)-5-(3,5-bis(trifluoromethyl)phenyl)-3-((5,5-dimethyl-2-(methylthio)-5-(trifluoromethoxy)phenyl)cyclohex-1-enyl)methyl)-4-methyloxazolidin-2-one;

(Z)-3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-cyano-1,1-dimethylguanidine;

(E)-1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-cyano-3-methylguanidine;

(E)-1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-cyano-1,3,3-trimethylguanidine;

(Z)-methyl N-3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl-N'-methylcarbamimidothioate;

1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-1,3,3-trimethylurea;

methyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)propanoate;

(4S,5R)-5-(3,5-bis(trifluoromethyl)phenyl)-3-((2-(2-methoxy-5-(1,1,1-trifluoropropan-2-ylamino)phenyl)-5,5-dimethylcyclohex-1-enyl)methyl)-4-methyloxazolidin-2-one;

(4S,5R)-5-(3,5-bis(trifluoromethyl)phenyl)-3-((2-(2-methoxy-5-(methyl(1,1,1-trifluoropropan-2-yl)amino)phenyl)-5,5-dimethylcyclohex-1-enyl)methyl)-4-methyloxazolidin-2-one N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2,2-trifluoroacetamide;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-bromoacetamide;

N-(2-(2-(((4S,5R)-5-(3,5-bis(trifluoromethyl)phenyl)-4-methyl-2-oxooxazolidin-3-yl)methyl)-4,4-dimethylcyclohex-1-enyl)-4-isopropylphenyl)acetamide;

(4S,5R)-5-(3,5-bis(trifluoromethyl)phenyl)-3-((2-(5-isopropyl-2-(methylamino)phenyl)-5,5-dimethylcyclohex-1-enyl)methyl)-4-methyloxazolidin-2-one;

(4S,5R)-5-(3,5-bis(trifluoromethyl)phenyl)-3-((2-(2-(dimethylamino)-5-isopropylphenyl)-5,5-dimethylcyclohex-1-enyl)methyl)-4-methyloxazolidin-2-one;

(4S,5R)-5-(3,5-bis(trifluoromethyl)phenyl)-3-((2-(2-methoxy-5-(2,2,2-trifluoroacetyl)phenyl)-5,5-dimethylcyclohex-1-enyl)methyl)-4-methyloxazolidin-2-one;

(4S,5R)-5-(3,5-bis(trifluoromethyl)phenyl)-3-((2-(2-methoxy-5-(perfluoroprop-1-en-2-yl)phenyl)-5,5-dimethylcyclohex-1-enyl)methyl)-4-methyloxazolidin-2-one;

(4S,5R)-5-(3,5-bis(trifluoromethyl)phenyl)-3-((2-(5-(1,1,1,3,3,3-hexafluoropropan-2-yl)-2-methoxyphenyl)-5,5-dimethylcyclohex-1-enyl)methyl)-4-methyloxazolidin-2-one;

tert-butyl 3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl(isopropyl)carbamate;

tert-butyl 3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl(ethyl)carbamate;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-ethylacetamide;

(4S,5R,Z)-5-(3,5-bis(trifluoromethyl)phenyl)-3-((2-(2-methoxy-5-(2,2,2-trifluoro-1-(methoxyimino)ethyl)phenyl)-5,5-dimethylcyclohex-1-enyl)methyl)-4-methyloxazolidin-2-one;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-(2-hydroxy-2-methylpropyl)acetamide;

(4S,5R)-5-(3,5-bis(trifluoromethyl)phenyl)-3-((2-(5-(3,3-difluoroazetidine-1-carbonyl)-2-methoxyphenyl)cyclohex-1-enyl)methyl)-4-methyloxazolidin-2-one;

(4S,5R)-5-(3,5-bis(trifluoromethyl)phenyl)-3-((2-(5-(1,1,1,3,3,3-hexafluoro-2-hydroxypropan-2-yl)-2-methoxyphenyl)-5,5-dimethylcyclohex-1-enyl)methyl)-4-methyloxazolidin-2-one;

(4S,5R)-5-(3,5-bis(trifluoromethyl)phenyl)-3-((2-(5-(1,1,1,3,3,3-hexafluoro-2-methoxypropan-2-yl)-2-methoxyphenyl)-5,5-dimethylcyclohex-1-enyl)methyl)-4-methyloxazolidin-2-one;

(4S,5R)-5-(3,5-bis(trifluoromethyl)phenyl)-3-((2-(5-((2-hydroxy-2-methylpropyl)(methyl)amino)-2-methoxyphenyl)-5,5-dimethylcyclohex-1-enyl)methyl)-4-methyloxazolidin-2-one;

(4S,5R)-3-((2-(5-acetyl-4-fluoro-2-methoxyphenyl)-5,5-dimethylcyclohex-1-enyl)methyl)-5-(3,5-bis(trifluoromethyl)phenyl)-4-methyloxazolidin-2-one;

(4S,5R)-5-(3,5-bis(trifluoromethyl)phenyl)-3-((2-(5-(4,5-dihydrooxazol-2-yl)-2-methoxyphenyl)-5,5-dimethylcyclohex-1-enyl)methyl)-4-methyloxazolidin-2-one;

(4S,5R)-5-(3,5-bis(trifluoromethyl)phenyl)-3-((2-(5-(3-hydroxyazetidine-1-carbonyl)-2-methoxyphenyl)-5,5-dimethylcyclohex-1-enyl)methyl)-4-methyloxazolidin-2-one;

(4S,5R)-5-(3,5-bis(trifluoromethyl)phenyl)-3-((2-(5-((R)-4-isopropyl-4,5-dihydrooxazol-2-yl)-2-methoxyphenyl)-5,5-dimethylcyclohex-1-enyl)methyl)-4-methyloxazolidin-2-one;

1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)cyclopropanecarbonitrile;

1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)cyclopropanecarboxamide;

(4S,5R)-5-(3,5-bis(trifluoromethyl)phenyl)-3-((2-(4-fluoro-2-methoxy-5-(2,2,2-trifluoroacetyl)phenyl)-5,5-dimethylcyclohex-1-enyl)methyl)-4-methyloxazolidin-2-one;

(4S,5R)-5-(3,5-bis(trifluoromethyl)phenyl)-3-((2-(5-(cyclopropanecarbonyl)-4-fluoro-2-methoxyphenyl)-5,5-dimethylcyclohex-1-enyl)methyl)-4-methyloxazolidin-2-one;

(4S,5R)-5-(3,5-bis(trifluoromethyl)phenyl)-3-((2-(2-methoxy-5-(trifluoromethyl)phenyl)-5-(trifluoromethyl)cyclohex-1-enyl)methyl)-4-methyloxazolidin-2-one;

(4S,5R)-5-(3,5-bis(trifluoromethyl)phenyl)-3-((2-(2-methoxy-5-nitrophenyl)-5-(trifluoromethyl)cyclohex-1-enyl)methyl)-4-methyloxazolidin-2-one;

(4S,5R)-3-((2-(5-amino-2-methoxyphenyl)-5-(trifluoromethyl)cyclohex-1-enyl)methyl)-5-(3,5-bis(trifluoromethyl)phenyl)-4-methyloxazolidin-2-one;

N-(3-(2-(((4S,5R)-5-(3,5-bis(trifluoromethyl)phenyl)-4-methyl-2-oxooxazolidin-3-yl)methyl)-4-(trifluoromethyl)cyclohex-1-enyl)-4-methoxyphenyl)acetamide;

methyl 5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxybenzoate;

5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxybenzoic acid;

(4S,5R)-5-(3,5-bis(trifluoromethyl)phenyl)-3-((2-(2-methoxy-5-nitro-4-(trifluoromethyl)phenyl)-5,5-dimethylcyclohex-1-enyl)methyl)-4-methyloxazolidin-2-one;

(4S,5R)-3-((2-(5-amino-2-methoxy-4-(trifluoromethyl)phenyl)-5,5-dimethylcyclohex-1-enyl)methyl)-5-(3,5-bis(trifluoromethyl)phenyl)-4-methyloxazolidin-2-one;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)trifluoro-N-methylmethanesulfonamide;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)-N-methylacetamide;

(4S,5R)-5-(3,5-bis(trifluoromethyl)phenyl)-3-((2-(2-methoxy-5-(methyl(4-(trifluoromethyl)thiazol-2-yl)amino)phenyl)-5,5-dimethylcyclohex-1-enyl)methyl)-4-methyloxazolidin-2-one;

(4S,5R)-5-(3,5-bis(trifluoromethyl)phenyl)-3-((2-(2-methoxy-5-(4-(trifluoromethyl)thiazol-2-ylamino)phenyl)-5,5-dimethylcyclohex-1-enyl)methyl)-4-methyloxazolidin-2-one;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxyphenyl)-N-methylacetamide;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxyphenyl)acetamide;

(4S,5R)-3-((2-(5-amino-4-fluoro-2-methoxyphenyl)-5,5-dimethylcyclohex-1-enyl)methyl)-5-(3,5-bis(trifluoromethyl)phenyl)-4-methyloxazolidin-2-one;

(4S,5R)-5-(3,5-bis(trifluoromethyl)phenyl)-3-((2-(4-fluoro-2-methoxy-5-nitrophenyl)-5,5-dimethylcyclohex-1-enyl)methyl)-4-methyloxazolidin-2-one;

tert-butyl 3-(((4S,5R)-5-(3,5-bis(trifluoromethyl)phenyl)-4-methyl-2-oxooxazolidin-3-yl)methyl)-4-(4-fluoro-5-isopropyl-2-methoxyphenyl)-5,6-dihydropyridine-1(2H)-carboxylate;

(4S,5R)-5-(3,5-bis(trifluoromethyl)phenyl)-3-((2-(4-fluoro-2-methoxy-5-(2,2,2-trifluoroethoxy)phenyl)-5,5-dimethylcyclohex-1-enyl)methyl)-4-methyloxazolidin-2-one;

(4S,5R)-5-(3,5-bis(trifluoromethyl)phenyl)-3-((2-(6-methoxybenzo[d][1,3]dioxol-5-yl)-5,5-dimethylcyclohex-1-enyl)methyl)-4-methyloxazolidin-2-one;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)-N-methylisobutyramide;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)-N-methylpropionamide;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)-N-methylmethanesulfonamide;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)-2,2,2-trifluoro-N-methylacetamide;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)trifluoromethanesulfonamide;

(4S,5R)-5-(3,5-bis(trifluoromethyl)phenyl)-3-((2-(2,4-dimethoxy-5-nitrophenyl)-5,5-dimethylcyclohex-1-enyl)methyl)-4-methyloxazolidin-2-one;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2,4-dimethoxyphenyl)-N-methylacetamide (4S,5R)-5-(3,5-bis(trifluoromethyl)phenyl)-3-((4-(4-fluoro-5-isopropyl-2-methoxyphenyl)-1-methyl-1,2,5,6-tetrahydropyridin-3-yl)methyl)-4-methyloxazolidin-2-one;

(4S,5R)-5-(3,5-bis(trifluoromethyl)phenyl)-3-((2-(4-hydroxy-2-methoxy-5-nitrophenyl)-5,5-dimethylcyclohex-1-enyl)methyl)-4-methyloxazolidin-2-one;

(4S,5R)-5-(3,5-bis(trifluoromethyl)phenyl)-3-((2-(2-methoxy-5-(methylamino)-4-(trifluoromethyl)phenyl)-5,5-dimethylcyclohex-1-enyl)methyl)-4-methyloxazolidin-2-one;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-ethyl-4-methoxyphenyl)-N-methylacetamide;

(4S,5R)-5-(3,5-bis(trifluoromethyl)phenyl)-3-((2-(5-((2-hydroxy-2-methylpropyl)(methyl)amino)-2-methoxy-4-(trifluoromethyl)phenyl)-5,5-dimethylcyclohex-1-enyl)methyl)-4-methyloxazolidin-2-one;

(4S,5R)-5-(3,5-bis(trifluoromethyl)phenyl)-3-((2-(5-cyclopropyl-4-fluoro-2-methoxyphenyl)-5,5-dimethylcyclohex-1-enyl)methyl)-4-methyloxazolidin-2-one;

1-((5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)(methyl)amino)-2-methyl-1-oxopropan-2-yl acetate;

(4S,5R)-5-(3,5-bis(trifluoromethyl)phenyl)-3-((2-(4-fluoro-5-isopropoxy-2-methoxyphenyl)-5,5-dimethylcyclohex-1-enyl)methyl)-4-methyloxazolidin-2-one;

1-((3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)(methyl)amino)-2-methyl-1-oxopropan-2-yl acetate;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-hydroxy-N,2-dimethylpropanamide;

(4S,5R)-5-(3,5-bis(trifluoromethyl)phenyl)-3-((4-(4-fluoro-5-isopropyl-2-methoxyphenyl)-1-(trifluoromethyl)-1,2,5,6-tetrahydropyridin-3-yl)methyl)-4-methyloxazolidin-2-one;

(4S,5R)-5-(3,5-bis(trifluoromethyl)phenyl)-3-((2-(2-methoxy-4-methyl-5-nitrophenyl)-5,5-dimethylcyclohex-1-enyl)methyl)-4-methyloxazolidin-2-one;

(4S,5R)-3-((2-(5-amino-2-methoxy-4-methylphenyl)-5,5-dimethylcyclohex-1-enyl)methyl)-5-(3,5-bis(trifluoromethyl)phenyl)-4-methyloxazolidin-2-one;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-methylphenyl)acetamide;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-methylphenyl)-N-methylacetamide;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-methylphenyl)trifluoromethanesulfonamide;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-methylphenyl)trifluoro-N-methylmethanesulfonamide;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-methylethanethioamide;

(4S,5R)-5-(3,5-bis(trifluoromethyl)phenyl)-3-((4-(4-fluoro-5-isopropyl-2-methoxyphenyl)-1-(2,2,2-trifluoroacetyl)-1,2,5,6-tetrahydropyridin-3-yl)methyl)-4-methyloxazolidin-2-one;

(4S,5R)-5-(3,5-bis(trifluoromethyl)phenyl)-3-((4-(4-fluoro-5-isopropyl-2-methoxyphenyl)-1-(trifluoromethylsulfonyl)-1,2,5,6-tetrahydropyridin-3-yl)methyl)-4-methyloxazolidin-2-one;

(4S,5R)-3-((1-acetyl-4-(4-fluoro-5-isopropyl-2-methoxyphenyl)-1,2,5,6-tetrahydropyridin-3-yl)methyl)-5-(3,5-bis(trifluoromethyl)phenyl)-4-methyloxazolidin-2-one;

(4S,5R)-5-(3,5-bis(trifluoromethyl)phenyl)-3-((4-(4-fluoro-5-isopropyl-2-methoxyphenyl)-1-(methylsulfonyl)-1,2,5,6-tetrahydropyridin-3-yl)methyl)-4-methyloxazolidin-2-one;

(4S,5R)-5-(3,5-bis(trifluoromethyl)phenyl)-3-((4-(4-fluoro-5-isopropyl-2-methoxyphenyl)-1-isopropyl-1,2,5,6-tetrahydropyridin-3-yl)methyl)-4-methyloxazolidin-2-one;

(4S,5R)-5-(3,5-bis(trifluoromethyl)phenyl)-3-((4-(4-fluoro-5-isopropyl-2-methoxyphenyl)-1,2,5,6-tetrahydropyridin-3-yl)methyl)-4-methyloxazolidin-2-one;

(4S,5R)-5-(3,5-bis(trifluoromethyl)phenyl)-3-((4-(4-fluoro-5-isopropyl-2-methoxyphenyl)-1-(2,2,2-trifluoroethyl)-1,2,5,6-tetrahydropyridin-3-yl)methyl)-4-methyloxazolidin-2-one;

N-(3-(2-(((4S,5R)-5-(3,5-bis(trifluoromethyl)phenyl)-4-methyl-2-thioxooxazolidin-3-yl)methyl)-4,4-dimethylcyclohex-1-enyl)-4-methoxyphenyl)-N-methylacetamide;

methyl 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)propanoate;

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)propanoic acid;

(4S,5R)-5-(3,5-bis(trifluoromethyl)phenyl)-3-((6-(4-fluoro-5-isopropyl-2-methoxyphenyl)spiro[2.5]oct-5-en-5-yl)methyl)-4-methyloxazolidin-2-one;

tert-butyl 6-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxyindoline-1-carboxylate;

(4S,5R)-5-(3,5-bis(trifluoromethyl)phenyl)-3-((2-(5-methoxyindolin-6-yl)-5,5-dimethylcyclohex-1-enyl)methyl)-4-methyloxazolidin-2-one;

(4S,5R)-3-((2-(1-acetyl-5-methoxyindolin-6-yl)-5,5-dimethylcyclohex-1-enyl)methyl)-5-(3,5-bis(trifluoromethyl)phenyl)-4-methyloxazolidin-2-one;

(4S,5R)-5-(3,5-bis(trifluoromethyl)phenyl)-3-((2-(5-methoxy-1-(2,2,2-trifluoroethyl)indolin-6-yl)-5,5-dimethylcyclohex-1-enyl)methyl)-4-methyloxazolidin-2-one;

(4S,5R)-5-(3,5-bis(trifluoromethyl)phenyl)-3-((2-(5-methoxy-1-(methylsulfonyl)indolin-6-yl)-5,5-dimethylcyclohex-1-enyl)methyl)-4-methyloxazolidin-2-one;

tert-butyl 4-(((4S,5R)-5-(3,5-bis(trifluoromethyl)phenyl)-4-methyl-2-oxooxazolidin-3-yl)methyl)-3-(4-fluoro-5-isopropyl-2-methoxyphenyl)-5,6-dihydropyridine-1(2H)-carboxylate;

(4S,5R)-5-(3,5-bis(trifluoromethyl)phenyl)-3-((3-(4-fluoro-5-isopropyl-2-methoxyphenyl)-1,2,5,6-tetrahydropyridin-4-yl)methyl)-4-methyloxazolidin-2-one;

(4S,5R)-5-(3,5-bis(trifluoromethyl)phenyl)-3-((3-(4-fluoro-5-isopropyl-2-methoxyphenyl)-1-(2,2,2-trifluoroethyl)-1,2,5,6-tetrahydropyridin-4-yl)methyl)-4-methyloxazolidin-2-one;

(4S,5R)-5-(3,5-bis(trifluoromethyl)phenyl)-3-((3-(4-fluoro-5-isopropyl-2-methoxyphenyl)-1-(trifluoromethylsulfonyl)-1,2,5,6-tetrahydropyridin-4-yl)methyl)-4-methyloxazolidin-2-one;

methyl 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2-dimethylpropanoate;

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2-dimethylpropanoic acid;

(R)—N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3,3,3-trifluoro-2-methoxy-2-phenylpropanamide;

(S)—N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3,3,3-trifluoro-2-methoxy-2-phenylpropanamide;

(4S,5R)-5-(3,5-bis(trifluoromethyl)phenyl)-3-((6-(2-methoxyphenyl)spiro[2.5]oct-5-en-5-yl)methyl)-4-methyloxazolidin-2-one;

(4S,5R)-5-(3,5-bis(trifluoromethyl)phenyl)-3-((6-(2-methoxy-5-nitrophenyl)spiro[2.5]oct-5-en-5-yl)methyl)-4-methyloxazolidin-2-one;

(4S,5R)-3-((6-(5-amino-2-methoxyphenyl)spiro[2.5]oct-5-en-5-yl)methyl)-5-(3,5-bis(trifluoromethyl)phenyl)-4-methyloxazolidin-2-one;

(R)—N-(3-(5-(((4S,5R)-5-(3,5-bis(trifluoromethyl)phenyl)-4-methyl-2-oxooxazolidin-3-yl)methyl)spiro[2.5]oct-5-en-6-yl)-4-methoxyphenyl)-3,3,3-trifluoro-2-methoxy-2-phenylpropanamide;

(S)—N-(3-(5-(((4S,5R)-5-(3,5-bis(trifluoromethyl)phenyl)-4-methyl-2-oxooxazolidin-3-yl)methyl)spiro[2.5]oct-5-en-6-yl)-4-methoxyphenyl)-3,3,3-trifluoro-2-methoxy-2-phenylpropanamide;

(R)—N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3,3,3-trifluoro-2-methoxy-N-methyl-2-phenylpropanamide;

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)propanamide;

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)propanenitrile;

(4S,5R)-3-((2-(5-(2-(2H-tetrazol-5-yl)ethyl)-2-methoxyphenyl)-5,5-dimethylcyclohex-1-enyl)methyl)-5-(3,5-bis(trifluoromethyl)phenyl)-4-methyloxazolidin-2-one;

(4S,5R)-5-(3,5-bis(trifluoromethyl)phenyl)-3-((2-(4-fluoro-2-methoxy-5-(1-methylcyclopropyl)phenyl)-5,5-dimethylcyclohex-1-enyl)methyl)-4-methyloxazolidin-2-one;

(4S,5R)-5-(3,5-bis(trifluoromethyl)phenyl)-3-((6-(4-fluoro-2-methoxy-5-(1-methylcyclopropyl)phenyl)spiro[2.5]oct-5-en-5-yl)methyl)-4-methyloxazolidin-2-one;

(4S,5R)-5-(3,5-bis(trifluoromethyl)phenyl)-3-((2-(3'-difluoro-4-methoxy-4'-(methoxymethoxy)biphenyl-3-yl)-5,5-dimethylcyclohex-1-enyl)methyl)-4-methyloxazolidin-2-one;

(4S,5R)-5-(3,5-bis(trifluoromethyl)phenyl)-3-((2-(3'-difluoro-4'-hydroxy-4-methoxybiphenyl-3-yl)-5,5-dimethylcyclohex-1-enyl)methyl)-4-methyloxazolidin-2-one;

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2-dimethylpropanamide;

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2-dimethylpropanenitrile;

methyl 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3-methylbutanoate;

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3-methylbutanoic acid;

methyl 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2-dimethylbutanoate;

4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2-dimethylbutanoic acid;

ethyl 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclobutanecarboxylate;

1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclobutanecarboxylic acid;

1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclobutanecarboxamide;

methyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-methylpropanoate;

(4S,5R)-5-(3,5-bis(trifluoromethyl)phenyl)-3-((2-(2-methoxy-5-(trifluoromethyl)pyridin-3-yl)-5,5-dimethylcyclohex-1-enyl)methyl)-4-methyloxazolidin-2-one;

methyl 2-(7-(2-(((4S,5R)-5-(3,5-bis(trifluoromethyl)phenyl)-4-methyl-2-oxooxazolidin-3-yl)methyl)-4,4-dimethylcyclohex-1-enyl)benzo[d][1,3]dioxol-5-yl)acetate;

2-(7-(2-(((4S,5R)-5-(3,5-bis(trifluoromethyl)phenyl)-4-methyl-2-oxooxazolidin-3-yl)methyl)-4,4-dimethylcyclohex-1-enyl)benzo[d][1,3]dioxol-5-yl)acetic acid;

2-(7-(2-(((4S,5R)-5-(3,5-bis(trifluoromethyl)phenyl)-4-methyl-2-oxooxazolidin-3-yl)methyl)-4,4-dimethylcyclohex-1-enyl)benzo[d][1,3]dioxol-5-yl)-N-methylacetamide;

2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-methylpropanoic acid;

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N,2,2-trimethylpropanamide;

methyl 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclopentanecarboxylate;

1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclopentanecarboxylic acid;

3-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxyphenyl)-2,2-dimethylpropanoic acid;

methyl 7-(2-(((4S,5R)-5-(3,5-bis(trifluoromethyl)phenyl)-4-methyl-2-oxooxazolidin-3-yl)methyl)-4,4-dimethylcyclohex-1-enyl)-6-methoxy-1,2,3,4-tetrahydronaphthalene-2-carboxylate;

7-(2-(((4S,5R)-5-(3,5-bis(trifluoromethyl)phenyl)-4-methyl-2-oxooxazolidin-3-yl)methyl)-4,4-dimethylcyclohex-1-enyl)-6-methoxy-1,2,3,4-tetrahydronaphthalene-2-carboxylic acid;

methyl 3-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxyphenyl)-2,2-dimethylpropanoate;

3-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxyphenyl)-2,2-dimethylpropanamide;

ethyl 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenethyl)cyclobutanecarboxylate;

1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenethyl)cyclobutanecarboxylic acid;

3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzonitrile;

(4S,5R)-5-(3,5-bis(trifluoromethyl)phenyl)-3-((2-(2-methoxy-5-(2H-tetrazol-5-yl)phenyl)-5,5-dimethylcyclohex-1-enyl)methyl)-4-methyloxazolidin-2-one;

(4R,5R)-5-(3,5-bis(trifluoromethyl)phenyl)-3-((2-(4-fluoro-5-isopropyl-2-methoxyphenyl)-5,5-dimethylcyclohex-1-enyl)methyl)-4-methyloxazolidin-2-one;

(4S,5S)-5-(3,5-bis(trifluoromethyl)phenyl)-3-((2-(4-fluoro-5-isopropyl-2-methoxyphenyl)-5,5-dimethylcyclohex-1-enyl)methyl)-4-methyloxazolidin-2-one;

(4R,5S)-5-(3,5-bis(trifluoromethyl)phenyl)-3-((2-(4-fluoro-5-isopropyl-2-methoxyphenyl)-5,5-dimethylcyclohex-1-enyl)methyl)-4-methyloxazolidin-2-one;

7-(2-(((4S,5R)-5-(3,5-bis(trifluoromethyl)phenyl)-4-methyl-2-oxooxazolidin-3-yl)methyl)-4,4-dimethylcyclohex-1-enyl)-6-methoxy-1,2,3,4-tetrahydronaphthalene-2-carboxamide;

(4S,5R)-5-(3,5-bis(trifluoromethyl)phenyl)-3-((2-(2-methoxy-5-(2-methyl-2H-tetrazol-5-yl)phenyl)-5,5-dimethylcyclohex-1-enyl)methyl)-4-methyloxazolidin-2-one;

(4S,5R)-5-(3,5-bis(trifluoromethyl)phenyl)-3-((2-(2-methoxy-5-(1-methyl-1H-tetrazol-5-yl)phenyl)-5,5-dimethylcyclohex-1-enyl)methyl)-4-methyloxazolidin-2-one;

(4S,5R)-5-(3,5-bis(trifluoromethyl)phenyl)-3-((2-(2-methoxy-5-(2-methyl-2-(2H-tetrazol-5-yl)propyl)phenyl)-5,5-dimethylcyclohex-1-enyl)methyl)-4-methyloxazolidin-2-one;

(4S,5R)-5-(3,5-bis(trifluoromethyl)phenyl)-3-((2-(2-methoxy-5-(2-methyl-2-(2-methyl-2H-tetrazol-5-yl)propyl)phenyl)-5,5-dimethylcyclohex-1-enyl)methyl)-4-methyloxazolidin-2-one;

tert-butyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzamido)acetate;

tert-butyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-N-methylbenzamido)acetate;

(R)-methyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzamido)-3-methylbutanoate;

(R)-methyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-N-methylbenzamido)-3-methylbutanoate;

(R)-2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzamido)-3-methylbutanoic acid;

methyl 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy benzyl)cyclobutanecarboxylate;

2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-N-methylbenzamido)acetic acid;

methyl 3-(5-(2-(((4S,5R)-5-(3,5-bis(trifluoromethyl)phenyl)-4-methyl-2-oxooxazolidin-3-yl)methyl)-4,4-dimethylcyclohex-1-enyl)-6-methoxypyridin-3-yl)-2,2-dimethylpropanoate;

3-(5-(2-(((4S,5R)-5-(3,5-bis(trifluoromethyl)phenyl)-4-methyl-2-oxooxazolidin-3-yl)methyl)-4,4-dimethylcyclohex-1-enyl)-6-methoxypyridin-3-yl)-2,2-dimethylpropanoic acid;

(4S,5R)-5-(3,5-bis(trifluoromethyl)phenyl)-3-((2-(5-chloro-2-methoxyphenyl)-5,5-dimethylcyclohex-1-enyl)methyl)-4-methyloxazolidin-2-one;

tert-butyl 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-5,6-dihydropyridine-1(2H)-carboxylate;

(4S,5R)-5-(3,5-bis(trifluoromethyl)phenyl)-3-((2-(5-(3,6-dihydro-2H-pyran-4-yl)-2-methoxyphenyl)-5,5-dimethylcyclohex-1-enyl)methyl)-4-methyloxazolidin-2-one;

(4S,5R)-5-(3,5-bis(trifluoromethyl)phenyl)-3-((2-(5-(hydroxymethyl)-2-methoxyphenyl)-5,5-dimethylcyclohex-1-enyl)methyl)-4-methyloxazolidin-2-one;

methyl 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-1,2,4-oxadiazole-5-carboxylate;

(4S,5R)-5-(3,5-bis(trifluoromethyl)phenyl)-3-((2-(2-methoxy-5-(1,2,3,6-tetrahydropyridin-4-yl)phenyl)-5,5-dimethylcyclohex-1-enyl)methyl)-4-methyloxazolidin-2-one;

methyl 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-5,6-dihydropyridine-1(2H)-carboxylate;

(S)-methyl 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)pyrrolidine-2-carboxylate;

(R)-methyl 2-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzylamino)-3-methylbutanoate;

4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)cyclohex-3-enecarboxylic acid;

(R)-methyl 2-((3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)(methyl)amino)-3-methylbutanoate;

(4S,5R)-5-(3,5-bis(trifluoromethyl)phenyl)-3-((2-(2-methoxy-5-(4R)-2-(trifluoromethyl)pyrrolidin-1-yl)methyl)phenyl)-5,5-dimethylcyclohex-1-enyl)methyl)-4-methyloxazolidin-2-one;

(4S,5R)-5-(3,5-bis(trifluoromethyl)phenyl)-3-((2-(6-isopropyl-3-methoxypyridin-2-yl)-5,5-dimethylcyclohex-1-enyl)methyl)-4-methyloxazolidin-2-one; and (4S,5R)-5-(3,5-bis(trifluoromethyl)phenyl)-3-((2-(5-(((S)-3-fluoropyrrolidin-1-yl)methyl)-2-methoxyphenyl)-5,5-dimethylcyclohex-1-enyl)methyl)-4-methyloxazolidin-2-one.

4. The cycloalkenyl aryl derivatives, stereoisomers thereof, pharmaceutically acceptable salts thereof, hydrates thereof or solvates thereof according to claim 3, wherein the cycloalkenyl aryl derivatives are selected from the group consisting of the following compounds:

(4S,5R)-5-(3,5-bis(trifluoromethyl)phenyl)-3-((2-(5-isopropyl-2-methoxyphenyl)-5,5-dimethylcyclohex-1-enyl)methyl)-4-methyloxazolidine-2-thione;

(4S,5R)-5-(3,5-bis(trifluoromethyl)phenyl)-3-((2-(4-fluoro-5-isopropyl-2-methoxyphenyl)-5,5-dimethylcyclohex-1-enyl)methyl)-4-methyloxazolidine-2-thione;

(4S,5R)-5-(3,5-bis(trifluoromethyl)phenyl)-3-((2-(2-methoxyphenyl)-5,5-dimethylcyclohex-1-enyl)methyl)-4-methyloxazolidin-2-one;

(4S,5R)-5-(3,5-bis(trifluoromethyl)phenyl)-3-((2-(4-fluoro-5-isopropyl-2-methoxyphenyl)-5,5-dimethylcyclohex-1-enyl)methyl)-4-methyloxazolidin-2-one;

(4S,5R)-5-(3,5-bis(trifluoromethyl)phenyl)-3-((2-(4-fluoro-5-isopropyl-2-methoxyphenyl)-5-methylcyclohex-1-enyl)methyl)-4-methyloxazolidin-2-one;

(4S,5R)-5-(3,5-bis(trifluoromethyl)phenyl)-3-((2-(4-fluoro-5-isopropyl-2-methoxyphenyl)-5-methylcyclohex-1-enyl)methyl)-4-methyloxazolidine-2-thione;

(4S,5R)-5-(3,5-bis(trifluoromethyl)phenyl)-3-((2-(4-fluoro-5-isopropyl-2-methoxyphenyl)cyclohex-1-enyl)methyl)-4-methyloxazolidin-2-one;

(4S,5R)-5-(3,5-bis(trifluoromethyl)phenyl)-3-((2-(4-fluoro-5-isopropyl-2-methoxyphenyl)cyclohex-1-enyl)methyl)-4-methyloxazolidine-2-thione;

methyl 3-(2-(((4S,5R)-5-(3,5-bis(trifluoromethyl)phenyl)-4-methyl-2-oxooxazolidin-3-yl)methyl)cyclohex-1-enyl)-4-methoxybenzoate;

(4S,5R)-5-(3,5-bis(trifluoromethyl)phenyl)-3-((2-(5-isopropyl-2-methoxyphenyl)-4,4-dimethylcyclohex-1-enyl)methyl)-4-methyloxazolidin-2-one;

(4S,5R)-5-(3,5-bis(trifluoromethyl)phenyl)-3-((2-(4-fluoro-5-isopropyl-2-methoxyphenyl)-5-(trifluoromethyl)cyclohex-1-enyl)methyl)-4-methyloxazolidin-2-one;

3-(2-(((4S,5R)-5-(3,5-bis(trifluoromethyl)phenyl)-4-methyl-2-oxooxazolidin-3-yl)methyl)cyclohex-1-enyl)-4-methoxybenzaldehyde;

(4S,5R)-5-(3,5-bis(trifluoromethyl)phenyl)-3-((2-(5-(1-hydroxyethyl)-2-methoxyphenyl)cyclohex-1-enyl)methyl)-4-methyloxazolidin-2-one;

(4S,5R)-5-(3,5-bis(trifluoromethyl)phenyl)-3-((2-(5-(2-hydroxypropan-2-yl)-2-methoxyphenyl)cyclohex-1-enyl)methyl)-4-methyloxazolidin-2-one;

N-(3-(2-(((4S,5R)-5-(3,5-bis(trifluoromethyl)phenyl)-4-methyl-2-oxooxazolidin-3-yl)methyl)cyclohex-1-enyl)-4-methoxyphenyl)-N-methylisobutyramide;

(4S,5R)-5-(3,5-bis(trifluoromethyl)phenyl)-3-((2-(2-methoxy-5-(trifluoromethyl)phenyl)-5,5-dimethylcyclohex-1-enyl)methyl)-4-methyloxazolidin-2-one;

(4S,5R)-5-(3,5-bis(trifluoromethyl)phenyl)-3-((5-tert-butyl-2-(4-fluoro-5-isopropyl-2-methoxyphenyl)cyclohex-1-enyl)methyl)-4-methyloxazolidin-2-one;

(4S,5R)-5-(3,5-bis(trifluoromethyl)phenyl)-3-((2-(5-(1-hydroxyethyl)-2-methoxyphenyl)-5,5-dimethylcyclohex-1-enyl)methyl)-4-methyloxazolidin-2-one;

(4S,5R)-5-(3,5-bis(trifluoromethyl)phenyl)-3-((2-(5-(2-hydroxypropan-2-yl)-2-methoxyphenyl)-5,5-dimethylcyclohex-1-enyl)methyl)-4-methyloxazolidin-2-one;

(4S,5R)-5-(3,5-bis(trifluoromethyl)phenyl)-3-((2-(5-isopropyl-2-methoxyphenyl)-5,5-dimethylcyclohex-1-enyl)methyl)-4-methyloxazolidin-2-one;

(4S,5R)-5-(3,5-bis(trifluoromethyl)phenyl)-3-((2-(5-isopropyl-2-methoxyphenyl)-5-(trifluoromethyl)cyclohex-1-enyl)methyl)-4-methyloxazolidin-2-one;

(4S,5R)-5-(3,5-bis(trifluoromethyl)phenyl)-3-((2-(4-fluoro-5-isopropyl-2-methoxyphenyl)-4,4-dimethylcyclohex-1-enyl)methyl)-4-methyloxazolidin-2-one;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)acetamide;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-methylacetamide;

(4S,5R)-5-(3,5-bis(trifluoromethyl)phenyl)-3-((2-(5-tert-butyl-2-methoxyphenyl)-5,5-dimethylcyclohex-1-enyl)methyl)-4-methyloxazolidin-2-one;

(4S,5R)-5-(3,5-bis(trifluoromethyl)phenyl)-3-((2-(2-methoxy-5-(trifluoromethoxy)phenyl)-5,5-dimethylcyclohex-1-enyl)methyl)-4-methyloxazolidin-2-one;

(4S,5R)-5-(3,5-bis(trifluoromethyl)phenyl)-3-((5,5-difluoro-2-(4-fluoro-5-isopropyl-2-methoxyphenyl)cyclohex-1-enyl)methyl)-4-methyloxazolidin-2-one;

methyl 3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl(methyl)carbamate;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N-methylmethanesulfonamide;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3,3,3-trifluoro-N-methylpropanamide;

(4S,5R)-5-(3,5-bis(trifluoromethyl)phenyl)-3-((2-(4-fluoro-2-methoxy-5-(1,1,1-trifluoropropan-2-yl)phenyl)-5,5-dimethylcyclohex-1-enyl)methyl)-4-methyloxazolidin-2-one;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)trifluoromethanesulfonamide;

(4S,5R)-5-(3,5-bis(trifluoromethyl)phenyl)-3-((2-(5-(1,1,1,3,3,3-hexafluoro-2-hydroxypropan-2-yl)-2-methoxyphenyl)-5,5-dimethylcyclohex-1-enyl)methyl)-4-methyloxazolidin-2-one;

(4S,5R)-5-(3,5-bis(trifluoromethyl)phenyl)-3-((2-(5-(1,1,1,3,3,3-hexafluoro-2-methoxypropan-2-yl)-2-methoxyphenyl)-5,5-dimethylcyclohex-1-enyl)methyl)-4-methyloxazolidin-2-one;

(4S,5R)-3-((2-(5-acetyl-4-fluoro-2-methoxyphenyl)-5,5-dimethylcyclohex-1-enyl)methyl)-5-(3,5-bis(trifluoromethyl)phenyl)-4-methyloxazolidin-2-one;

(4S,5R)-5-(3,5-bis(trifluoromethyl)phenyl)-3-((2-(5-(4,5-dihydrooxazol-2-yl)-2-methoxyphenyl)-5,5-dimethylcyclohex-1-enyl)methyl)-4-methyloxazolidin-2-one;

(4S,5R)-5-(3,5-bis(trifluoromethyl)phenyl)-3-((2-(5-((R)-4-isopropyl-4,5-dihydrooxazol-2-yl)-2-methoxyphenyl)-5,5-dimethylcyclohex-1-enyl)methyl)-4-methyloxazolidin-2-one;

1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)cyclopropanecarbonitrile;

1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)cyclopropanecarboxamide;

(4S,5R)-5-(3,5-bis(trifluoromethyl)phenyl)-3-((2-(4-fluoro-2-methoxy-5-(2,2,2-trifluoroacetyl)phenyl)-5,5-dimethylcyclohex-1-enyl)methyl)-4-methyloxazolidin-2-one;

(4S,5R)-5-(3,5-bis(trifluoromethyl)phenyl)-3-((2-(5-(cyclopropanecarbonyl)-4-fluoro-2-methoxyphenyl)-5,5-dimethylcyclohex-1-enyl)methyl)-4-methyloxazolidin-2-one;

(4S,5R)-5-(3,5-bis(trifluoromethyl)phenyl)-3-((2-(2-methoxy-5-(trifluoromethyl)phenyl)-5-(trifluoromethyl)cyclohex-1-enyl)methyl)-4-methyloxazolidin-2-one;

(4S,5R)-5-(3,5-bis(trifluoromethyl)phenyl)-3-((2-(2-methoxy-5-nitrophenyl)-5-(trifluoromethyl)cyclohex-1-enyl)methyl)-4-methyloxazolidin-2-one;

(4S,5R)-3-((2-(5-amino-2-methoxyphenyl)-5-(trifluoromethyl)cyclohex-1-enyl)methyl)-5-(3,5-bis(trifluoromethyl)phenyl)-4-methyloxazolidin-2-one;

N-(3-(2-(((4S,5R)-5-(3,5-bis(trifluoromethyl)phenyl)-4-methyl-2-oxooxazolidin-3-yl)methyl)-4-(trifluoromethyl)cyclohex-1-enyl)-4-methoxyphenyl)acetamide;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)trifluoro-N-methylmethanesulfonamide;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)-N-methylacetamide;

(4S,5R)-5-(3,5-bis(trifluoromethyl)phenyl)-3-((2-(2-methoxy-5-(methyl(4-(trifluoromethyl)thiazol-2-yl)amino)phenyl)-5,5-dimethylcyclohex-1-enyl)methyl)-4-methyloxazolidin-2-one;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxyphenyl)-N-methylacetamide;

(4S,5R)-5-(3,5-bis(trifluoromethyl)phenyl)-3-((2-(4-fluoro-2-methoxy-5-(2,2,2-trifluoroethoxy)phenyl)-5,5-dimethylcyclohex-1-enyl)methyl)-4-methyloxazolidin-2-one;

(4S,5R)-5-(3,5-bis(trifluoromethyl)phenyl)-3-((2-(6-methoxybenzo[d][1,3]dioxol-5-yl)-5,5-dimethylcyclohex-1-enyl)methyl)-4-methyloxazolidin-2-one;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)-2,2,2-trifluoro-N-methylacetamide;

(4S,5R)-5-(3,5-bis(trifluoromethyl)phenyl)-3-((4-(4-fluoro-5-isopropyl-2-methoxyphenyl)-1-methyl-1,2,5,6-tetrahydropyridin-3-yl)methyl)-4-methyloxazolidin-2-one;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-ethyl-4-methoxyphenyl)-N-methylacetamide;

(4S,5R)-5-(3,5-bis(trifluoromethyl)phenyl)-3-((2-(5-cyclopropyl-4-fluoro-2-methoxyphenyl)-5,5-dimethylcyclohex-1-enyl)methyl)-4-methyloxazolidin-2-one;

(4S,5R)-5-(3,5-bis(trifluoromethyl)phenyl)-3-((2-(4-fluoro-5-isopropoxy-2-methoxyphenyl)-5,5-dimethylcyclohex-1-enyl)methyl)-4-methyloxazolidin-2-one;

1-((3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)(methyl)amino)-2-methyl-1-oxopropan-2-yl acetate;

N-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2-hydroxy-N,2-dimethylpropanamide;

(4S,5R)-5-(3,5-bis(trifluoromethyl)phenyl)-3-((4-(4-fluoro-5-isopropyl-2-methoxyphenyl)-1-(trifluoromethyl)-1,2,5,6-tetrahydropyridin-3-yl)methyl)-4-methyloxazolidin-2-one;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-methylphenyl)-N-methylacetamide;

N-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-methylphenyl)trifluoro-N-methylmethanesulfonamide;

(4S,5R)-5-(3,5-bis(trifluoromethyl)phenyl)-3-((4-(4-fluoro-5-isopropyl-2-methoxyphenyl)-1-(trifluoromethylsulfonyl)-1,2,5,6-tetrahydropyridin-3-yl)methyl)-4-methyloxazolidin-2-one;

(4S,5R)-5-(3,5-bis(trifluoromethyl)phenyl)-3-((4-(4-fluoro-5-isopropyl-2-methoxyphenyl)-1-isopropyl-1,2,5,6-tetrahydropyridin-3-yl)methyl)-4-methyloxazolidin-2-one;

(4S,5R)-5-(3,5-bis(trifluoromethyl)phenyl)-3-((4-(4-fluoro-5-isopropyl-2-methoxyphenyl)-1-(2,2,2-trifluoroethyl)-1,2,5,6-tetrahydropyridin-3-yl)methyl)-4-methyloxazolidin-2-one;

methyl 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)propanoate;

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)propanoic acid;

(4S,5R)-5-(3,5-bis(trifluoromethyl)phenyl)-3-((6-(4-fluoro-5-isopropyl-2-methoxyphenyl)spiro[2.5]oct-5-en-5-yl)methyl)-4-methyloxazolidin-2-one;

methyl 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2-dimethylpropanoate;

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-2,2-dimethylpropanoic acid;

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)propanenitrile;

(4S,5R)-5-(3,5-bis(trifluoromethyl)phenyl)-3-((2-(4-fluoro-2-methoxy-5-(1-methylcyclopropyl)phenyl)-5,5-dimethylcyclohex-1-enyl)methyl)-4-methyloxazolidin-2-one;

(4S,5R)-5-(3,5-bis(trifluoromethyl)phenyl)-3-((6-(4-fluoro-2-methoxy-5-(1-methylcyclopropyl)phenyl)spiro[2.5]oct-5-en-5-yl)methyl)-4-methyloxazolidin-2-one;

methyl 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3-methylbutanoate;

1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclobutanecarboxylic acid;

(4S,5R)-5-(3,5-bis(trifluoromethyl)phenyl)-3-((2-(2-methoxy-5-(trifluoromethyl)pyridin-3-yl)-5,5-dimethylcyclohex-1-enyl)methyl)-4-methyloxazolidin-2-one;

methyl 2-(7-(2-(((4S,5R)-5-(3,5-bis(trifluoromethyl)phenyl)-4-methyl-2-oxooxazolidin-3-yl)methyl)-4,4-dimethylcyclohex-1-enyl)benzo[d][1,3]dioxol-5-yl)acetate;

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-N,2,2-trimethylpropanamide;

methyl 1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclopentanecarboxylate;

1-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxybenzyl)cyclopentanecarboxylic acid;

3-(5-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4-methoxyphenyl)-2,2-dimethylpropanamide;

(4S,5R)-5-(3,5-bis(trifluoromethyl)phenyl)-3-((2-(2-methoxy-5-(2-methyl-2H-tetrazol-5-yl)phenyl)-5,5-dimethylcyclohex-1-enyl)methyl)-4-methyloxazolidin-2-one;

(4S,5R)-5-(3,5-bis(trifluoromethyl)phenyl)-3-((2-(2-methoxy-5-(2-methyl-2-(2H-tetrazol-5-yl)propyl)phenyl)-5,5-dimethylcyclohex-1-enyl)methyl)-4-methyloxazolidin-2-one;

(4S,5R)-5-(3,5-bis(trifluoromethyl)phenyl)-3-((2-(2-methoxy-5-(2-methyl-2-(2-methyl-2H-tetrazol-5-yl)propyl)phenyl)-5,5-dimethylcyclohex-1-enyl)methyl)-4-methyloxazolidin-2-one;

3-(5-(2-(((4S,5R)-5-(3,5-bis(trifluoromethyl)phenyl)-4-methyl-2-oxooxazolidin-3-yl)methyl)-4,4-dimethylcyclohex-1-enyl)-6-methoxypyridin-3-yl)-2,2-dimethylpropanoic acid;

(4S,5R)-5-(3,5-bis(trifluoromethyl)phenyl)-3-((2-(5-chloro-2-methoxyphenyl)-5,5-dimethylcyclohex-1-enyl)methyl)-4-methyloxazolidin-2-one; and (4S,5R)-5-(3,5-bis(trifluoromethyl)phenyl)-3-((2-(6-isopropyl-3-methoxypyridin-2-yl)-5,5-dimethylcyclohex-1-enyl)methyl)-4-methyloxazolidin-2-one;

(4S,5R)-5-(3,5-bis(trifluoromethyl)phenyl)-3-((2-(5-(((S)-3-fluoropyrrolidin-1-yl)methyl)-2-methoxyphenyl)-5,5-dimethylcyclohex-1-enyl)methyl)-4-methyloxazolidin-2-one.

5. Pharmaceutical compositions comprising cycloalkenyl aryl derivatives of formula I, stereoisomers thereof, pharmaceutically acceptable salts thereof, hydrates thereof or solvates thereof according claim 1 together with pharmaceutically acceptable carriers.

6. The pharmaceutical compositions according to claim 5, wherein the compositions are used for prevention or treatment of dyslipidemia and atherosclerosis associated with dyslipidemia, through increasing of High-density Lipoprotein Cholesterol (HDL-C) and decreasing of Low-density Lipoprotein Cholesterol (LDL-C) by CETP activity inhibition.

7. A method for preparing cycloalkenyl aryl derivatives of formula 1, the method comprising the steps of:

subjecting a compound of the following formula 2 to a Vilsmeier reaction to prepare a compound of the following formula 3;

subjecting the obtained compound of the formula 3 to a Suzuki reaction with a compound of the following formula 4 in the presence of palladium to prepare a compound of the following formula 5; and subjecting the obtained compound of the formula 5 and a compound of the following formula 6 to the reduction to prepare a compound of the following formula 7, and then subjecting the obtained compound of the formula 7 to formation of a ring:

[Formula 1]

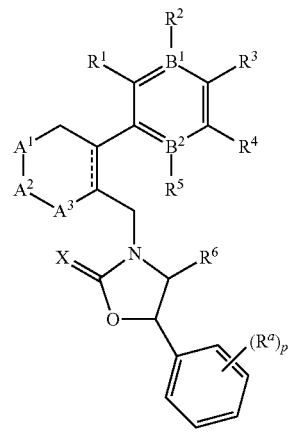

(I)

[Formula 2]

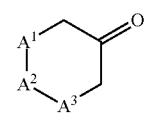

(II)

[Formula 3]

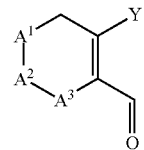

(III)

[Formula 4]

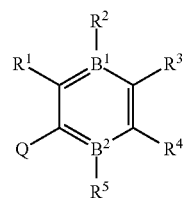

(IV)

[Formula 5]

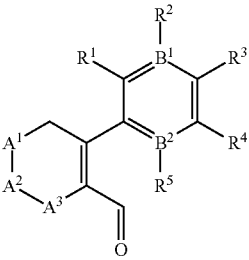

(V)

[Formula 6]

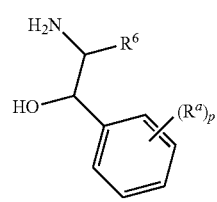

(VI)

233

-continued

[Formula 7]

(VII)

wherein, $A^1, A^2, A^3, B^1, B^2, R^1, R^2, R^3, R^4, R^5, R^6, R^a$, p and X are same as defined in claim 1; Y is Cl or Br; and Q is —B(OH)$_2$ or

8. A method for preparing cycloalkenyl aryl derivatives of formula 1, the method comprising the steps of:

subjecting compound of the following formula 3 and a compound of the following formula 6 to the reduction to prepare a compound of the following formula 8, and then subjecting the obtained compound of the formula 8 to formation of a ring; and subjecting the obtained compound of the formula 9 to a Suzuki reaction with a compound of the following formula 4 in the presence of palladium to prepare a compound of the following formula 1:

[Formula 1]

(I)

234

-continued

[Formula 3]

(III)

[Formula 4]

(IV)

[Formula 6]

(VI)

[Formula 8]

(VIII)

[Formula 9]

(IX)

wherein, $A^1, A^2, A^3, B^1, B^2, R^1, R^2, R^3, R^4, R^5, R^6, R^a$, p, and X are same as defined in claim 1; Y is Cl or Br; and Q is —B(OH)$_2$ or

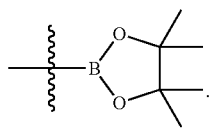 [SMILES: *B1OC(C)(C)C(C)(C)O1]

9. Pharmaceutical compositions comprising cycloalkenyl aryl derivatives of formula I, stereoisomers thereof, pharmaceutically acceptable salts thereof, hydrates thereof or solvates thereof according to claim 3 together with pharmaceutically acceptable carriers.

10. Pharmaceutical compositions comprising cycloalkenyl aryl derivatives of formula I, stereoisomers thereof, pharmaceutically acceptable salts thereof, hydrates thereof or solvates thereof according to claim 2 together with pharmaceutically acceptable carriers.

* * * * *